United States Patent
Rangaramanujam et al.

(10) Patent No.: US 10,561,673 B2
(45) Date of Patent: *Feb. 18, 2020

(54) DENDRIMER BASED NANODEVICES FOR THERAPEUTIC AND IMAGING PURPOSES

(71) Applicants: Wayne State University, Detroit, MI (US); The United States of America as Represented by the Secretary, Department of Health and Human Service, Bethesda, MD (US)

(72) Inventors: Kannan Rangaramanujam, Highland, MD (US); Sujatha Kannan, Highland, MD (US); Roberto Romero, Grosse Pointe, MI (US); Raghavendra S Navath, Detroit, MI (US); Hui Dai, Detroit, MI (US); Anupa R. Menjoge, Detroit, MI (US)

(73) Assignees: Wayne State University, Detroit, MI (US); The United States of America as Represented by the Secretary, Department of Health and Human Service, Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 16/223,793

(22) Filed: Dec. 18, 2018

(65) Prior Publication Data
US 2019/0247407 A1 Aug. 15, 2019

Related U.S. Application Data

(63) Continuation of application No. 14/477,725, filed on Sep. 4, 2014, now Pat. No. 10,172,951, which is a
(Continued)

(51) Int. Cl.
*A61K 9/00* (2006.01)
*A61K 31/65* (2006.01)
(Continued)

(52) U.S. Cl.
CPC ............ *A61K 31/65* (2013.01); *A61K 31/198* (2013.01); *A61K 31/405* (2013.01); *A61K 31/43* (2013.01);
(Continued)

(58) Field of Classification Search
CPC .................................... A61K 31/65
See application file for complete search history.

(56) References Cited

U.S. PATENT DOCUMENTS

| | | | |
|---|---|---|---|
| 2009/0192227 A1* | 7/2009 | Tirouvanziam | A61K 31/195 514/562 |
| 2010/0074932 A1* | 3/2010 | Talsma | A01N 59/16 424/409 |

(Continued)

FOREIGN PATENT DOCUMENTS

WO 2009046446 A2 4/2009 ........... A61K 9/0048

OTHER PUBLICATIONS

Office Action dated Jan. 21, 2016 for European Application No. 10789963.5.
(Continued)

*Primary Examiner* — Paul W Dickinson
(74) *Attorney, Agent, or Firm* — Pabst Patent Group LLP

(57) ABSTRACT

A nanodevice composition including N-acetyl cysteine linked to a dendrimer, such as a PAMAM dendrimer or a multiarm PEG polymer, is provided. Also provided is a nanodevice for targeted delivery of a compound to a location in need of treatment. The nanodevice includes a PAMAM dendrimer or multiarm PEG polymer, linked to the compound via a disulfide bond. There is provided a nanodevice composition for localizing and delivering therapeutically active agents, the nanodevice includes a PAMAM dendrimer or multiarm PEG polymer and at least one therapeutically active agent attached to the PAMAM dendrimer or multiarm (Continued)

PEG polymer. A method of site-specific delivery of a therapeutically active agent, by attaching a therapeutically active agent to a PAMAM dendrimer or multiarm PEG polymer using a disulfide bond, administering the PAMAM dendrimer or multiarm PEG polymer to a patient in need of treatment, localizing the dendrimer or multiarm PEG polymer to a site in need of treatment, and releasing the therapeutically active agent at the site in need of treatment.

20 Claims, 101 Drawing Sheets

Specification includes a Sequence Listing.

Related U.S. Application Data continuation of application No. 12/797,657, filed on Jun. 10, 2010, now Pat. No. 8,889,101.

(60) Provisional application No. 61/319,285, filed on Mar. 31, 2010, provisional application No. 61/187,263, filed on Jun. 15, 2009.

(51) Int. Cl.

| | | |
|---|---|---|
| *A61K 47/64* | (2017.01) | |
| *A61K 47/59* | (2017.01) | |
| *A61K 47/60* | (2017.01) | |
| *A61K 38/10* | (2006.01) | |
| *A61K 31/198* | (2006.01) | |
| *A61K 31/405* | (2006.01) | |
| *A61K 31/43* | (2006.01) | |
| *A61K 31/57* | (2006.01) | |
| *A61K 31/573* | (2006.01) | |
| *C08G 83/00* | (2006.01) | |

(52) U.S. Cl.
CPC ............ *A61K 31/57* (2013.01); *A61K 31/573* (2013.01); *A61K 38/10* (2013.01); *A61K 47/595* (2017.08); *A61K 47/60* (2017.08); *A61K 47/64* (2017.08); *C08G 83/004* (2013.01)

(56) References Cited

U.S. PATENT DOCUMENTS

2010/0215631 A1\* 8/2010 Hartog ................. A61K 31/198
424/94.1
2012/0003155 A1 1/2012 Kannan et al.

OTHER PUBLICATIONS

Office Action dated Aug. 24, 2015 in Israeli Application No. 75189.
Alexandre, et al., "Accumulation of Hydrogen Peroxide is an Early and Crucial Step for Paclitaxel-Induced Cancer Cell Death Both in Vitro and in Vivo", Int. J. Cancer, 119(1), 2006, pp. 41-48.
Allard, et al., "Convection-Enhanced Delivery of Nanocarriers for the Treatment Brain Tumors", Biomaterials, 30(12), 2009, pp. 2302-2318.
Almutairi, et al., "Biodegradable dendritic positron-emitting nanoprobes for the noninvasive imaging of angiogenesis.", Proc. Natl. Acad. Sci. USA. 106(3), 2009, pp. 685-690.
Almutairi, et al., "Monitoring the Biodegradation of Dendritic Near-infrared Nanoprobes by in Vivo Fluorescence Imaging", Mol. Pharm. 5(6), 2008, pp. 1103-1110.
Alving, et al., "Therapy of Leishmaniasis: Superior Efficacies of Liposome-Encapsulated Drugs", Proc. Natl. Acad. Sci. U.S. A. 75(6), 1978, pp. 2959-2963.
Arrick, et al., "Glutathione Metabolism as a Determinant of Therapeutic Efficacy: A Review", Cancer Res, 44(10), 1984, pp. 4224-4232.
Aslam, et al., "Antibacterial and Antifungal Activity of Cicerfuran and Related 2-Arylbenzofurans and Stilbenes", Microbial Res, 164(2), 2009, pp. 191-195.
Ballatori, et al., "N-acetylcysteine as an antidote in methylmercury poisoning." EnViron. Health Perspect. 106(5), 1998, pp. 267-271.
Balogh, et al., "Dendrimer-Silver Complexes and Nanocomposites as Antimicrobial Agents", Nano Lett, 1(1), 2001, pp. 18-21.
Barrett, et al., "Dendrimers in Medical Nanotechnology", IEEE. Eng. Med. Biol. Mag., 28(1), 2009, pp. 12-22.
Beloosesky, et al., "N-Acetyl-Cysteine Suppresses Amniotic Fluid and Placenta Inflammatory Cytokine Responses to Lipopolysaccharide in rats.", Am. J. Obstet. Gynecol. 194(1), 2006. pp. 268-273.
Beloosesky, et al., "Maternal N-Acetylcysteine Suppresses Fetal Inflammatory Cytokine Responses to Maternal Lipopolysaccharide." Am. J. Obstet. Gynecol., 195, 2006, pp. 1053-1057.
Ben-Ari, et al., "N-Acetylcysteine in Acute Hepatic Failure (Non-Paracetamol-Induced)", Hepatogastroenterology, 47 (33), pp. 786-789.
Bennewitz, et al., "Nanotechnology for Delivery Drugs to the Brain for Epilepsy", Neurotherapeutics 6(2), 2009, pp. 323-336.
Benz, "Structure and Function of Porins from Gram-Negative Bacteria", Ann. Rev. Microbiol. vol. 42, 1988, pp. 359-393.
Block, et al., "Microglia-Mediated Neurotoxicity: Uncovering the Molecular Mechanisms", Nat. Rev. Neurosci. 8(1), 2007, pp. 57-69.
Borgstrom, et al., "Pharmacokinetics of N-acetylcysteine in Man", Eur. J. Clin. Pharmacol. vol. 31, 1986, pp. 217-222.
Bourne, et al., "Dendrimers, a New Class of Candidate Topical Microbicides with Activity Against Herpes Simplex Virus Infection", Antimicrobial Agents and Chemotherapy vol. 44, 2000, pp. 2471-2474.
Bracci, et al., "Synthetic Peptides in the Form of Dendrimers Become Resistant to Protease Activity", J Biol Chem, 2003, 278(47), pp. 46590-46595.
Breitkreutz, et al., "Improvement of Immune Functions in HIV Infection by Sulfur Supplementation: Two Randomized Trials", J. Mol. Med., 78(1), 2000, pp. 55-62.
Buhimschi, et al., "Protective Effect of N-acetylcysteine Against Fetal Death and Preterm Labor Induced by Maternal Inflammation", Am. J. Obstet. Gynecol. vol. 188, 2003, pp. 203-208.
Cakara, et al., "Microscopic Protonation Equilibria of Poly(amidoamine) Dendrimers from Macroscopic Titrations", Macromolecules, vol. 36, 2003, pp. 4201-4207.
Cakara, et al., "Microscopic Protonation Mechanism of Branched Polyamines: Poly(amidoamine) Versus Poly (propyleneimine) Dendrimers", Croat Chem Acta, vol. 8, 2007, pp. 421-428.
Calabretta, et al., "Antibacterial Activities of Poly(amidoamine) Dendrimers Terminated with Amino and Poly(ethylene glycol) Groups", Biomacromolecules vol. 8, 2007, pp. 1807-1811.
Carbonell, et al., "Migration of Perilesional Microglia After Focal Brain Injury and Modulation by CC Chemokine Receptor 5: An in Situ Time-lapse Confocal Imaging Study", J Neurosci, 27, 25, 2005, pp. 7040-7047.
Chaim, et al. "The Relationship Between Bacterial Vaginosis and Preterm Birth. A Review" Archives of Gynecology and Obstetrics, 1997, 259, pp. 51-58.
Chandrasekar, et al., "The Development of Folate-PAMAM Dendrimer Conjugates for Targeted Delivery of Antiarthritic Drugs and their Pharmacokinetics and Biodistribution in Arthritic Rats", Biomaterials 28(3), 2007, pp. 504-512.
Chen, et al., "Interactions Between Dendrimer Biocides and Bacterial Membranes", Biomaterials 23 (2002), pp. 3359-3368.
Chen, et al., "Quaternary Ammonium Functionalized Poly(propylene imine) Dendrimers as Effective Antimicrobials:? Structure-Activity Studies" Biomacromolecules 1 (3), 2000, pp. 473-480.
Cheng,, et al., "Pharmaceutical Applications of Dendrimers: Promising Nanocarriers for Drug Deliver", . Front. Biosci. vol. 13, 2008, pp. 1447-1471.
Cheng, et al., "Polyamidoamine (PAMAM) Dendrimers as Biocompatible Carriers of Quinolone Antimicrobials: An In Vitro Study" European Journal of Medicinal Chemistry, 2007, 42(7), pp. 1032-1038.

(56) References Cited

OTHER PUBLICATIONS

Cloninger, "Biological Applications of Dendrimers" Current Opinion in Chemical Biology, vol. 6, Issue 6, Dec. 2002, pp. 742-748.

Cuchelkar, et al., "Synthesis and Biological Evaluation of Disulfide-Linked HPMA Copolymer-Mesochlorin e6 Conjugates", Macromolecular Bioscience, 2008, vol. 8, pp. 375-383.

De Jesus, et al., "Polyester Dendritic Systems for Drug Delivery Applications: In Vitro and in Vivo Evaluation", Bioconjug Chem 2002, vol. 13, pp. 453-461.

Dekhuijzen PNR, "Antioxidant Properties of N-Acetyl Cysteine; Their Relevance in Relation to Chronic Obstructive Pulmonary Disease", Eur Respiratory Journal, 2004, vol. 23, pp. 629-636.

Dickenson, et al., "Transient Lipopolysaccharide-Induced Cytokine Responses in the Maternal Serum and Amniotic Fluid of the Guinea Pig", Am. J. Obstet. Gynecol, 2009, vol. 200, pp. 534.e1-534.e6.

Dilger, et al, "Excess Dietary L- cysteine, but not L-cystine, is Lethal for Chicks But not for Rats or Pigs", J. Nutr. vol. 322, 2007, pp. 331-338.

Dilger, et al., "Oral N-acetyl L-cysteine is a Safe and Effective Precursor of Cysteine", J. Anim. Sci. 19, 2006, pp. 1-26.

Duncan, et al. "Dendrimer Biocompatibility and Toxicity", Adv Drug Deliv Rev 2005;57:2215-37.

Duncan,et al., "The Dawning Era of Polymer Therapeutics", Nat. Rev. Drug Discovery 2,347-360. D, 2003, EFS Web.

Dutta, et al., "Poly(propyleneimine) Dendrimer and Dendrosome Mediated Genetic Immunization Against Hepatitis B", Vaccine 26, 2008, pp. 389-3394.

El-Remessy, et al., Neuroprotective Effects of Cannabidiol in Endotoxin-induced Uveitis: Critical Role of p38 MAPK Activation. Mol. Vis. vol. 14, 2008, pp. 2190-2203.

Ellison, et al., "Damage of the Outer Membrane of Enteric Gram-negative Bacteria by Lactoferrin and Transferrin", Infect Immun 56, 1988, pp. 2774-2781.

Examination Report dated Nov. 22, 2013 in Australia Application No. 2010260349.

Examination Report dated Apr. 30, 2014 in EP Application No. 10789963.5.

Esfand, et al., "Poly(amidoamine) (PAMAM) Dendrimers: From Biomimicry to Drug Delivery and Biomedical Applications", Drug Discov Today 2001 ;6:427-36.

Estensen, et al., "N-Acetyl Cysteine Suppression of the Proliferative Index in the Colon of Patients with Previous Adenomatous Colonic Polyps", Cancer Lett. vol. 147, 1999, pp. 109-114.

Ethier-Chiasson, et al., "Modulation of Placental Protein Expression of OLR1: Implication in Pregnancy-related Disorders or Pathologies", . Reproduction 136:, 2008, pp. 491-502.

Ferrari, et al., "NAcetylcysteine (D- and L-stereoisomers) Prevents Apoptotic Death of Neuronal Cells", J. Neurosci. vol. 15, 1995, pp. 2857-2866.

Filipovska, et al., Delivery of Antisense Peptide Nucleic Acids (PNAs) to the Cytosol by Disulphide Conjugation to a Lipophilic Cation, FEBS Lett. vol. 556, 2004, pp. 180-186.

Roy, et al., Reactive Oxygen Species Upregulate CD11b in Microglia via Nitric Oxide: Implications for Neurodegenerative diseases, 2008, Free Radic. Biol. Med. 26, 116-121.

Rui, et al., Diplasmenylcholine-folate Liposomes: An Efficient Vehicle for Intracellular Drug Delivery. J. Am. Chem. Soc. vol. 120,1998, pp. 11213-11218.

Saadani-Makki, et al., "Intrauterine Administration of Endotoxin Leads to Motor Deficits in a Rabbit Model: A Link Between Prenatal Infection and Cerebral Palsy", Am. J. Obstet. Gynecol. 199(6), 2008, pp. 651-659.

Saito, et al., "Drug Delivery Strategy Utilizing Conjugation via Reversible Disulfide Linkages: Role and Site of Cellular Reducing Activities", Adv Drug Deliv Rev 2003;55:199-215.

Sarin, et al."Effective Transvascular Delivery of Nanoparticles Across the Blood-brain Tumor Barrier into Malignant Glioma Cells." Journal of Translational Medicine, Dec. 2008, vol. 6:80, pp. 1-15.

Sato, et al., "Pharmacokinetics and Enhancement Patterns of Macromolecular MR Contrast Agents With Various Sizes of Polyamidoamine Dendrimer Cores", Magn Reson Med 2001 ;46:1169-73.

Search Report dated Nov. 15, 2010 in PCT Application No. PCT/US2010/38068.

Search Report dated Mar. 27, 2014 in EP Application No. 10789963.5.

Stence, et al., "Dynamics of Microglial Activation: A Confocal Time-lapse Analysis in Hippocampal Slices", Glia. 33(3), 2001, pp. 256-266.

Svenson, et al., "Dendrimers in Biomedical Applications—Reflections on the Field", Adv. Drug Delivery Rev. 57, (15). 2005, pp. 2106-2129.

Tang, et al., "Insertion Mode of a Novel Anionic Antimicrobial Peptide MDpep5 (Val-Glu-Ser-Trp-Val) from Chinese Traditional Edible Larvae of Housefly and its Effect on Surface Potential of Bacterial Membrane", J Pharm Biomed Anal vol. 48, 2008, pp. 1187-1194.

Tepel, et al., "Prevention of Radiographic-contrast-agent-induced Reductions Inrenal Function by Acetylcysteine", N. Engl. J. Med., 2000, vol. 343, pp. 180-184.

Tulu, et al., "Synthesis, Characterization and Antimicrobial Activity of Water Soluble Dendritic Macromolecules", Eur J Med Chem vol. 44, 2009, pp. 1093-1099.

Tziveleka, et al., "Synthesis, Characterization and Antimicrobial Activity of Water Soluble Dendritic Macromolecules", Eur J Med Chem vol. 44, 2009, pp. 1093-1099.

Ugwumadu, "Role of Antibiotic Therapy for Bacterial Vaginosis and Intermediate Flora in Pregnancy", Best Practice & Research vol. 21, 2007, pp. 391-402.

Ulbrich, et al., "HPMA Copolymers with PH-controlled Release of doxorubicin: In Vitro Cytotoxicity and in Vivo Antitumor Activity", J. Controlled Release vol. 87, 2003, pp. 33-47.

Urakuboa, et al., "Prenatal Exposure to Maternal Infection Alters Cytokine Expression in the Placenta, Amniotic Fluid, and Fetal Brain", Schizophrenia Research. vol. 47, 2001, pp. 27-36.

Vale, et al., "Paracetamol (acetaminophen) Poisoning", 1995, Lancet, 1995 vol. 346, pp. 547-552.

Van Schayck, et al., "Are Anti-oxidant and Anti-inflammatory Treatments Effective in Different Subgroups of COPD", A hypothesis. Respir, Med. vol. 92, 1998, pp. 1259-1264.

Verma, et al., "Tunable Reactivation and Nanoparticle-Inhibited-Galactosidase by Glutathione at Intracellular Concentrations". 2004, J. Am. Chem. Soc. 129, 13987-13991.

Villalonga-Barber et al., "Dendrimers as Biopharmaceuticals: Synthesis and Properties." Curr. Top Chem. 8 (14), 1294-1309.

Wagner. et al., "DNA-Binding transferrin Conjugates as Functional Gene-Delivery Agents: Synthesis by Linkage of Polylysine or Ethidium Homodimer to the Transferrin Carbohydrate Moiety", Bioconjugate Chem. vol. 2, 1991, pp. 226-231.

Wang, et al., "Anti-inflammatory and Anti-oxidant Activity of Anionic Dendrimer-N-acetyl Cysteine Conjugates in Activated Microglial Cells", Int. J. Pharm. 377(1-2), 2009, pp. 159-168.

Wang, et al., N-acetylcysteine Reduces Lipopolysaccharide-Sensitive Hypoxic-ischemic Brain Injury, Ann. Neuro. 61, 2007, pp. 263-271.

Waseem, et al., Exogenous Ghrelin modulates Release of Pro-inflammatory and Anti-inflammatory Cytokines in LPS Stimulated Macrophages Through Distince Signaling Pathways. Surgery 143, 334-342.

Wiegand, et al., "Agar and Brot Dilution Methods to Determine the Minimal Inhibitory Concentration (MIC) of Antimicrobial Substances", . Nature protocols vol. 3, 2008, pp. 163-175.

Winterboum, et al., "Reactivity of Biologically Important Thiol Compounds with Superoxide and Hydrogen Peroxide", Free Radic Bioi Med 1999;27:322-8. D 38.

Wiwattanapatapee, et al., "Anionic PAMAM Dendrimers Rapidly Cross Adult Rat Intestine in Vitro: A Potential Oral Delivery System". 2004, Pharm. Res. 2, 991-998.

Wiwattanapatapee, et al., "Dendrimers Conjugates for Colonic Delivery of 5-aminosalicylic Acid", J Control Release 2003;88:1-9.

(56) References Cited

OTHER PUBLICATIONS

Wolinsky, et al., "Therapeutic and Diagnostic Applications of Dendrimers for Cancer Treatment", Adv. Drug Deliv. Rev. vol. 60 (9), 2008. pp. 1037-1055.
Xu, et al., Effect of N-acetylcysteine on Lipopolysaccharide-induced intra-uterine Fetal Death and Intra-uterine Growth Retardation in Mice , Toxicol. Sci vol. 88, 2005, pp. 525-533.
Yan, et al., "Distribution of Intracerebral Ventricularly Administered Neurotrophins in Rat Brain and its Correlation with TRK Receptor Expression", Exp Neurol. vol. 127, 1994. pp. 23-36.
Yang, et al., "Stealth Dendrimers for Drug Delivery: Correlation Between PEGylation, Cytocompatibility, and Drug Payload", J Mater Sci Mater Med vol. 19, 2008, pp. 1991-1997.
Yeh, et al., "A Study of Glutathione Status in the Blood Tissues of Patients with Breast Cancer", Cell. Biochem. Funct. 24, 555-559.
Yip, et al., "Intravenous Administration of Oral N-acetyl Cysteine", Crit Care Med 1998;26:40-3.
You, et al., "Reducible Ploy(2-dimethylaminoethyl Methacrylate): Synthesis, Cytotoxicity, and Gene Delivery Activity", 2007, J. Controlled Release 122, 217-225.
Zafarullah, et al., Molecular Mechanisms of N-acetyl Cysteine Actions, Cell Mol Life Sci 2003;60:6-20.
Zhang, et al., "Evaluation of Multivalent Dendrimers Based on Melamine: Kinetics of Thiol-Disulfide Exchange Depends on the Structure of the Dendrimer", JAm Chem Soc 2003;25:5086-94.
Zhuo et al., "In Vitro Release of 5-fluorouracil with Cyclic Core Dendrite Polymer", J Control Release 1999;57:249-57.
Zugates, er al., "Synthesis of of poly(_-amino esters) with Thiol-reactive Side Chains for DNA Delivery", J. Am. Chem. Soc. 128, 2006, pp. 12726-12734.
Beichert, et al., "Improvement of Immune Functions in HIV Infection by Sulfur Supplementation: Two Randomized Trials", J. Mol. Med., vol. 78, 2000, pp. 55-62.
Examination Report dated Mar. 6, 2015 in Australian Application No. 2010260349.
Examination Report dated May 29, 2015 in Australian Application No. 2010260349.
Flora, et al., Lead Induced Oxidative Stress and its Recovery Following Co-administration of Melatonin or N-acetyl Cysteine During Chelation with Succimer in Male Rats. Cell Mol Bioi 2004;50:543-5.
Fung, et al., "Chemotherapeutic Drugs Released from Polymers: Distribution of 1, 3-bis(2-chloroethyl)-1-Nitrosourea in the Rat Brain", Pharm, Res. vol. 13, 1996, pp. 671-682.
Gillies, et al., "Dendrimers and Dendritic Polymers in Drug Delivery", Drug Discovery Today 10, 2005, pp. 35-43.
Giri, et al., "Stimuli-responsive Controlled-release Delivery System Based on Mesoporous Silica Nanorods Capped with Magnetic Nanoparticles." Agnew. Chem., Int Ed. 44, 5038-5044.
Gomez, et al., "Antibiotic Administration to Patients with Preterm Premature Rupture of Membranes Does Not Eradicate intra-amniotic Infection", J. Matern. Fetal Neonatal Med. vol. 20, 2007, pp. 167-173.
Gurdag, et al., "Activity of Dendrimer-Methotrexate Conjugates in Sensitive and Resistant Cell Lines", Bioconjugate Chem. vol. 17, 2005, pp. 275-283.
Halford, "Dendrimers Branch Out", C&EN. 83, 2005, pp. 30-36.
Harada, et al., "Kinetic Analysis of Covalent Binding Between N-acetyl-l-cysteine and Albumin Through the Formation of Mixed Disulfides in Human and Rat Serum in Vitro", Pharm Res 2002;19:1648-54.
Harnett, et al., "Lipopolysaccharide-induced Fetal Brain Injury in the Guinea Pig", American Journal of Obstetrics and Gynecology 197, 179 e171-177. 2007.
Helander, et al., "Fluorometric Assessment of Gram-negative Bacterial Permeabilization", J Appl Microbiol vol. 88, 2000, pp. 213-219.

Hinman, et al., "Upeslacis, Preparation and Characterization of Monoclonal Antibody Conjugates of the Calicheamicins: A Novel and Potent Family of Antitumor Antibiotics", J. Cancer Res. vol. 3, 1993, pp. 3336-3342.
Hong, et al., "Interaction of Polycationic Polymers with Supported Lipid Bilayers and Cells: Nanoscale Hole Formation and Enhanced Membrane Permeability", Bioconjug Chem vol. 17, 2006, pp. 728-734.
Hong, et al., "Glutathione-mediiated Delivery and Release Using Monolayer Protected Nanoparticle Carrier", 2006, J. Am. Chem. Soc. 128, 1078-1079.
Hou, et al., "Antimicrobial Dendrimer Active against *Escherichia coli* Biofilms", Bioorg Med Chem Lett vol. 19, 2009, pp. 5478-5481.
Huang, et al., "Efficient Gene Delivery Targeted to the Brain Using a Transferrin-conjugated Polyethyleneglycol-modified Polyamidoamine Dendrimer", FASEB, 21(4), 2007, pp. 1117-1125.
Ibrahim, et al., Antimicrobial Effects of Lysozyme Against Gram-Negative Bacteria Due to Covalent Binding of Palmitic Acid, J Agric Food Chem vol. 39, 1991, pp. 2077-2082.
Je, et al., "Antimicrobial Action of Novel Chitin Derivative", Biochim Biophys Acta 1760, 2006a, pp. 104-109.
Je, et al., "Chitosan Derivatives Killed Bacteria by Disrupting the Outer and Inner Membrane", J Agric Food Chem vol. 54, 2006b, pp. 6629-6633.
Jevprasesphant, et al., "The Influence of Surface Modification on the Cytotoxicity of PAMAM Dendrimers", Int J Pharm vol. 252, 2003, pp. 263-266.
Jucker, et al., "Adsorption of Bacterial Surface Polysaccharides on Mineral Oxides is Mediated by Hydrogen Bonds Colloids and Surfaces B", Biointerfaces, 1997, pp. 9331-9343.
Jucker, et al. "Quantification of Polymer Interactions in Bacterial Adhesion" Environ. Sol. Technol, 1998, 32, pp. 2909-2915.
Karm, et al. "Functionalizing of Carbon Nanotubes via Cleavable Disulfide Bonds for Efficient Intracellular Delivery of siRNA and Potent Gene Silencing," 2005 J. Am. Chem. Soc. 127. 12492-12493.
Kang, et al., "Tat-conjugated PAMAM Dendrimers as Delivery Agents for Antisense and siRNA Oligonucleotides", Pharm. Res. 22, 2005, pp. 2099-2106.
Kannan et al., "Dendrimer-Based Postnatal Therapy for Neuroinflammation and Cerebral Palsy in a Rabbit Model", Science Translational Medicine, vol. 4, Apr. 18, 2012, pp. 1-11.
Kannan, et al., "Dendrimer Based Nanodevices for Therapeutic and Imaging Purposes", U.S. Appl. No. 611187,263, filed 2009.
Kannan, et al., "Dendrimer-containing Particles for Sustained Release of Compounds", (USIinternational patent filed, U.S. Appl. No. 60/997,967.
Kannan, et al., "Dynamics of Cellular Entry and Drug Delivery by Dendritic Polymers Into Human Epithelial Carcinoma Cells", J. Biomater. Sci. Polym. Edn 15, 2004, pp. 311-330.
Kannan et al., "Microglial Activation in Perinatal Rabbit Brain Induced by Intrauterine Inflammation: Detection with11C-(R)-PK11195 and Small-animal PET", J. Nucl. Med. 48(6), 2007, pp. 946-954.
Keelan, et al., "Cytokine Abundance in Placental Tissues: Evidence of Inflammatory Activation in Gestational Membranes with Term and Preterm Parturition", American Journal of Obstetrics and Gynecology vol. 181, 1999, pp. 1530-1536.
Khan, et al., "Administration of N-acetyl Cysteine After Focal Cerebral Ischemia Protects Brain and Reduces Inflammation in a Rat Model of Experimental Stroke", J Neurosci Res 2004;4:519-27.
Khan, et al., "Bactericidal Action of Egg Yolk Phosvitin against *Escherichia coli* under Thermal Stress", J Agric Food Chem vol. 48, 2000, pp. 1503-1506.
Khan, et al., In Vivo Biodistribution of Dendrimers and Dendrimer Nanocomposites—Implications for Cancer Imaging and Therapy. Technol. Cancer. Res. Treal. 4(6), 2005, pp. 603-613.
Khandare, et al., "Synthesis, Cellular Transport, and Activity of Polyamidoamine Dendrimer-Methylprednisolone Conjugates", Bioconjugate Chem. vol. 16, 2005, pp. 330-337.

(56) References Cited

OTHER PUBLICATIONS

Kim, et al., "Mutagenesis of the SupF Gene of pSP189 Replicating in AD293 Cells Cocultivated with Activated Macrophages: Roles of Nitric Oxide and Reactive Oxygen Species", Chem. Res. Toxicol. vol. 19, 2006, pp. 1483-1491.
Kim, et al., Systematic Investigation of Polyamidoamine Dendrimers Surface-modified with Poly(ethylene glycol} for Drug delivery Applications; Synthesis, Characterization, and Evaluation of Cytotoxicity, Sioconjug Chem vol. 19, 2008, pp. 1660-1672.
Kirpotin, et al., "Antibody Targeting of Long-circulating Lipidic Nanoparticles Does Not Increase Tumor Localization But Does Increase Internalization in Animal Models", Cancer Res. 66(13), 2006, pp. 6732-4670.
Kitchens, et al., "Endocytosis and Interaction of Poly(amidoamine) Dendrimers with Caco-2 cells", Pharm Res 2007;24:2138-45.
Kobayashi, et al., "Multimodal Nanoprobes for Radionuclide and Live-Color Near-infrared Optical Lymphatic Imaging", ACS Nano. 1 (4), 2007, pp. 258-264.
Kolhatkar, et al., Surface Acetylation of Polyamidoamine (PAMAM) Dendrimers Decreases Cytotoxicity While Maintaining Membrane Permeability, Bioconjug Chem vol. 18, 2007, pp. 2054-2060.
Kolhe, et al., "Drug Complexation, in Vitro Release and Cellular Entry of Dendrimers and Hyperbranched Polymers", Int. J. Pharm. vol. 259, 2003, pp. 143-160.
Kolhe, et al., "Preparation, Cellular Transport, and Activity of Polyamidoamine-based Dendritic Nanodevices with a High Drug Payload", Biomaterials vol. 27, pp. 660-669.
Kommareddy, et al., "Preparation and Evaluation Ofthiol-modified Gelatin Nanoparticles for Intracellular DNA Delivery in Response to Glutathione", Bioconjugate Chem. 16, 2005, pp. 1423-1432.
Kou, et al., "Glutathione-and Cysteine-induced Tranverse Overgrowth on Gold Nanorods", J. Am. Chem. Soc. 2007, 129, 6402-6404.
Kukowska-Latallo, et al., "Nanoparticie Targeting of Anticancer Drug Improves Therapeutic Response in Animal Model of Human Epithelial Cancer", Cancer Res 2005;65:5317-24.
Kurtoglu, et al., "Dendrimer-drug Conjugates for Tailoredl Intracellular Drug Release Based on Glutathione Levels", Bioconjug. Chem. vol. 19, 2008, pp. 2446-2455.
Kurtoglu, et al., "Poly(amidoamine) Dendrimer-drug Conjugates with Disulfide Linkages for Intracellular Drug Delivery"Biomaterials vol. 30, 2009, pp. 2112-2121.
Lebreton, "Antibacterial Single-bead Screening", Tetrahedron vol. 59, 2003, pp. 10213-10222.
Lee, et al., "Designing Dendrimers for Biological Applications", Biotechnology vol. 23, 2005, pp. 1517-1526.
Lee, et al., "A Single Dose of Doxorubicin-functionalized Bow-tie Dendrimer Cures Mice Bearing C-26 Colon Carcinomas", Proc Natl Acad Sci USA 2006:103:16649-56.
Lesniak, et al., "Synthesis and Characterization of PAMAM Dendrimer-based Multifunctional Nanodevices for Targeting Alphavbeta3 Integrins", Bioconjug. Chem. 18(4), 2007, pp. 1148-1154.
Lessio, et al., "Cyclosporine A and NAC on the Inducible Nitric Oxide Synthase Expression and Nitric Oxide Synthesis in Rat renal artery cultured cells", Kidney Int. vol. 68, 2005, pp. 2508-2516.
Li, et al., "Pharmacokinetics and Biodistribution of Nanoparticles", Mol. Pham. 5(4), 2008, pp. 496-504.
Lopez, et al., "Antibacterial Activity and CytotoxiCity of PEGylated Poly(amidoamine) Dendrimers", Mol Biosyst vol. 5, 2009, pp. 1148-1156.
Louwerse, et al., "Randomized Acetylcysteine in Amyotrophic Lateral Sclerosis", Arch. Neurol. vol. 52, 1995, pp. 559-564.
Lu, et al., "YC-1 Attenuates LPS-induced Proinflammatory Responses and Activation of Nuclear Factor-kB in Microglia", Br. J. Pharmacal. vol. 151, 2007, pp. 396-405.
Makki, et al., "Intrauterine Administration of Endotoxin Leads to Motor Deficits in a Rabbit Model: A link Between Prenatal Infection and Cerebral Palsy", Am. J. Obstet. Gynecol. vol. 199, 2008, pp. 651-1651.

Malik, et al., "Dendrimer-Platinate: A Novel Approach to Cancer Chemotherapy", Anticancer Drugs 1999;10:767-76.
Malik, et al., Dendrimers: Relationship Between Structure and Biocompatibility in Vitro, and Preliminary Studies on the Biodistribution of 125I-labelled Polyamidoamine Dendrimers in Vivo. J. Control Release, vol. 2000, 65, pp. 133-148.
Matsumura, et al., A new Concept for Macromolecular Therapeutics in Cancer Chemotherapy: Mechanism of Tumoritropic Accumulation of Proteins and the Antitumor Agent. Cancer Res 1986;46:6387-92.
Mecke, et al., Lipid Bilayer Disruption by Polycationic Polymers; The Roles of Size and Chemical Functional Group, Langmuir vol. 21, 2005, pp. 10348-10354.
Meister, et al., "Glutathione", Annu Rev Biochem 1983;52:711-60.
Menjoge et al., "Transfer of PAMAM Dendrimers Across Human Placenta: Prospects of its Use as a Drug Carrier During Pregnancy", Journal of Controlled Release. vol. 150, Dec. 1, 2010, pp. 326-338.
Meyer-Luehmann, et al., "Rapid Appearance and Local Toxicity of Amyloid-beta Plaques in a Mouse Model of Alzheimer's Disease", Nature; 451, 2008, pp. 720-724.
Milovic, et al., "Immobilized N-alkylated Polyethylenimine Avidly Kills Bacteria by Rupturing Cell Membranes with No Resistance Developed", Biotechnol Bioeng vol. 90, 2005, pp. 715-722.
Min, et al., "Plasminogen-induced IL-1Beta and TNFa Production in Microglia is Regulated by Reactive Oxygen Species", Biochem. Biophys. Res. Commun. vol. 312, 2003, pp. 969-974.
Mishra et al., "PAMAM Dendrimer-azithromycin Conjugate Nanodevices for the Treatment of Chalamydia Trachomatis", Nanomedicine:NBM, May 19, 2011, vol. 9, pp. 935-944.2011.
Mumper, et al., "Formulating a Sulfonated Antiviral Dendrimer in a Vaginal Microbicidal Gel Having Dual Mechanisms of Action", Drug development and Industrial Pharmacy vol. 35, 2009, pp. 515-524.
Myers, "The Effect of Hydroxyl Ion Concentration on the Thermal Death Rate of Bacterium *coli*", J Bacteriol vol. 15, 1928, pp. 341-356.
Naberezhnykh, et al., "Interaction of Chitosans and their N-acylated Derivatives with Lipopolysaccharide of Gram-negative Bacteria", Biochemistry (Mosc) vol. 73, 2008, pp. 432-441.
Najlah, et al., "Synthesis, Characterization and Stability of Dendrimer Prodrugs", . Int J Pharm 2006;308:175-82.
Najlah, et al., "In Vitro Evaluation of Dendrimer Prodrugs for Oral Drug Delivery", Inl. J. Pharm. vol. 336, 2007, pp. 183-190.
Napoli, et al., "Microglial Clearance Function in Health and Disease" Neuroscience. vol. 158, 2009, pp. 1030-1038.
Navath, et al., "Dendrimer-drug Conjugates for Tailored Intracellular Drug Release Based on Glutathione Levels", Bioconjug. Chem. vol. 19, 2008, pp. 2446-2455.
Neeves, et al., "Dilation and Degradation of the Brain Extracellular Matrix Enhances Penetration of Infused Polymer Nanoparticles", Brain Res. vol. 1180, 2007, pp. 121-132.
Nigavekar, et al., "3H Dendrimer Nanoparticle Organ/Tumor Distribution", Pharm. Res, 21 (3), 2004, pp. 476-483.
Nimmerjahn, et al., "Resting Microglial Cells are Highly Dynamic Surveillants of Brain Parenchyma in Vivo" Science. vol. 308, 2005, pp. 1314-1318.
Noack, et al., "Nitrosative Stress in Primary Glial Cultures After Induction of the Inducible Isoform of Nitric Oxide Synthase (i-NOS)", Toxicology, 2000, 148, pp. 133-142.
Office Action dated Nov. 7, 2012 in U.S. Appl. No. 12/797,657.
Office Action dated Jul. 30, 2013 in U.S. Appl. No. 12/797,657.
Ortega, et al., "Amine and Ammonium Functionalization of Chloromethylsilane-ended Dendrimers", Antimicrobial activity studies. Org Biomol Chem. vol. 6, 2008, pp. 3264-3269.
Oupicky, et al., "Laterally Stabilized Complexes of DNA with Linear Reducible Polycations: Strategy for Triggered Intracellular Activation of DNA Delivery Vectors", J. Am. Chem. Soc. 2002, vol. 124, pp. 8-9.
Paintlia, et al., "Lipopolysaccharide-Induced Peroxisomal Dysfunction Exacerbates Cerebral White Matter Injury: Attention by N-acetyl Cyctein", Exp. Neurol. 2008, 210, pp. 560-576.

(56) References Cited

OTHER PUBLICATIONS

Paintlia, et al., "Lipopolysaccharide-Induced Peroxisomal Dysfunction Exacerbates Cerebral White Matter Injury: Attenuation by N-Acetyl Cysteine", Exp Neurol, Apr. 2008, 210 (2), pp. 560-576.
Palmer, et al., "S-Nitrosothiol Signal Hypoxia-mimetic Vascular Pathology", J. Clin. InVest. 117, 1998, pp. 2592-2601.
Pardridge, et al., "Blood-brain Barrier Delivery", Drug. Discov. Today. 12(1-2), 2007, pp. 54-61.
Patil, et al., "Internally Cationic Polyamidoamine PAMAM-OH Dendrimers for siRNA Delivery: Effect of the Degree of Quaternization and Cancer Targeting", Biomacromolecules 10 (2), 2009, pp. 258-256.
Path, et al., "Targeted Drug Delivery with Dendrimers: Comparison of the Release Kinetics of Covalently Conjugated Drug and Noncovalent Drug Inclusion Complex", Adv Drug Deliv Rev 2005;57:2203-14.
Patrick, et al., "Development of a Guinea Pig Model of Chorioamnionitis and Fetal Brain Injury", American Journal of Obstetrics and Gynecology vol. 191, 2004, pp. 1205-1211.
Perry, et al., "Glutathione Levels and Variability in Breast Tumors and Normal Tisue", 1993, Cancer 72, 783-787.
Perumal, et al., "The Effect of Surface Functionality on Cellular Trafficking of Dendrimers", Biomaterials 29(24-25), 2008, pp. 3469-3476.
Pillai, et al., "The Effect of Surface Functionality on Cellular Trafficking of Dendrimers", Biomaterials, vol. 29, 2006, pp. 3469-3476.
Rajur, et al., "Covalent Protein-Oligonucleotide Conjugates for Efficient Delivery of Antisense Molecules", Bioconjugate Chem. vol. 8, 1997, pp. 935-940.
Regina, et al., "Antiturnour Activity of ANG1005, a Conjugate Between Paclitaxel and the New Brain Delivery Vector Angiopep-2", Br. J. Pharmacol. 155(2), 2008, pp. 185-197.
Reiter, et al., "Cytotoxic and Antitumor Activity of a Recombinant Immunotoxin Composed of Disulfide-Stabilized anti-TAC Fv Fragment and Truncated Pseudomonas Exotoxin", Int J. Cancer, vol. 58, 1994, pp. 142-149.
Romero, et al., "Micronutrients and Intrauterine Infection, Preterm Birth and the Fetal Inflammatory Response Syndrome", The Journal of Nutrition, 2003, 1668S-1673S.
Romero, et al., A Fetal Systemic Inflammatory Response is Followed by the Spontaneous Onset of Preterm Parturition, Am. J. Obstet. Gynecol. 1998, pp. 186-193.
Romero, et al., "Inflammation in Pregnancy: Its Role in Reproductive Physiology, Obstetrical Complications, and Fetal Injury." Nutr. 2007. Rev. 65, S194-S202.
Romero, et al., The Preterm Parturition Syndrome. Int. J. Obstet. Gynaecol, 113, 17-42, 2006.
Romero, et al., "The Role of Inflammation and Infection in Preterm Birth", Semim. Reprod. Med. 25, 21-39, 2007b.
Roy, et al., "Oral Gene Delivery with Chitosan—DNA Nanoparticles Generates Immunologic Pprotection in a Murine Model of Peanut Allergy", Nature. Med. vol. 5, 1999, pp. 387-391.
Liang, PAMAM dendrimers and branched polyethyleneglycol (nanoparticles) prodrugs of (-)-beta-delta-(2R, 4R)-dioxolanethymine (DOT) and their anti-HIV activity, Antiviral Chemistry & Chemotherapy, 2006, 17, 321-329.

* cited by examiner

*P<0.05, **P<0.01 VS group of LPS
▲P<0.05, ▲▲ P<0.01 VS group of NAC in same concentration

*P<0.05, **P<0.01 VS group of LPS
▲P<0.05, ▲▲ P<0.01 VS group of NAC in same concentration

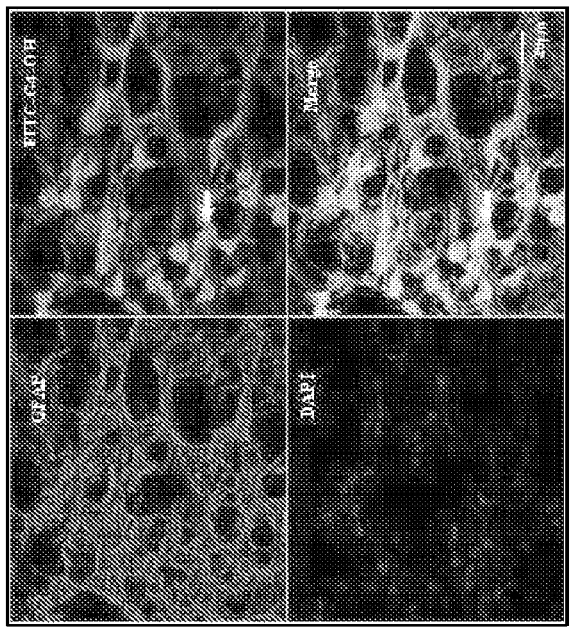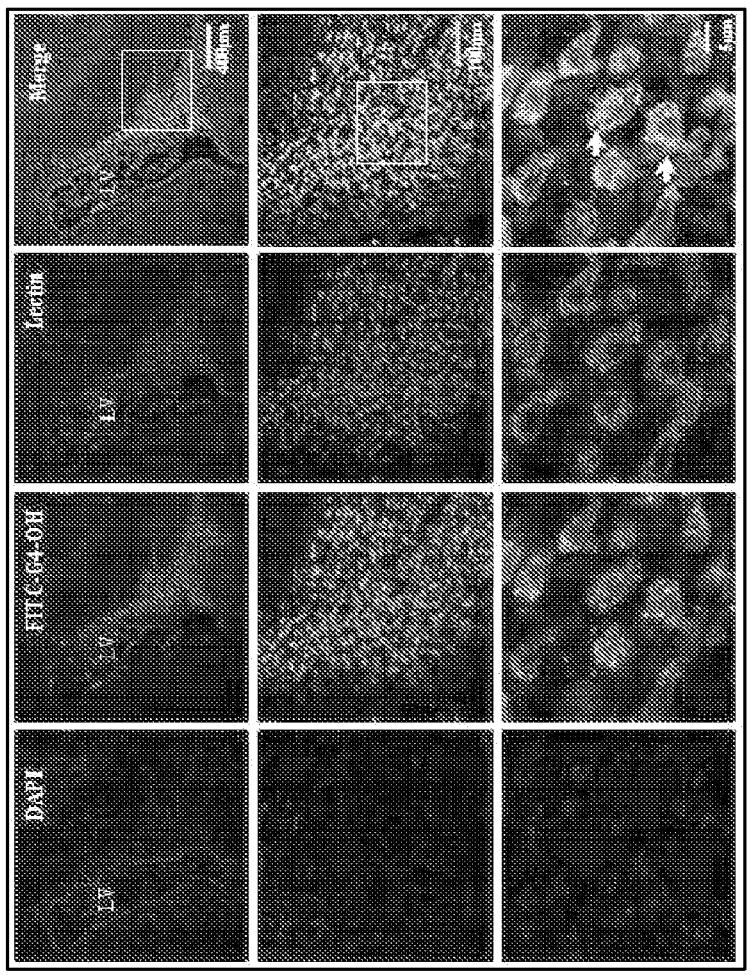
FIG-25

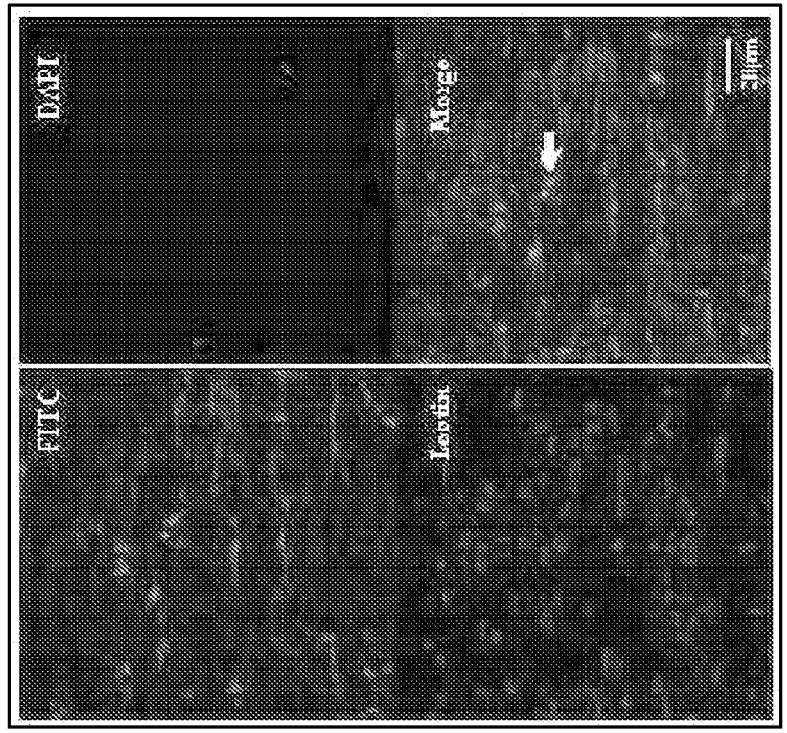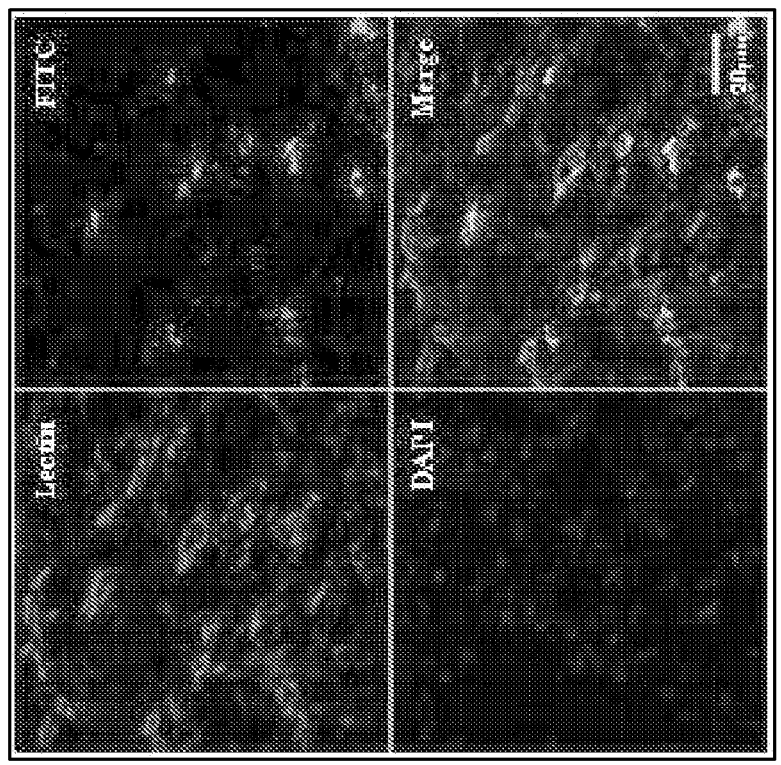
FIG-27

| Polymer | Polymer Surface | Linker | Drug Loading | M.W confirmed MALDI-TOF / NMR | Release Time |
|---|---|---|---|---|---|
| G4 PAMAM Dendrimers | -OH (Neutral) | -Co-GABA-NH-CO-Pr-S- | 15 | 19.3 kDa | 3 hours |
| G4 PAMAM Dendrimers | -COOH (Anionic) | -NH-GS-S- | 18 | 19.7 kDa | 2 hours |
| G4 PAMAM Dendrimers | -NH₂ (Cationic) | -CO-Pr-S- | 16 | 18.3 kDa | 2 hours |
| Polyethylene glycol (PEG) | -SH (Thiol) | Direct attachment | 8.9 | 10.9 kDa | 1.5 hours |

FIG - 30

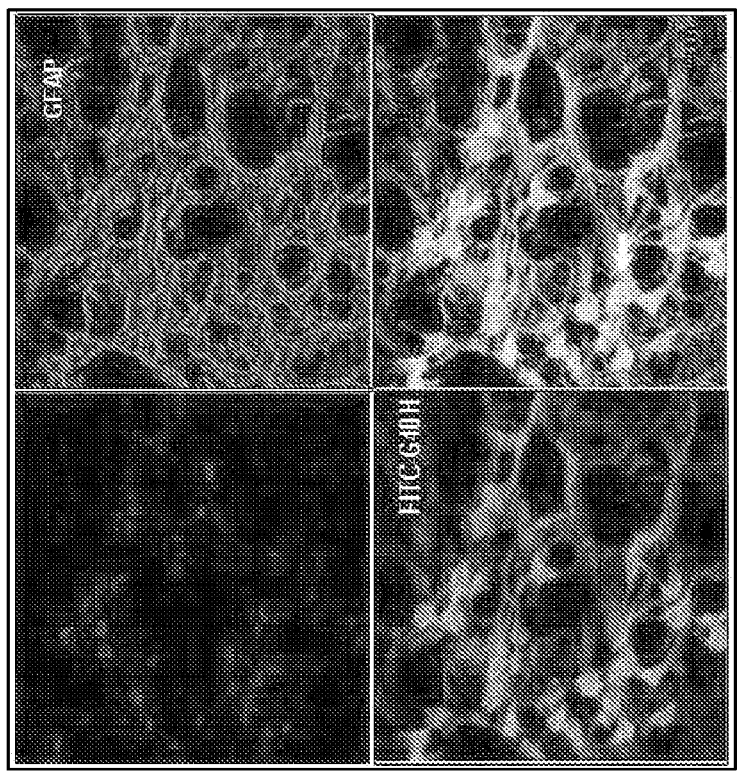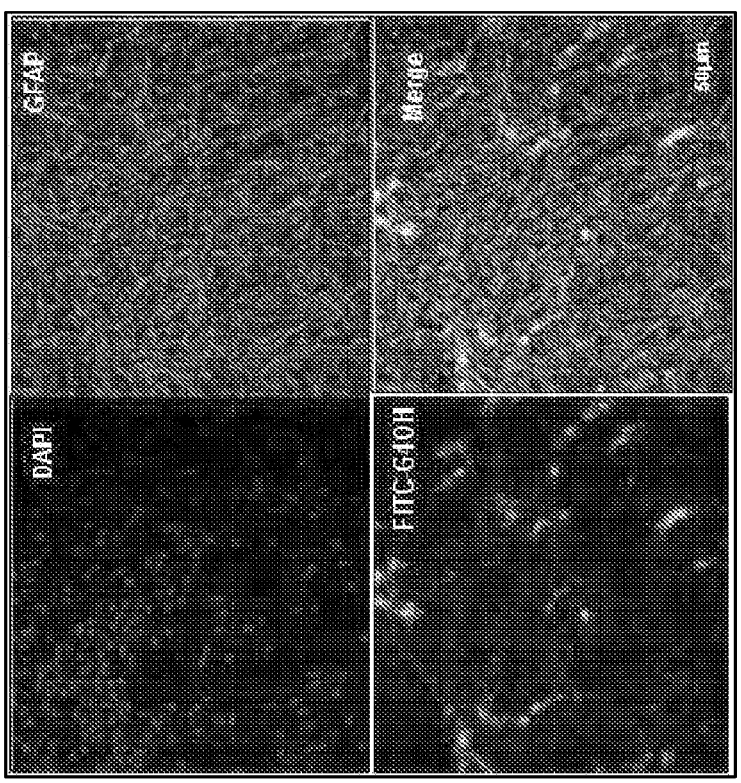
FIG-41

Control-Day 5

Endotoxin-PBS treatment

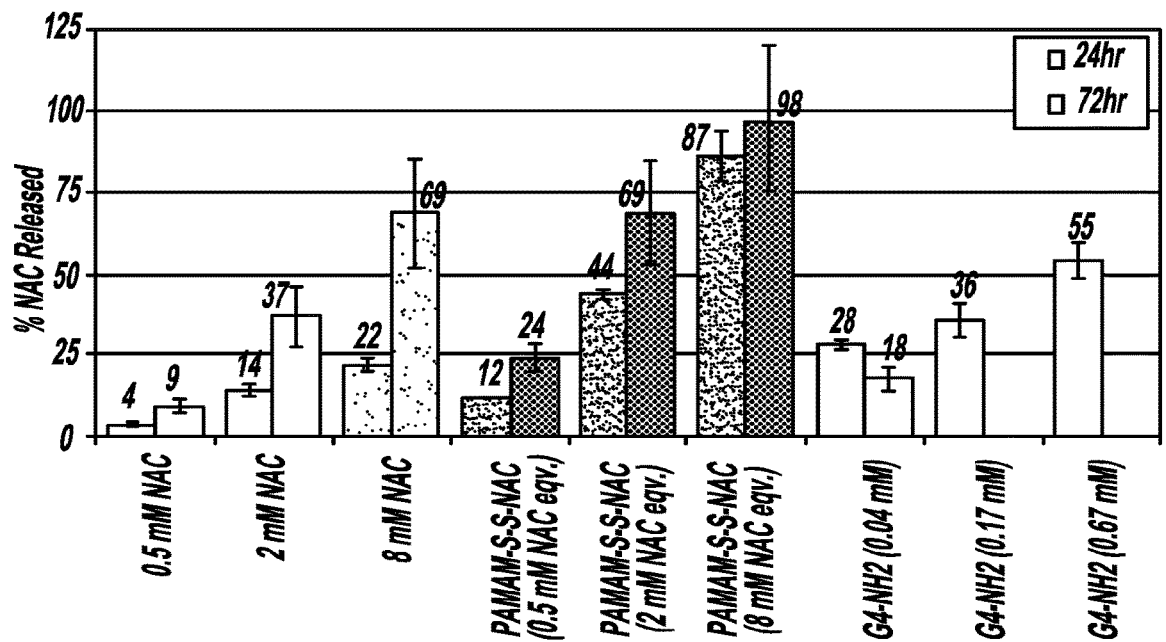
FIG - 64
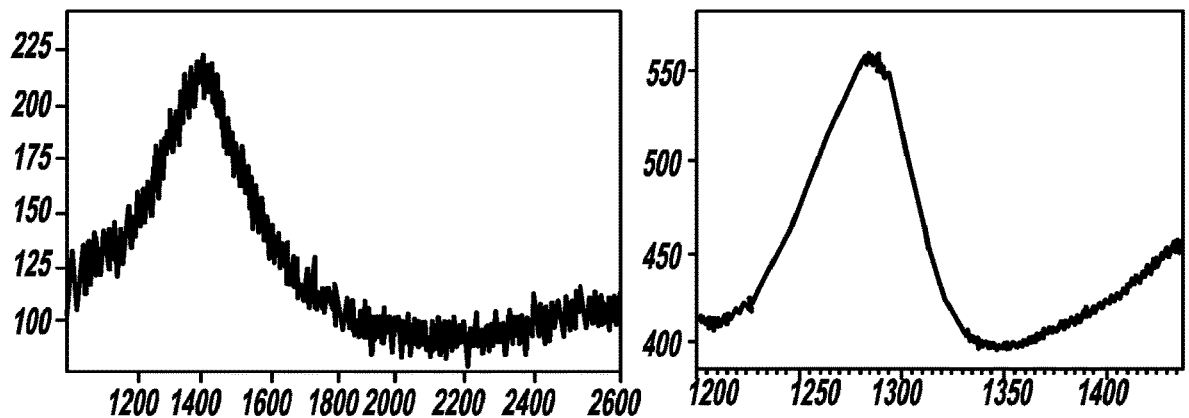
FIG - 65a
FIG - 65b

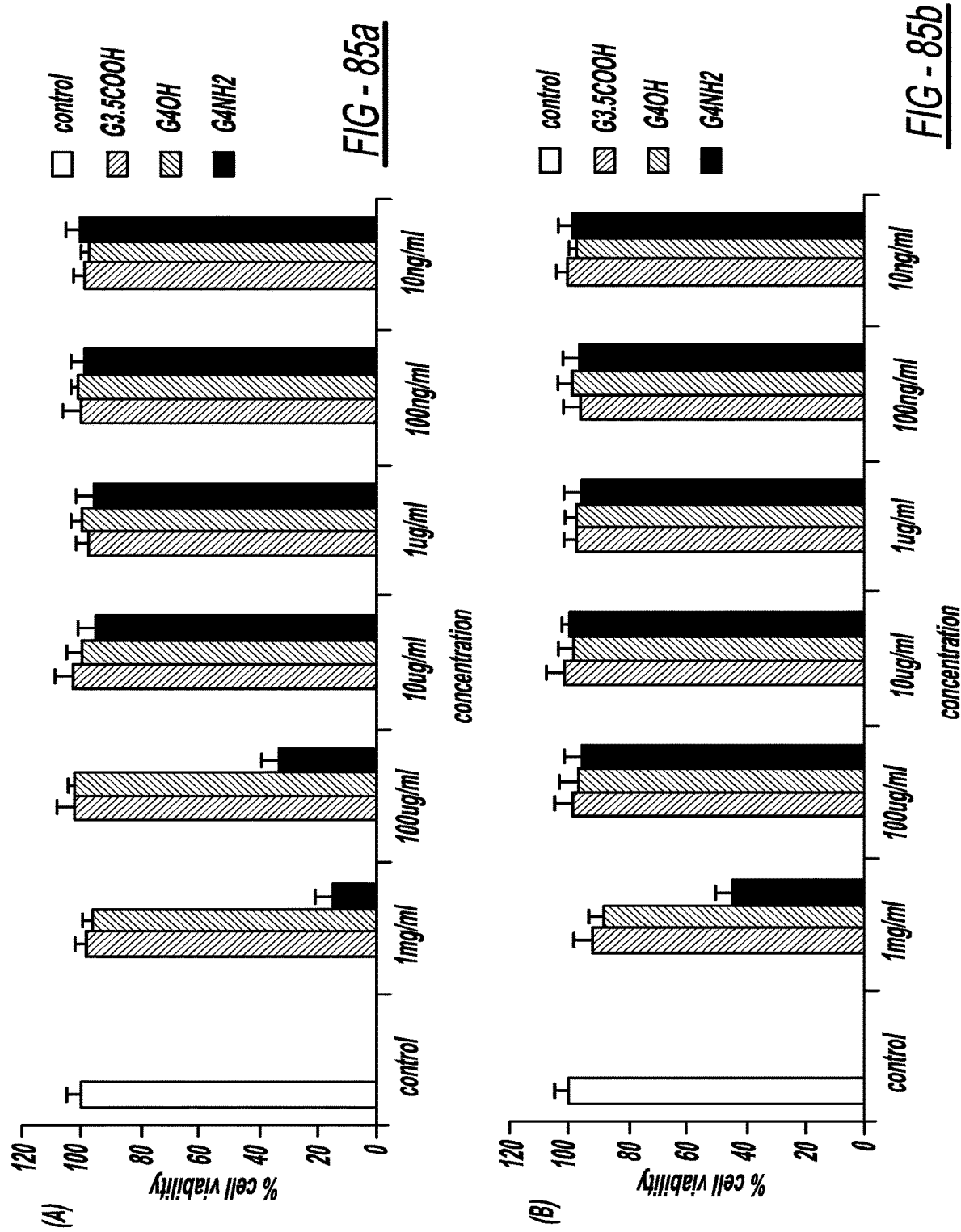

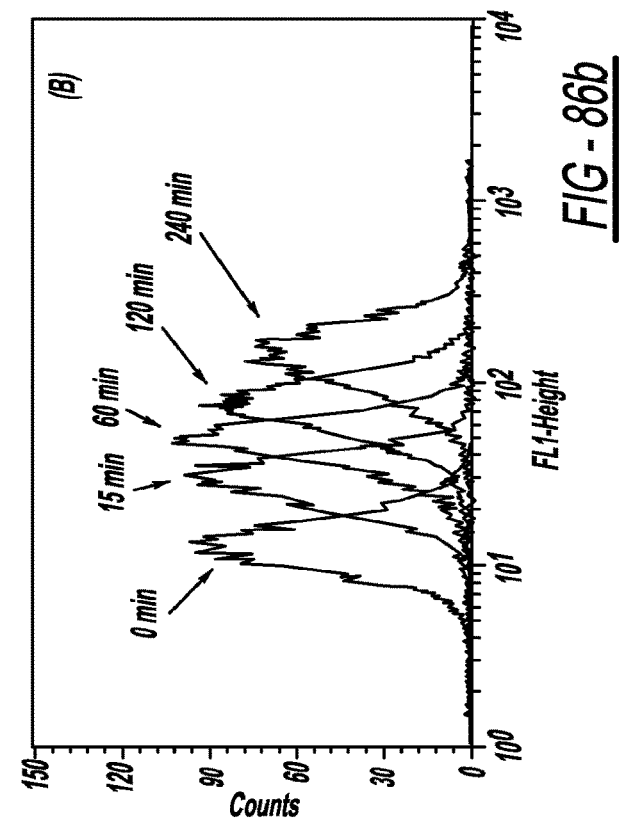
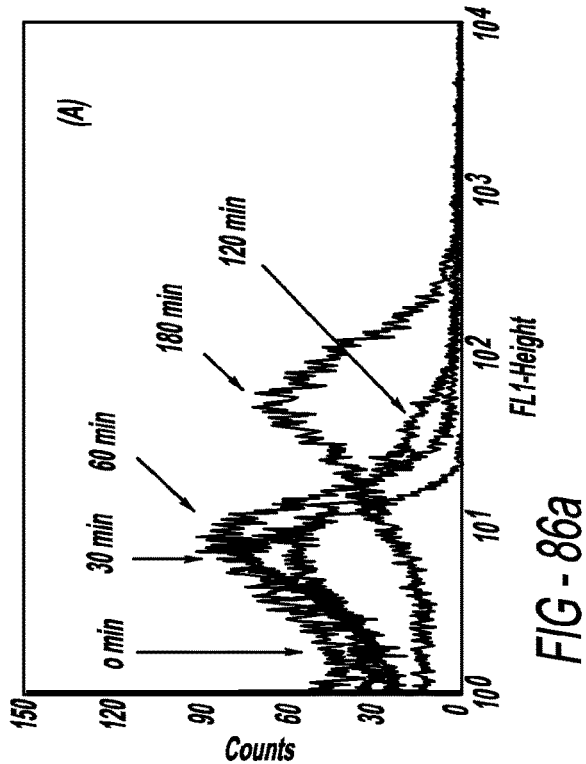
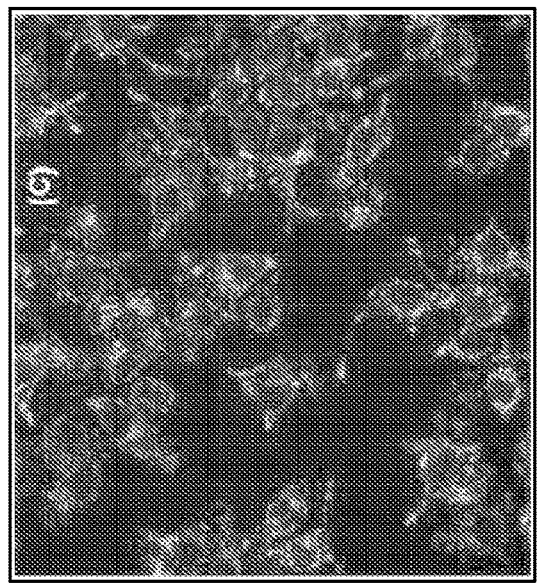
FIG-86b
FIG-86c
FIG-86a

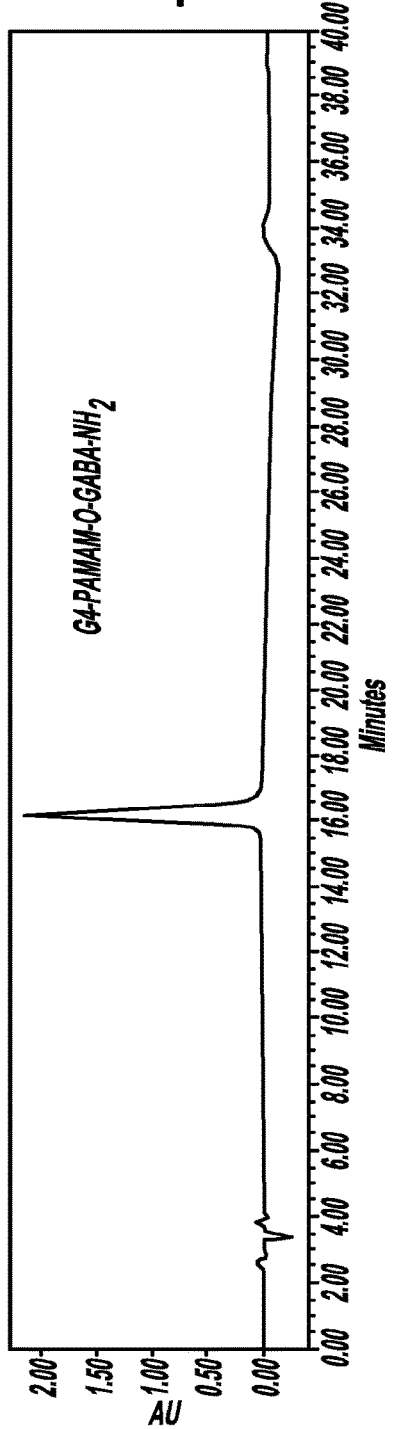
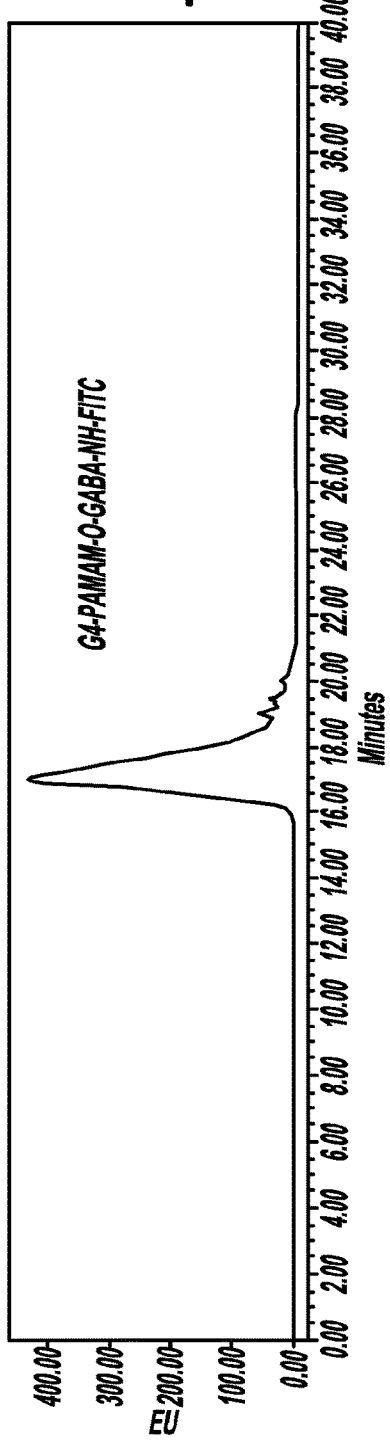
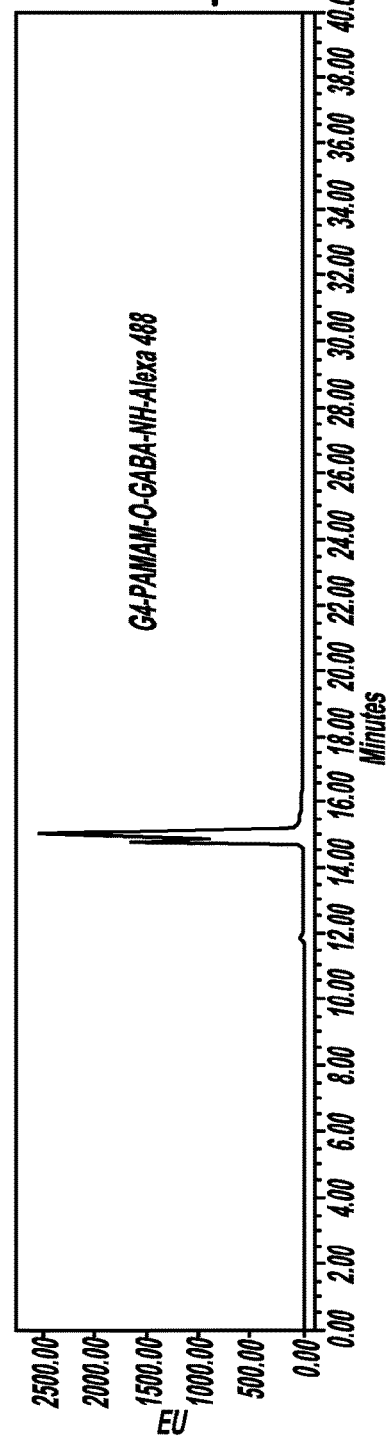
FIG - 89a  G4-PAMAM-O-GABA-NH₂
FIG - 89b  G4-PAMAM-O-GABA-NH-FITC
FIG - 89c  G4-PAMAM-O-GABA-NH-Alexa 488

SEQUENCE LISTING

<160> NUMBER OF SEQ ID NOS: 7

<210> SEQ ID NO 1
<211> LENGTH: 19
<212> TYPE: RNA
<213> ORGANISM: Artificial Sequence
<220> FEATURE:
<223> OTHER INFORMATION: Linker

<400> SEQUENCE: 1
agucggaggc uuaauuaca                                                19

<210> SEQ ID NO 2
<211> LENGTH: 19
<212> TYPE: RNA
<213> ORGANISM: Artificial Sequence
<220> FEATURE:
<223> OTHER INFORMATION: Linker

<400> SEQUENCE: 2
caggaaauuu gccuauuga                                                19

<210> SEQ ID NO 3
<211> LENGTH: 19
<212> TYPE: RNA
<213> ORGANISM: Artificial Sequence
<220> FEATURE:
<223> OTHER INFORMATION: Linker

<400> SEQUENCE: 3
uaaggaccaa gaccaucca                                                19

<210> SEQ ID NO 4
<211> LENGTH: 4
<212> TYPE: PRT
<213> ORGANISM: Artificial Sequence
<220> FEATURE:
<223> OTHER INFORMATION: Spacer

<400> SEQUENCE: 4

Arg Gly Asp Cys
1

<210> SEQ ID NO 5
<211> LENGTH: 5
<212> TYPE: PRT
<213> ORGANISM: Artificial Sequence
<220> FEATURE:
<223> OTHER INFORMATION: Spacer
<220> FEATURE:
<221> NAME/KEY: MISC_FEATURE
<222> LOCATION: (1)..(5)
<223> OTHER INFORMATION: Cyclic peptide
<220> FEATURE:
<221> NAME/KEY: MISC_FEATURE
<222> LOCATION: (4)..(4)
<223> OTHER INFORMATION: D enantiomer

<400> SEQUENCE: 5

Arg Gly Asp Phe Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Spacer

```
<220> FEATURE:
<221> NAME/KEY: MISC_FEATURE
<222> LOCATION: (1)..(5)
<223> OTHER INFORMATION: Cyclic peptide
<220> FEATURE:
<221> NAME/KEY: MISC_FEATURE
<222> LOCATION: (4)..(4)
<223> OTHER INFORMATION: D enantiomer

<400> SEQUENCE: 6

Arg Gly Asp Tyr Cys
1               5

<210> SEQ ID NO 7
<211> LENGTH: 5
<212> TYPE: PRT
<213> ORGANISM: Artificial Sequence
<220> FEATURE:
<223> OTHER INFORMATION: Spacer
<220> FEATURE:
<221> NAME/KEY: MISC_FEATURE
<222> LOCATION: (1)..(2)
<223> OTHER INFORMATION: Cyclic peptide
<220> FEATURE:
<221> NAME/KEY: MISC_FEATURE
<222> LOCATION: (4)..(4)
<223> OTHER INFORMATION: D enantiomer

<400> SEQUENCE: 7

Arg Ala Asp Tyr Cys
1               5
```

DENDRIMER BASED NANODEVICES FOR THERAPEUTIC AND IMAGING PURPOSES

CROSS REFERENCE TO RELATED APPLICATIONS

This application is a continuation of U.S. application Ser. No. 14/477,725, filed Sep. 4, 2014, which is a continuation of U.S. patent application Ser. No. 12/797,657, filed Jun. 10, 2010, which claims priority to U.S. Provisional Patent Application No. 61/319,285, filed Mar. 31, 2010 and U.S. Provisional Patent Application No. 61/187,263, filed Jun. 15, 2009 all of which are incorporated herein by reference.

REFERENCE TO SEQUENCE LISTING

The Sequence Listing submitted Apr. 28, 2010 as a text file named "ATL.WSU_09-945_CON(2)_ST25.txt," created on Apr. 16, 2019, and having a size of 2,154 bytes is hereby incorporated by reference pursuant to 37 C.F.R. § 1.52(e)(5).

BACKGROUND ART

1. Field of the Invention

Generally, the present invention relates to therapeutic nanodevices based on dendritic polymers. More specifically, the present invention relates to nanodevices for use in treating neuroinflammation and infections in maternal-fetal medicine.

2. Description of Related Art

Currently, there is a need to develop techniques and compounds that are able to effectively deliver bioactive agents to cells. While there are numerous systems under review for effectuating the delivery, the problems surrounding the delivery mechanisms have outweighed the usefulness of the systems. Examples of such systems include viral transfection systems and non-viral transfection systems. Viral systems typically have higher transfection efficiency than non-viral systems, but there have been questions regarding the safety of viral systems. In addition, viral vector preparation tends to be a complicated and expensive process. Although non-viral transfection systems generally are less efficient than viral systems, they have received significant attention because they are generally believed to be safer and easier to prepare than viral systems.

A number of non-viral transfection systems involve the use of cationic polymers that are complexed to bioactive agents. Examples of cationic polymers that have been used as gene carriers include poly(L-lysine) (PLL), polyethyleneimine (PEI), chitosan, PAMAM dendrimers, and poly(2-dimethylamino)ethyl methacrylate (pDMAEMA). Unfortunately, transfection efficiency is typically poor with PLL, and high molecular weight PLL has shown significant toxicity to cells. Unfortunately, PEI-dendrimers have been reported to be toxic to cells, thus limiting the potential for using PEI as a gene delivery tool in applications to human patients.

Dendrimers, as the term is used herein, are a class of polymers often called starburst polymers because of their shape. These dendrimers have a molecular architecture with an interior core, interior layers (or "generations") of repeating units regularly attached to this interior core, and an exterior surface of terminal groups attached to the outermost generation. These starburst polymers are radially symmetrical and have a branched or tree-like structure. The number of generations can be controlled by the conditions of manufacture, leading to different size molecules having different numbers of terminal groups. U.S. Pat. No. 4,587,329 entitled Dense Star Polymers Having Two Dimensional Molecular Diameter, issued May 6, 1986 to the Dow Chemical Company, the disclosure of which is incorporated by reference, describes these starburst dendrimers and methods of their manufacture. These starburst dendrimers can be made to exact, repeatable molecular weights with the same number of functional groups on each dendrimer. These functional groups can react with a material to be carried, such as a pharmaceutical or agricultural product, or the material to be carried can be associated with this dendrimer in a non-reactive manner.

One family of dendrimers is based on an amidoamine repeat structure, forming what are known as poly(amidoamine) dendrimers ("PAMAM"). PAMAM dendrimers are grown from an amine containing core structure such as ethylene diamine, or the like. Normally ethylene diamine is used as the core or initiator of the reaction. The basic synthesis for PAMAM starburst dendrimers begins with ethylene diamine (EDA) being reacted with methyl acrylate under control conditions such that a Michael addition of one molecule of EDA to four molecules of methyl acrylate occurs. This forms the initiator or core adduct. Following the removal of excess methyl acrylate, the core adduct is reacted with an excess of EDA to form a 0 generation molecule having four amidoamine groups. The excess EDA is removed and the 0 generation molecule can be reacted with methyl acrylate in another Michael addition reaction to form a first generation molecule containing eight primary amine groups. A continuation of this stepwise procedure forms the other generations in sequence.

These delivery systems are being developed to increase the bioavailability of the bioactive agents that are administered. The bioavailability of many compositions is limited when the compound is administered orally. This low bioavailability is often due to incomplete absorption and first-pass metabolism of the compounds. Additionally, rapid degradation of antioxidants in the body fluid and elimination of antioxidants from the body further decreases the beneficial effects of antioxidants. Further, some compounds may be limited by their stoichiometric quantities. By combining the compounds with a dendrimer the goal is to overcome these problems. However, as stated above, currently available systems have met with little to no success. It would therefore be useful to develop a delivery system that both overcomes the problems outlined above as well as increasing the bioavailability of the administered compounds.

SUMMARY OF THE INVENTION

According to the present invention, there is provided a nanodevice composition including N-acetyl cysteine linked to a PAMAM dendrimer or a multiarm PEG (polyethylene glycol) polymer.

Also provided is a nanodevice for targeted delivery of a compound to a location in need of treatment. The nanodevice includes a PAMAM dendrimer or or a multiarm PEG (polyethylene glycol) polymer linked to the compound via a disulfide, amide, or ester bond. There is provided a nanodevice composition for localizing and delivering therapeutically active agents, the nanodevice includes a PAMAM dendrimer or or a multiarm PEG and at least one therapeutically active agent attached to the PAMAM dendrimer or said multiarm PEG.

A method of site-specific delivery of a therapeutically active agent, by attaching a therapeutically active agent to a PAMAM dendrimer or or a multiarm PEG using a disulfide bond, administering the PAMAM dendrimer or or a multi-arm PEG to a patient in need of treatment, localizing the dendrimer or or a multiarm PEG to a site in need of treatment, and releasing the therapeutically active agent at the site in need of treatment is further provided.

BRIEF DESCRIPTION OF THE DRAWINGS

FIG. 25 depicts the biodistribution of FITC-G4OH in endotoxin exposed kits (SD Injection). Rabbit kits exposed to maternal inflammation G4OH-FITC localizes to activated microglial cells and astrocytes in the brain far removed from the site of injection.

FIG. 27 depicts the biodistribution of FITC-G4OH following intravenous injection. Dendrimer-FITC localizes in activated microglia and astrocytes on intravenous injection in endotoxin kits but not in controls.

FIG. 30 show polymers, linkers, and drug release times.

FIG. 41 depicts subdural injection astrocytes (GFAP staining).

FIG. 64 shows a ROS assay, percent reduction in $H_2O_2$ levels with 3 hours NAC, PAMAM-S—S-NAC or dendrimer treatment followed by LPS stimulation. 100% reduction denotes $H_2O_2$ concentration of cells with no induction by LPS (control group). The amount of ROS released into the media was measured using Amplex Red. Data are mean±SD of three samples per group, and assessed by t-test. The solid bars are the efficacy data for 24 hours, whereas the patterned bars denote the response after 72 hours. For free dendrimers, equivalent concentrations of the dendrimers that correspond to the amount present in the conjugate at the given NAC concentration are shown in brackets.

FIG. 65 shows a MALDI-TOF analysis of modified PAMAM dendrimers to determine the average number of coupled Ethyl-S—S-NAC groups. PAMAM-NH$_2$ before (A) and after (B) reaction with SPDP and followed by NAC reaction.

FIG. 85 depicts a cytotoxicity assay. (A) Human cervical epithelial End1/E6E7 cells and (B) mouse microglial cells were treated with the $G_4$-PAMAM-OH, G3.5-PAMAM-COOH and $G_4$-PAMAM-$NH_2$ dendrimers at concentrations indicated for MIC values. Three samples were in each group. Cell viability was assessed by MTT method. The proportion of viable cells in the treated group was compared to that of negative control.

FIG. 86 show the flow cytometry of the cell entry dynamics of (A) $G_4$-PAMAM-OH-FITC in *E. coli* and (B) BV-2 microglial cell line. The log of FITC absorption intensity (FL1-H on x-axis) is plotted against the number of cells (counts on y-axis). The maximum uptake of $G_4$-PAMAM-OH-FITC in *E. coli* occurs at 3 hours. The rapid cellular uptake of G4-PAMAM-OH-FITC within 15 minutes in microglial cells is evident. The transport of conjugate into microglial cell increased with increasing time. Confocal microscopy images (400×) showed that $G_4$-PAMAM-OH-FITC appeared to be mainly localized in the cytoplasm of BV-2 cells while the nucleus appeared to be relatively free of the presence of any fluorescence at this time point (C).

FIG. 89 are HPLC chromatograms for G4-PAMAM-O-GABA-$NH_2$ (6) (UV channel), G4-PAMAM-O-GABA-NH-FITC (1) (Fluorescent channel) and G4-PAMAM-O-GABA-NH-Alexa 488 (2) (Fluorescent channel). The retention time of G4-PAMAM-O-GABA-$NH_2$ is 16.2 minutes and the FITC and Alexa tagged G4-PAMAM-O-GABA-$NH_2$ show a peak appearing at 17.5 and 15.5 minutes respectively.

(FIG. 91A) The transport of $G_4$-PAMAM-O-GABA-NH-FITC (D-FITC) and FITC (unconjugated) across the chorion stripped off fetal membrane. The amnion was placed in the side by side diffusion chamber over 30 h to study the transport of dendrimers.

(FIG. 92A) The transport of $G_4$-PAMAM-O-GABA-NH-FITC (D-FITC) and FITC (unconjugated) across the amnion stripped off fetal membrane. The chorion was placed in the side by side diffusion chamber over 30 hours to study the transport of dendrimers.

DETAILED DESCRIPTION OF THE INVENTION

Figure 1:
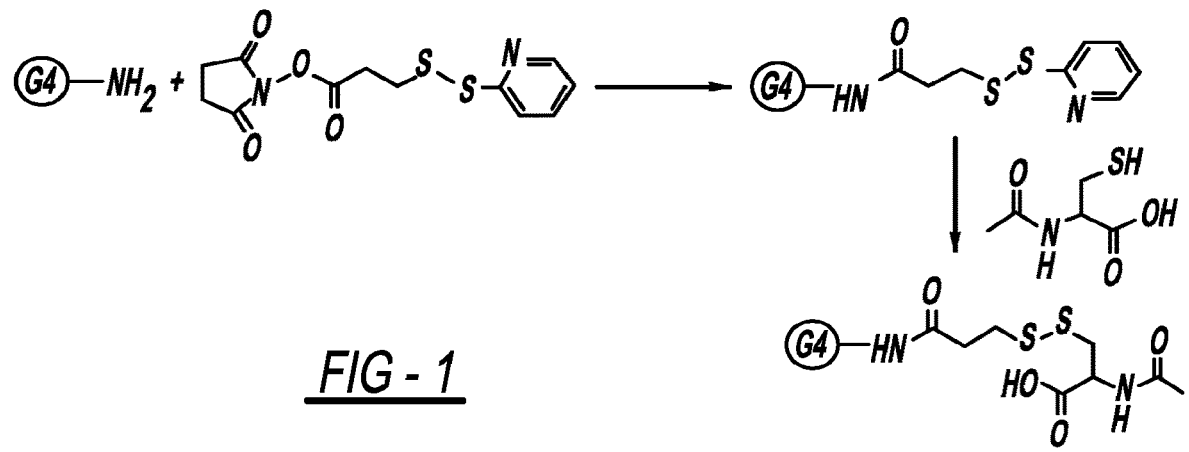
FIG. 1 depicts N-Acetyl Cysteine (NAC) linked to G4-PAMAM-NH$_2$ dendrimer by disulfide bond using the spacer SPDP such that the bond between NAC and SPDP appended on dendrimer surface is disulfide.
Figure 2:
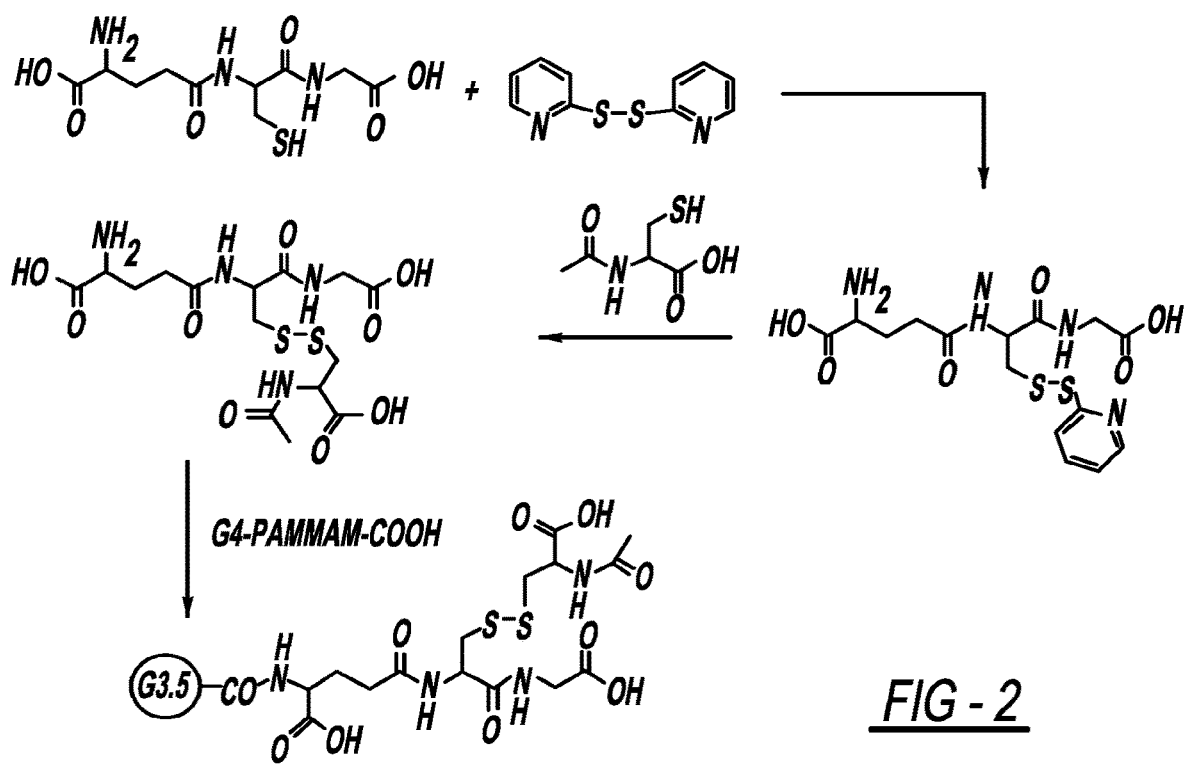
FIG. 2 depicts N-Acetyl Cysteine (NAC) linked to G4-PAMAM-COOH dendrimer by disulfide bond using the spacer Glutathione (GSH) such that the bond between NAC and GSH on appended on dendrimer surface is disulfide.
Figure 3:
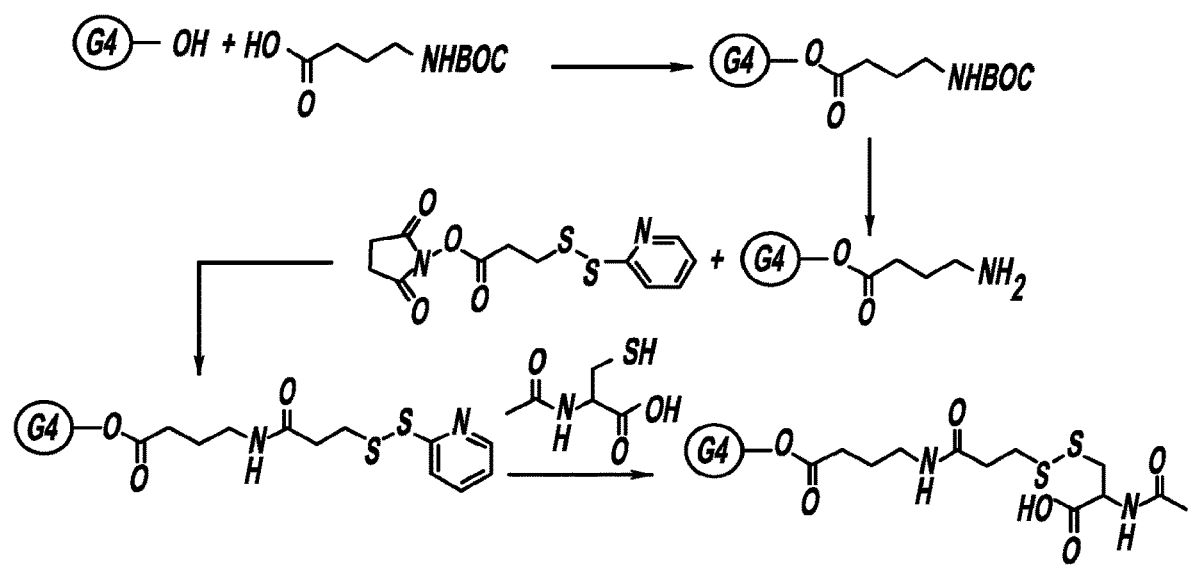
FIG. 3 depicts N-Acetyl Cysteine (NAC) linked to G4-PAMAM-OH dendrimers by disulfide bond using the two spacer molecules, Gamma-aminobutyric acid (GABA) and SPDP such that the bond between NAC and SPDP appended on dendrimer surface is disulfide
Figure 4:
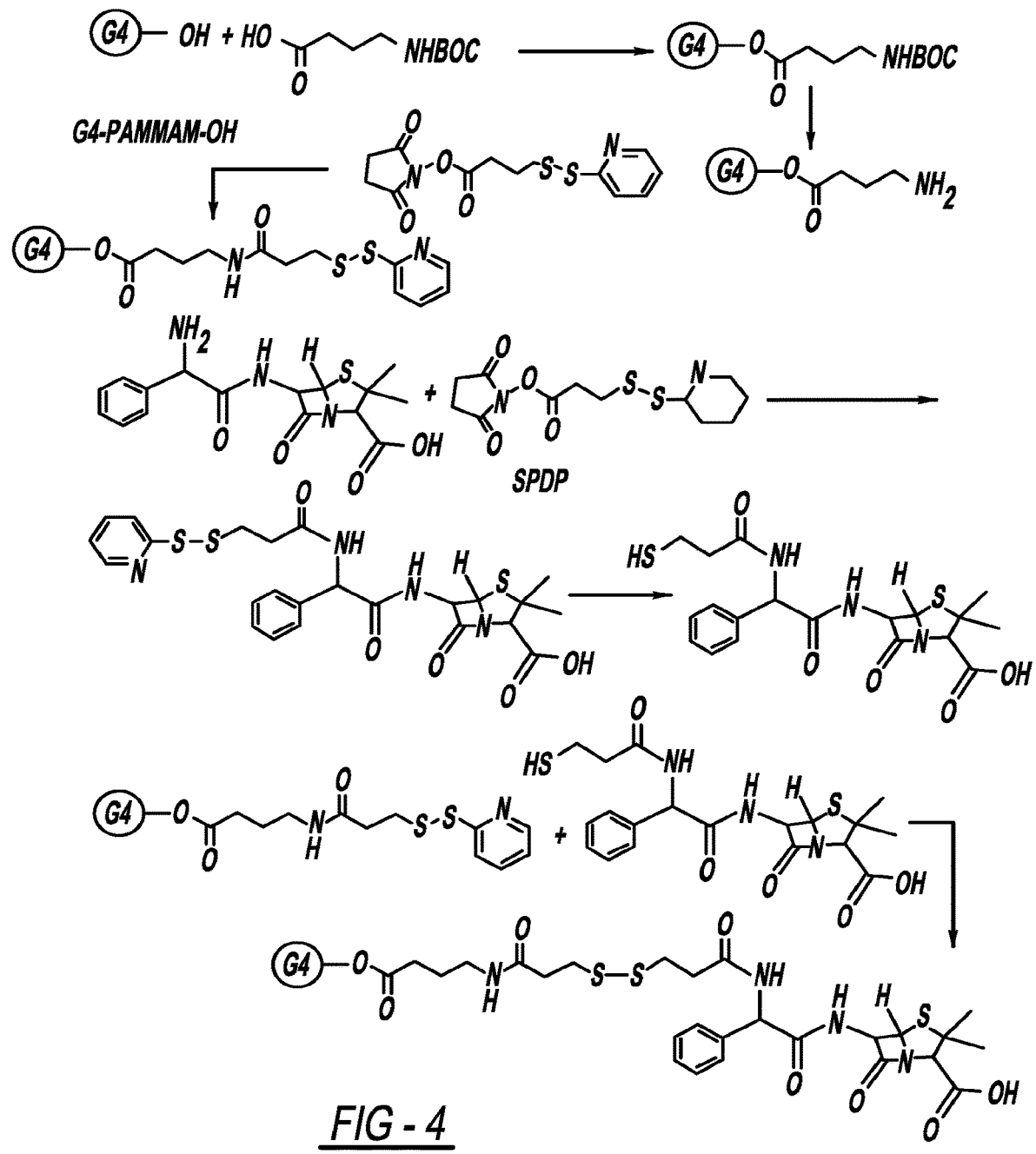
FIG. 4 depicts Ampicillin linked to G4-PAMAM-OH dendrimers by disulfide bond using the two spacer molecules, Gamma-aminobutyric acid (GABA) and SPDP such that the bond between Ampicillin and SPDP appended on dendrimer surface is disulfide.
Figure 5:
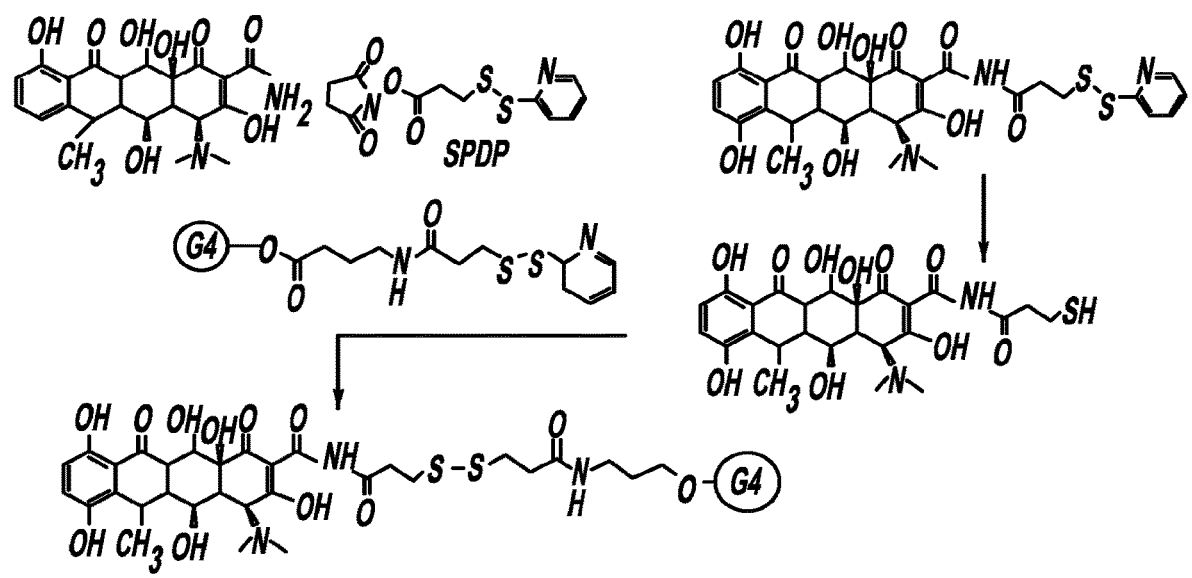
FIG. 5 depicts Doxycycline linked to G4-PAMAM-OH dendrimer by disulfide bond using the spacer SPDP such that the bond between doxycycline and SPDP appended on dendrimer surface is disulfide.
Figure 6:
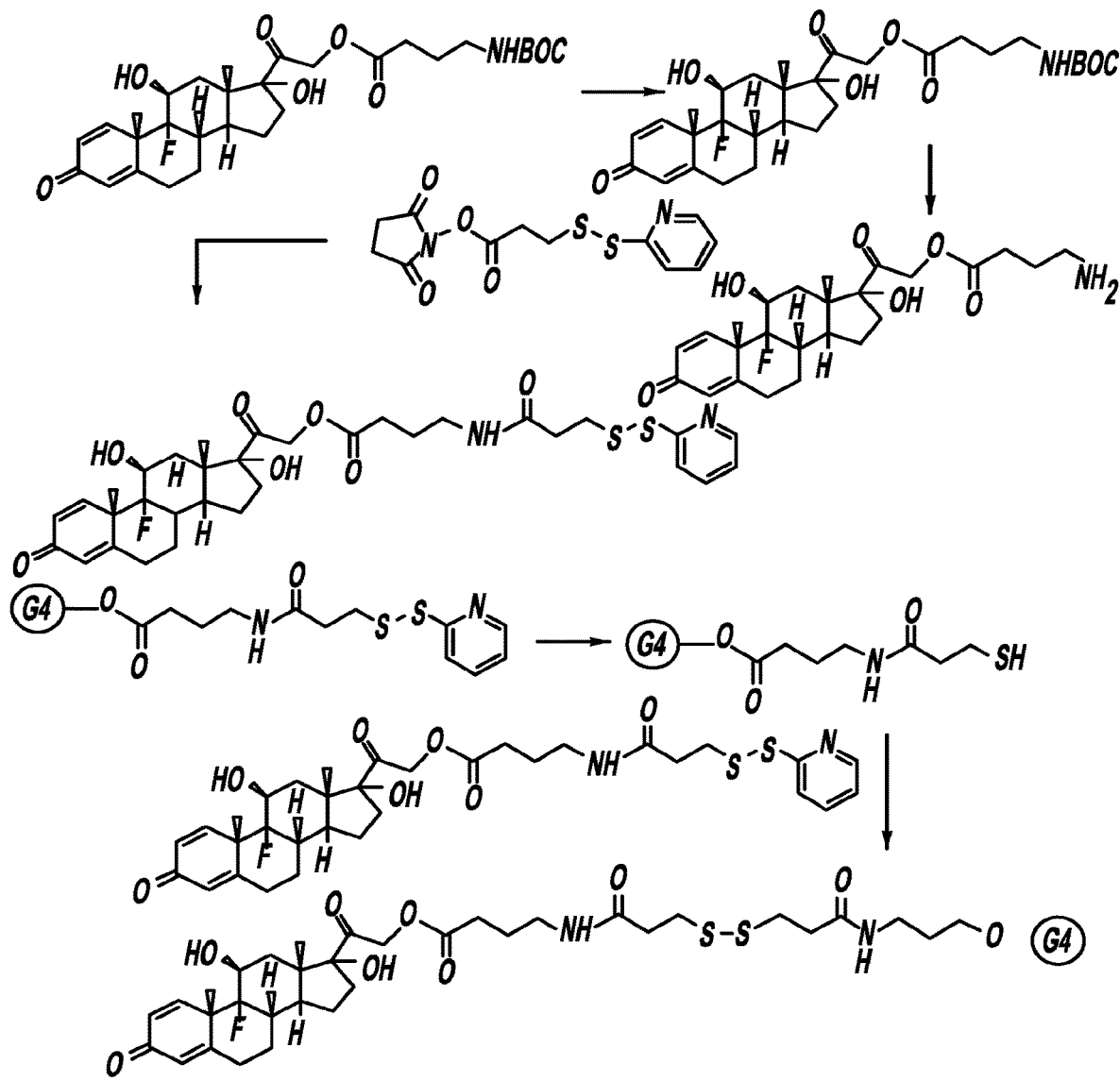
FIG. 6 depicts Dexamethasone linked to G4-PAMAM-OH dendrimers by disulfide bond using the three spacer molecules, Gamma-aminobutyric acid (GABA), SPDP and SPDP such that the bond between Dexamethasone and SPDP appended on dendrimer surface is disulfide.
Figure 7:
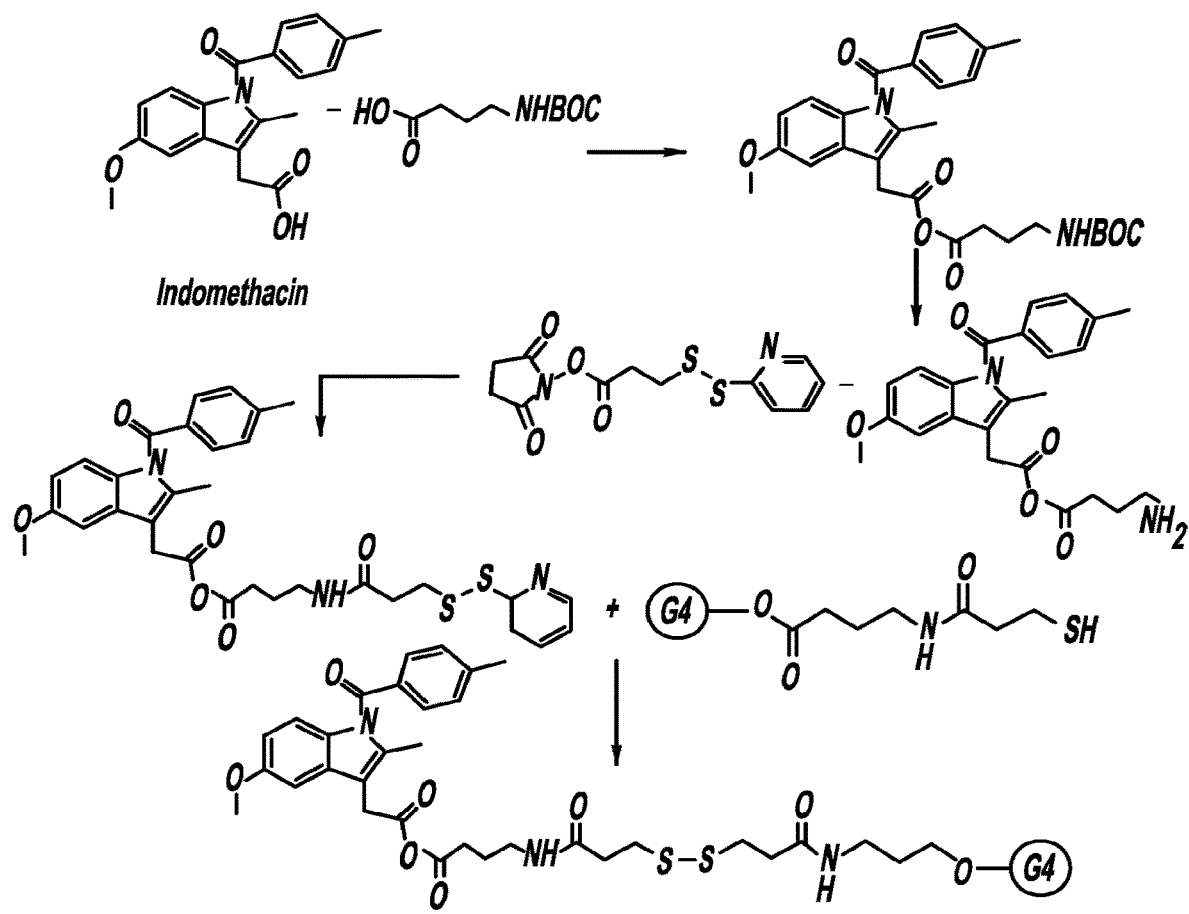
FIG. 7 depicts Indomethacin linked to G4-PAMAM-OH dendrimers by disulfide bond using the three spacer molecules, Gamma-aminobutyric acid (GABA), SPDP and SPDP such that the bond between Indomethacin and SPDP appended on dendrimer surface is disulfide.
Figure 8:
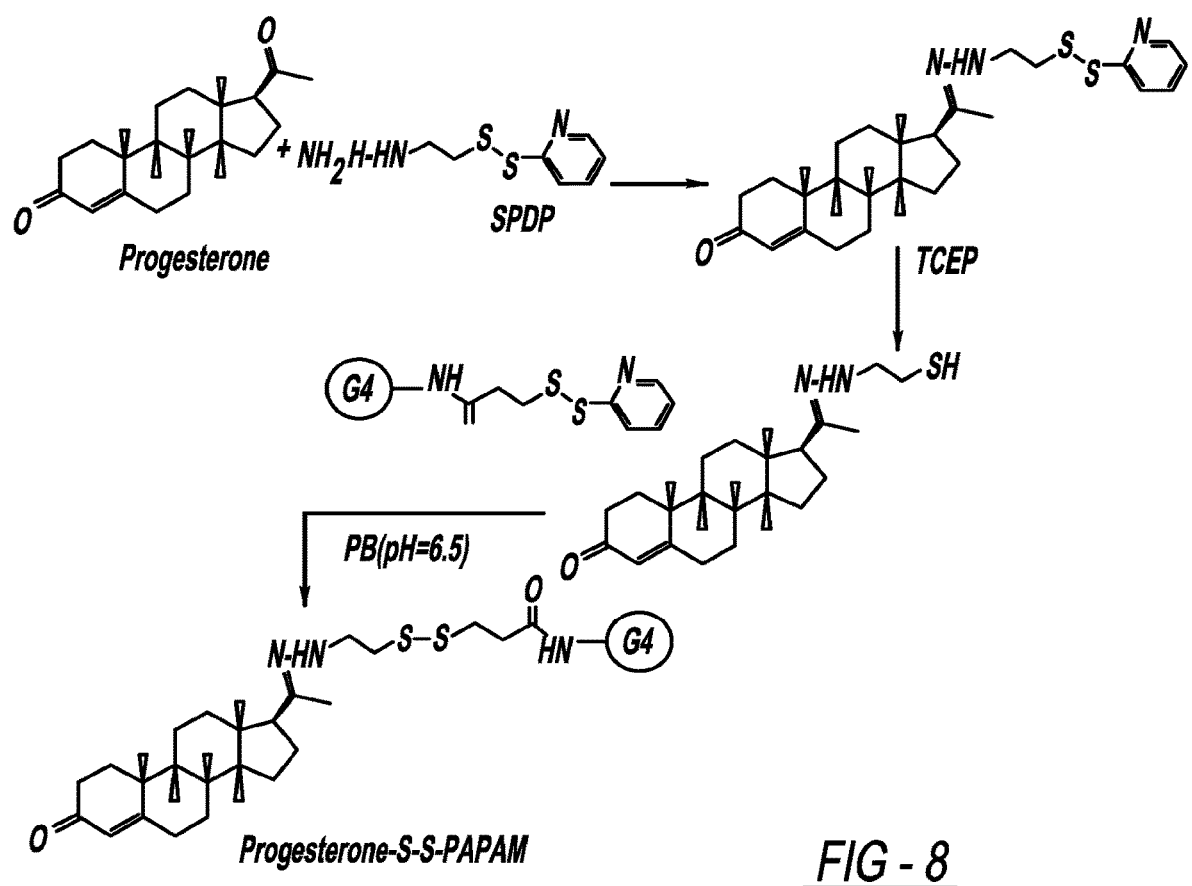
FIG. 8 depicts Progesterone linked to G4-PAMAM-OH dendrimers by disulfide bond using the two spacer molecules of SPDP linked to each other such that the bond between Progesterone and SPDP appended on dendrimer surface is disulfide.
Figure 9:
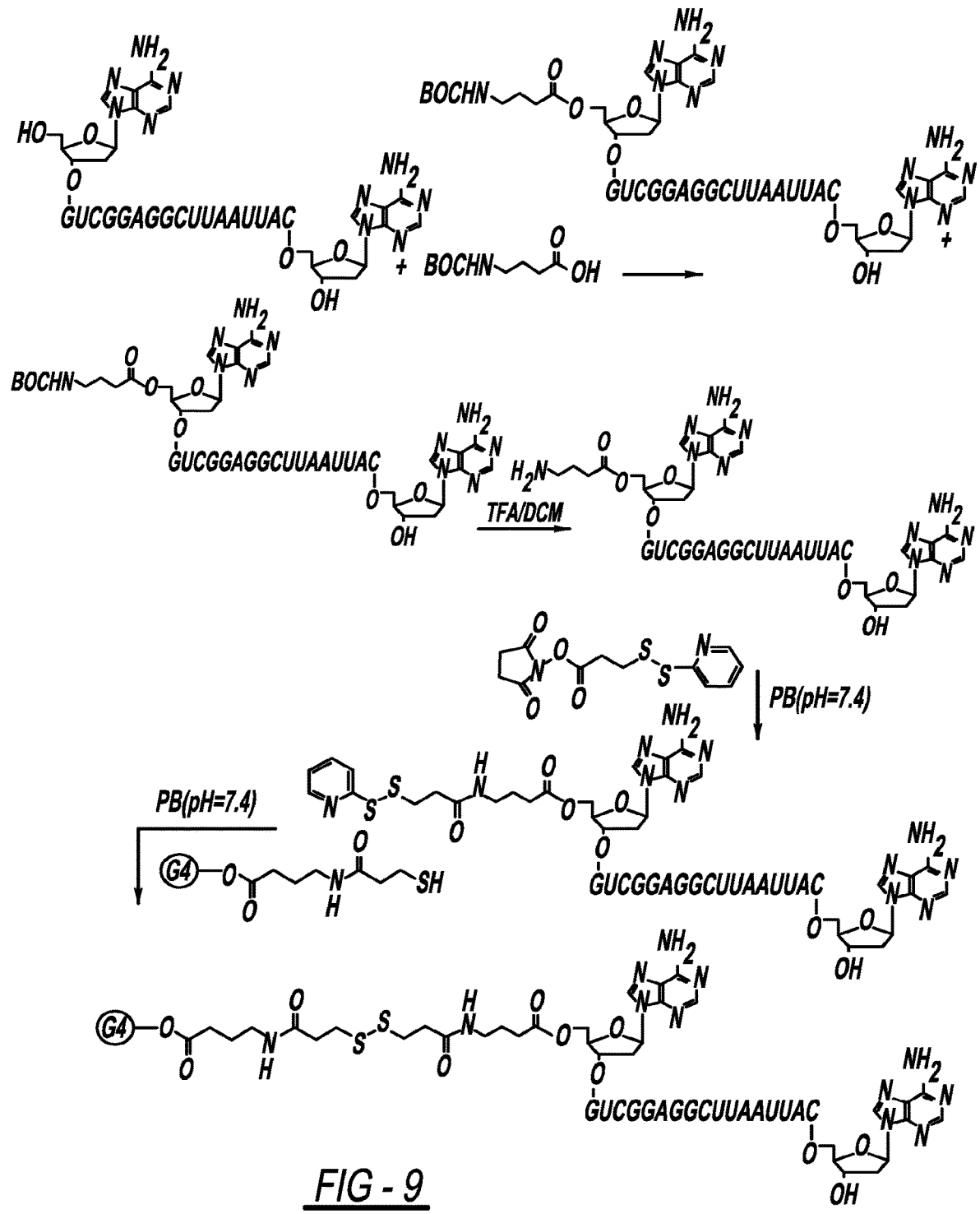
FIG. 9 depicts 5$^1$Adenine-GUCGGAGGC-UUAAUUACA-3$^1$ (SEQ ID NO: 1) nucleotide linked to G4-PAMAM-OH dendrimers by disulfide bond using four spacer molecules of linked in order GABA-SPDP-SPDP-GABA linked to each other such that the bond between Adenine nucleotide and SPDP-GABA appended on dendrimer surface is disulfide.
Figure 10:
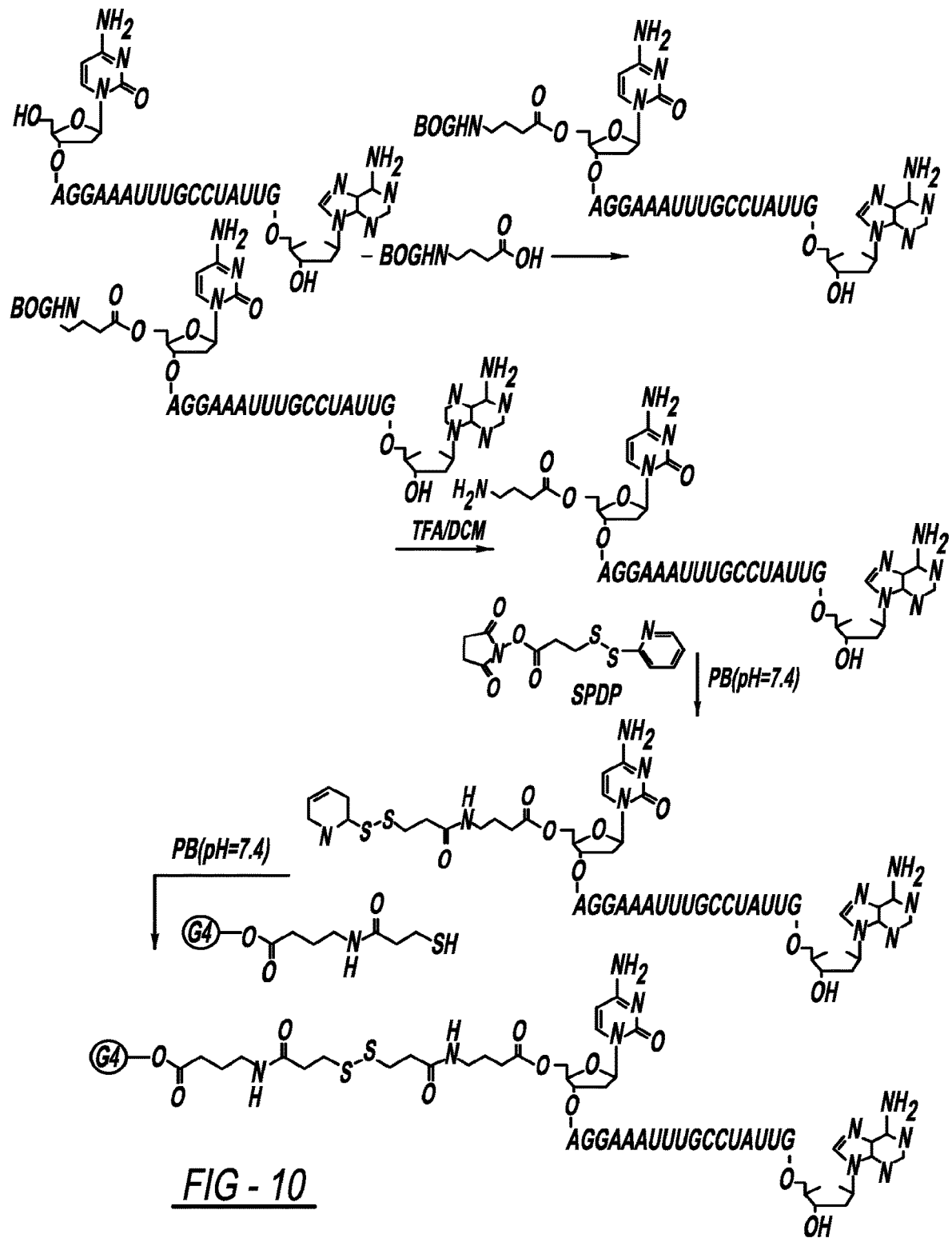
FIG. 10 depicts 5$^1$Cytosine-AGGAAAUUUGC-CUAUUGA-3$^1$ (SEQ ID NO: 2) nucleotide linked to G4-PAMAM-OH dendrimers by disulfide bond using four spacer molecules of linked in order GABA-SPDP-SPDP-GABA linked to each other such that the bond between Cytosine nucleotide and SPDP-GABA appended on dendrimer surface is disulfide.
Figure 11:
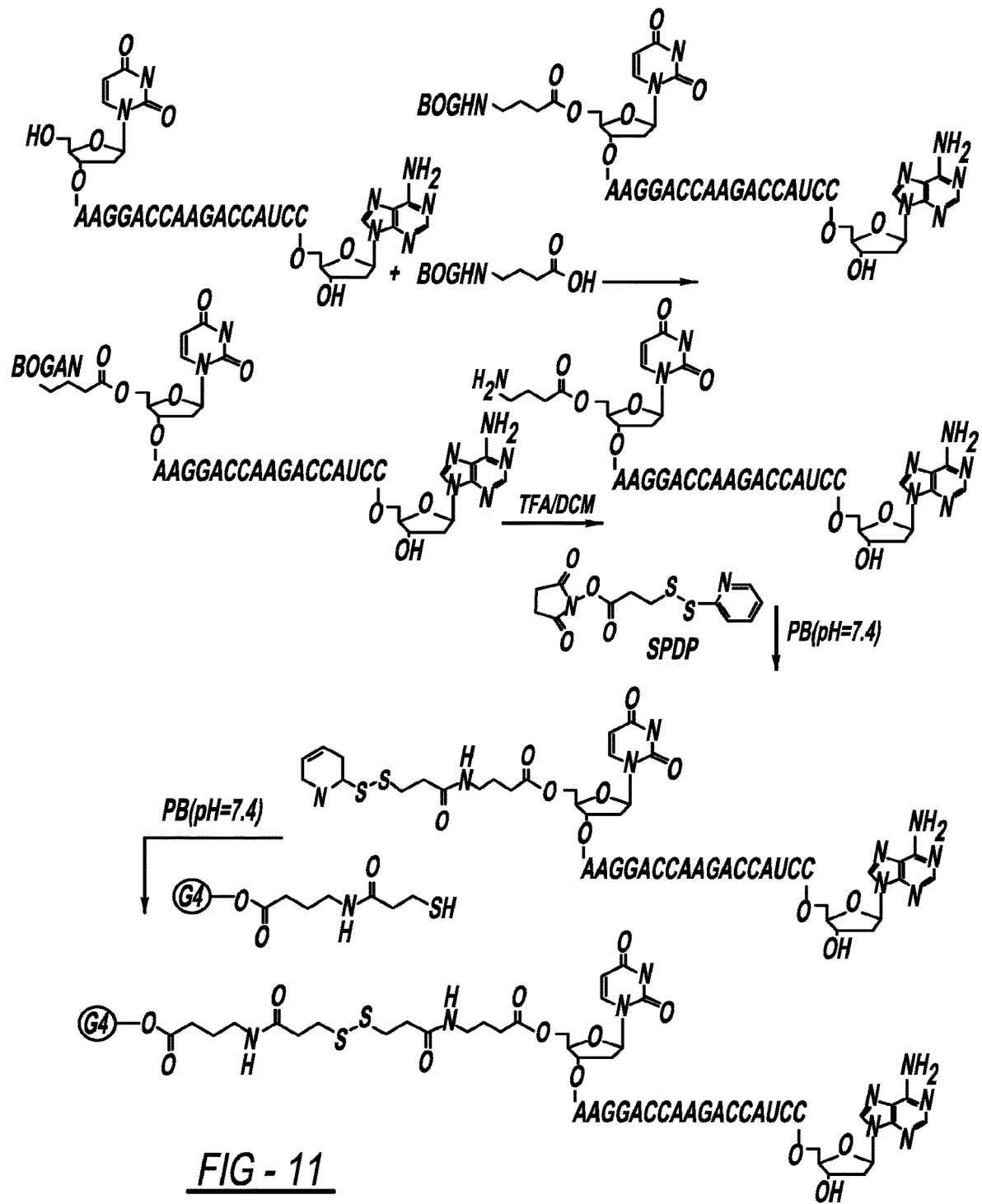
FIG. 11 depicts 5$^1$Uracil-AAGGACCAAGACCAUCCA-3$^1$ (SEQ ID NO: 3) nucleotide linked to G4-PAMAM-OH dendrimers by disulfide bond using four spacer molecules of linked in order GABA-SPDP-SPDP-GABA linked to each other such that the bond between Uracil nucleotide and SPDP-GABA appended on dendrimer surface is disulfide.
Figure 12:
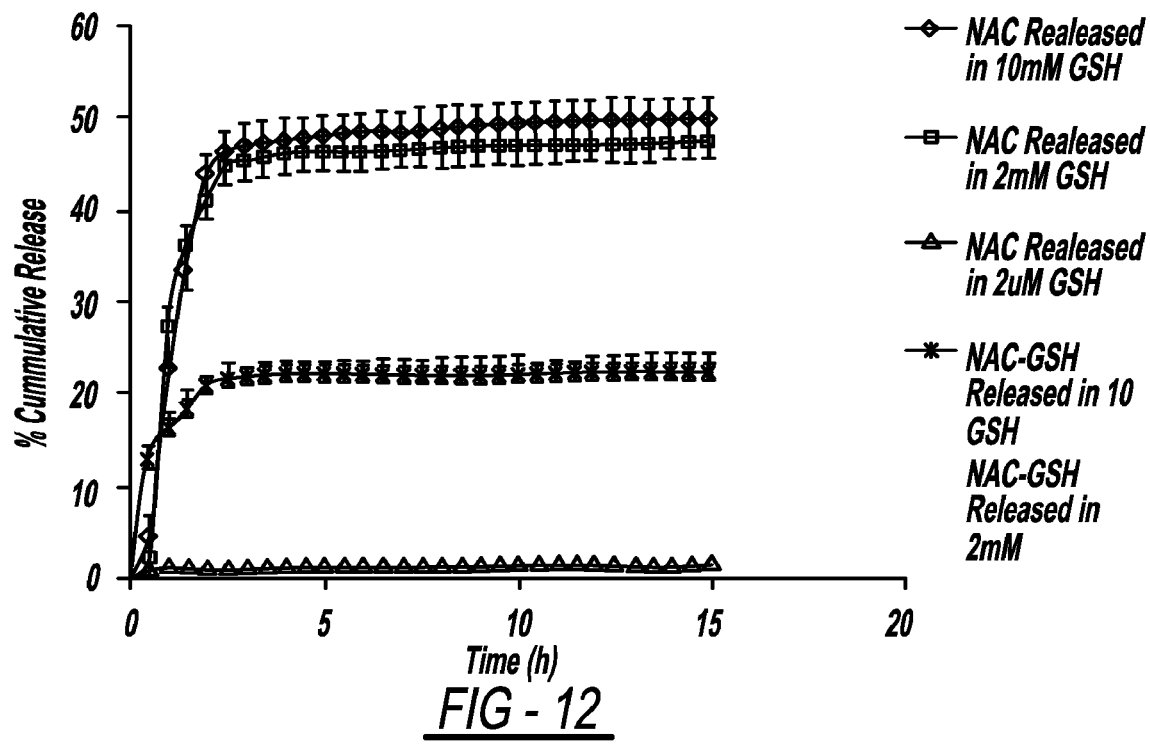
FIG. 12 shows the rapid release of NAC from 6 arm-PEG-S—S-NAC
Figure 13:
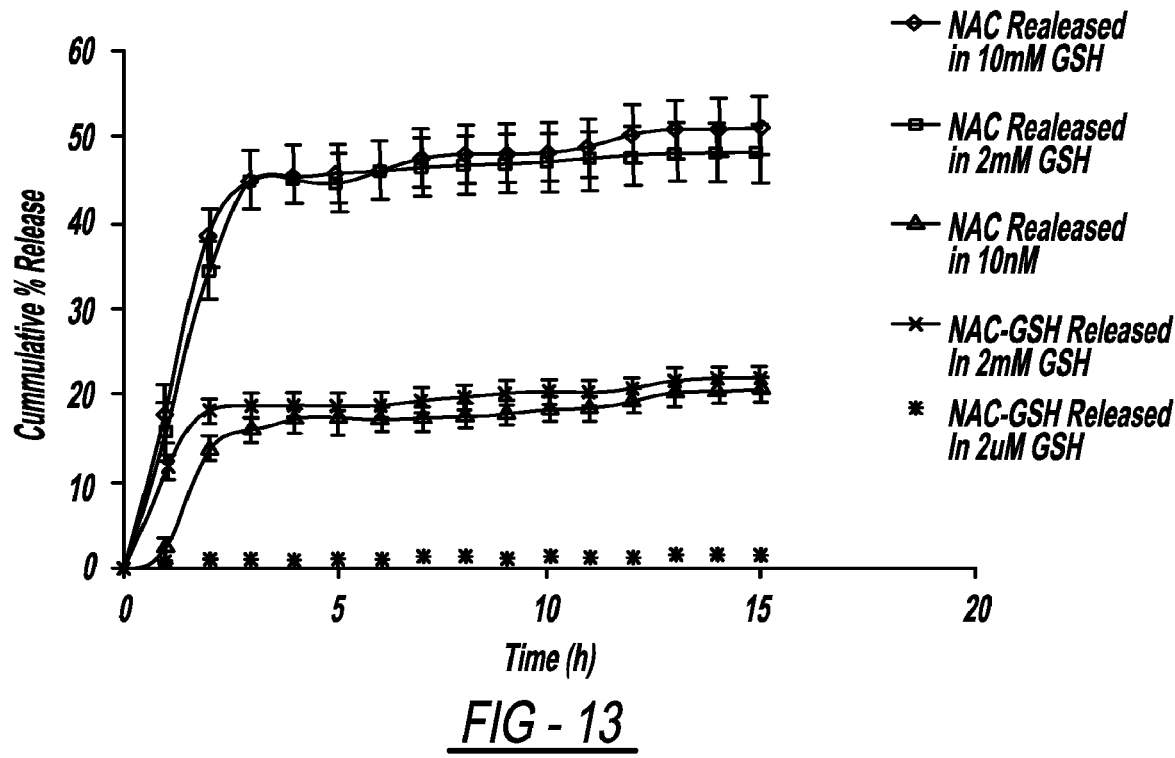
FIG. 13 shows the rapid release of NAC from 8 arm-PEG-S—S-NAC
Figure 14A:
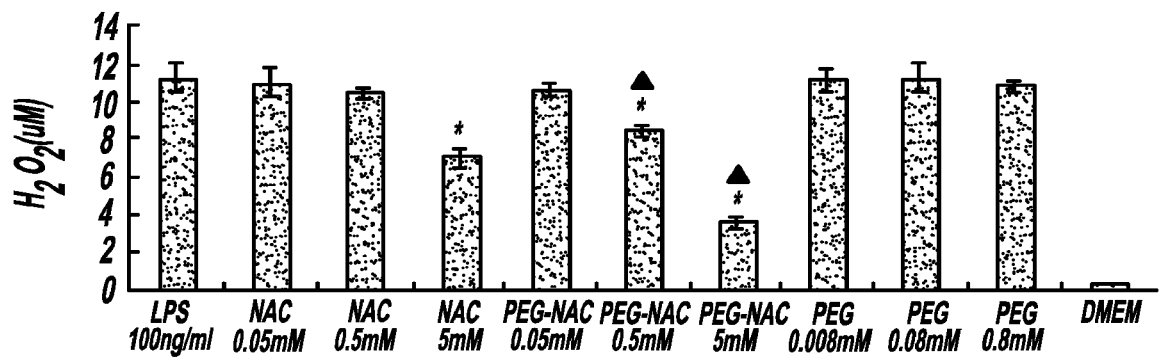
FIG. 14 shows an ROS assay. (A) BV-2 cells (passage 22) were co-treated with 100 ng/mL of LPS and the indicated concentration of NAC, PEG-NAC conjugate 1 and its corresponding PEG for 72 hours. (B) BV-2 cells were co-treated with 100 ng/mL of LPS and the indicated concentration of NAC, PEG-NAC conjugate 2 and its corresponding PEG for 72 hours. The amount of ROS released into the media was measured using Amplex Red.
Figure 14B:
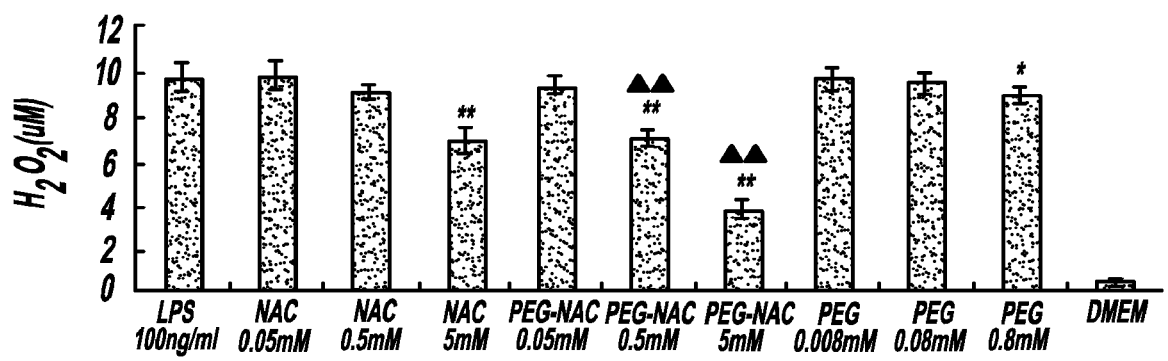
Figure 15A:
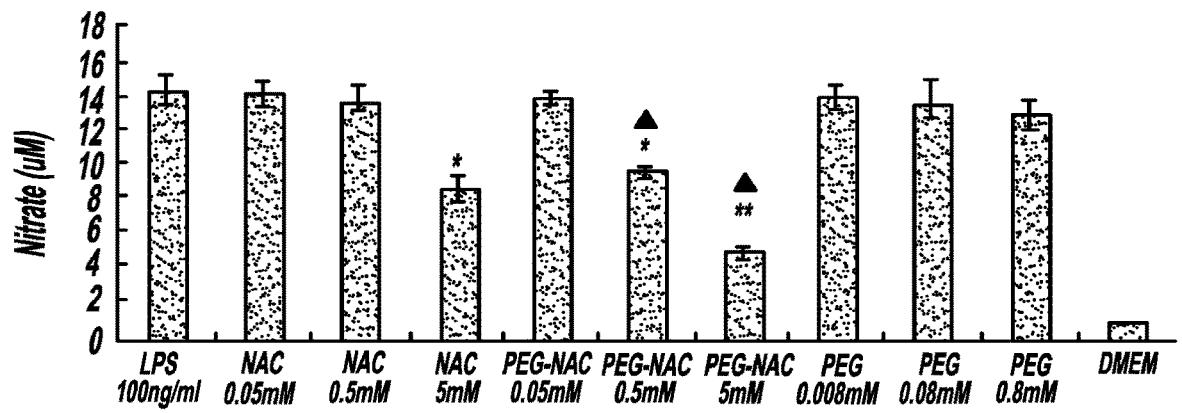
FIG. 15 shows a NO release assay. (A) BV-2 cells (passage 22) were co-treated with 100 ng/mL of LPS and the indicated concentration of NAC, PEG-NAC conjugate land its corresponding PEG for 72 hours. (B) BV-2 cells were co-treated with 100 ng/mL of LPS and the indicated concentration of NAC, PEG-NAC conjugate 2 its corresponding PEG for 72 hours. Nitrite in culture medium was measured using Griess reagent system.
Figure 15B:
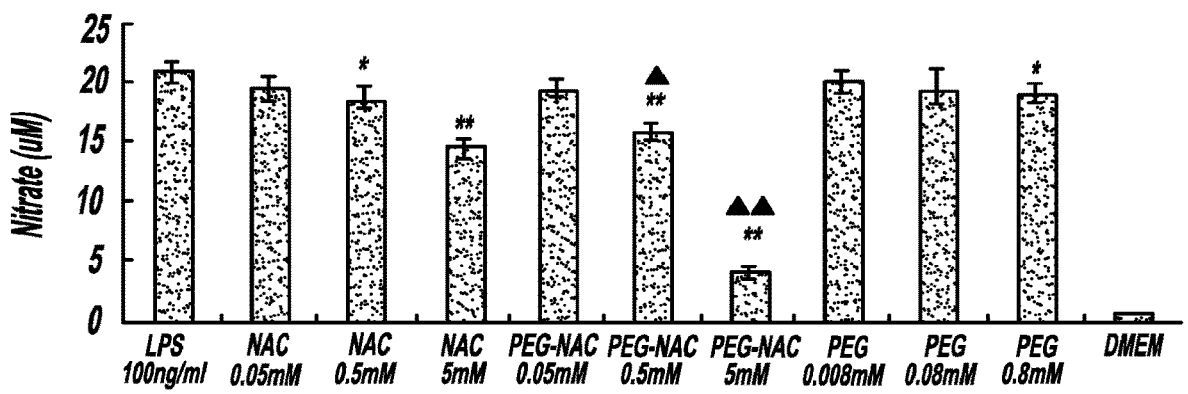
Figure 16A:
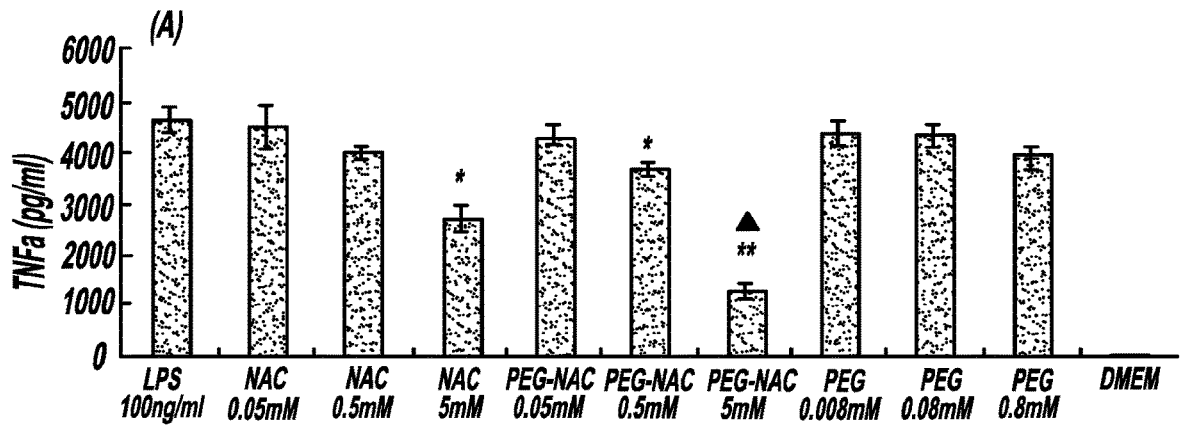
FIG. 16 shows an TNF-α release assay. (A) BV-2 cells (passage 22) were co-treated with 100 ng/mL of LPS and the indicated concentration of NAC, 6-Arm-PEG-S—S-NAC conjugate (1) and its correspond 6-Arm-PEG-SH for 72 hours (B) BV-2 cells were co-treated with 100 ng/mL of LPS and the indicated concentration of NAC, 8-Arm-PEG-S—S-NAC conjugate (3) and its correspond PEG for 72 hours. Three samples were in each group. TNF-α in culture medium was measured using mouse TNF-α ELISA Kit.
Figure 16B:
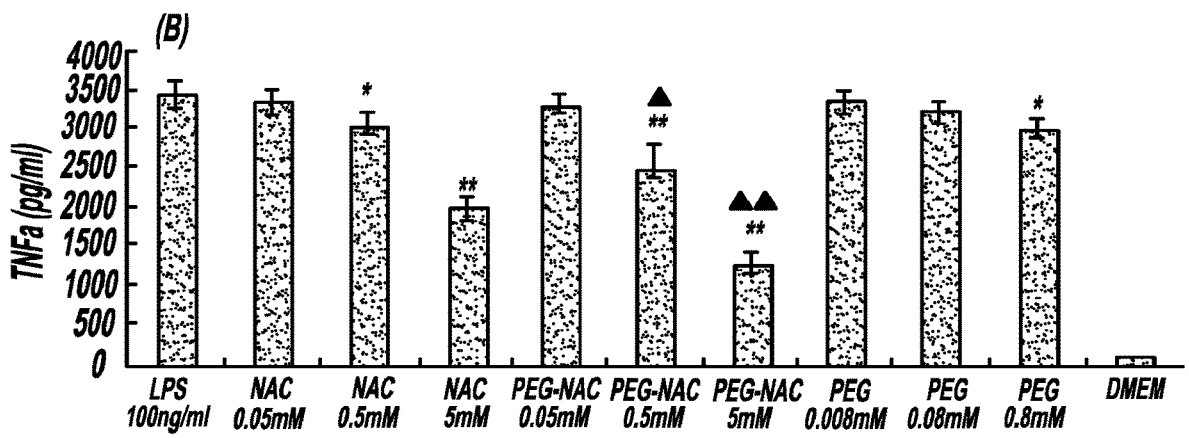
Figure 17:
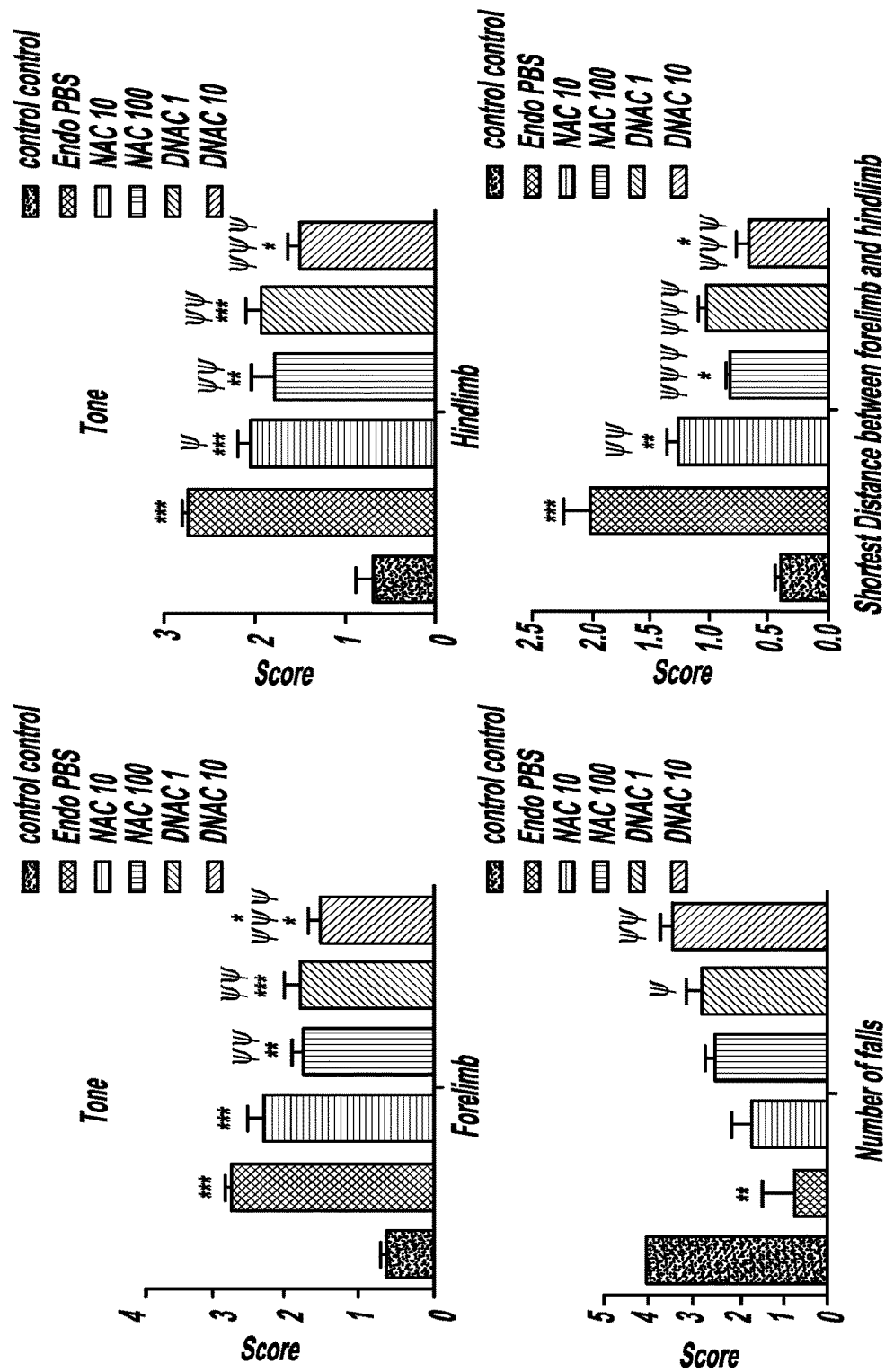
FIG. 17 shows the neurobehavioral scoring of rabbits treated with NAC, G4-PAMAM-NAC conjugate and endotoxin treated rabbits.
Figure 18:
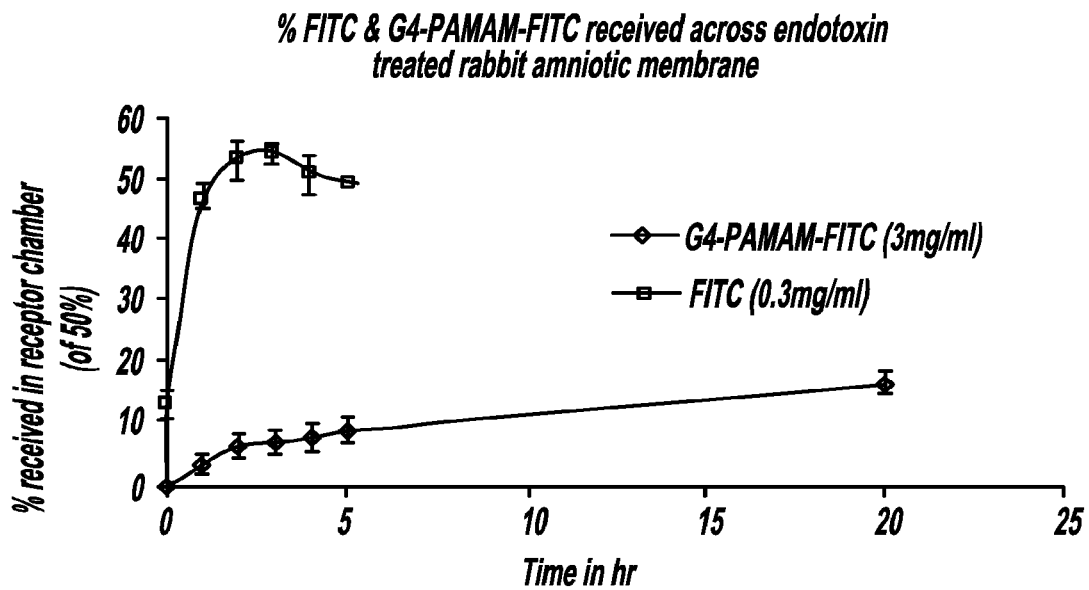
FIG. 18 shows the transport of G4-PAMAM-FITC across the rabbit amniotic membrane (in-vitro evaluation).
Figure 19:
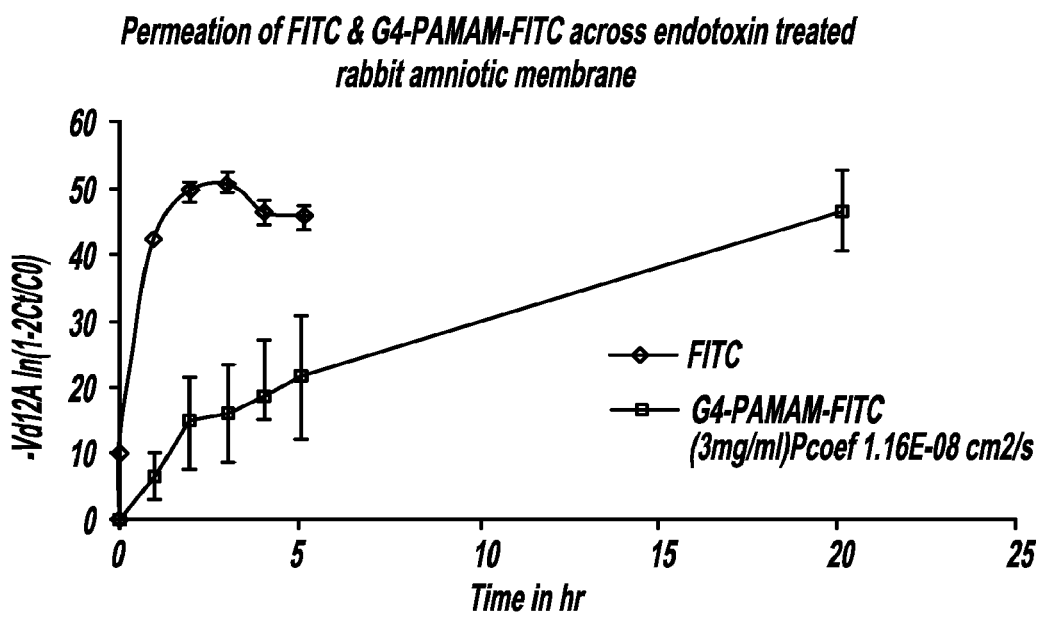
FIG. 19 depicts the permeation coefficient determination for G4-PAMAM-FITC across the rabbit amniotic membrane (in vitro evaluation).
Figure 20:
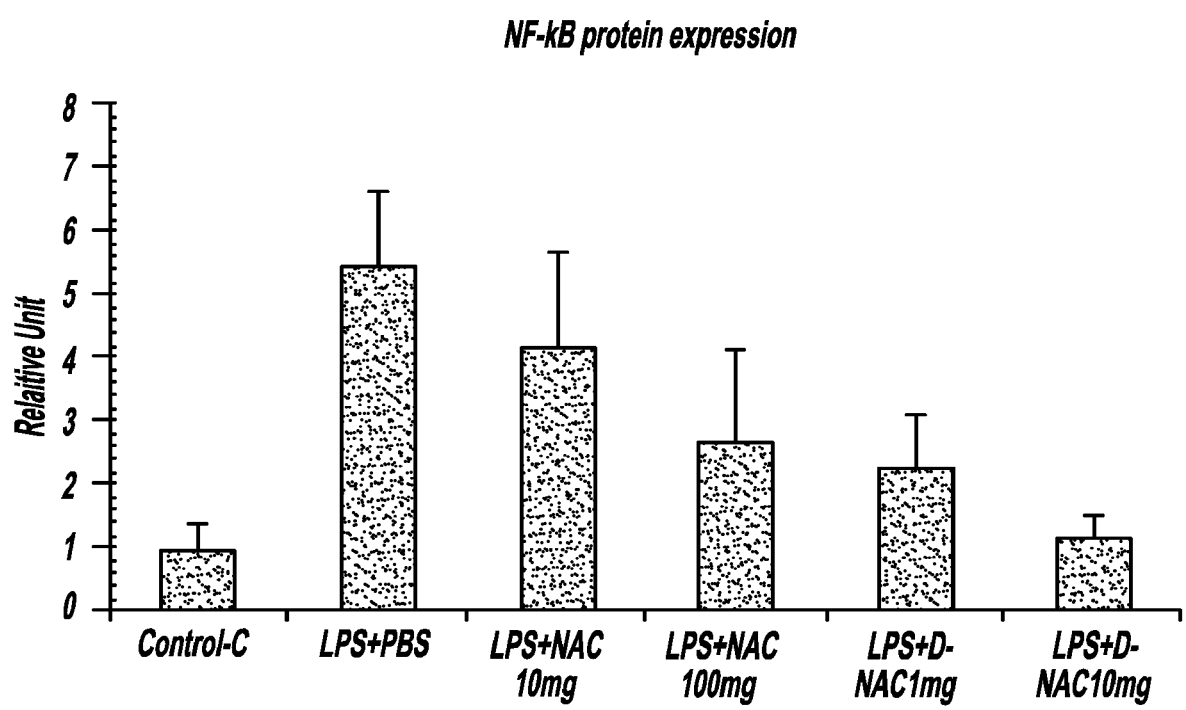
FIG. 20 shows the NF-κB protein expression.
Figure 21:
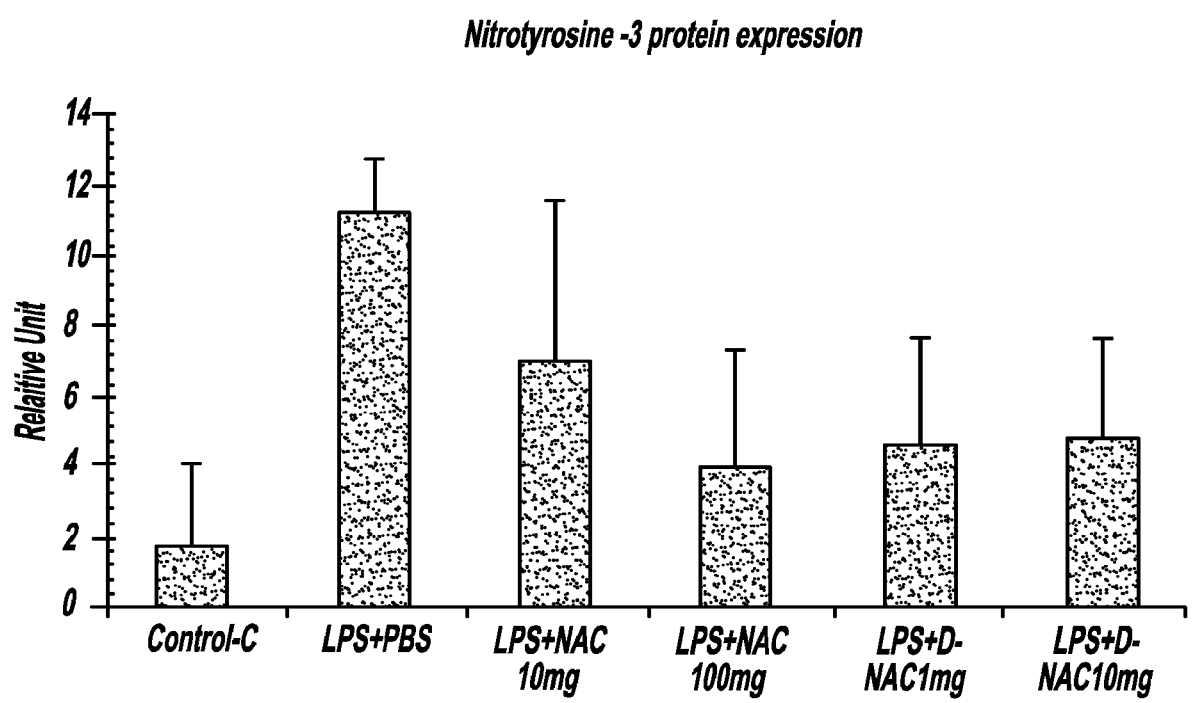
FIG. 21 shows the NT-3 expression indicated oxidative injury.
Figure 22:
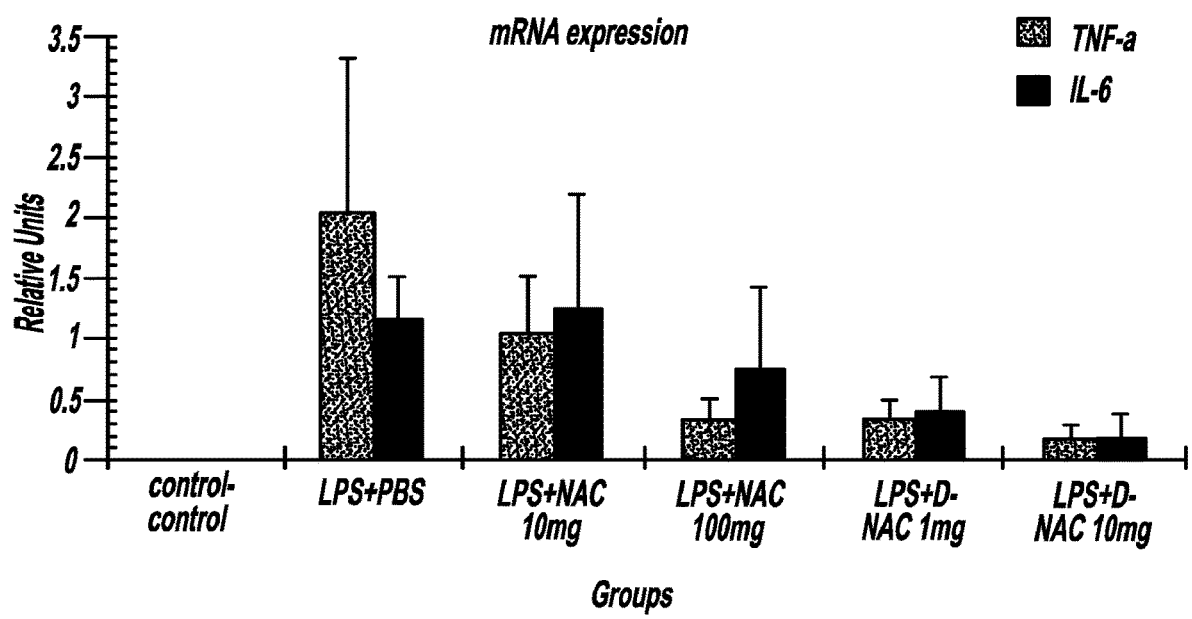
FIG. 22 shows the mRNA expression of TNF-α and IL-6 in the brain.
Figure 23:
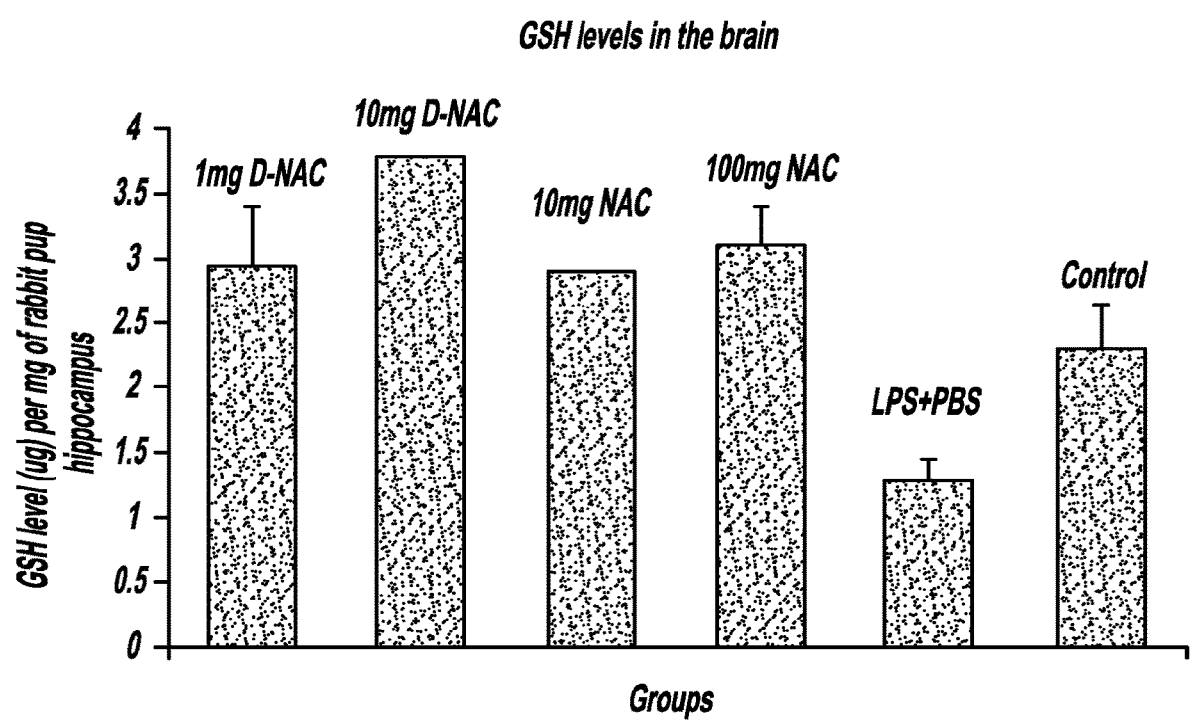
FIG. 23 shows the GSH qualification in the hippocampus.
Figure 24:
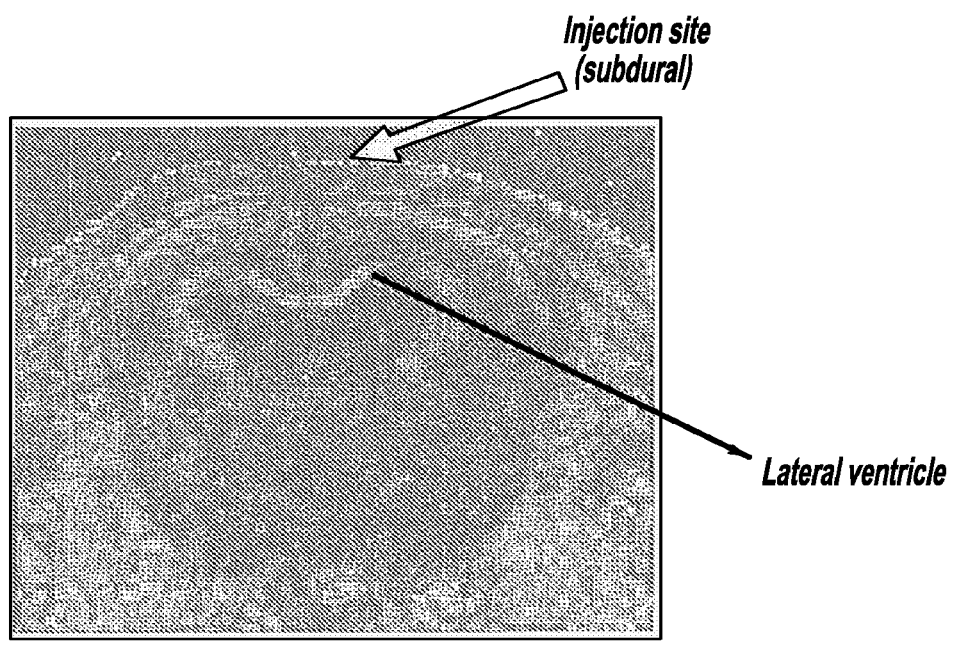
FIG. 24 shows the Uptake of FITC-G4OH in activated microglial cells through subdural injection.
Figure 26:
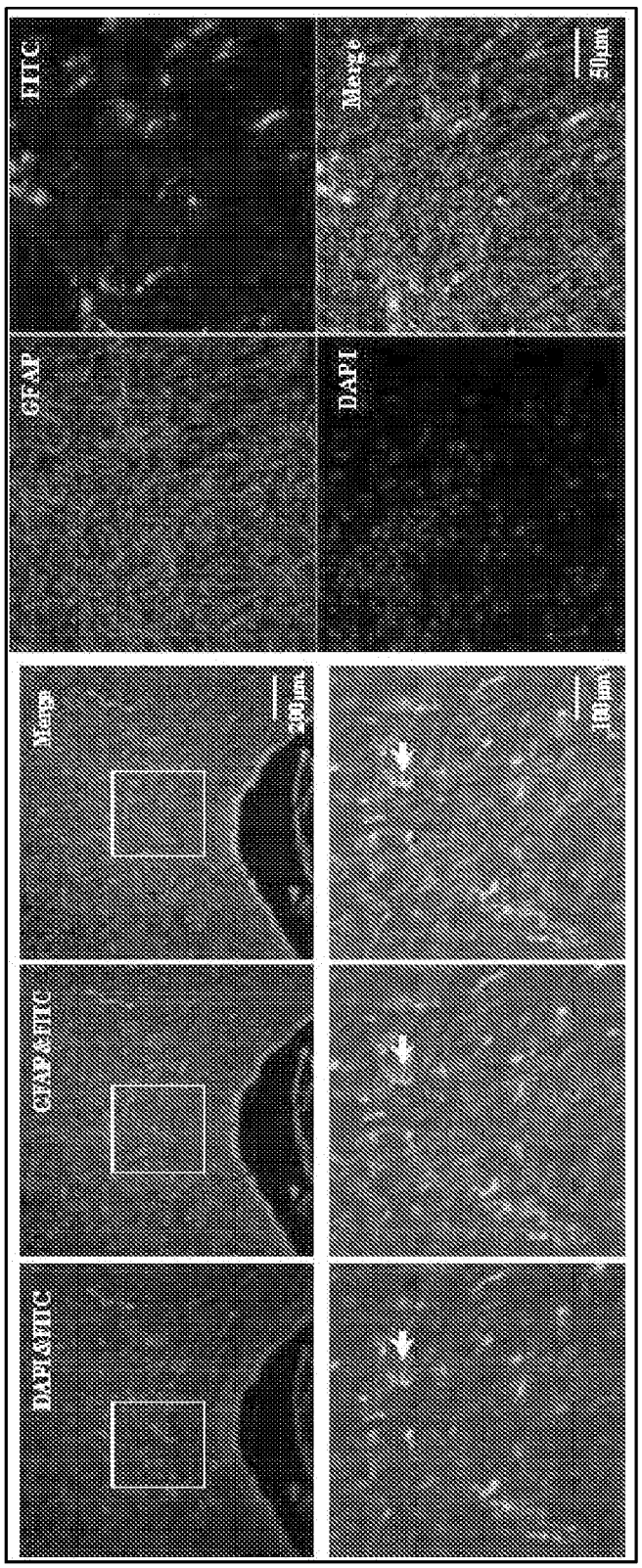
FIG. 26 depicts the biodistribution of FITC-G4OH after subdural injection in controls. G4OH-FITC is taken up by some microglial cells along the lateral ventricle in control kits while no uptake is seen in astrocytes.
Figure 28:
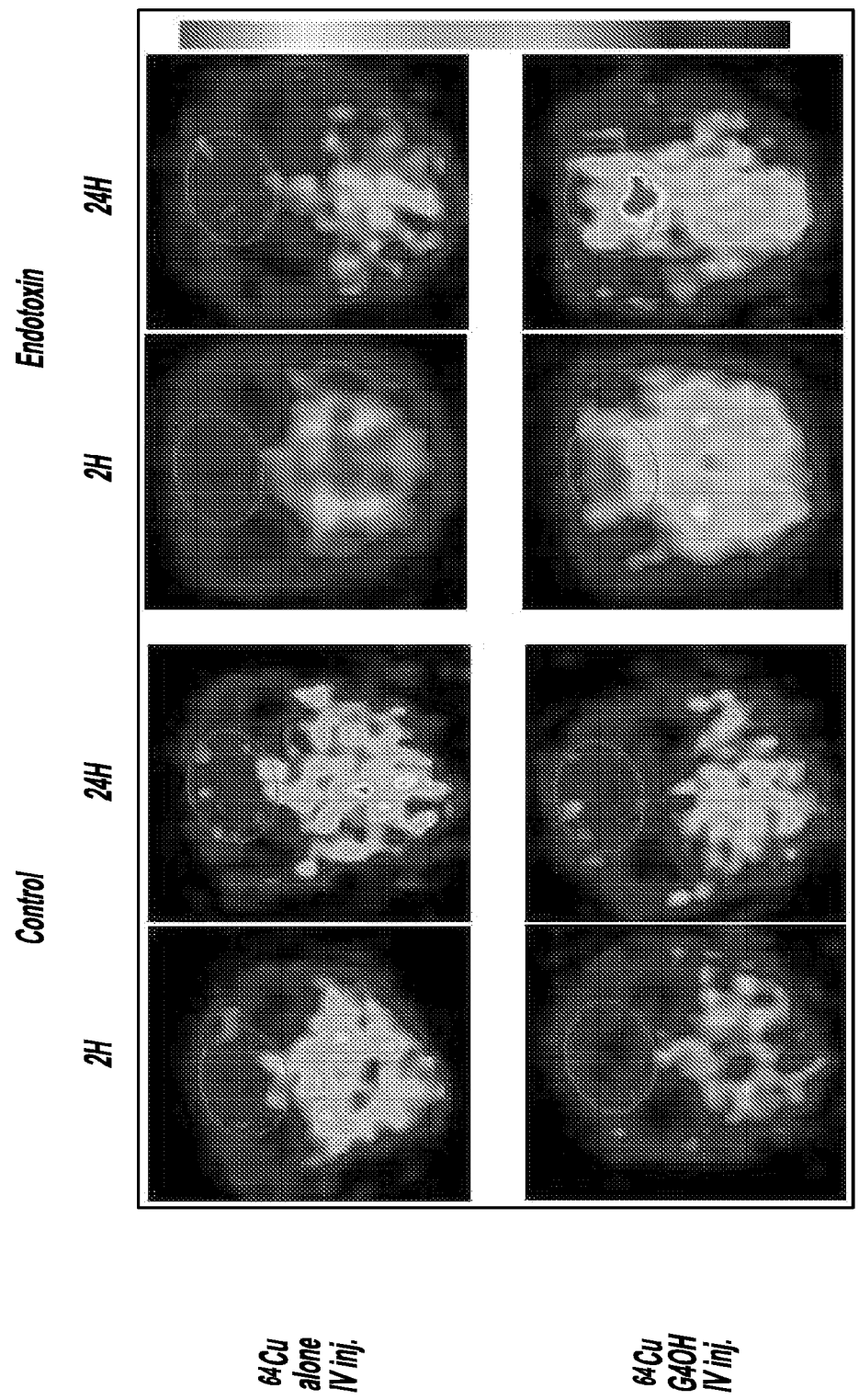
FIG. 28 depicts the brain uptake of G4OH—Cu[64] in fetal neuroinflammation using PET imaging. Increased uptake of G4OH—Cu[64] was noted in the newborn rabbit kits exposed to maternal inflammation.
Figure 29:
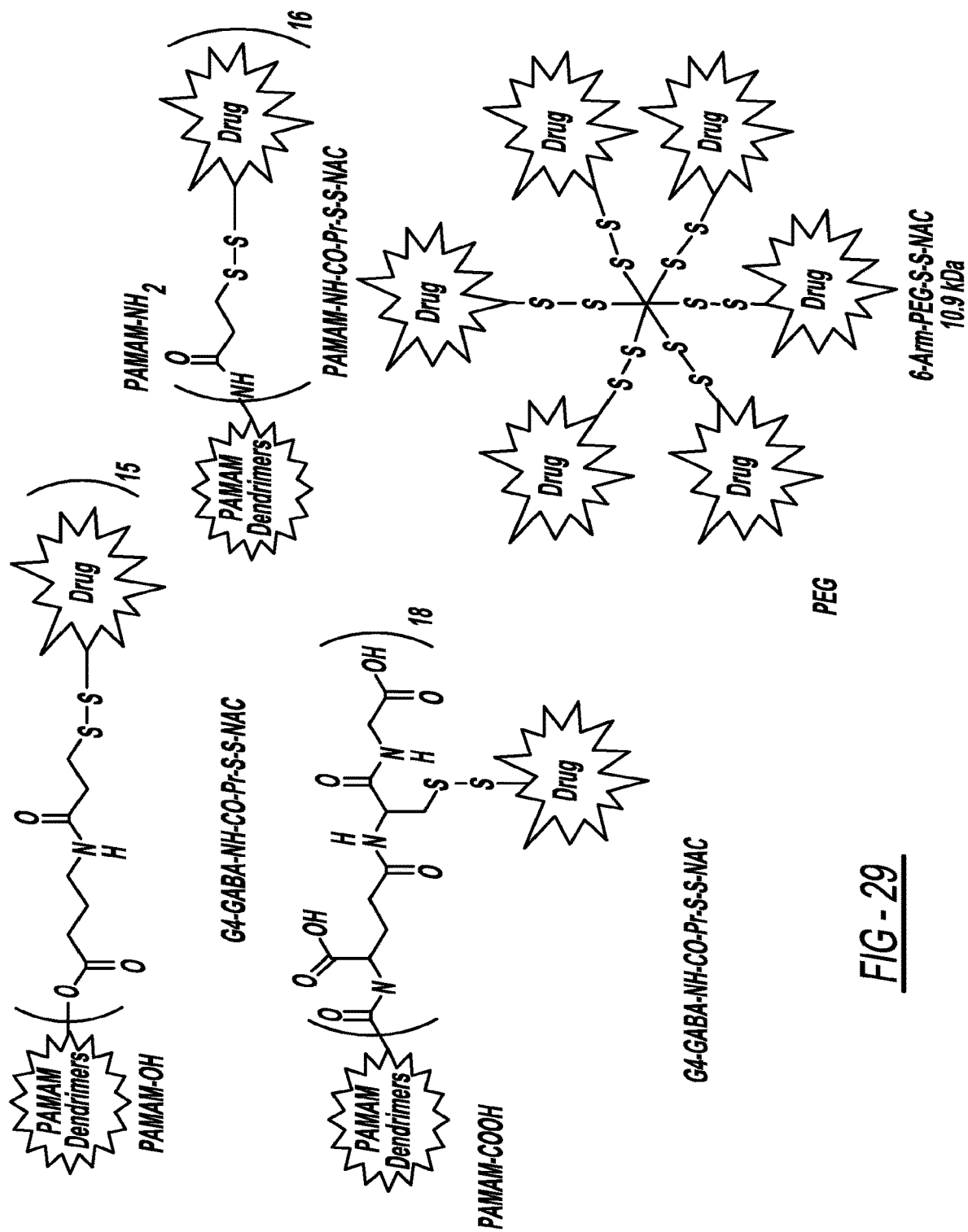
FIG. 29 shows a library of D-NAC nanodevices.
Figure 31:
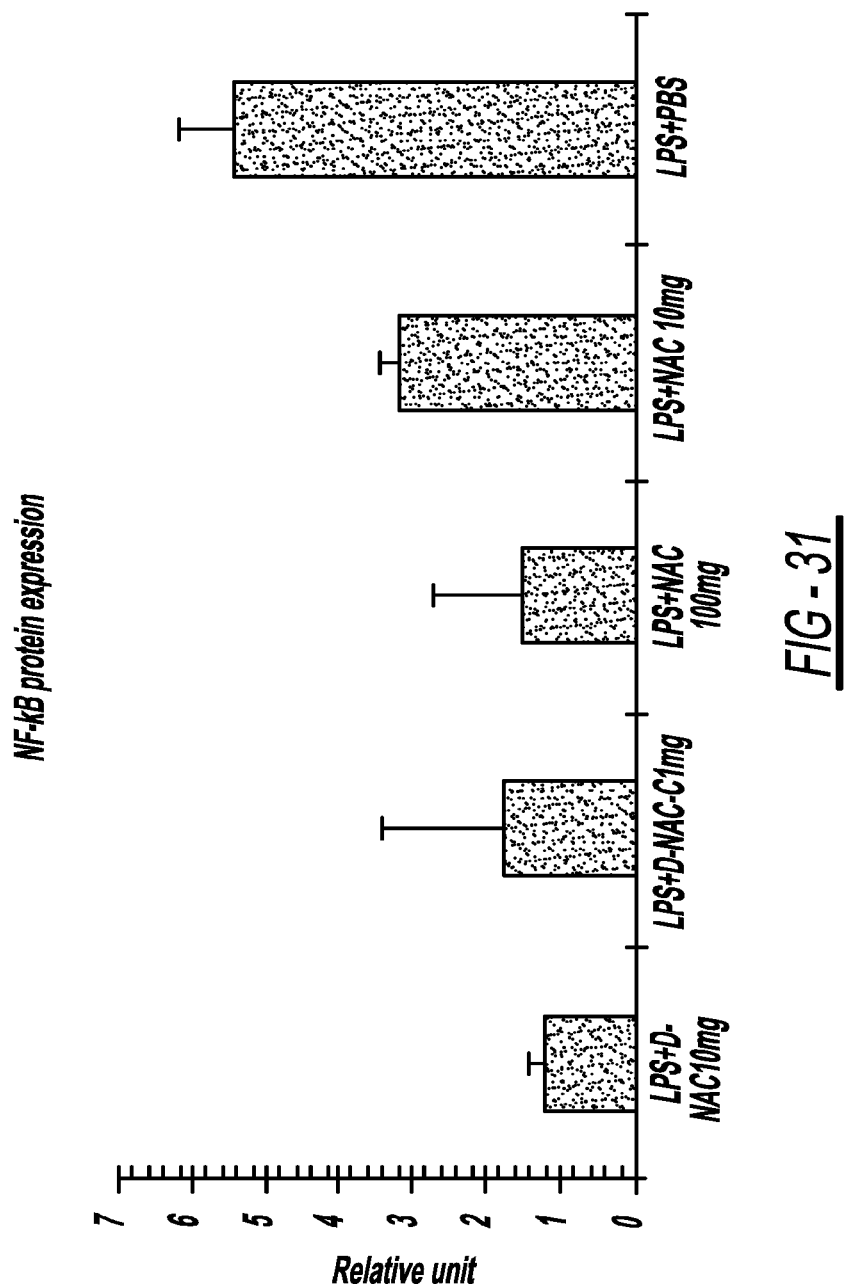
FIG. 31 shows the efficacy of Dendrimer-NAC Conjugates for suppression of neuroinflammation (protein level). Dendrimer-NAC Conjugates result in 10-100 greater suppression of NF-kB protein expression in the hippocampus of 5 day old rabbits exposed to maternal inflammation in utero (n=3-4 pups/group).
Figure 32:
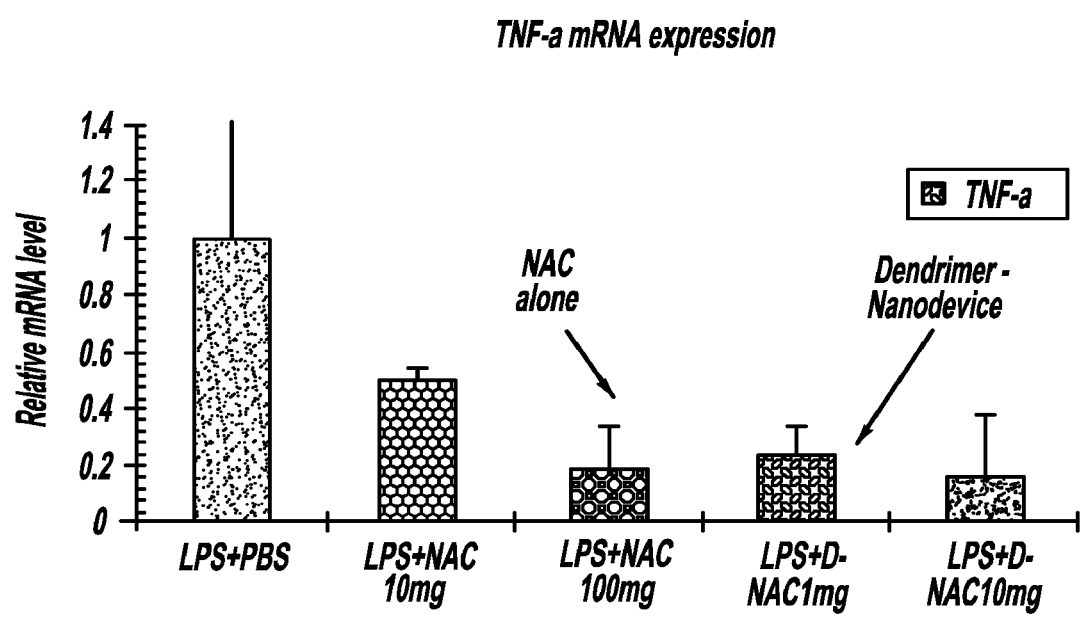
FIG. 32 shows the dendrimer-NAC Conjugates for suppression of neuroinflammation (RNA level). The dendrimer nanodevice is 10-100 times more effective in suppressing mRNA expression of TNF-alpha in the hippocampus of endotoxin kits at 5 days of age (n=3 pups/group).
Figure 33:
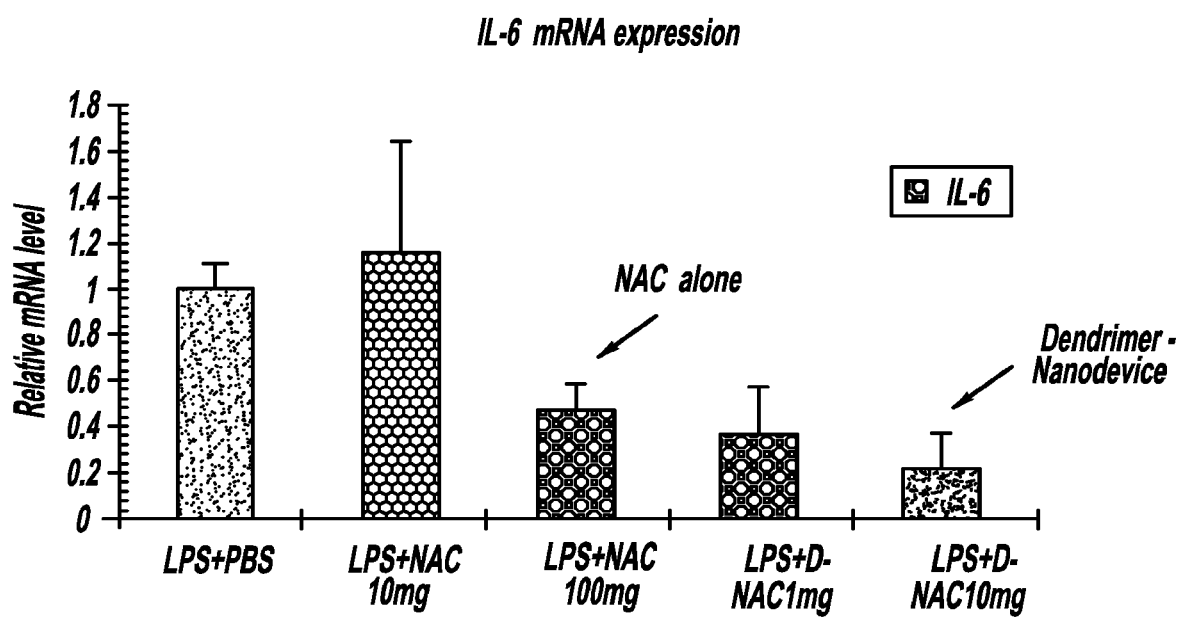
FIG. 33 show the dendrimer-NAC Conjugates for suppression of neuroinflammation (RNA level). The dendrimer nanodevice is 10-100 times more effective than the free drug for suppression of IL-6 in the hippocampus (n=3 pups/group).
Figure 34:
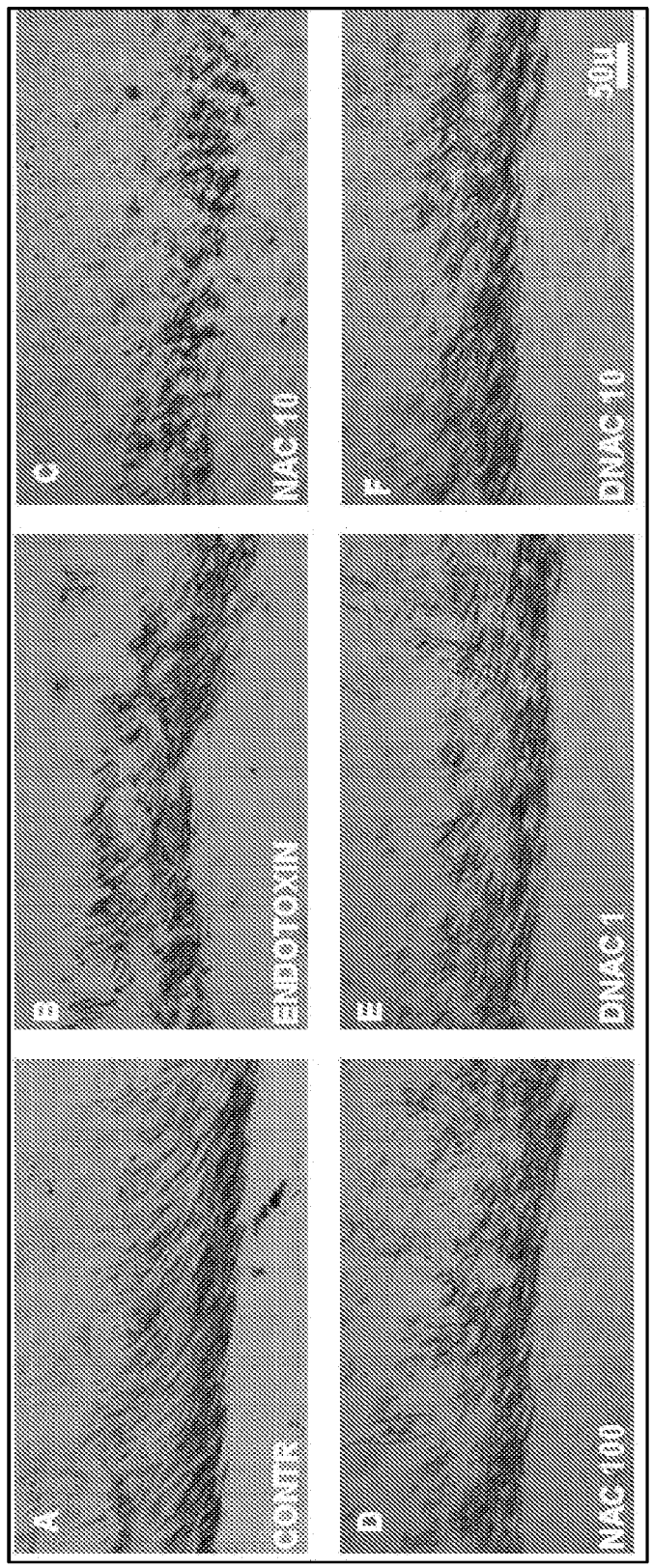
FIG. 34 shows the therapeutic Efficacy of Dendrimer-NAC Conjugates (effects on myelination). Treatment with dendrimer-NAC results in increased myelination and better organization of myelin tracts when compared to the drug alone.
Figure 35:
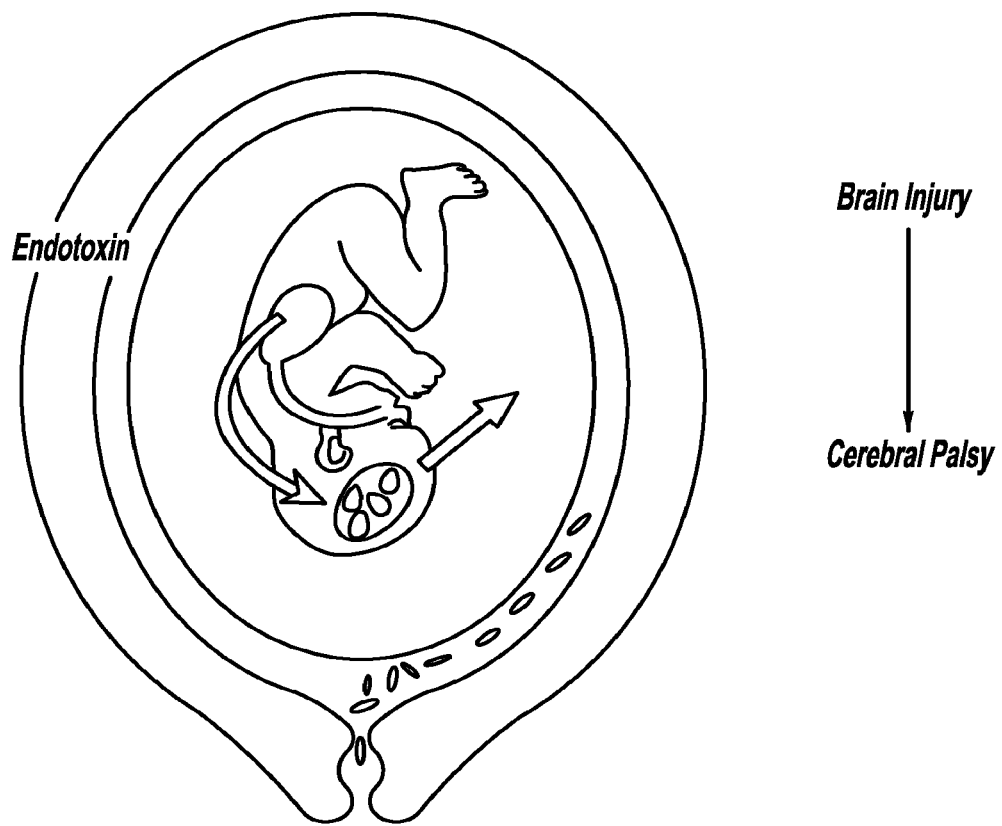
FIG. 35 depicts the Maternal Infection and FIRS.
Figure 36:
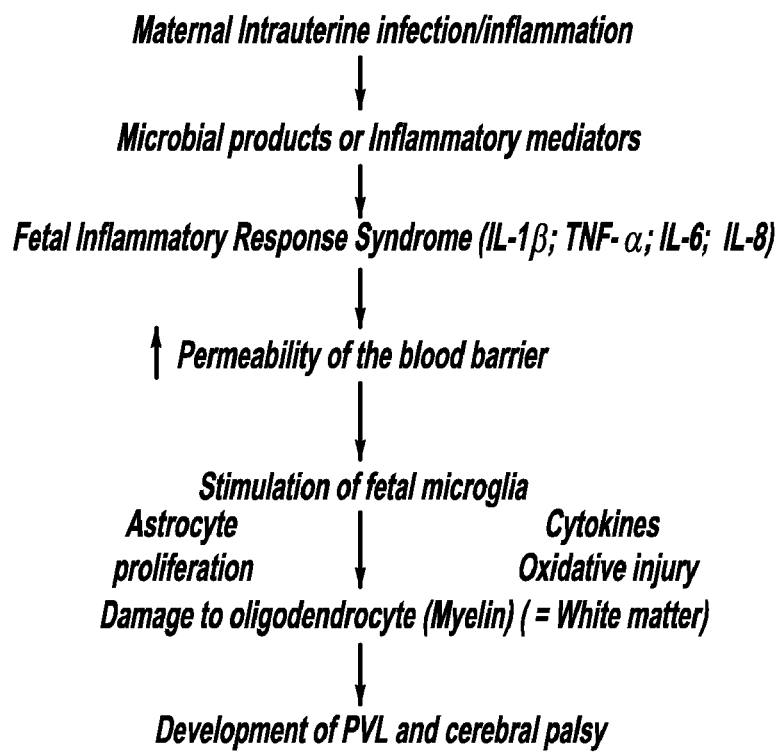
FIG. 36 depicts the mechanism of Brain Injury.
Figure 37:
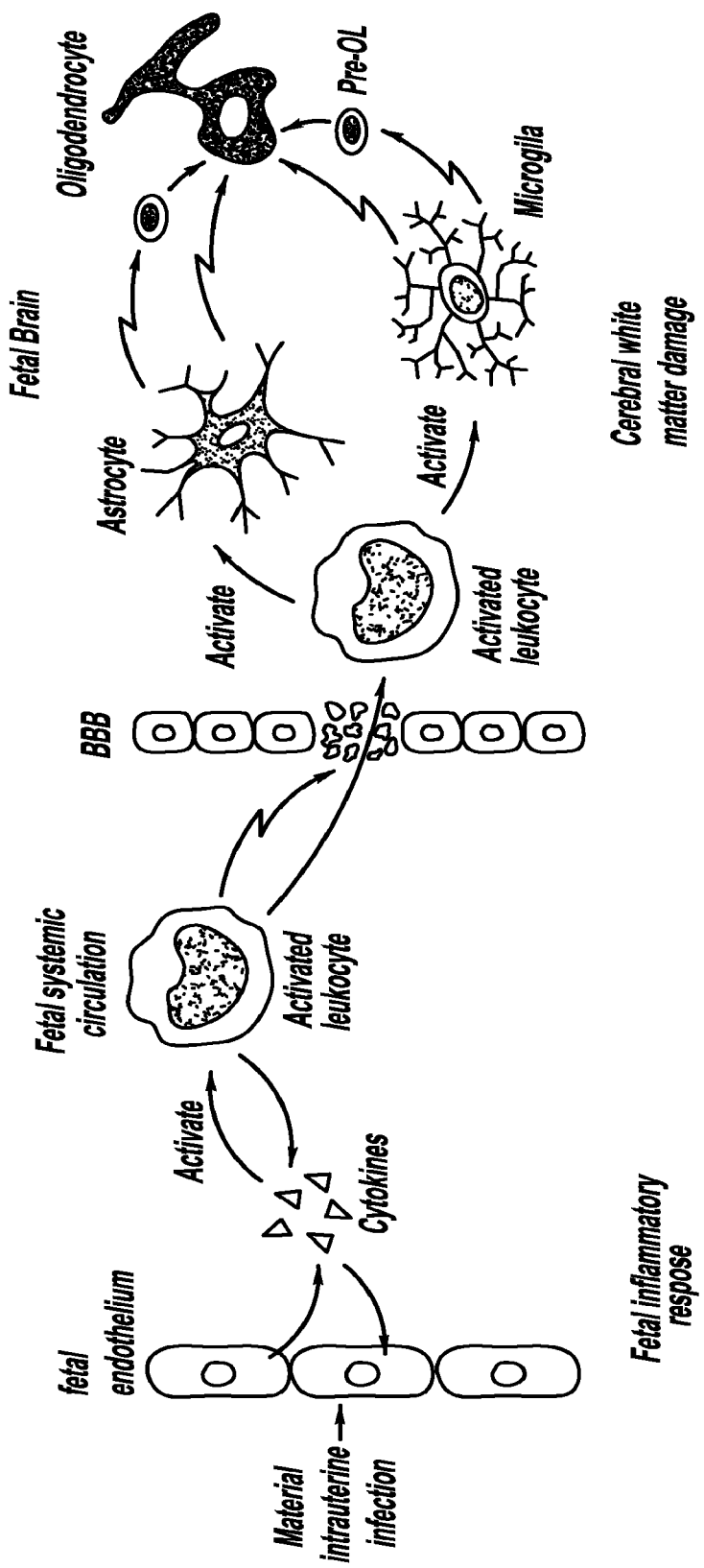
FIG. 37 depicts neonatal white matter damage and cerebral palsy.
Figure 38:
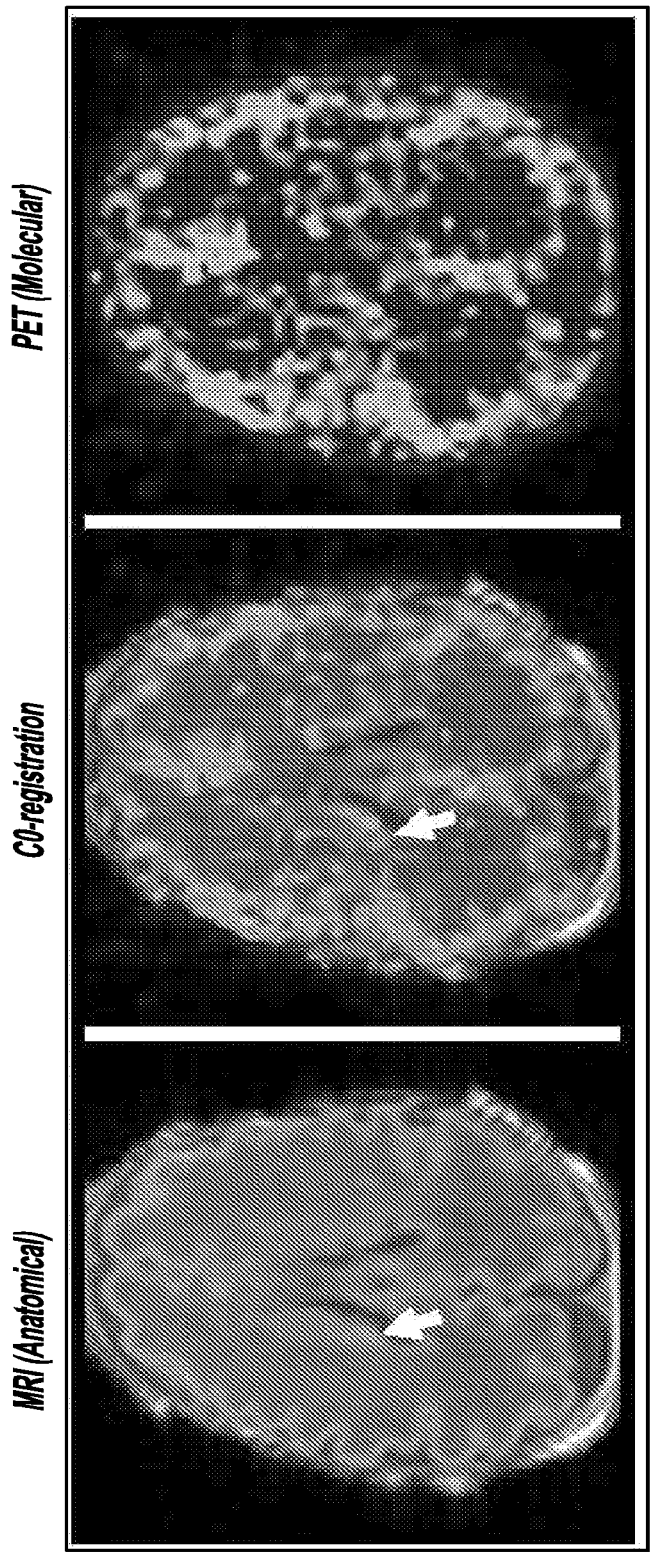
FIG. 38 shows the clinical translation-PET imaging babies. PK11195 imaging of neonate born to mother with severe chorioamnionitis with funisitis at GA 28 5/7. Patient was asymptomatic at birth. Arrow points to increased tracer uptake in the periventricular regions.
Figure 39:
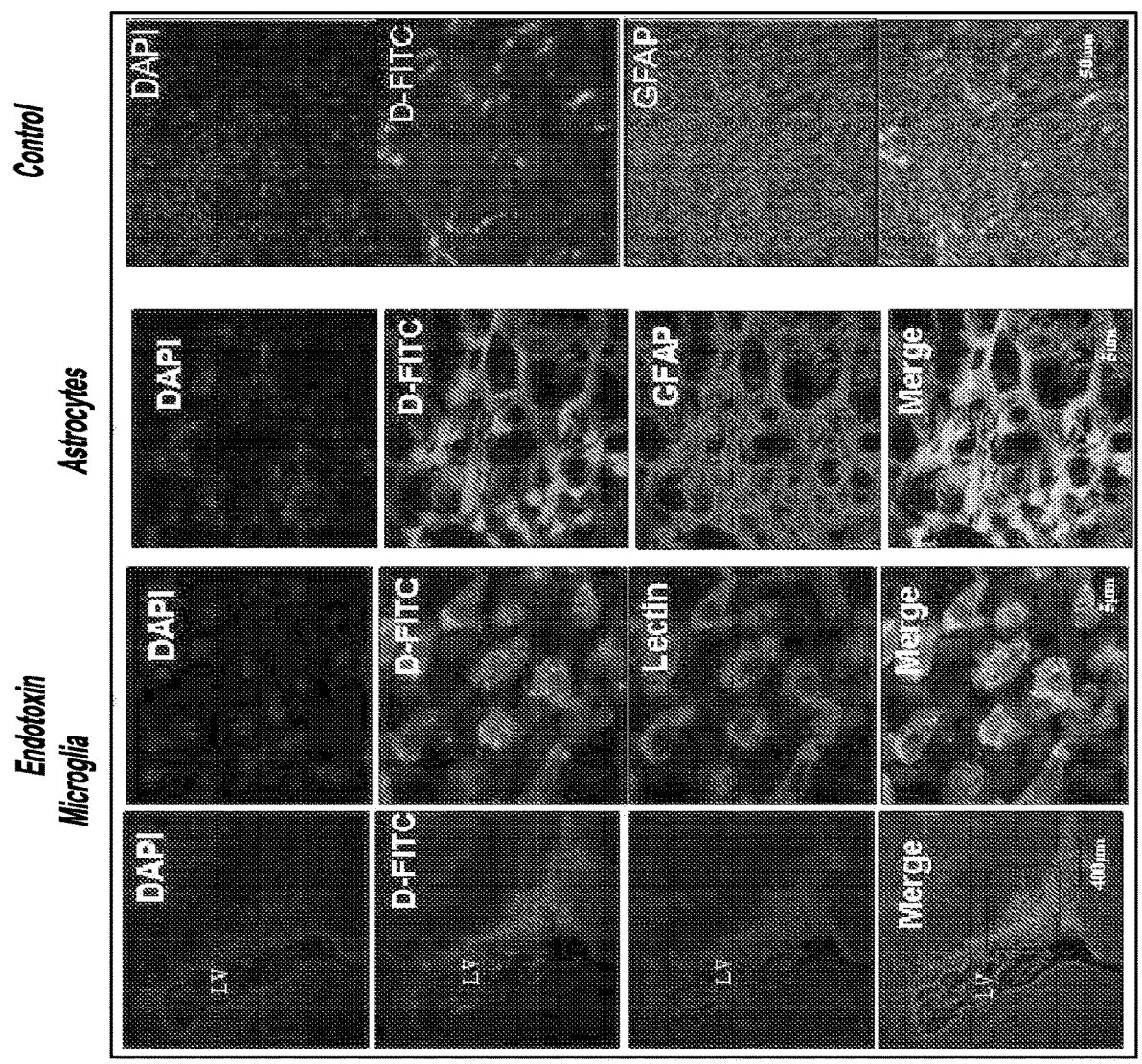
FIG. 39 shows the biodistribution of dendrimers administered via subdural injection. Dendrimers preferentially localize in activated microglia and astrocytes in the endotoxin kits but not in the controls. No localization seen in neuronal cells.
Figure 40:
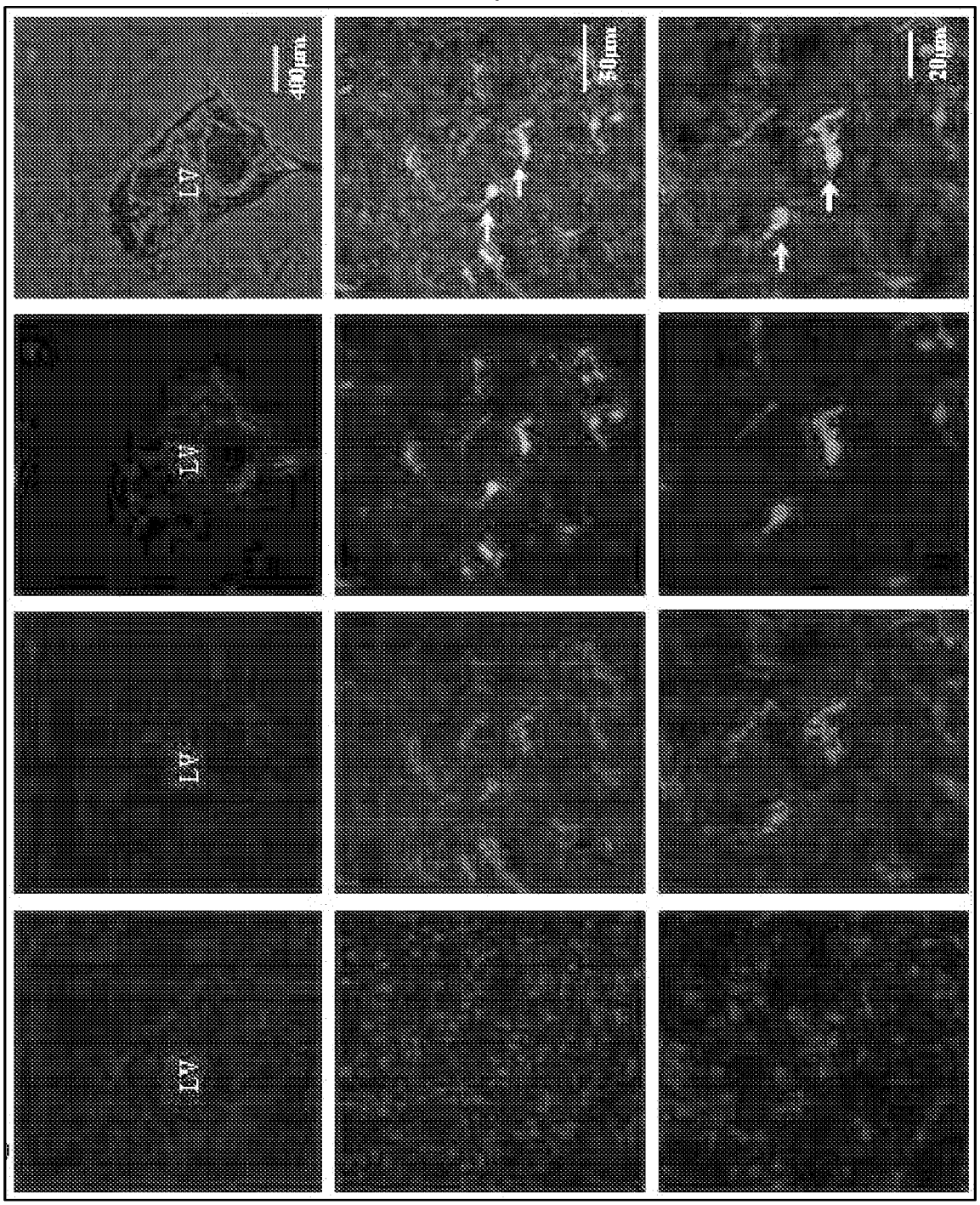
FIG. 40 depicts the control administered via subdural injection microglial (lectin) staining.
Figure 42:
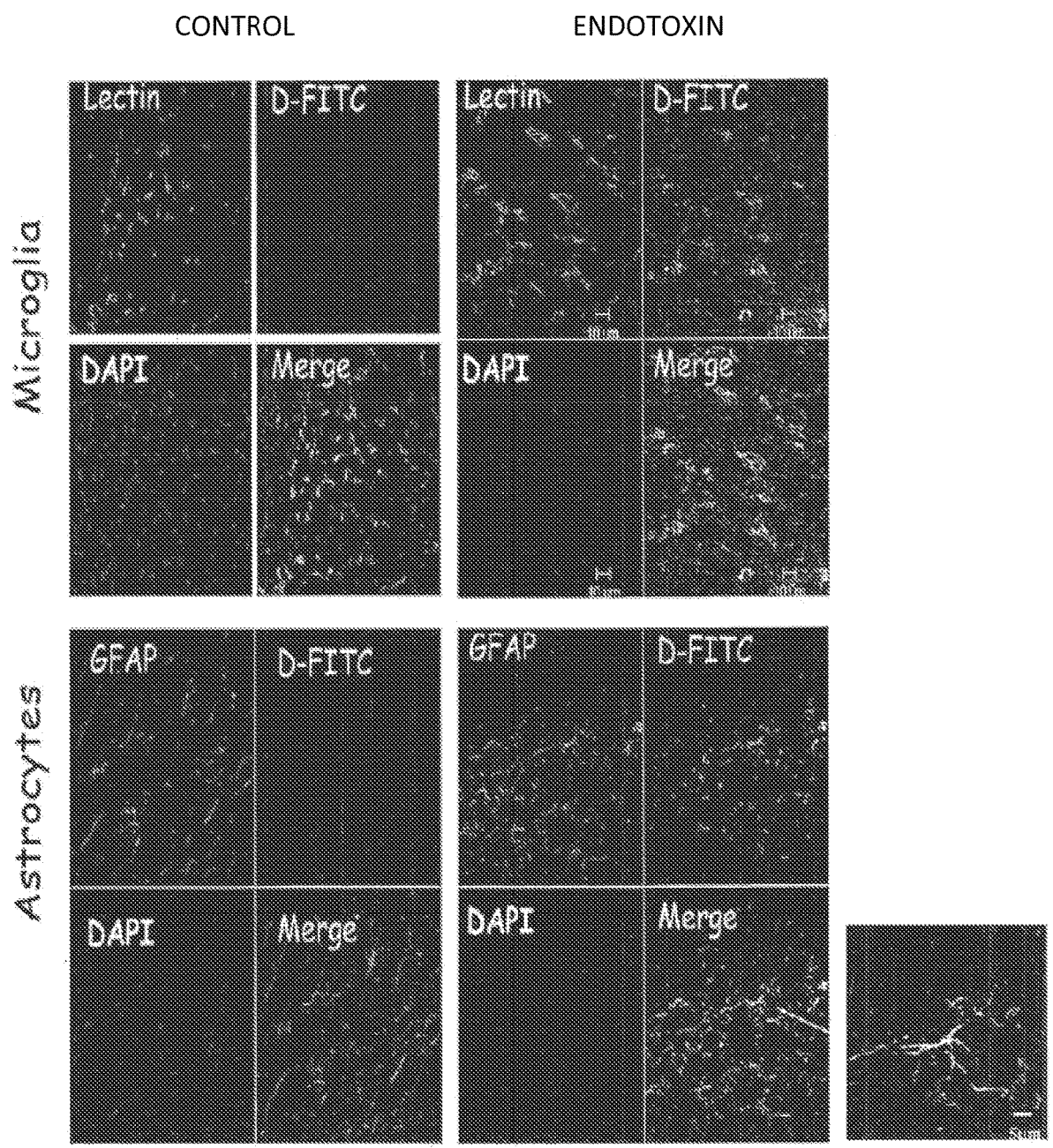
FIG. 42 shows the biodistribution of dendrimers administered via intravenous (IV). Dendrimers were seen in activated microglia and astrocytes in endotoxin kits and not in controls following IV administration.
Figure 43:
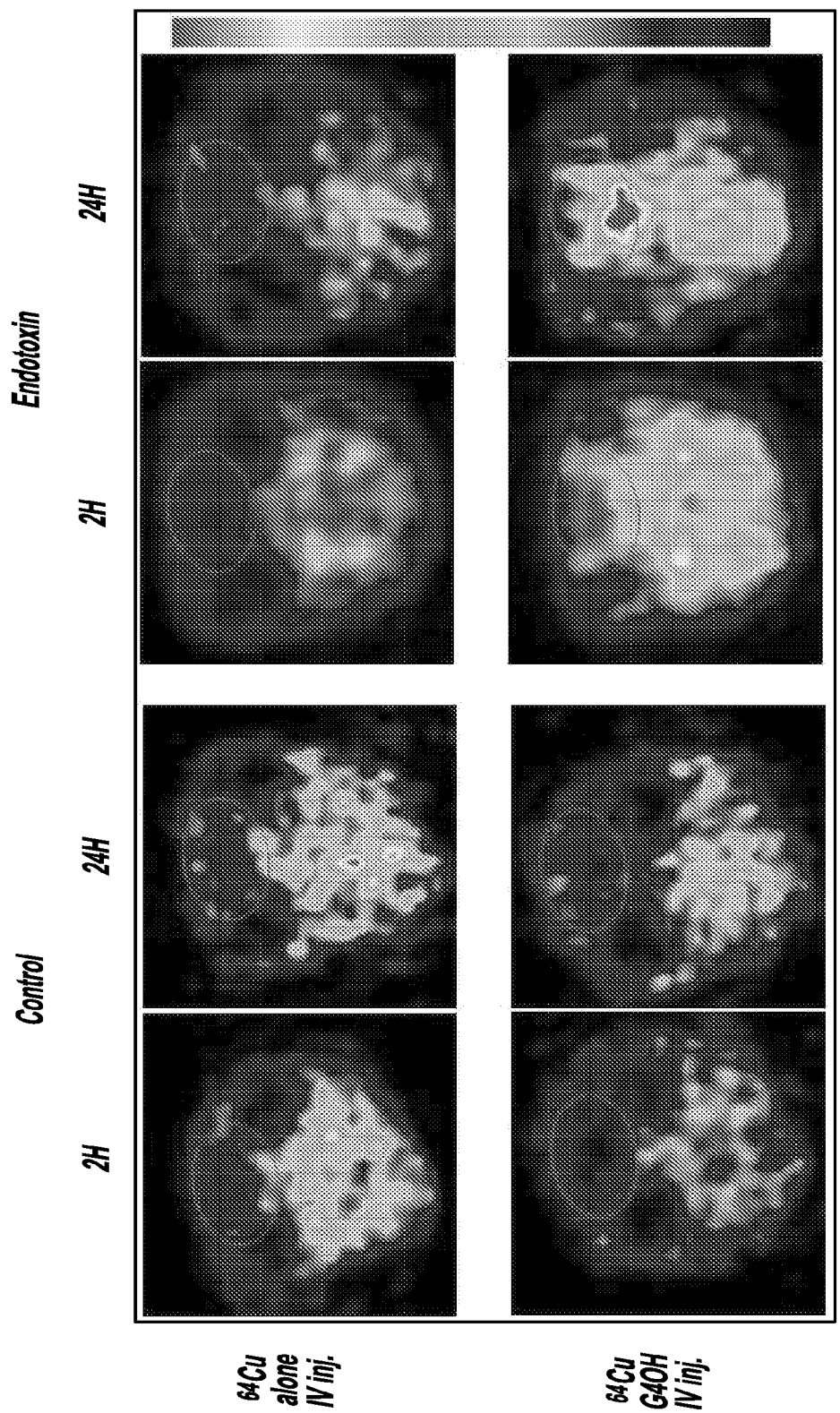
FIG. 43 shows the brain uptake of Dendrimer-$^{64}$Cu[64] in fetal neuroinflammation via PET imaging. Increased uptake of G4OH-$^{64}$Cu was noted in the newborn rabbits kits exposed to maternal inflammation.
Figure 44:
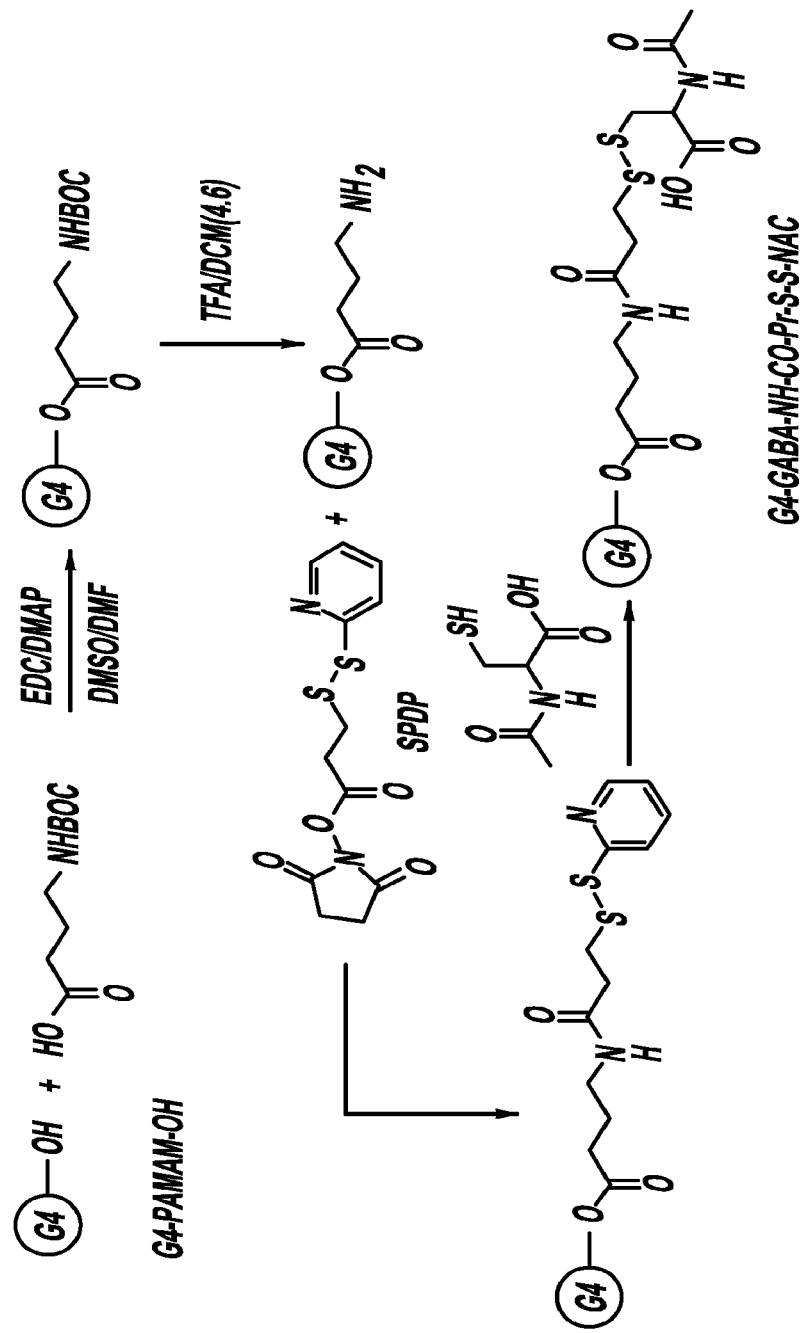
FIG. 44 shows a synthesis scheme for PAMAM-OH-NAC.
Figure 45:
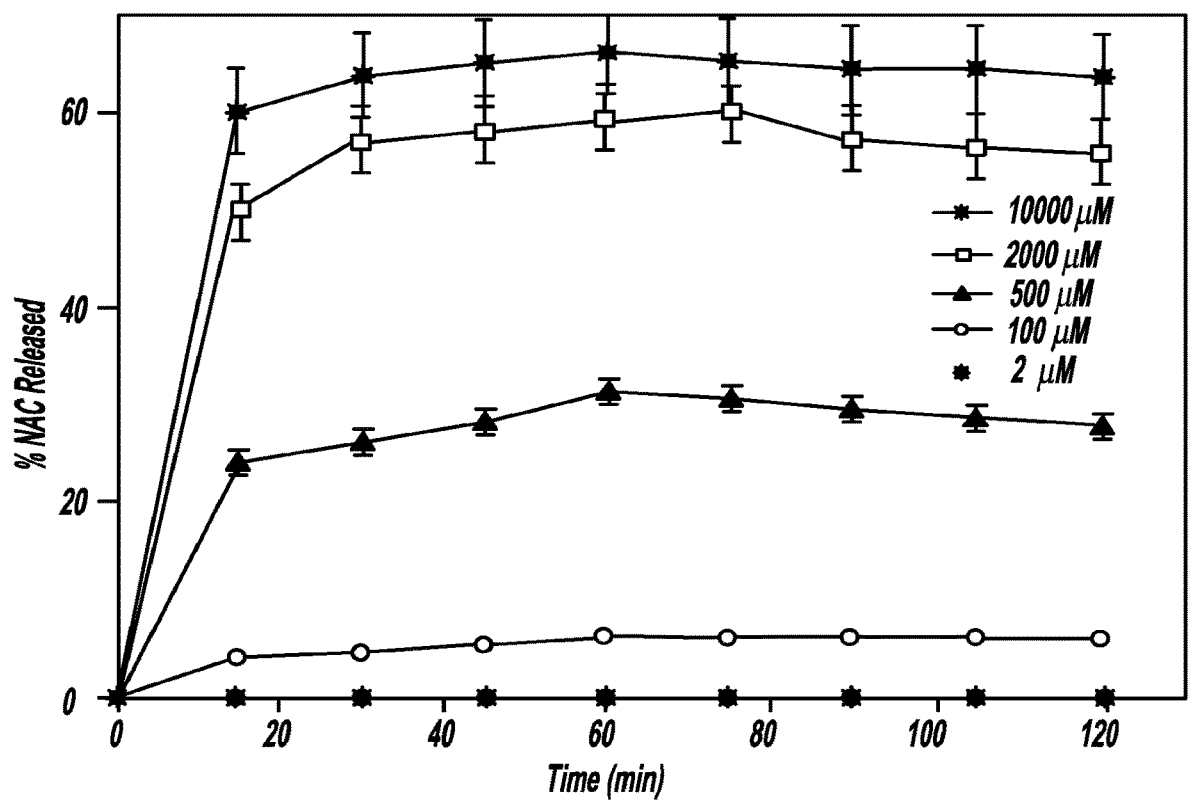
FIG. 45 shows the in vitro release in the presence of GSH (pH=7.4). G4-PAMAM-NH$_2$—CO-Ethyl-S—S-NAC conjugate was dissolved in PBS at 1 mg/ml concentration. G4-PAMAM-NH$_2$—CO-Ethyl-S—S-NAC conjugate release media contained 730 μM NAC in conjugated form. More than 60% of the drug was released in less than two hours at intracellular GSH levels.
Figure 46:
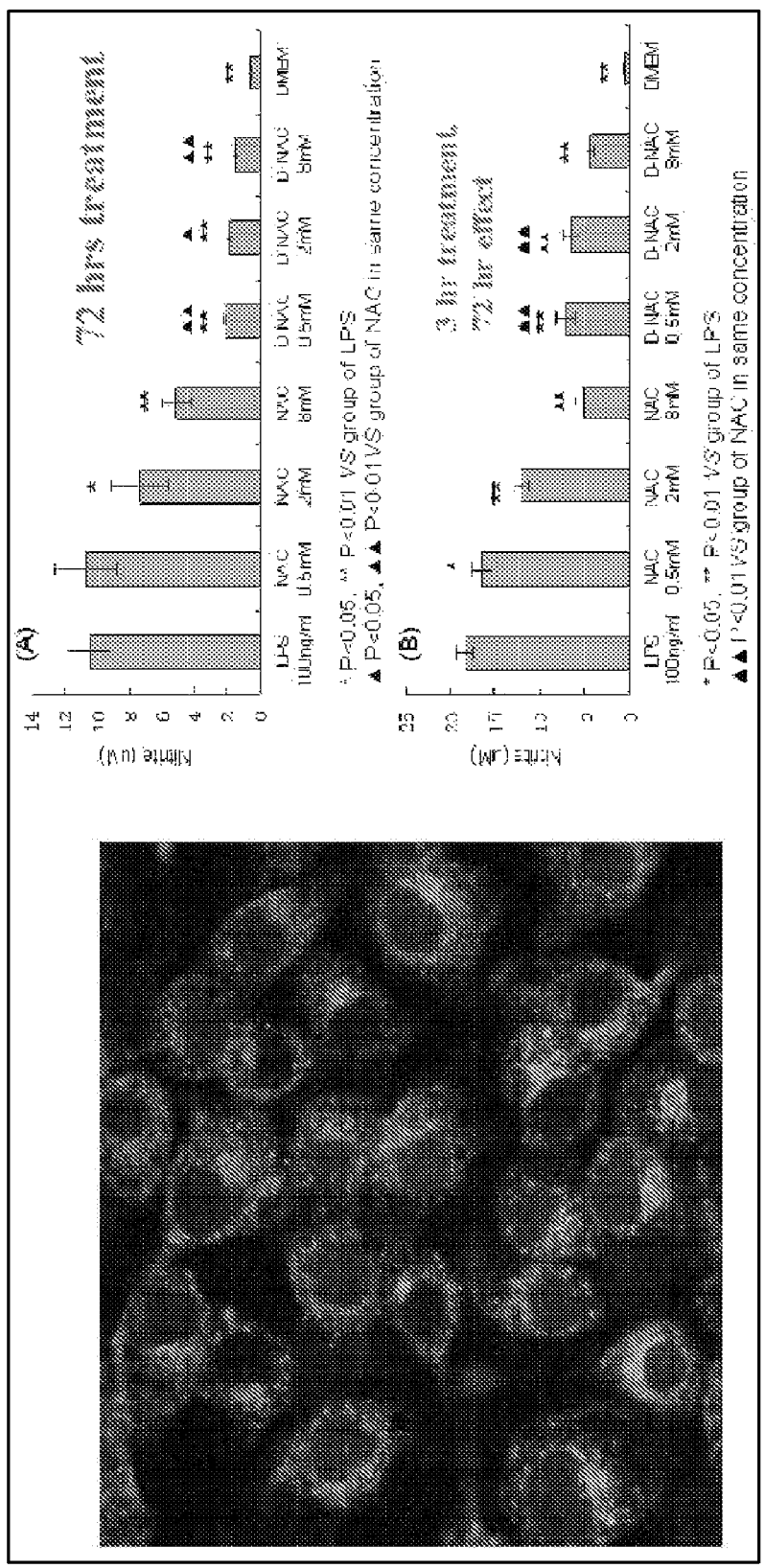
FIG. 46 shows in vitro efficacy: NO release assay. Even at the lowest doses, dendrimer nanodevices showed better efficacy than free NAC at the highest doses. Similar results for ROS, TNF-alpha, GSH depletion assays.
Figure 47:
FIG. 47 depicts a rabbit model (neurobehavioral assessment) showing phenotype change upon dendrimer treatment. All endotoxin treated animals looked the same on day 1. Control had no disease. Endo had PBS treatment. Free drug administered at 100 mg/kg NAC. Dendrimer administered at 1 mg/kg NAC and 10 mg/kg NAC.
Figure 48:
FIG. 48 depicts a rabbit model (neurobehavioral assessment). On day one, one injection was administered. Control had no disease. Endo had PBS treatment. Free drug administered at 100 mg/kg NAC. Dendrimer administered at 1 mg/kg NAC and 10 mg/kg NAC.
Figure 49:
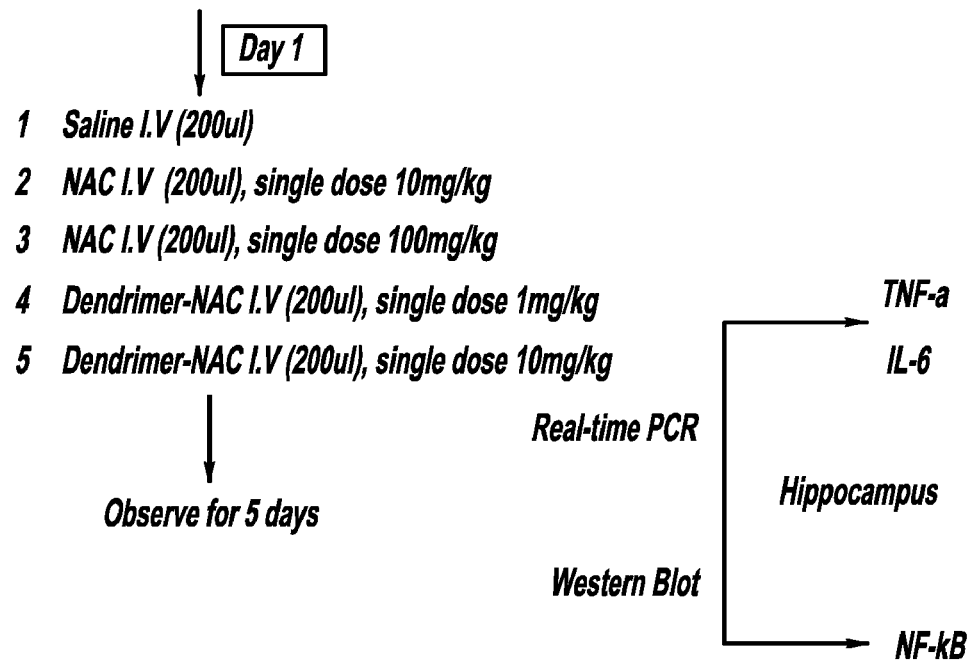
FIG. 49 shows real-time RT-PCR Assays: Fetal brain.
Figure 50:
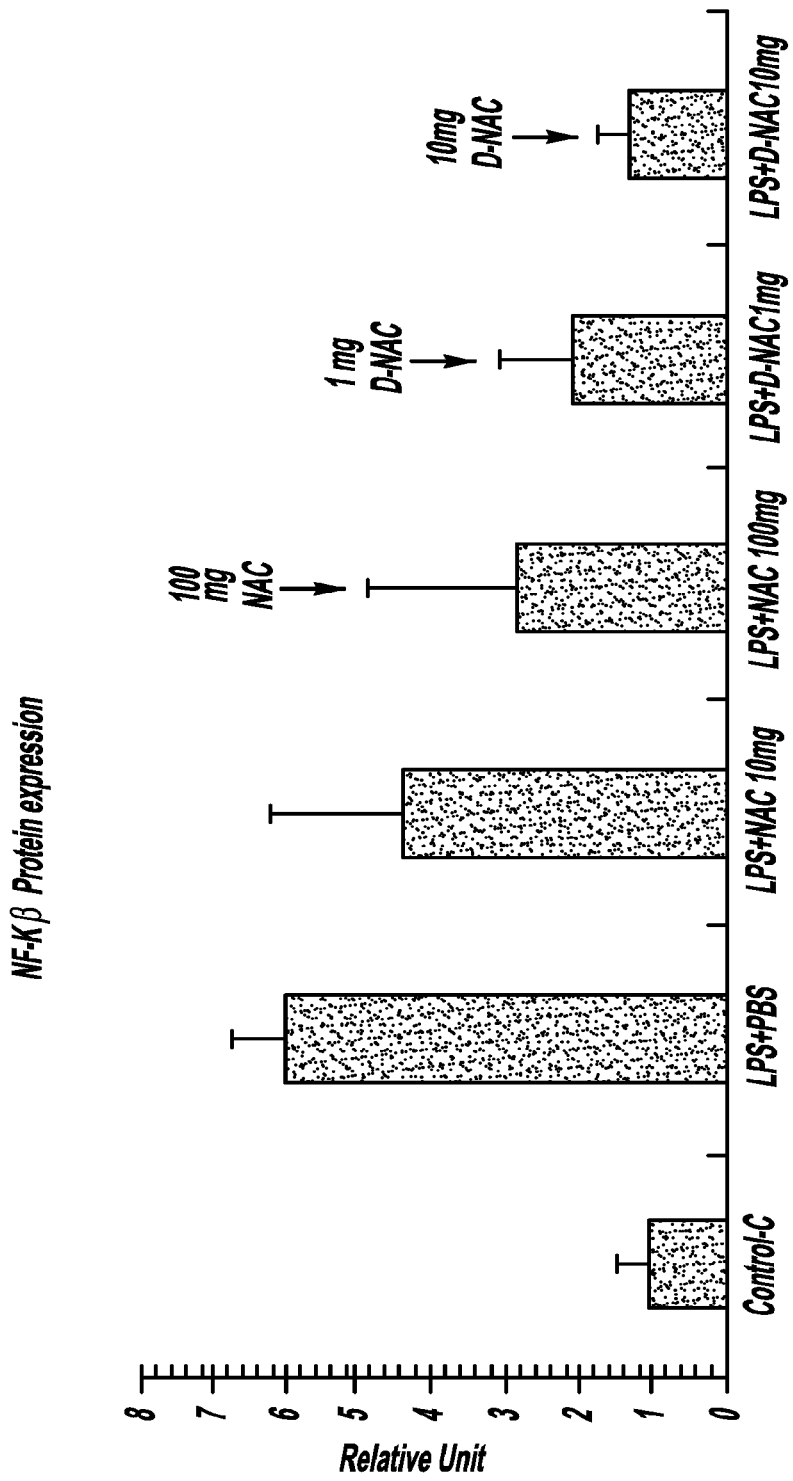
FIG. 50 shows a dendrimer-NAC conjugates in vivo. 1 mg/kg of D-NAC was as effective as 100 mg/kg of NAC alone in suppressing NF-κB. Endotoxin kits were treated with a single dose of NAC or $\frac{1}{10}^{th}$ or $\frac{1}{100}^{th}$ the dose of D-NAC on PND-1. Kits euthanized on PND 5 and NF-κB expression in hippocampus determined.

Generally, the present invention provides nanodevices formed of therapeutically active agents or compounds (hereinafter "agent") conjugated or attached to a dendrimer or multiarm PEG. The attachment can occur via an appropriate spacer that provides a disulfide bridge between the agent and the dendrimer. The nanodevices are capable of rapid release of the agent in vivo by thiol exchange reactions under the reduced conditions found in body. The dendrimers disclosed herein can include, but are not limited to, PAMAM dendrimers. The embodiments disclosed herein are not limited to this class, and other types of dendrimer such as polyester or PPI can be used. The multiarm PEG polymer comprises polyethylene glycol having 2 and more branches bearing sulfhydryl or thiopyridine terminal groups; however, embodiments disclosed herein are not limited to this class and PEG polymers bearing other terminal groups such as succinimidyl or maleimide terminations can be used. The PEG polymers in the molecular weight 10 kDa to 80 kDa can be used.

The term "nanodevices" as used herein it intended to be defined as a combination of a dendrimer with a therapeutically active agent. These nanodevices include an agent that is attached or conjugated to PAMAM dendrimers or multiarm PEG, which are capable of preferentially releasing the drug intracellularly under the reduced conditions found in vivo. In other words, the nanodevice is a dendrimer linked to an active molecule. The nanodevices, when administered by i.v. injection, can preferentially cross the blood brain barrier (BBB) only under diseased condition and not under normal conditions. The nanodevices can also be useful for targeted delivery of the therapeutics in neuro-inflammation, cerebral palsy, ALS and other CNS diseases.

The nanodevices can be administered via parenteral, topical and oral route either by itself or as a part of a formulation such as hydrogels, nanoparticle or microparticles, suspensions, gels, ointments, powders, tablets, capsules and solutions. The nanodevice composition can be administered parenterally by subdural, intravenous, intra-amniotic, intraperitonial, subcutaneous routes, topically on skin, eye and other mucosal membranes such as vaginal, orally either as solid or liquid dosage form. Further, the nanodevice can be formed for oral or topical application wherein the composition is administered in form of solution, suspension, powder, tablet or capsule for oral administration and as gel, ointment, solution or as a patch for topical administration. The nanodevice is capable of targeting and or rapidly releasing or delivering the therapeutically active agent at the site of action or absorption either intracellularly or in interstitial spaces.

The term "dendrimer" as used herein is intended to include, but is not limited to, a molecular architecture with an interior core, interior layers (or "generations") of repeating units regularly attached to this initiator core, and an exterior surface of terminal groups attached to the outermost generation. Examples of dendrimers include, but are not limited to, PAMAM, polyester, polylysine, and PPI. The PAMAM dendrimers can have carboxylic, amine and hydroxyl terminations and can be any generation of dendrimers including, but not limited to, generation 1 PAMAM dendrimers, generation 2 PAMAM dendrimers, generation 3 PAMAM dendrimers, generation 4 PAMAM dendrimers, generation 5 PAMAM dendrimers, generation 6 PAMAM dendrimers, generation 7 PAMAM dendrimers, generation 8 PAMAM dendrimers, generation 9 PAMAM dendrimers, or generation 10 PAMAM dendrimers. Dendrimers suitable for use with the present invention include, but are not limited to, polyamidoamine (PAMAM), polypropylamine (POPAM), polyethylenimine, polylysine, polyester, iptycene, aliphatic poly(ether), and/or aromatic polyether dendrimers. Each dendrimer of the dendrimer complex may be of similar or different chemical nature than the other dendrimers (e.g., the first dendrimer may include a PAMAM dendrimer, while the second dendrimer may comprises a POPAM dendrimer). In some embodiments, the first or second dendrimer may further include an additional agent. The multiarm PEG polymer includes a polyethylene glycol having at least two branches bearing sulfhydryl or thiopyridine terminal groups; however, embodiments disclosed herein are not limited to this class and PEG polymers bearing other terminal groups such as succinimidyl or maleimide terminations can be used. The PEG polymers in the molecular weight 10 kDa to 80 kDa can be used.

In another embodiment of the present invention, the dendrimer complex can include multiple dendrimers. For example, the nanodevice can include a third dendrimer; wherein the third-dendrimer is complexed with at least one other dendrimer. Further, a third agent can be complexed with the third dendrimer. In another embodiment, the first and second dendrimers are each complexed to a third dendrimer, wherein the first and second dendrimers are PAMAM dendrimers and the third dendrimer is a POPAM dendrimer. Additional dendrimers can be incorporated without departing from the spirit of the invention. When multiple dendrimers are utilized, multiple agents can also be incorporated. The present invention is not limited by the number of dendrimers complexed to one another.

The term "spacers" as used herein is intended to include compositions used for linking a therapeutically active agent to the dendrimer. The spacer can be either a single chemical entity or two or more chemical entities linked together to bridge the polymer and the therapeutic agent or imaging agent. The spacers can include any small chemical entity, peptide or polymers having sulfydryl, thiopyridine, succinimidyl, maleimide, vinylsulfone, and carbonate terminations.

The spacer can be chosen from among a class of compounds terminating in sulfhydryl, thiopyridine, succinimidyl, maleimide, vinylsulfone and carbonate group. The spacer can comprise thiopyridine terminated compounds such as dithiodipyridine, N-Succinimidyl 3-(2-pyridyldithio)-propionate (SPDP), Succinimidyl 6-(3-[2-pyridyldithio]-propionamido)hexanoate LC-SPDP or Sulfo-LC-SPDP. The spacer can also include peptides wherein the peptides are linear or cyclic essentially having sulfhydryl groups such as glutathione, homocysteine, cysteine and its derivatives, arg-gly-asp-cys (RGDC) (SEQ ID NO: 4), cyclo (Arg-Gly-Asp-d-Phe-Cys) (c(RGDFC)) (SEQ ID NO: 5), cyclo(Arg-Gly-Asp-D-Tyr-Cys) (SEQ ID NO: 6), cyclo (Arg-Ala-Asp-d-Tyr-Cys) (SEQ ID NO: 7). The spacer can be a mercapto acid derivative such as 3 mercapto propionic acid, mercapto acetic acid, 4 mercapto butyric acid, thiolan-2-one, 6 mercaptohexanoic acid, 5 mercapto valeric acid and other mercapto derivatives such as 2 mercaptoethanol and 2 mercaptoethylamine. The spacer can be thiosalicylic acid and its derivatives, (4-succinimidyloxycarbonyl-methyl-alpha-2-pyridylthio)toluene, (3-[2-pyridithio]propionyl hydrazide, The spacer can have maleimide terminations wherein the spacer comprises polymer or small chemical entity such as bis-maleimido diethylene glycol and bis-maleimido triethylene glycol, Bis-Maleimidoethane, bismaleimidohexane. The spacer can comprise vinylsulfone such as 1,6-Hexane-bis-vinylsulfone. The spacer can comprise thioglycosides such as thioglucose. The spacer can be reduced proteins such as bovine serum albumin and human serum albumin, any thiol terminated compound capable of forming disulfide bonds. The spacer can include polyethylene glycol having maleimide, succinimidyl and thiol terminations.

The term "therapeutically active agents" or "bioactive compounds" as used herein is intended to include antibiotics, antioxidants, steroids, NSAIDs, progesterone, and thalidomide. The therapeutic agent can also include a drug or modified form of drug such as prodrugs and analogs. The therapeutic agent can also be siRNAs, microRNAs, DNA, RNA, and peptide drugs. Other examples of agents include, but are not limited to, β-lactum, tetracycline and microlides antibiotics, wherein the β-lactam antibiotics comprise penicillins such as ampicillin, cephalosporins selected in turn from the group consisting of cefuroxime, cefaclor, cephalexin, cephadroxil and cepfodoxime proxetil the tetracycline antibiotics comprise doxycycline and minocycline, the microlide antibiotics comprise azithromycin, erythromycin, rapamycin and clarithromycin, fluroquinolones selected in turn from the group consisting of ciprofloxacin, enrofloxacin, ofloxacin, gatifloxacin, levofloxacin and norfloxacin, an antioxidant drug comprises N-acetylcysteine. An anti-inflammatory drug can be a nonsteroidal drug such as indomethacin, aspirin, acetaminophen, diclofenac sodium and ibuprofen; the steroidal anti-inflammatory drug can be dexamethasone. The corticosteroids can be fluocinolone acetonide and methylprednisolone. The peptide drug can be streptidokinase. The therapeutic agent can be a PAMAM dendrimer with amine or hydroxyl terminations. The targeting moiety can be folic acid, RGD peptides either linear or cyclic, TAT peptides, LHRH and BH3.

More specifically, the nanodevices linked to a bioactive compound or therapeutically active agent, examples of which are disclosed in embodiments, can be used to perform several functions including targeting, localization at a diseased site, releasing the drug, and imaging purposes. The nanodevice linked to the bioactive compounds or therapeutically active agents can be used in therapies. For example, the nanodevices of the present invention can incorporate agents and/or imaging agents with the dendrimers or multiarm PEG polymer. The nanodevices can be tagged with or without targeting moieties such that a disulfide bond between the dendrimer and the agent or imaging agent is formed via a spacer or linker molecule. The nanodevices disclosed herein can rapidly release the agent by the cleavage of the disulfide bond in-vivo. For example, G4 PAMAM-NAC, as disclosed herein, can be administered to a patient for treatment of inflammation associated with maternal fetal infections involving neuro-inflammation associated with cerebral palsy. Because of the site specific delivery, less of the agent has to be administered. This has no impact on the bioavailability of the agent, and in fact the agent is delivered via the nanodevice is ten to a hundred times more efficacious than the free drug. The enhanced bioavailability of the agent is due to the inhibition of the plasma protein binding and enhancement of the intracellular delivery. In conjunction with the decreased amount of agent being administered, there are fewer side effects without a corresponding decrease in efficacy. The disclosed nanodevices deliver agents having a higher efficacy than the drug itself. The nanodevices comprising PAMAM dendrimer or PEG linked to several drugs by disulfide linkage offers the advantage of rapid drug release, site specific delivery of drugs. Unlike drugs linked by amide or ester bonds where the hydrolysis takes place slowly, the disulfide linkages deliver the drug rapidly. As shown in the Examples, the compounds are ten to a hundred times more efficacious than the free drug.

The nanodevices of the present invention have selective permeabilities. For example, the nanaodevices do not cross the placenta and the amniotic membranes such that on injection into the amnion or intra-amniotic fluids the nanodevices exhibit no or minimal leaching into the tissues and vasculature of the pregnant woman, restricting the exposure to the baby or fetus. Alternatively, the nanodevice, including a dendrimer linked to a bioactive compound or therapeutically active agent, can be used to treat the pregnant woman, thereby restricting the exposure of the nanodevices into the fetus or the conceptus.

In light of the selective permeability, the nanodevice, a dendrimer linked to a bioactive compound or therapeutically active agent, can be used for treating maternal fetal infections such as chorioamnionitis or bacterial vaginosis or any other ascending genital infection, urinary tract infections, HIV/AIDS, herpes, Group B streptococcus and listeriosis. Specifically, the nanodevice includes a polymer, and a therapeutically active agent. Alternatively, an imaging agent and/or targeting moiety can also be incorporated. The therapeutically active agent, or imaging agent, and/or targeting moiety can be either covalently attached or intra-molecularly dispersed or encapsulated within the dendrimer. The attachment occurs via one or more spacer molecules. The spacer molecules, as disclosed above, can end in disulfide, ester or amide bonds. The nanodevice is administered either in form of injectable solution or suspension or topically in form of a patch, gel, ointment or solution.

Additionally, the nanodevice composition, including a dendrimer linked to a bioactive compound or therapeutically active agent, can also selectively cross the blood-brain barrier. Thus, the nanodevices of the present invention can be used to administer an agent to the brain of a patient. The nanodevice only crosses the blood-brain barrier in appreciable amounts when diseased conditions of the central nervous system especially in neuroinflammatory conditions such as white matter injury and cerebral palsy and does not cross the blood brain barrier in normal conditions. The nanodevices can therefore be used to selectively administer agents to brain tissues while limiting the side effects of the agents.

The nanodevice composition, including a dendrimer linked to a bioactive compound or therapeutically active agent, can also selectively target microglia and astrocytes. Thus, the nanodevices of the present invention can be used to target and treat neuroinflammation. After the nanodevices localize at the microglia and astrocytes, which play a key role in the pathogenesis of several neurodegenerative diseases, including cerebral palsy. The agent that is incorporated into the nanodevice can deliver the agent to and near the site of localization This enables the nanodevice to be used to locate and treat inflammation.

A specific nanodevice for treating maternal fetal infections can include a dendrimer or multiarm PEG polymer and a therapeutically active agent. Alternatively, an imaging agent and/or targeting moiety can also be included. The therapeutically active agent, imaging agent, and/or targeting moiety can be either covalently attached or intra-molecularly dispersed or encapsulated. The dendrimer is preferably a PAMAM dendrimer up to generation 10, having carboxylic, hydroxyl, or amine terminations. The PEG polymer is a star shaped polymer having 2 or more arms and a molecular weight of 10 kDa to 80 kDa. The PEG polymer has has sulfhydryl, thiopyridine, succinimidyl, or maleimide terminations. The dendrimer is linked to the targeting moiety, imaging agents, and/or therapeutic agents via a spacer ending in disulfide, ester or amide bonds.

The nanodevice can also be used for intrauterine administration. For such uses, the nanodevice is administered in the form of an injectable solution, hydrogel or suspension directly into the uterus, and includes a dendrimer or multiarm PEG polymer and a therapeutically active agent.

In a specific embodiment, the nanodevice is based on PAMAM dendrimers or multiarm PEG polymers linked to drugs by disulfide linkages via appropriate spacer or linker molecules. These G4 PAMAM-drug or PEG-drug conjugates can be used as funtionalized nanocarriers or nanodevices capable of rapid release of the drugs at the target site, ensuring the bioavailability of the drugs. One suitable linker between the drug and the dendrimer or multiarm PEG polymer is a disulfide linker, to facilitate the cleavage of the drug into active form in the presence of reducing agents such as glutathione, a chemical entity found in the human body.

These nanodevices based on the PAMAM dendrimers or multiarm PEG polymer linked to various drugs, targeting moieties, imaging agent by disulfide linkages offer several advantages: (1) the composition in itself acts as a device capable of targeting, localizing and releasing the drug; (2) the drugs are only released in the redox environment usually found in infected tissues or cells such as tumor, inflammation associated with several infections; (3) the composition can preferentially deliver the drug only to the mother in pregnant woman sparing the baby and conceptus and vice versa, for example to treat the fetus or conceptus without affecting the pregnant woman; and (4) the nanodevices can be formulated in new dosage forms including tablets, injections, gels powders capsules, films, etc. Since, PEGs are approved for human use there is an additional benefit to using the nanodevices of the present invention.

Thus, the nanodevices of the present invention can be used to treat diseases related to chronic inflammation. Examples of such diseases include, but are not limited to, heart attack, Alzheimer's disease, congestive heart failure, stroke, arthritis, aortic valve stenosis, kidney failure, lupus, asthma, psoriasis, pancreatitis, allergies, fibrosis, surgical complications, anemia, fibromyalgia, and other inflammatory diseases including, but not limited to, neuroinflammation. The nanodevices can also be used as antibacterial and/or antimicrobial devices.

By way of example, NAC is a drug very extensively investigated and studied. It is also investigated for neuroinflammation associated in maternal fetal infections. However, NAC suffers from low bioavailability due to high plasma protein binding. The nanodevice compositions disclosed herein are designed to overcome the plasma protein binding without affecting the activity of NAC.

In fact, G4 PAMAM-NAC can be ten to a hundred times more efficacious in vivo than the free drug NAC by single i.v. administration. The free drug NAC exhibits very high plasma protein binding resulting in reduced bioavailability. One of the major advantages of this nanodevice is that it enhances the bioavailability by restricting the unwanted drug plasma protein interactions and selectively results in rapid release of the drug intracellularly to exhibit the desired therapeutic action. The enhanced efficacy of the nanodevices without any significant toxicity in vitro and in vivo is exemplified in the embodiments disclosed herein.

The high payload of the drug NAC in the G4 PAMAM-NAC requires very small quantities (over 10 mg) of the carrier, PAMAM dendrimer, thereby reducing the amounts administered daily. A decreased quantity of agent limits the side effects associated with the agent. Since the bioavailability of the agent remains high, the positive effects of the agent are not lowered despite the administration of smaller quantities of agent.

The nanodevices including the dendrimer-drug conjugates, restricts its biodistribution to tissues and organ and preferentially deliver the drug at the target site thereby reducing the undesired side effects.

Dendrimer nanodevices effectively transport across the BBB, and offer a new method for targeted drug delivery in brain injuries. The results disclosed herein demonstrate that G4-PAMAM-S—S-NAC conjugates can be used to specifically target activated microglial cells and astrocytes in neuroinflammatory disorders. The therapeutic efficacy of G4-PAMAM-S—S-NAC dendrimer conjugate was evaluated after two days of animal treatment with lipopolysaccharide (LPS) to induce white matter injury and hypomyelination in the developing rabbit brain (an animal model of Cerebral Palsy).

NAC selectively delivered from the G4-PAMAM-S—S-NAC nanodevices strongly suppressed pro-inflammatory cytokines (TNF-α, IL-6 mRNA), inflammatory signaling factors, including NFκB and nitrotyrosine, and enhanced GSH level. The G4-PAMAM-S—S-NAC was found to be ten to a hundred times more efficacious compared with free NAC. This supports a conclusion that the G4-PAMAM-S—S-NAC traversed across the BBB. The targeted delivery of NAC from dendrimer nanodevice to actived microglial cells improved the motor deficits and attenuated recovery from the LPS-induced brain injury in a neonatal rabbit model of cerebral palsy.

A significant reduction in proinflammatory cytokines (TNF-α, IL-6 mRNA) was observed on administration of G4-PAMAM-S—S-NAC nanodevices. The kits treated with NAC and G4-PAMAM-S—S-NAC showed a decrease in fetal inflammation response with improvement of motor deficits when compared to the kits that were treated with saline. The kits that were treated with G4-PAMAM-S—S-NAC conjugates had less behavioral changes and lower microglial activation in the brain when compared to the kits that received NAC alone due to the sustained delivery of NAC from G4-PAMAM-S—S-NAC conjugate. The results indicate that G4-PAMAM-S—S-NAC conjugates have a greater effect than NAC alone since it is preferentially taken up by activated macrophages and microglial cells, reducing the inflammatory and oxidative and nitrosative effects.

Treatment with G4-PAMAM-S—S-NAC nanodevices reduced white matter injury and microglia activation. A significant reduction in dose of NAC was observed when administered as G4-PAMAM-S—S-NAC to elicit the similar response as that observed for free NAC. Both free NAC at concentration 100 mg/kg and G4-PAMAM-S—S-NAC at concentration 10 mg/kg, 10 mg elicit identical responses, demonstrating that on conjugating to dendrimer a reduction in dose is achieved. G4-PAMAM-S—S-NAC at lower concentrations than free NAC shows significant protective effects against LPS-induced brain injuries, suppression of TNF-α and down-regulation of IL-6 activity. This activity of the dendrimer-NAC conjugates may be attributed to its ability to interfere with the early inflammatory responses by blocking or modifying the signal transduction factor NF-κB and nitrotyrosine, thereby modulating cellular activation.

The down-regulation of TNF-α and IL-6 in hippocampus, is likely to be attributed to the preferential biodistribution of dendrimer nonodevices with specific cell uptake by microglia cell in the brain. The dendrimer-NAC nanodevices can be used for treatment of pregnant women developing clinical symptoms associated with maternal infection, with increased risk of developing PVL and CP in infants. The results show that inhibition of microglial cells, astrocytes with Dendrimer-NAC decreased the white matter injury in the newborn rabbit brain. Further, the dendrimers exhibit sustained release of conjugated drugs, and enhance the effectiveness of drugs over a prolonged period. At lower dose, Dendrimer-NAC conjugates were more effective than NAC alone. The dendrimer-NAC conjugates seem to offer more advantages including significant dose reduction, enhanced bioavailability, and reduction in dosing.

As another example, 6 and 8 arm PEG-NAC conjugates released 74% of NAC in the intracellular GSH concentration (2 and 10 mM), within 2 hours. At a concentration range of between 0.008-0.8 mM, the conjugates were nontoxic to the microglial cells. At an equimolar concentration of NAC (0.5 mM) the 6-arm-PEG-S—S-NAC and 8-arm-PEG-S—S-NAC were more efficient in inhibition of GSH depletion than the free NAC. Both 6 and 8-arm-PEG-S—S-NAC conjugates, each at 0.5 mM and 5 Mm concentration showed significant inhibition in ROS production when compared to free NAC at equimolar concentrations. The studies demonstrate that the conjugates are superior in inhibition of the NO production as compared to the free NAC. At the highest concentration (5 mM), the free drug reduced the $H_2O_2$ levels and nitrite levels by 30-40%, whereas the conjugates reduced the $H_2O_2$ and nitrite levels by more than 70%. This shows that the conjugates are able to traffic the drug inside the cells, and release the drug in the free form and are significantly more efficacious than the free drug. At 5 mM concentration 6-arm-PEG-S—S-NAC conjugate (1) showed significant inhibition (70%) of TNF-α production when compared to equivalent concentration of NAC (Pb0.05). 8-arm-PEG-S—S-NAC conjugate (3) showed significant inhibition of TNF-α production (70%) at 5 mM when compared to equivalent concentration of NAC (Pb0.05 and Pb0.01). PEGylated NAC is a nanodevice with utility for the pharmaceutical industry, as PEGs are approved for human use and this device addresses limitations of NAC and provides greater efficacy.

The Examples below are included to demonstrate preferred embodiments of the invention. It should be appreciated by those of skill in the art that the techniques disclosed in the Examples represent techniques and compositions discovered by the inventors to function well in the practice of embodiments disclosed herein, and thus can be considered to constitute preferred modes for its practice. However, those of skill in the art should, in light of the present disclosure, appreciate that many changes can be made in the specific embodiments which are disclosed and stil obtain a like or similar result without departing from the spirit and scope of embodiments disclosed herein.

EXAMPLES

Example 1

PAMAM-NH—CO-Ethyl-S—S-NAC Conjugate

For the preparation of PAMAM-PDP generation 4, SPDP (0.5 equivalent) in ethanol (10 mL) was added to a solution of PBS buffer pH 7.4 (20 mL) and PAMAM-NH$_2$ dendrimer (1 equivalent) to provide sufficient modification whilst preventing loss of product due to the precipitation of highly modified dendrimer. The reaction was stirred at room temperature for 2 hours. To this reaction N-Acetyl cysteine was added (1 equivalent) at once, and the reaction was stirred at room temperature for 4 hours. The reaction was monitored with HPLC. After completion of reaction, the reaction mixture was diluted with water and lyophilized to get crude product. The solid crude product was diluted with water and dialyzed against DMSO followed by PBS (pH=7.4) to remove by-products and the excess of reactants, and then replaced with deionized water (1 in 41 times) for 12 h to remove salts. The water was lyophilized to get pure product in good yield (71%).

Example 2

PAMAM-CO-GS-S-NAC Conjugate
Step 1. S-(2-thiopyridyl) glutathione
S-(2-thiopyridyl) glutathione was prepared from the reaction of 2, 2$^1$-dithiodipyridine (2 equivalent) and GSH (1 equivalent) in a mixture of methanol and water (1:1) stirred for 15 hours at room temperature. Upon completion of the reaction (monitored by TLC), most of methanol was removed in vacuo and the residue was dissolved in water washed with dichloromethane. The aqueous solution was subjected to reverse phase (RP) HPLC purification, and lyophilization of the eluent gave the pure product as a white solid in 80% yield. Calculated mass: 416. ESI m/z 417 (M+H). $^1$H-NMR (300 MHz, d$_6$-DMSO) δ/ppm 1.98-2.11 (2H, m), 2.22-3.02 (2H, m), 2.98-3.08 (1H, m), 3.18-3.22 (1H, m), 3.65-3.71 (2H, m), 3.95-402 (1H, m), 4.57-4.62 (1H, m), 7.0-7.07 (1H, m), 7.72-7.87 (2H, m), 8.24 (2H, br.s., NH), 8.42-8.48 (3H, m, NH$_2$, aromatic).
Step 2. N-Acetyl-glutathione
S-(2-thiopyridyl) glutathione (1 equivalent) was dissolved in PBS buffer pH=7.4 (5 mL) and added NAC (1 equivalent) at once, and the reaction mixture was stirred at room temperature for 2 hours. After completion of the reaction, dichloromethane was added and the organic layer was separated to remove the corresponding thione by-product, this process was repeated five times. The aqueous solution was subjected to reverse phase (RP) HPLC purification, and lyophilization of the eluent gave the pure product as a white solid in 79% yield. Calculated mass: 468. ESI m/z 467 (M−H). $^1$H NMR (300 MHz, d$_6$-DMSO) δ/ppm, 1.81 (3H, s), 1.90-2.0 (2H, m), 2.28-2.37 (2H, m), 2.79-2.86 (3H, m), 3.07-3.17 (2H, m), 3.69-3.78 (2H, m), 4.40-4.46 (1H, m), 4.52-4.58 (1H, m). $^{13}$C-NMR (75, MHz d$_6$-DMSO) δ/ppm, 22.35, 26.09, 30.86, 51.26, 51.32, 51.64, 52.02, 169.36, 169.44, 170.89, 171.27, 172.02, 172.07.
Step 3. PAMAM-CO-GS-S-NAC Conjugate
The anionic PAMAM-COOH generation-3.5 dendrimer (1 equivalent) was dissolved in DMSO/DMF (3:2, 20 mL) and DIEA (1 equivalent) and PyBop (1 equivalent) were added and the reaction stirred for 1 hour. To this a solution of N-Acetyl-glutathione (1.5 equivalent) was added in DMSO (10 mL) was stirred for 12 hours at room temperature. The reaction was monitored with HPLC. After completion of reaction, it was diluted with water and lyophilized to get crude product. The solid crude product was diluted with water and dialyzed against DMSO followed by PBS (pH=7.4) to remove by-products and the excess of reactants and then replaced with deionized water for 12 hours to remove salts. The water was lyophilized get pure product in 78% yield. Raghu/Bing Efficacy data for COOH dendrimer were determined.

Example 3

PAMAM-O-GABA-NH—CO-Ethyl-S—S-NAC
Step 1. Synthesis of PAMAM-O-GABA-BOC
A solution of BOC-GABA-OH (1.5 equivalent)) in DMSO/DMF (3:1) was cooled to 0° C. and then treated with a solution of EDC (1.5 equivalent), DMAP (0.01 eq) and G4-OH, PAMAM dendrimer (1 equivalent) in DMSO/DMF (3:1). This was left to stir at room temperature for 24 hours. The reaction mixture was purified on dialysis with DMSO (3 times) to remove by-products and the excess of reactants and after dialysis the solvent was removed under lyophilization to get pure compound.
Step 2. Synthesis of PAMAM-O-GABA-NH$_2$
To a stirred solution of PAMAM-O-GABA-BOC (1 equivalent) was treated with trifloroacetic acid and dichloromethane (1:1, 10 mL). The reaction was stirred at room temperature for 10 min. After completion of the reaction trifloroacetic acid/dichloromethane was removed under rotavapor. Reaction mixture was neutralized with PBS (pH=7.4) on dialysis with water (3 times) and solvent was removed under lyophilization to get pure compound.
Step 3. PAMAM-O-GABA-NH—CO-Ethyl-S—S-NAC
For the preparation of PAMAM-O-GABA-PDP generation 4, SPDP (1 equivalent) in ethanol (10 mL) was added to a solution of PBS buffer pH 7.4 (20 mL) and PAMAM-O-GABA-NH$_2$ dendrimer (1 equivalent) to provide sufficient modification whilst preventing loss of product due to the precipitation of highly modified dendrimer. Reaction was stirred at room temperature for 2 hours. To this reaction N-Acetyl cysteine was added (1 eq) at once, and stirred the reaction at room for 4 hours. The reaction was monitored with HPLC. After completion of reaction, the reaction mixture was diluted with water and lyophilized to get crude product. The solid crude product was diluted with water and dialyzed against PBS (pH=7.4) to remove by-products and the excess of reactants and then replaced with deionized water (3 times) dialyzed for 12 hours to remove salts. The water was lyophilized to get pure product in good yield.

Example 4

In Vivo Evaluation of the Efficacy of G4-PAMAM-S—S-NAC Nanodevices in Rabbit Model of Cerebral Palsy
New Zealand White rabbits (CoVance Research Products Inc., Kalamazoo, Mich.) with timed pregnancies confirmed with breeders (having a history of delivering 7-11 kits per litter) underwent laparotomy under general anesthesia (2-3% isoflurane by mask) on gestational day 28 (E28, term pregnancy is 31-32 days). 1 mL of saline for the control group (n=6) or 1 mL of saline containing 20 µg/kg of LPS (*Escherichia coli* serotype O127: B8 from Sigma-Aldrich, St Louis, Mo.) for the endotoxin group (n=6), was equally divided and injected into the uterine wall using a 27 gauge needle between the fetuses taking care not to enter the amniotic sac. This ensured that all the kits were exposed to the same amount of endotoxin. 0.5% NaHCO$_3$ was infused at end of surgery and additional dose NaHCO$_3$ was given at 2 hour after surgery according blood gas.
Normothermia was maintained using a water circulating blanket, and heart rate, oxygen saturations, and arterial blood pressure measured through a 20 G arterial catheter placed in the marginal ear artery, were monitored continuously during the procedure. Maternal serum was collected before laparotomy (0 hours) and at 6, 24 hours following endotoxin injection. The dams were monitored daily for changes in activity, feeding and fever. A surveillance camera was placed in the rabbit room and the dams monitored remotely to determine the time of delivery. The kits were all born spontaneously at 31 or 32 days gestational age and the litter size ranged from 7-12 kits. The number of live and dead kits, and weight of all live kits was recorded.

The following animal groups were enrolled and used for this example:
Group 1: Pups exposed to 20 μg/kg E.coli LPS in utero treated with saline I.V. (200 ul), Observe for 5 days (N=5-7)
Group 2: Pups exposed to 20 μg/kg E.coli LPS in utero treated with NAC I.V. (200 ul), single dose 10 mg/kg. Observe for 5 days (N=5-7)
Group 3: Pups exposed to 20 μg/kg E.coli LPS in utero treated with NAC I.V. (200 ul), single dose 100 mg/kg. Observe for 5 days (N=5-7)
Group 4: Pups exposed to 20 μg/kg E.coli LPS in utero treated with G4-PAMAM-S—S-NAC I.V (200 ul), single dose 1 mg/kg (based on preliminary data). Observe for 5 days (N=5-7)
The dose of the saline, NAC, and G4-PAMAM-S—S-NAC used for this example are as follows:
  a) Saline I.V (200 ul)
  b) NAC I.V (200 ul), single dose 10 mg/kg.
  c) NAC I.V (200 ul), single dose 100 mg/kg
  d) Dendrimer-NAC I.V (200 ul), single dose 1 mg/kg
  e) Dendrimer-NAC I.V (200 ul), single dose 10 mg/kg
  f) Dendrimer-linker I.V (200 ul), single dose 10 mg/kg
Behavioral testing of kits administered with G4-PAMAM-S—S-NAC All live postnatal day 1 (PND1) control and endotoxin kits from four consecutive litters in each group were tested to reduce the risk of selection bias. The rabbit kits were assessed and scored for behavioral testing, as described by Derrick et al. Briefly, the kits were videotaped and scored on a scale of 0 (worst) to 3 (best) by two blinded observers for (1) posture (ability to maintain prone posture), (2) righting reflex (ability to right itself from supine to prone position for 10 attempts), (3) activity and locomotion on a flat surface (assessed by grading the quality, intensity, and duration of spontaneous movement of the head and front and back legs), (4) ability to move in a straight line and in circles, (5) coordination of suck and swallow assessed by feeding the rabbit kits artificially with formula from a syringe with a dropper, and (6) ability to move head during feeding (scored from 0-3 in which 0 is no movement of head and 3 is forceful movement of head and body). The tone on passive flexion and extension was assessed using the scoring based on the Ashworth scale, as described by Derrick et al, in which 0 indicated no increase in tone and 4 indicated the limb was rigid in flexion or extension.

Example 5

6 Arm-PEG-S—S-NAC Conjugate
Step 1. S-(2-thiopyridyl) N-Acetyl Cysteine

S-(2-thiopyridyl) N-Acetyl Cysteine was prepared from the reaction of 2, 2$^1$-dithiodipyridine (5.398 g, 0.0245 mol) and NAC (2 g, 0.0122 mol) in a mixture of methanol and water (1:1) stirred for 15 hours at room temperature. Upon completion of the reaction (monitored by TLC), most of methanol was removed in vacuo and the residue was dissolved in water extracted into dichloromethane concentrated on rotavapor under reduced pressure to get crude product. Crude product was purified on silicagel column chromatography with dichloromethane/methanol (8:2) gave the pure product as a light yellow solid (2.66 g, 0.098 mole, in 80%). Calculated mass: ESI m/z (M+H) 273, $^1$H-NMR (400 MHz, CD$_3$OD) δ, 1.99 (s, 3H), 3.10-3.20 (m, 1H), 2.30-2.38 (m, 1H), 4.65-4.70 (m, 1H) 7.20-7.27 (m, 1H, Ar), 7.80-7.85 (m, 2H Ar), 8.40-8.45 (m, 1H). $^{13}$C-NMR (100 MHz, CD$_3$OD), 21.22, 39.91, 52.05, 120.26, 121.37, 122.08, 137.98, 149.00, 159.56, 172.14.

Step 2. Preparation of 6 Arm-PEG-S—S-NAC Conjugate

For the preparation of 6Arm-PEG-S—S-NAC, NAC-TP (0.245 g, 0.897 mmole) in ethanol (10 mL) was added to a solution of 6-Arm-PEG-SH (1 g, 0.1 mmole) in a PBS buffered pH 7.4 (20 mL) and reaction was stirred at room temperature for 4 hours. The reaction was monitored with HPLC. After completion of reaction, the reaction mixture was purified using a sephadex LH-20 column (Amersham Pharmacia Biotech, 3.8×45 cm) with water as mobile phase. Water was removed under lyophilization to get pure compound in good yields (0.102 g, 0.0094 mmole, 95%). $^1$H-NMR (400 MHz, CD$_3$OD) δ, 2.00 (s, 3H), 2.95-3.10 (m, 1H), 3.30-2.38 (m, 1H), 3.58-3.80 (br, m, 4H, —OCH$_2$—CH$_2$O—) 4.40-4.50 (m, 1H), 6.95 (br, s 1H, NH amide).

Example 6

8 Arm-PEG-S—S-NAC Conjugate
Step 1. S-(2-thiopyridyl) N-Acetyl Cysteine

S-(2-thiopyridyl) N-Acetyl Cysteine was prepared from the reaction of 2, 2$^1$-dithiodipyridine (5.398 g, 0.0245 mol) and NAC (2 g, 0.0122 mol) in a mixture of methanol and water (1:1) stirred for 15 hours at room temperature. Upon completion of the reaction (monitored by TLC), most of methanol was removed in vacuo and the residue was dissolved in water extracted into dichloromethane concentrated on rotavapor under reduced pressure to get crude product. Crude product was purified on silicagel column chromatography with dichloromethane/methanol (8:2) gave the pure product as a light yellow solid (2.66 g, 0.098 mole, in 80%). Calculated mass: ESI m/z (M+H) 273, $^1$H-NMR (400 MHz, CD$_3$OD) δ, 1.99 (s, 3H), 3.10-3.20 (m, 1H), 2.30-2.38 (m, 1H), 4.65-4.70 (m, 1H) 7.20-7.27 (m, 1H, Ar), 7.80-7.85 (m, 2H Ar), 8.40-8.45 (m, 1H). $^{13}$C-NMR (100 MHz, CD$_3$OD), 21.22, 39.91, 52.05, 120.26, 121.37, 122.08, 137.98, 149.00, 159.56, 172.14.

Step 2. Preparation of 8 Arm-PEG-S—S-NAC Conjugate

To a stirred solution of NAC-TP (0.163 g, 0.599 mmole) in ethanol (2 mL) was added a solution of 8Arm-PEG-SH (1 g, 0.05 mmol) in PBS buffered pH 7.4 (20 mL) and reaction was stirred at room temperature for 4 hours. The reaction was monitored with HPLC. After completion of reaction, the reaction mixture was purified using a sephadex LH-20 column (Amersham Pharmacia Biotech, 3.8×45 cm) with water as mobile phase. Water was removed under lyophilization to get pure compound in good yields (92%). $^1$H-NMR (400 MHz, CD$_3$OD) δ, 2.00 (s, 3H), 2.95-3.10 (m, 1H), 3.30-2.38 (m, 1H), 3.58-3.80 (br m 4H, —OCH$_2$—CH$_2$O—) 4.40-4.50 (m, 1H), 6.95 (br, s 1H, NH amide).

Example 7

In Vitro NAC Release Studies from PEG Conjugates

The in vitro release of NAC from the 6-Arm-PEG-S—S-NAC and 8-Arm-PEG-S—S-NAC conjugates was performed in PBS (pH=7.4) at 37° C. Appropriate amounts of PEG-S—S-NAC conjugate were dissolved in release media (PBS buffered) to form a solution of 1 mg/ml into eppendorf tube and GSH was added to the conjugates to form 10 mM, 2 mM, or 2 µM concentrations and to initiate the release of NAC. All samples were run as triplicates for statistical analysis. As control samples, conjugates were analyzed in PBS buffered media in the absence of reducing agents. The solutions were kept at 37° C. and stirred continuously. At predetermined time intervals, 30 µL of samples were withdrawn and immediately analyzed release of NAC and GS-NAC with RP-HPLC and the concentrations of analytes were determined by using appropriate calibrations prepared under same conditions.

Example 8

Confirmation of Antioxidative Properties of 6Arm and 8Arm PEG-S—S-NAC Conjugates by Reactive Oxygen Species (ROS) and Free Radical NO, and Inhibition of TNF-α Production
(a) Measurement of ROS $H_2O_2$ released from BV-2 cells was measured using 10-acetyl-3,7-dihydroxyphenoxazine (Amplex Red), following the manufacturer's instructions. Briefly, the procedure for cell culture and drug treatment was the same as described in previous section. The supernatant was mixed with 0.05 U/mL of horseradish peroxidase and 1 µM of Amplex Red in 96-well plates. After 30 min incubation, the fluorescence intensity was measured using spectrofluorometry. Excitation and emission wavelengths were 530 nm and 590 nm.
(b) NO Release Assay Production of NO was assayed by measuring the levels of nitrite, the stable NO metabolite, in supernatant. Accumulation of nitrite in supernatant was determined by colorimetric assay with Griess reagent system, which uses sulfanilamide and N-(1-Naphthyl)-ethylene diamine. 100 µL of the supernatant was incubated with 50 µL of Griess reagent 1 (sulfanilamide) and 50 µL of Griess reagent 2 N-(1-Naphthyl)-ethylenediamine for 10 min at room temperature. The absorbance at 540 nm was then measured, and nitrite concentration was determined using a curve calibrated with nitrite standards.
(c) Detection of TNF-α

The procedure for cell culture and drug treatment was the same as described in an earlier example. TNF-α secretion was measured using an ELISA Kit according to the manufacturer's instruction. In brief, 50 µL of supernatant from each sample was added in 96-well ELISA plates. Biotinylated antibody reagent was applied to each well and incubated the plate at room temperature for 2 hours. After washing the plate with PBS-Tween 20, diluted streptavidin-HRP was added, and the plate was incubated at room temperature for 30 min. After washing the plate, premixed TMB substrate solution was added. The plate was developed in the dark for 30 min, and read at 450 nm using a microplate reader. The concentration of TNF-α was calculated using murine rTNF-α as standard.

Both 6-Arm-PEG-S—S-NAC conjugate and 8-Arm-PEG-S—S-NAC conjugate inhibited TNF-α production in a dose-dependent manner similar to that observed for free NAC at equimolar concentrations of NAC for conjugates and free NAC, as shown in the Figures. PEG-S—S conjugates showed significant inhibition of nitrite production at the equivalent dose of NAC (0.5 mM and 5 mM) when compared to the same concentration of free NAC (as shown in the Figures) PEG-S-SNAC conjugates showed significant inhibition of ROS production at the equivalent dose of NAC (0.5 mM and 5 mM) compared to the same concentration of free NAC ($p<0.05$ and $p<0.01$, respectively, as shown in the Figures.

Example 9

G4-PAMAM-O-GABA-Ethyl-S—S-Ethyl-Ampicillin
Step 1: Synthesis of Ampicillin-PDP

For the preparation of Ampicillin-PDP, SPDP (1 equivalent) in ethanol (10 mL) was added to a solution of Ampicillin (1 equivalent) in PBS buffer pH 7.4 (20 mL) and the reaction was stirred at room temperature for 2 hours. The reaction was monitored with HPLC and purified on HPLC to get pure product in good yield (71%).
Step 2: Synthesis of Ampicillin-NH-Ethyl-SH To a stirred solution of Ampicillin-PDP (1 equivalent) in PBS (pH=7.4) was added a solution of TCEP (1.5 equivalent) in PBS (pH=7.4) and the reaction was continued for 1 hour at room temperature. After completion of reaction, crude product was purified on RP-HPLC to get pure compound in good yield.
Step 3: Synthesis of G4-PAMAM-O-GABA-Ethyl-S—S-Ethyl-Ampicillin To a stirred solution of compound from example 3 (PA-MAM-O-GABA-NH2) (1 equivalent) in PBS (pH=7.4) was added ethanolic solution of SPDP (0.5 equivalent) in PBS (pH=7.4) and the reaction was continued for 1 hour at room temperature. After completion of the reaction, was added Ampicillin-NH-Ethyl-SH and continued the reaction for 2 hours at room temperature. After completion of the reaction the reaction was monitored with HPLC. The reaction mixture was dialyzed against PBS (pH=7.4) to remove by-products and the excess of reactants and then replaced with deionized water (3 times) dialyzed for 12 hours to remove salts. The water was lyophilized to get pure product in good yield.

Example 10

G4-PAMAM-O-GABA-Ethyl-S—S-Ethyl-Doxycycline
Step 1: Synthesis of Doxycycline-PDP For the preparation of Doxycycline-PDP, SPDP (1.3 equivalent) in ethanol (10 mL) was added to a solution of Doxycycline (1 equivalent) in PBS buffer pH 7.4 (20 mL) and the reaction was stirred at room temperature for 2 hours. The reaction was monitored with HPLC and purified on HPLC to get pure product in good yield.
Step 2: Synthesis of Doxycycline-NH-Ethyl-SH To a stirred solution of Doxycycline-PDP (1 equivalent) in PBS (pH=7.4) was added a solution of TCEP (0.1.2 equivalent) in PBS (pH=7.4) and the reaction was continued for 1 hour at room temperature. After completion of reaction, crude product was purified on RP-HPLC to get pure compound in good yield.
Step 3: Synthesis of G4-PAMAM-O-GABA-Ethyl-S—S-Ethyl-Doxycycline.

To a stirred solution of compound from example 3 (PA-MAM-O-GABA-NH$_2$) (1 equivalent) in PBS (pH=7.4) was added ethanolic solution of SPDP (1 equivalent) in PBS (pH=7.4) and the reaction was continued for 1 hour at room temperature. After completion of the reaction, was added Doxycycline-NH-Ethyl-SH and continued the reaction for 2 hours at room temperature. After completion of the reaction the reaction was monitored with HPLC. The reaction mixture was dialyzed against PBS (pH=7.4) to remove by-products and the excess of reactants and then replaced with

Example 11

PAMAM-NH-Ethyl-S—S-Ethyl-CO—NH-GABA-O-Dexamethasone

Step 1: Synthesis of Dexamethasone-O-GABA-BOC

A solution of BOC-GABA-OH (mg, mmol)) in DMF (3:1) was cooled to 0° C. and then treated with a solution of EDC (mg, mmol), DMAP (mg, mmol) and Dexamethasone, The reaction was stirred at room temperature for 24 hours. The reaction mixture was purified on silicagel column chromatography with ethyl acetate hexane as eluent to get pure compound.

Step 2: Synthesis of Dexamethasone-O-GABA-$NH_2$

To a stirred solution of Dexamethasone-O-GABA-BOC (1 g) was treated with trifloroacetic acid and dichloromethane (1:1, 10 mL). The reaction was stirred at room temperature for 10 min. After completion of the reaction trifloroacetic acid/dichloromethane was removed under rotavapor. Reaction mixture was neutralized with PBS (pH=7.4) and purified on silicagel column chromatography with ethyl acetate hexane as eluent to get pure compound.

Step 3: Dexamethasone-O-GABA-NH—CO-PDP

SPDP (1.2 equivalent) in ethanol (10 mL) was added to a solution of Dexamethasone-O-GABA-$NH_2$ (1 equivalent) in PBS buffer pH 7.4 (20 mL) and the reaction was stirred at room temperature for 2 hours. After completion of reaction compound was extracted into ethyl acetate, solvent was evaporated under reduced pressure to get crude product. The crude product was purified on silicagel column chromatography with ethyl acetate and hexane as eluent to get pure compound in good yield.

Step 4 PAMAM-O-GABA-NH—CO-PDP

For the preparation of PAMAM-O-GABAB-NH—CO-PDP, to a stirred solution of compound from example 3 (PAMAM-O-GABA-$NH_2$) (1 equivalent) in PBS (pH=7.4) SPDP (1.2 equivalent) in ethanol (10 mL) was added to a solution of PBS buffer pH 7.4 (20 mL) and PAMAM-O-GABA-$NH_2$ dendrimer (1 equivalent) to provide sufficient modification whilst preventing loss of product due to the precipitation of highly modified dendrimer. Reaction was stirred at room temperature for 2 hours. The reaction was monitored with HPLC. After completion of reaction, the reaction mixture was dialyzed against DMSO remove by-products and the excess of reactants and then lyophilized to get pure product in good yield (71%).

Step 5: PAMAM-O-GABA-NH—CO-Ethyl-SH

To a stirred solution of PAMAM-NH—CO-PDP (1 equivalent) in PBS (pH=7.4) was added a solution of TCEP (1.2 equivalent) in PBS (pH=7.4) and the reaction was continued for 1 hour at room temperature. After completion of reaction, crude product was purified on RP-HPLC to get pure compound in good yield.

Step 6: Synthesis of PAMAM-O-GABA-NH—CO-Ethyl-S—S-Ethyl-CO—NH-GABA-O-Dexamethasone To a stirred solution of Dexamethasone-O-GABA-NH-PDP (1 equivalent) in PBS (pH=7.4) was added PAMAM-NH-Ethyl-SH (1 equivalent) and the reaction was continued for 2 hours at room temperature. After completion of the reaction the reaction was monitored with HPLC. The reaction mixture was dialyzed against PBS (pH=7.4) to remove by-products and the excess of reactants and then replaced with deionized water (3 times) dialyzed for 12 hours to remove salts. The water was lyophilized to get pure product in good yield.

Example 12

PAMAM-O-GABA-NH-Ethyl-S—S-Ethyl-CO—NH-GABA-O-Indomethacin Carrier (VII)

Step 1: Synthesis of Indomethacin-O-GABA-$NH_2$

To a stirred solution of Indomethacin-O-GABA-BOC (1 g) was treated with trifloroacetic acid and dichloromethane (1:1, 10 mL). The reaction was stirred at room temperature for 1 hour. After completion of the reaction trifloroacetic acid/dichloromethane was removed under rotavapor. Reaction mixture was neutralized with PBS (pH=7.4) and purified on silicagel column chromatography with ethyl acetate hexane as eluent to get pure compound.

Step 2: Indomethacin-O-GABA-NH—CO-PDP

Solution of SPDP (1.2 equivalent) in ethanol (10 mL) was added to a solution of Indomethacin-O-GABA-$NH_2$ (1 equivalent) in PBS buffer pH 7.4 (20 mL) and the reaction was stirred at room temperature for 2 hours. After completion of reaction compound was extracted into ethyl acetate, solvent was evaporated under reduced pressure to get crude product. The crude product was purified on silicagel column chromatography with ethyl acetate and hexane as eluent to get pure compound in good yield.

Step 3: PAMAM-O-GABA-NH-Ethyl-S—S-GABA-Indomethacin

To a stirred solution of compound from example 11 (PAMAM-O-GABAB-NH—CO-Ethyl-SH) (1 equivalent) in PBS (pH=7.4) was added to a solution of Indomethacin-O-GABA-NH-PDP (1 equivalent) in PBS buffer pH 7.4 (20 mL) and continued the reaction for 2 hours at room temperature. After completion of the reaction, the reaction was monitored with HPLC. The reaction mixture was dialyzed against PBS (pH=7.4) to remove by-products and the excess of reactants and then replaced with deionized water (3 times) dialyzed for 12 hours to remove salts. The water was lyophilized to get pure product in good yield.

Example 13

PAMAM-O-GABA-NH—CO-Ethyl-S—S-Ethyl-NH—NH-Progesterone Carrier (VII)

Step 1: Synthesis of Progesterone-PDPH

Solution of PDPH (2 equivalent) in DMSO (10 mL) was added to a solution of Progesterone (1 equivalent) and the reaction was stirred at room temperature for 12 hours. After completion of reaction compound was extracted into ethyl acetate, solvent was evaporated under reduced pressure to get crude product. The crude product was purified on silicagel column chromatography with ethyl acetate and hexane as eluent to get pure compound in good yield.

Step 2: PAMAM-O-GABA-NH—CO-Ethyl-S—S-GABA-Progesterone

To a stirred solution of compound from example 12 (PAMAM-O-GABA-NH—CO-Ethyl-SH) (1 equivalent) in PBS (pH=7.4) was added to a solution of Progesterone-PDPH (1 equivalent) n PBS buffer pH 7.4 (20 mL) and continued the reaction for 2 hours at room temperature. After completion of the reaction, the reaction was monitored with HPLC. The reaction mixture was dialyzed against PBS (pH=7.4) to remove by-products and the excess of reactants and then replaced with deionized water (3 times) dialyzed

Example 14

PAMAM-O-GABA-NH—CO-Ethyl-S—S-Ethyl-NH-GABA-O-5[1]-AGUCGGAGGCUUAAUUACA-3[1] (SEQ ID NO: 1)

Step 1: Synthesis of Boc-NH-GABA-O-5[1]-AGUCGGAG-GCUUAAUUACA-3[1](SEQ ID NO: 1)

A solution of BOC-GABA-OH (1.5 equivalent)) in DMF (3:1) was cooled to 0° C. and then treated with a solution of EDC (1.5 equivalent), DMAP (0.01 equivalent) and 5[1]-AGUCGGAGGCUUAAUUACA-3' (SEQ ID NO: 1) and the reaction was stirred at room temperature for 24 hours. The reaction mixture was purified on HPLC to get pure compound.

Step 2: Synthesis of NH$_2$-GABA-O-5[1]-AGUCGGAGGC-UUAAUUACA-3[1] (SEQ ID NO: 1)

To a stirred solution of Boc-NH-GABA-O-5[1]-AGUCG-GAGGCUUAAUUACA-3[1] (SEQ ID NO: 1) (1 equivalent) was treated with trifloroacetic acid and dichloromethane (1:1, 20 equivalent). The reaction was stirred at room temperature for 1 hour. After completion of the reaction trifloroacetic acid/dichloromethane was removed under rotavapor. Reaction mixture was neutralized with PBS (pH=7.4) and the reaction mixture was purified on HPLC to get pure compound.

Step 3: PDP-NH-GABA-O-5[1]-AGUCGGAGGC-UUAAUUACA-3[1] (SEQ ID NO: 1)

Solution of SPDP (1.2 equivalent) in ethanol (10 mL) was added to a solution of NH$_2$-GABA-O-5[1]-AGUCGGAGGC-UUAAUUACA-3[1] (SEQ ID NO:1) (1 equivalent) in PBS buffer pH 7.4 (2 mL) and the reaction was stirred at room temperature for 2 hours. After completion of the reaction the reaction mixture was purified on HPLC to get pure compound.

Step 4: AMAM-O-GABA-NH—CO-Ethyl-S—S-Ethyl-NH-GABA-O-5[1]-AGUCGGAGGCUUAAUUACA-3[1] (SEQ ID NO: 1)

To a stirred solution of compound from example 12 (PAMAM-O-GABAB-NH—CO-Ethyl-SH) (1 equivalent) in PBS (pH=7.4) was added to a solution of PDP-NH-GABA-O-5[1]-AGUCGGAGGCUUAAUUACA-3[1](SEQ ID NO: 1) (1 equivalent) in PBS buffer pH 7.4 (20 mL) and continued the reaction for 2 hours at room temperature. After completion of the reaction, the reaction mixture was purified on HPLC to get pure compound.

Example 15

PAMAM-O-GABA-NH—CO-Ethyl-S—S-Ethyl-NH-GABA-O-5[1]-CAGGAAAUUUGCCUAUUGA-3[1] (SEQ ID NO: 2)

Step 1: Synthesis of Boc-NH-GABA-O-5[1]-CAG-GAAAUUUGCCUAUUGA-3[1] (SEQ ID NO: 2)

A solution of BOC-GABA-OH (1.5 equivalent)) in DMF (3:1) was cooled to 0° C. and then treated with a solution of EDC (1.5 equivalent), DMAP (0.01 equivalent) and 5[1]-CA-GGAAAUUUGCCUAUUGA-3' (SEQ ID NO: 2) and the reaction was stirred at room temperature for 24 h. The reaction mixture was purified on HPLC to get pure compound.

Step 2: Synthesis of NH$_2$-GABA-O-5[1]-CAG-GAAAUUUGCCUAUUGA-3[1] (SEQ ID NO:2)

To a stirred solution of Boc-NH-GABA-O-5[1]-CAG-GAAAUUUGCCUAUUGA-3[1] (SEQ ID NO: 2) (1 equivalent) was treated with trifloroacetic acid and dichloromethane (1:1, 20 equivalent). The reaction was stirred at room temperature for 1 hour. After completion of the reaction trifloroacetic acid/dichloromethane was removed under rotavapor. Reaction mixture was neutralized with PBS (pH=7.4) and the reaction mixture was purified on HPLC to get pure compound.

Step 3: PDP-NH-GABA-O-5[1]-CAGGAAAUUUGC-CUAUUGA-3[1] (SEQ ID NO: 2)

Solution of SPDP (1.2 equivalent) in ethanol (10 mL) was added to a solution of NH$_2$-GABA-O-5[1]-CAG-GAAAUUUGCCUAUUGA-3[1] (SEQ ID NO: 2) (1 equivalent) in PBS buffer pH 7.4 (2 mL) and the reaction was stirred at room temperature for 2 hours. After completion of the reaction the reaction mixture was purified on HPLC to get pure compound.

Step 4: AMAM-O-GABA-NH—CO-Ethyl-S—S-Ethyl-NH-GABA-O-5[1]-CAGGAAAUUUGCCUAUUGA-3[1] (SEQ ID NO: 2)

To a stirred solution of compound from example 12 (PAMAM-O-GABAB-NH—CO-Ethyl-SH) (1 equivalent) in PBS (pH=7.4) was added to a solution of PDP-NH-GABA-O-5[1]-AGUCGGAGGCUUAAUUACA-3[1] (SEQ ID NO: 1) (1 equivalent) in PBS buffer pH 7.4 (20 mL) and continued the reaction for 2 hours at room temperature. After completion of the reaction, the reaction mixture was purified on HPLC to get pure compound.

Example 16

PAMAM-O-GABA-NH—CO-Ethyl-S—S-Ethyl-NH-GABA-O-5[1]-UAAGGACCAAGACCAUCCA-3[1] (SEQ ID NO: 3)

Step 1: Synthesis of Boc-NH-GABA-O-5[1]-UAAGGAC-CAAGACCAUCCA-3[1] (SEQ ID NO: 3)

A solution of BOC-GABA-OH (1.5 equivalent)) in DMF (3:1) was cooled to 0° C. and then treated with a solution of EDC (1.5 equivalent), DMAP (0.01 equivalent) and 5[1]-UAAGGACCAAGACCAUCCA-3' (SEQ ID NO: 3) and the reaction was stirred at room temperature for 24 hours. The reaction mixture was purified on HPLC to get pure compound.

Step 2: Synthesis of NH$_2$-GABA-O-5[1]-UAAGGAC-CAAGACCAUCCA-3[1] (SEQ ID NO: 3)

To a stirred solution of Boc-NH-GABA-O-5[1]-UAAGGACCAAGACCAUCCA-3[1] (SEQ ID NO: 3) (1 equivalent) was treated with trifloroacetic acid and dichloromethane (1:1, 20 equivalent). The reaction was stirred at room temperature for 1 hour. After completion of the reaction trifloroacetic acid/dichloromethane was removed under rotavapor. Reaction mixture was neutralized with PBS (pH=7.4) and the reaction mixture was purified on HPLC to get pure compound.

Step 3: PDP-NH-GABA-O-5[1]-UAAGGACCAAGAC-CAUCCA-3[1] (SEQ ID NO: 3)

Solution of SPDP (1.2 equivalent) in ethanol (10 mL) was added to a solution of NH$_2$-GABA-O-5[1]-UAAGGAC-CAAGACCAUCCA-3[1] (SEQ ID NO: 3) (1 equivalent) in PBS buffer pH 7.4 (2 mL) and the reaction was stirred at room temperature for 2 hours. After completion of the reaction the reaction mixture was purified on HPLC to get pure compound.

Step 4: PAMAM-O-GABA-NH—CO-Ethyl-S—S-Ethyl-NH-GABA-O-5[1]-UAAGGACCAAGACCAUCCA-3[1] (SEQ ID NO: 3)

To a stirred solution of compound from example 12 (PAMAM-O-GABAB-NH—CO-Ethyl-SH) (1 equivalent)

in PBS (pH=7.4) was added to a solution of PDP-NH-GABA-O-5[1]-UAAGGACCAAGACCAUCCA-3[1] (SEQ ID NO: 3) (1 equivalent) in PBS buffer pH 7.4 (20 mL) and continued the reaction for 2 hours at room temperature. After completion of the reaction, the reaction mixture was purified on HPLC to get pure compound.

Example 17

Permeability of G4-PAMAM-FITC Across the Rabbit Amniotic Membrane

The permeability of the G4-PAMAM-FITC across the normal rabbit amniotic membrane and endotoxin treated rabbit amniotic membrane was studied using a side by side Permegear diffusion chamber at 37° C. for 48 hours. Endotoxin treated membranes were used to mimic the condition of E. coli infection in uterus. The freshly excised rabbit membranes obtained after sacrificing the rabbit was placed in between the donor and receptor chamber. The donor chambers were filled with 3 ml of FITC (0.9 mg/ml) and G4-PAMAM-FITC (3 mg/ml) solution in sterile PB buffer pH 7.4 respectively and samples were collected from the receptor chamber filled with 3 ml sterile PB buffer pH 7.4 at regular intervals and analyzed by UV and fluorescent plate reader. The permeation of dendrimer (G4-PAMAM-FITC) was compared against the small molecule (FITC alone).

The permeation of the G4-PAMAM-FITC was significantly lower than the FITC. 50% of FITC crossed the membrane in 1 hour as compared to the G4-PAMAM-FITC, which crossed 17% in 1 hour.

Example 18

Anti-Inflammatory and Anti-Oxidant Activity of Anionic Dendrimer-N-Acetyl Cysteine Conjugates in Activated Microglial Cells Perinatal brain damage is a major cause of disability and death in infants. A significant fraction of babies who suffer brain damage during and around birth develop cerebral palsy. There is increasing evidence suggesting that infection involving the uterus during pregnancy can lead to cerebral palsy in the baby (Makki et al., 2008; Romero et al., 1998, 2006, 2007a,b; Gomez et al., 2007). Recent studies demonstrate that the main mechanism of brain damage is due to the activation of microglial cells in the fetal brain that release inflammatory markers leading to the death of normal brain cells. These activated cells are not normally found in the brain. Infection or inflammation can activate microglial cells and cause them to migrate to the brain where they damage the normal brain cells. Therefore, developing intracellular drug delivery strategies to deliver drugs to activated microglial cells may help in decreasing the neuroinflammation and in the attenuation of the white matter injury. However, diagnosis and drug therapy during pregnancy is still a challenge. Recent work on a pregnant rabbit model has been able to successfully capture neuroinflammation-induced cerebral palsy, and its treatment using an anti-inflammatory drug, N-acetyl cysteine.

Developments in the rapidly expanding field of nanomedicine are offering a variety of nanoscale delivery vehicles such as liposomes, nanoparticles, and dendrimers (Lee et al., 2005; Cheng et al., 2008; Villalonga-Barber et al., 2008). Dendrimers are monodisperse, tree-like polymers with a large density of tailorable, functional groups that have potential to deliver drugs in a targeted manner to the site of action (Wolinsky and Grinstaff, 2008). Their nanoscale branching architecture size (~5 nm) enables them to be transported into cells. When this is combined with appropriate targeting mechanism and intracellular drug release profiles, conjugates of dendrimers can be potentially potent for a variety of therapeutic applications. Anionic PAMAM dendrimers are being explored as drug delivery vehicles in this study (Wiwattanapatapee et al., 2004). In addition to being highly non-cytotoxic compared to the cationic dendrimers, anionic dendrimers have shown to be highly effective in transcellular transport and has been used for oral delivery applications. Previous studies in cancer cells have also shown that efficacy of anionic PAMAM dendrimer-methotrexate (MTX) conjugates were significantly better than cationic PAMAM dendrimer-MTX conjugates (Gurdag et al., 2005). This difference has been at least partially attributed to differences in lysosomal residence times and intracellular drug release from anionic and cationic dendrimer-drug conjugates. There was previously reported the synthesis, efficacy, and drug release from cationic PAMAM-generation-4 dendrimer-N-acetyl-L-cysteine conjugates, where the conjugate showed a significantly better efficacy than the free drug, perhaps due to superior intracellular transport of the drug by the dendrimer, and its subsequent rapid release from the glutathione sensitive disulfide linker (Navath et al., 2008). Anionic PAMAM dendrimers may be more effective in vivo platforms compared to cationic PAMAM dendrimers for drug delivery applications, because of their better cytotoxicity profiles, and reduced protein binding (Malik et al., 2000). The efficacy of the anionic dendrimer conjugates will be compared with those of the previous conjugates, where other drugs (e.g. methotrexate and methyl prednisolone) were investigated (Khandare et al., 2005; Kolhe et al., 2003, 2006; Kannan et al., 2004).

N-acetyl-L-cysteine (NAC) is an anti-inflammatory and antioxidant agent used in a wide range of clinical applications (Wang et al., 2007). It is being explored for use in neuroinflammation in perinatal applications (Paintlia et al., 2008). NAC could effectively block CD11 b expression in mouse BV-2 cells and primary microglia, which is correlated to the severity of microglial activation in various neuroinflammatory diseases reported (Roy et al., 2008). However, early pharmacokinetic studies suggested that oral NAC bioavailability was low, between 6% and 10%, due to low blood concentration of NAC. The biological half-life of NAC is only 1.5 hours in the blood stream. Building on the recent findings that suggest that PAMAM dendrimers can target neuroinflammation, even after intravenous administration, this study seek build conjugates by understanding the efficacy in target cells (Kannan et al., 2007). Specifically, the anti-inflammatory and anti-oxidative effects of PAMAM dendrimer-NAC conjugate, compared to free NAC, were investigate on activated microglial cells, which are the target cells for this drug in vivo. The unique aspect of this study arises from the fact that the activity of the conjugated drug is being explored using multiple assays, for dendrimer-drug conjugates in non-cancer applications.

Synthesis of PAMAM-(COOH)$_{46}$-(NAC)$_{18}$ Conjugate

PAMAM-(COOH)$_{46}$-(NAC)$_{18}$ was prepared in three steps. n the first step, S-(2-thiopyridyl) glutathione was prepared from the reaction of 2-2[1]-dithiodipyridine in excess and the corresponding peptide in a mixture of methanol and water at room temperature. Upon completion of the reaction, methanol was removed in vacuo and the residue was washed with dichloromethane. The aqueous solution was subjected to reverse phase (RP)-HPLC purification, and lyophilization of the eluent gave the pure product as a white solid. In the second step, the above compound was reacted with NAC (1 eq) in PBS in pH 7.4 to get desired GS-NAC intermediate and purified. In third step, to introduce the GS-NAC, PAMAM-COOH was reacted with GS-NAC (64 eq/dendrimer) in the presence of PyBop/DIEA to give desired PAMAM-(COOH)$_{46}$-(NAC)$_{18}$ conjugate. Introduction of 18 GS-NAC was confirmed using HPLC, $^1$H NMR (FIG. 51) and MALDI. The MALDI analysis of the PAMAM-(COOH)$_{46}$-(NAC)$_{18}$ conjugate suggested a molecular weight of 19.7 kDa (18 GS-S-NAC molecules on one PAMAM-COOH dendrimer, Table 2). The attachment of GS-S-NAC groups to the dendrimer was also confirmed using $^1$H NMR analysis, as evidenced by the appearance of methyl protons at 1.70, 1.92 ppm that indicate the formation of GS-S-NAC conjugate with dendrimer.

Cell Culture

Mouse microglial cell line (BV-2) was obtained from Children's Hospital of Michigan Cell Culture Facility. Cells were grown in 75 mm$^2$ culture flasks using Dulbecco's Modified Eagle Medium (DMEM) supplemented with 5% fetal bovine serum (FBS) and 1% penicillin-streptomycin at 37° C. with 5% CO$_2$ in an incubator. The cells were subcultured every 48 hours and harvested from subconfluent cultures (60-70%) using 0.05% trypsin-EDTA.

Cells Treatment with PAMAM-(COOH)$_{46}$-(NAC)$_{18}$ Conjugate

BV-2 cells (passage 16) were seeded in 24 well plates at 10$^5$/mL/well and incubated for 24 hours. The medium was removed, and the cells were exposed to 100 ng/mL of LPS and varying concentrations of PAMAM-(COOH)$_{46}$-(NAC)$_{18}$ conjugate in 500 µL of serum free medium for 3 hours. The medium was removed again, and 500 µL of fresh serum free medium containing 100 ng/mL of LPS was added and incubated for 24 hours and 72 hours. Control treatment with varying concentrations of free NAC, positive control with 100 ng/mL of LPS induction, but negative control without any LPS induction and treatment were also studied. The culture medium was collected at specific time intervals of 24 hours and 72 hours, and spun at 1500 rpm for 5 min. The supernatant was stored at –80° C. for further assays.

Measurement of ROS

H$_2$O$_2$ released from BV-2 cells was measured using 10-acetyl-3,7-dihydroxyphenoxazine (Amplex Red), following the manufacturer's instructions (Alexandre et al., 2006; Min et al., 2003). The procedure for cell culture and drug treatment was the same as described in previous section. The supernatant was mixed with 0.05 U/mL of horseradish peroxidase and 1 µM of Amplex Red in 96-well plates. After 30 min incubation, the fluorescence intensity was measured using spectrofluorometry. Excitation and emission wavelengths were 530 nm and 590 nm respectively.

NO Release Assay

Production of NO was assayed by measuring the levels of nitrite, the stable NO metabolite, in the culture medium. Accumulation of nitrite in the medium was determined by colorimetric assay with Griess reagent system, which uses sulfanilamide and N-(1-Naphthyl)-ethylene diamine. From the treated cells in the medium, 100 µL of the supernatant was incubated with 50 µL of Griess reagent 1 (sulfanilamide) and 50 µL of Griess reagent 2 N-(1-Naphthyl)-ethylenediamine for 10 min at room temperature. The absorbance at 540 nm was then measured, and nitrite concentration was determined using a calibration curve prepared using nitrite standards.

Detection of TNF-α

The procedure for cell culture and drug treatment was the same as described in previous section. TNF-α secretion was measured using an ELISA kit according to the manufacturer's instructions. In brief, 50 µL of supernatant from each sample was added in 96-well ELISA plates. Biotinylated antibody reagent was applied to each well and the plate was incubated at room temperature for 2 hours. After washing the plate with PBS-Tween 20, diluted streptavidin-HRP was added, and the plate was incubated at room temperature for 30 min. After washing the plate, the premixed TMB substrate solution was added. The plate was developed in the dark for 30 min, and read at 450 nm using a microplate reader. The concentration of TNF-α was calculated using murine rTNF-α as standard.

Statistical Analysis

Data are presented as mean±SD. Specific comparisons between control and individual experiment were analyzed by Student's t-test with P-value less than 0.05 considered as statistical significance.

Results

Preparation and Characterization of Dendrimer-NAC Conjugates

A PAMAM dendrimer conjugate [PAMAM-(COOH)$_{46}$-(NAC)$_{18}$] has been developed, using a disulfide linker, for glutathione (GSH)-mediated intracellular release of NAC. To facilitate the linking of NAC to dendrimer via disulfide bond spacer group, glutathione (GSH) were used. To prepare GS-NAC, GSH was reacted with 2,2$^1$-dithiodipyridine to give GS-TP, which was further reacted with NAC to give GS-NAC. To introduce the GS-NAC, PAMAM-COOH was reacted with GS-NAC in the presence of PyBop/DIEA to give the desired PAMAM-(COOH)$_{46}$-(NAC)$_{18}$ conjugate.

PAMAM-(COOH)$_{46}$-(NAC)$_{18}$ Conjugate

Figure 51:
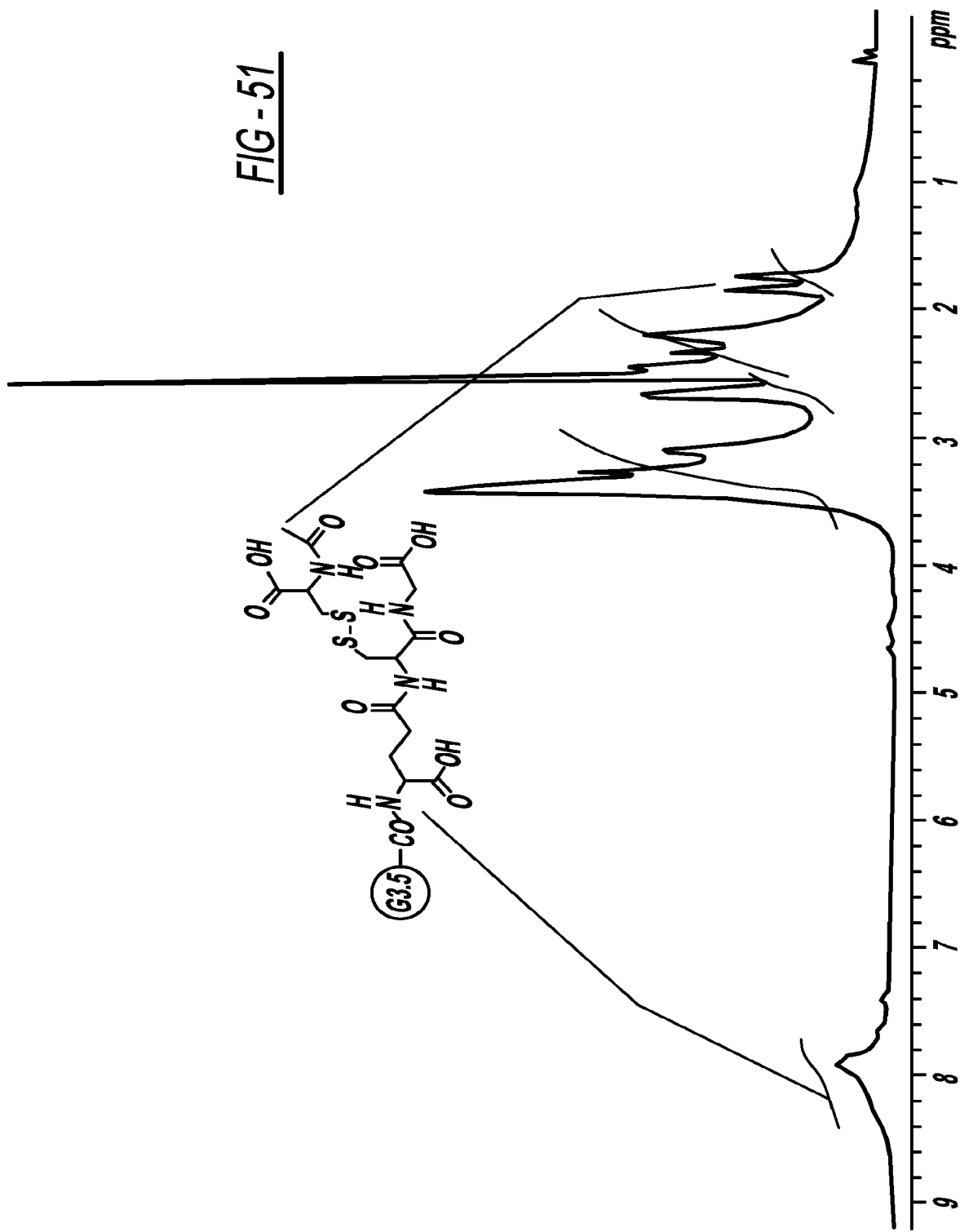
FIG. 51 shows an $^1$H NMR spectrum of the PAMAM-(COOH)$_{46}$-(NAC)$_{18}$ conjugate. The appearance of methyl protons at 1.70, 1.92 ppm indicating the formation of GS-NAC conjugates with dendrimer.

PAMAM-(COOH)$_{46}$-(NAC)$_{18}$ conjugates having cleavable disulfide linkages are designed for intracellular delivery based on glutathione levels. PAMAM-(COOH)$_{46}$-(NAC)$_{18}$ conjugate was synthesized using a three-step sequence. S-(2-thiopyridyl) glutathione was prepared from the reaction of 2,2$^1$-dithiodipyridine and GSH, and purified through HPLC. This compound was reacted with NAC in PBS (pH 7.4) to get the desired Glutathione-N-Acetyl Cysteine (GS-S-NAC) intermediate upon purification. The formation of disulfide bond was confirmed by $^1$H NMR and ESI-MS. Appearance of methyl groups in $^1$H NMR at 1.90 ppm indicates the formation of disulfide bond between the GSH and NAC. To introduce the GS-SNAC, PAMAM-COOH was reacted with GS-S-NAC in the presence of PyBop/DIEA to obtain the desired PAMAM-(COOH)$_{46}$-(NAC)$_{18}$ conjugate (FIG. 51). Introduction of GS-S-NAC was confirmed HPLC, $^1$H NMR and MALDI. MALDI analysis yielded a molecular weight of 19.7 kDa (FIG. 51) (18 GS-S-NAC molecules for one molecule of PAMAM-COOH dendrimer). The number of GS-S-NAC groups was also determined using H NMR analysis (FIG. 51), with the appearance of methyl protons at 1.70, 1.92 ppm indicating the formation of GS-NACconjugate with dendrimer. The $^1$H NMR and the MALDI data for the drug payload agree very well with each other, as summarized in Table 1.

TABLE 1

Molecular weight estimation (by MALDI-TOF, and ESI-MS) of NAC, FITC in PAMAM-(COOH)$_{46}$-(NAC)$_{18}$, (COOH)$_{62}$-(FITC)$_2$, respectively.

| Name of the compound | Molecular weight | Pay load | Purity of conjugate | Solubility in PBS/H$_2$O |
|---|---|---|---|---|
| GS-S-NAC | 468 kDa | — | 99.1% | Soluble |
| PAMAM-- (COOH)$_{46}$-(NAC)$_{18}$ | 19.7 kDa | 18 | 99.5% | Highly soluble |

TABLE 1-continued

Molecular weight estimation (by MALDI-TOF, and ESI-MS) of NAC, FITC in PAMAM-(COOH)$_{46}$-(NAC)$_{18}$, (COOH)$_{62}$-(FITC)$_2$, respectively.

| Name of the compound | Molecular weight | Pay load | Purity of conjugate | Solubility in PBS/H$_2$O |
|---|---|---|---|---|
| FITC | 389 kDa | — | 99.5% | Not soluble |
| PAMAM-CO—NH—CH$_2$—NH$_2$ | 13.7 kDa | 37 | 99.5% | Highly soluble |
| PAMAM-(COOH)$_{62}$-(FITC)$_2$ | ~14.7 kDa | 2 | 99.5% | Highly soluble |

Release of NAC from PAMAM-(COOH)$_{46}$-(NAC)$_{18}$ Conjugate

N-acetyl cysteine release from PAMAM-(COOH)$_{46}$-(NAC)$_{18}$ conjugate was analyzed at intracellular GSH concentration (10 mM). The detailed mechanism and kinetics of the drug release have been described elsewhere (Kurtoglu et al., 2009). Briefly, the results suggest that the conjugate was able to release significant amounts of free NAC within an hour, in the presence of GSH. In the absence of GSH, or at GSH levels in the blood (20 µM), no drug release was seen. PAMAM-(COOH)$_{46}$-(NAC)$_{18}$ conjugate released 39% of NAC in the free form and another 6% in the GS-S-NAC form within 1 hours, yielding a total of 45% NAC release. The eventual application, where neuroinflammation in the newborn rabbit pups is treated with the conjugates, requires relatively fast release of NAC from the conjugates. The release is desired over a period of a few days. The timescales for the cellular efficacy has been chosen to be 24 hours or 72 hours, with this in vivo requirement in mind.

Anti-Oxidative Activity of PAMAM-(COOH)$_{46}$-(NAC)$_{18}$ Conjugate

Figure 52:
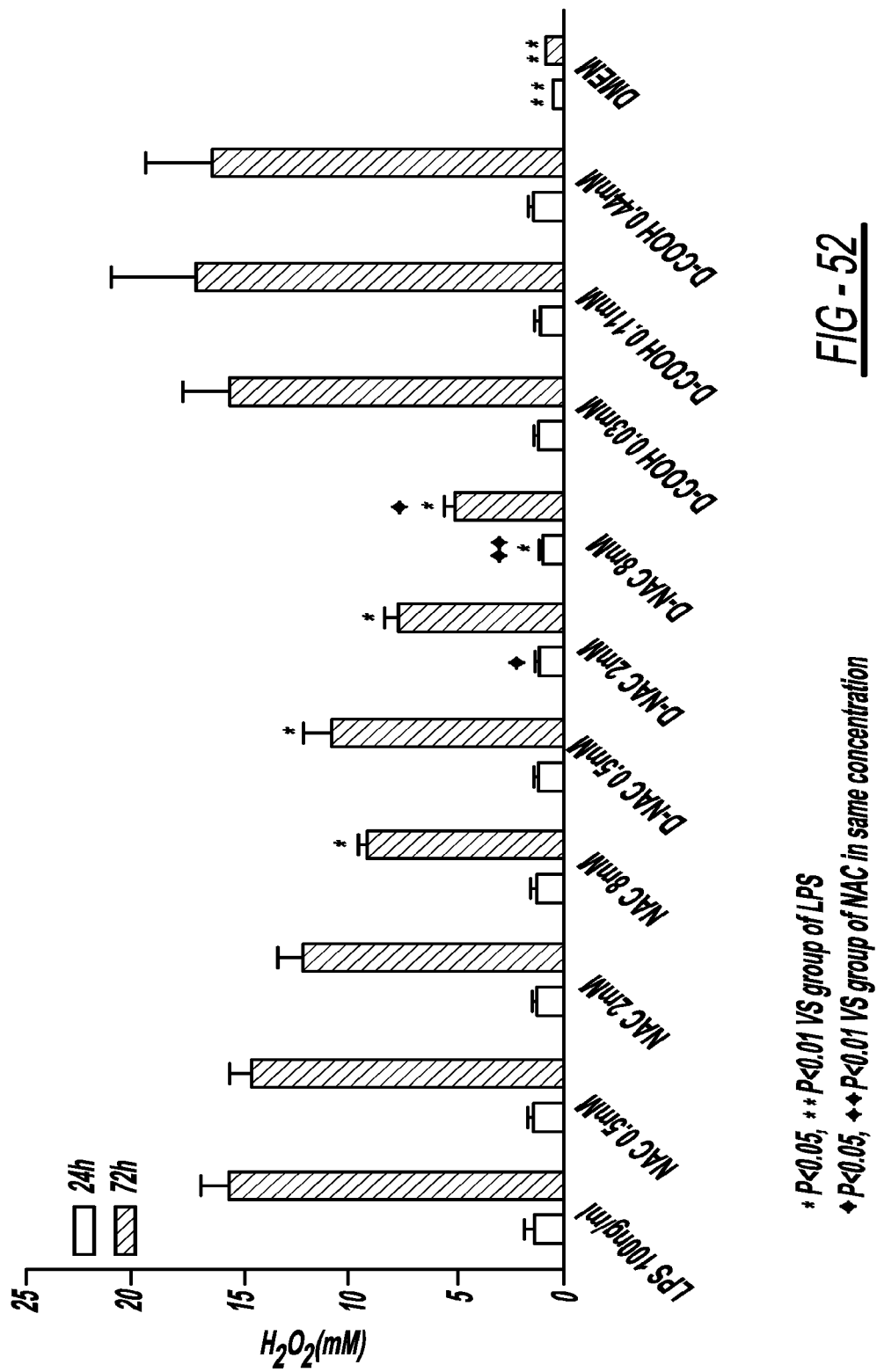
FIG. 52 shows an ROS assay. BV-2 cells (passage 16) were stimulated with 100 ng/mL of LPS for 24 hours and 72 hours after 3 hours pre-treatment with the indicated concentration of NAC, PAMAM-(COOH)$_{46}$-(NAC)$_{18}$ conjugate and the corresponding amount of free dendrimer. Three samples were used for each group. The amount of ROS released into the media was measured using Amplex Red. *P<0.05, **P<0.01 vs. group of LPS; ♦P<0.05, ♦♦P<0.01 vs. group of NAC in same concentration.
Figure 53:
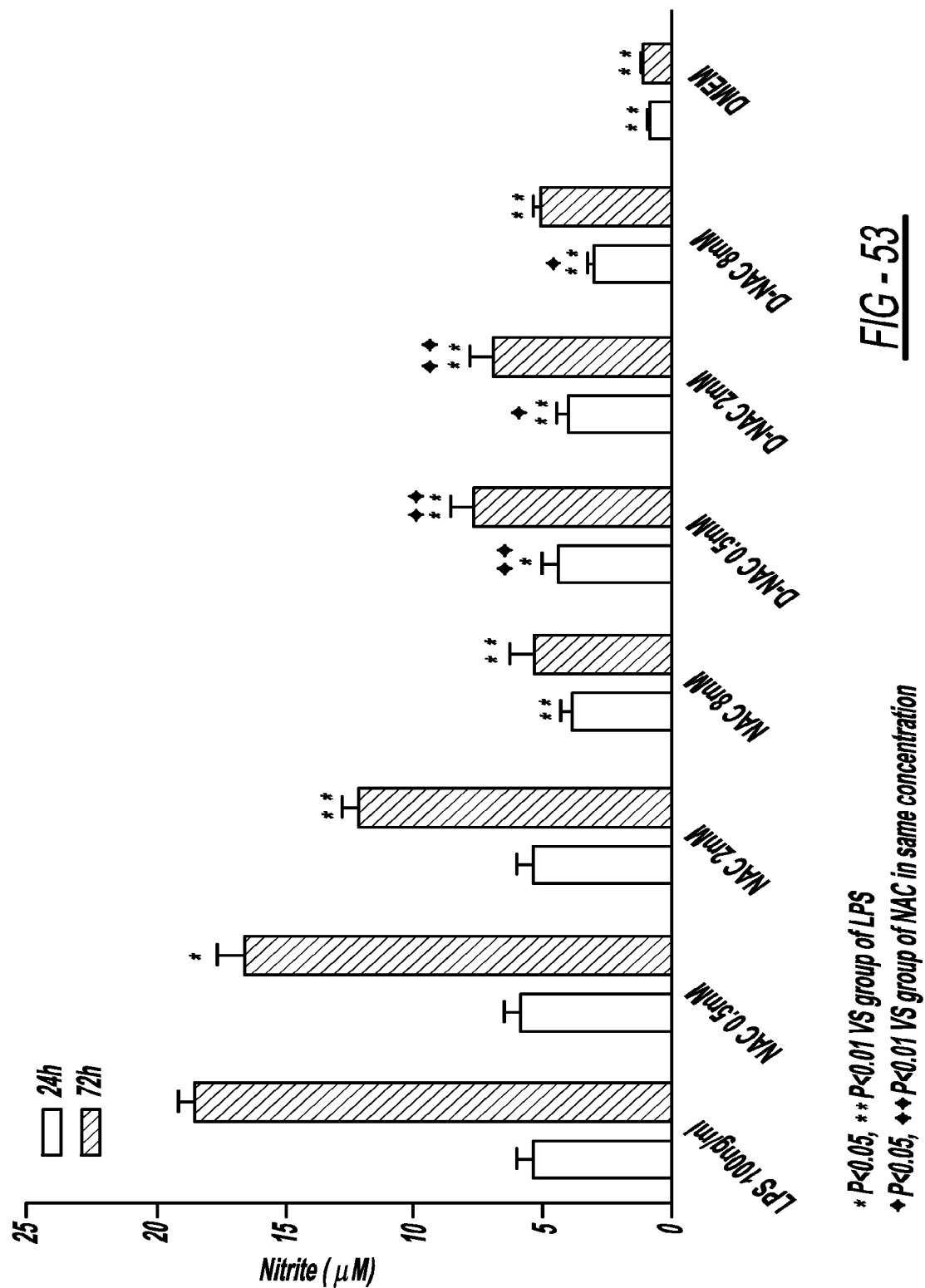
FIG. 53 shows an NO release assay. BV-2 cells (passage 16) were stimulated with 100 ng/mL of LPS for 24 and 72 hours after 3 hours pre-treatment with the indicated concentration of NAC, PAMAM-(COOH)$_{46}$-(NAC)$_{18}$ conjugate and the corresponding amount of free dendrimer. Three samples were used for each group. Nitrite in culture medium was measured using Griess reagent system. *P<0.05, **P<0.01 vs. group of LPS; ♦P<0.05, ♦♦P<0.01 vs. group of NAC in same concentration.

The anti-oxidative properties of the conjugate were tested by measuring the reactive oxygen species (ROS) and free radical NO in activated microglial cells. This is an indication of the ability of the conjugates to treat neuroinflammation, since these cells play a central role in the disease process. In prior studies in activated cells, it has been observed that ROS and NO production at 72 hours after activation was significantly higher than that at 24 hr after activation. This is also seen in the studies (FIGS. 52 and 53).

ROS Assay

ROS has been known to play important roles in oxidation and inflammation. PAMAM-(COOH)$_{46}$-(NAC)$_{18}$ conjugate inhibited the release of ROS induced by LPS in BV-2 cells. After 24 hours of stimulation with LPS following 3 hours pre-treatment, free NAC did not affect ROS production over a concentration range of 0.5-8 mM (P>0.05). In contrast, the PAMAM-(COOH)$_{46}$-(NAC)$_{18}$ conjugate showed significant inhibition of ROS production at 2 mM and 8 mM when compared to the same concentration of free NAC. After 72 hours of activation with LPS following 3 hours pre-treatment, only the highest concentration of free NAC (8 mM) inhibited ROS release moderately (30%), whereas the lowest concentration of PAMAM-(COOH)$_{46}$-(NAC)$_{18}$ conjugate (0.5 mM) showed inhibition of ROS production (25%). The conjugate significantly inhibited ROS production at 8 mM when compared to the same concentration of free NAC (68%). The inhibition showed a dose-dependent response. The corresponding concentrations of PAMAM-COOH dendrimer did not affect the cells ROS production after 24 hours and 72 hours stimulation of LPS following 3 hours pre-treatment (FIG. 52, Table 2).

Nitrite Assay

Figure 54:
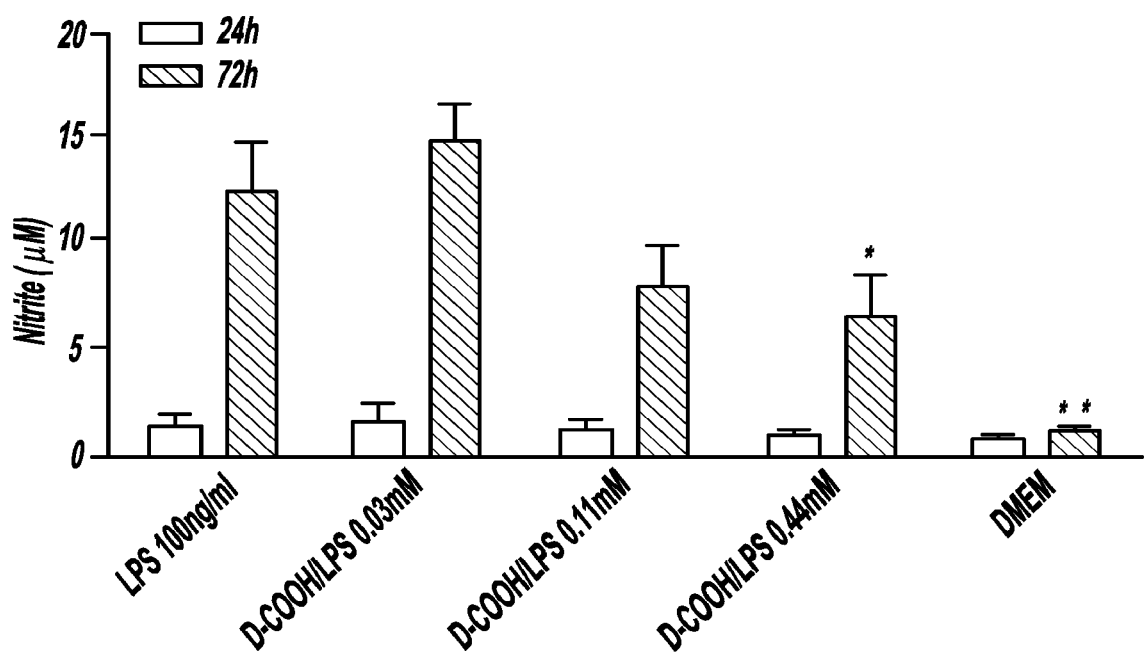
FIG. 54 shows the effect of dendrimer on NO release. BV-2 cells (passage 16) were stimulated with 100 ng/mL of LPS for 24 hours and 72 hours after 3 hours pre-treatment with the indicated concentration of PAMAM-COOH dendrimer. Three samples were used for each group. Nitrite in culture medium was measured using Griess reagent system. *P<0.05, **P<0.01 vs. group of LPS.

After 24 hours of activation with LPS following 3 hours pre-treatment, only the highest concentration of free NAC (8 mM) significantly reduced nitrite release (~70%), though there was a dose-dependent response. In contrast, the PAMAM-(COOH)$_{46}$-(NAC)$_{18}$ conjugate reduced nitrite release at the lowest equivalent dose of NAC (0.5 mM) (~61%). The conjugate significantly reduced nitrite release at all the three equivalent concentrations compared to free NAC. After 72 hours of activation with LPS following 3 hours pre-treatment, free NAC reduced nitrite release in a dose-dependent manner. PAMAM-(COOH)$_{46}$-(NAC)$_{18}$ conjugate showed significant reduction of nitrite release even at the lowest concentration (0.5 mM) when compared to the same concentration of free NAC (by ~60%). In fact, 0.5 mM NAC in the conjugated form, showed better efficacy compared to 2 mM of free NAC. The conjugate showed a dose-dependent response (FIG. 53, Table 2). The free PAMAM-COOH dendrimer control slightly decreased the nitrite release only at the highest concentration (0.44 mM) after 72 hours stimulation of LPS following 3 hours pre-treatment (FIG. 54, Table 2).

Anti-Inflammatory Activity of PAMAM-(COOH)$_{46}$-(NAC)$_{18}$ Conjugate

Figure 55:
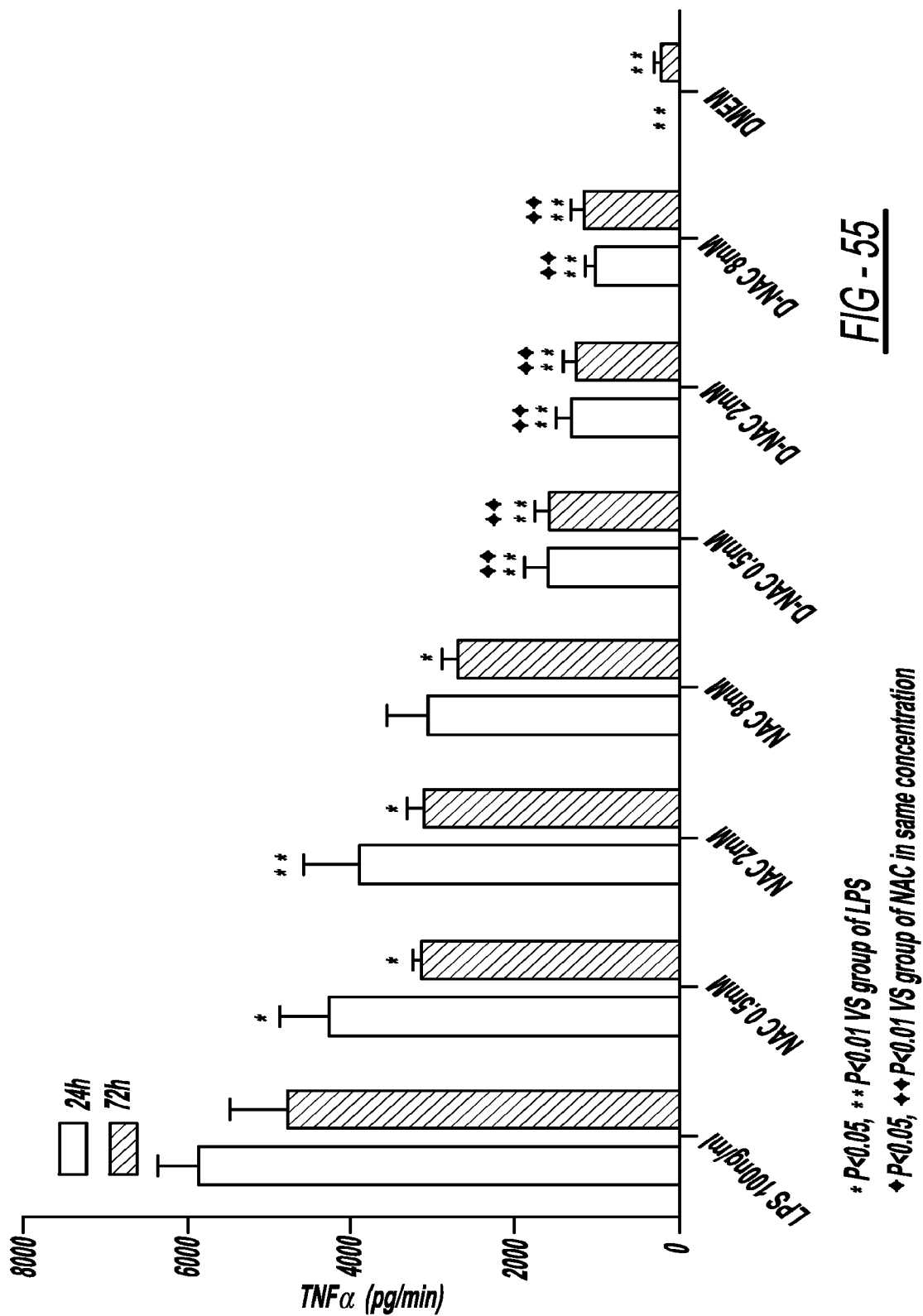
FIG. 55 Is a TNF-α release assay. BV-2 cells (passage 16) were stimulated with 100 ng/mL of LPS for 24 hours and 72 hours after 3 hours pre-treatment with the indicated concentration of NAC and PAMAM-(COOH)$_{46}$-(NAC)$_{18}$ conjugate. Three samples were used for each group. TNF-α in culture medium was measured using mouse TNF-α ELISA Kit. *P<0.05, **P<0.01 vs. group of LPS; ♦♦P<0.01 vs. group of NAC in same concentration.
Figure 56:
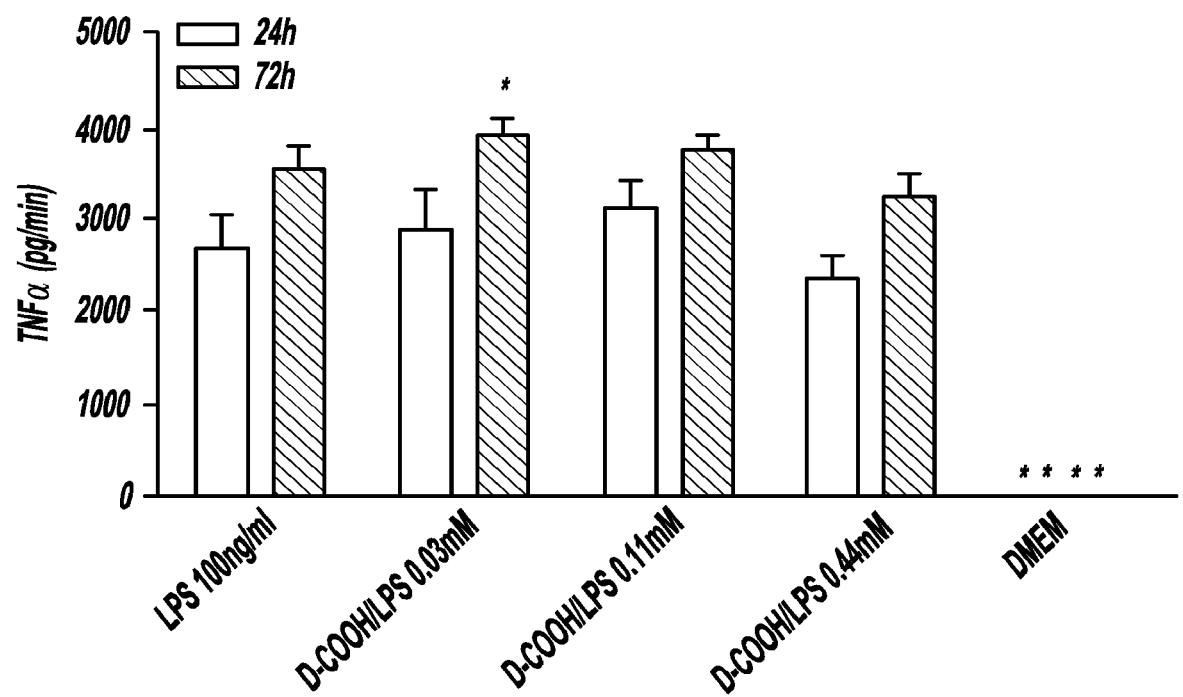
FIG. 56 shows the effect of dendrimer on TNF-α release. BV-2 cells (passage 16) were stimulated with 100 ng/mL of LPS for 24 hours and 72 hours after 3 hours pre-treatment with the chosen concentration (in mM) of PAMAM-COOH dendrimer. Three samples were used for each group. TNF-α in culture medium was measured using mouse TNF-α ELISA Kit. *P<0.05, **P<0.01 vs. group of LPS.

Anti-inflammatory activity of PAMAM-(COOH)$_{46}$-(NAC)$_{18}$ conjugate was evaluated in vitro using BV-2 cells, which were activated with LPS to induce TNF-α synthesis. In contrast to ROS and NO levels after activation, TNF-α levels have been shown to be appreciably faster, with significant increases at 24 hours (Waseem et al., 2008; El-Remessy et al., 2008). This is consistent with the present study, where high TNF-α levels were seen after 24 hours. After 24 hours and 72 hours of activation with LPS following 3 hours pre-treatment, free NAC inhibited TNF-α production in a dose-dependent manner, with a maximum reduction of ~45% at 8 mM concentration. In comparison, the PAMAM-(COOH)$_{46}$-(NAC)$_{18}$ conjugate reduced the TNF-α production very significantly (~67%) even at the lowest equivalent dose of NAC (0.5 mM). Typically, the conjugate showed better efficacy at 0.5 mM compared to free NAC at 8 mM in all the three assays. The inhibitory effect did not show a significant dose dependence (FIG. 55, Table 2), perhaps because appreciable reduction was seen even at the lowest dose. The free PAMAM-COOH dendrimer control did not inhibit TNF-α production (FIG. 56, Table 2).

TABLE 2

Inhibitory rate of NAC, conjugate and dendrimer in markers of oxidative stress and inflammation after 72 hours stimulation of LPS following 3 hours treatment.

| | Drug dose | H$_2$O$_2$ reduction (%) | Nitrite reduction (%) | TNF-α reduction (%) |
|---|---|---|---|---|
| NAC | 0.5 mM | 5.54 ± 6.38 | 10.52 ± 6.43 | 34.98 ± 2.43 |
| | 2 mM | 22.28 ± 8.33 | 34.66 ± 3.22 | 35.13 ± 4.44 |
| | 8 mM | 41.31 ± 2.33 | 72.70 ± 5.56 | 44.57 ± 4.35 |
| Dendrimer | 0.03 mM | 2.09 ± 14.53 | −20.16 ± 12.90 | −10.21 ± 5.07 |
| | 0.11 mm | −9.37 ± 24.63 | 38.29 ± 17.74 | −5.82 ± 4.58 |
| | 0.44 mM | −3.16 ± 21.02 | 46.77 ± 15.32 | 8.64 ± 6.73 |
| D-NAC | 0.5 mM | 30.81 ± 8.08 | 60.82 ± 6.05 | 67.46 ± 3.91 |
| | 2 mM | 51.13 ± 4.93 | 64.85 ± 5.12 | 74.43 ± 3.54 |
| | 8 mM | 68.75 ± 4.14 | 75.75 ± 1.85 | 77.37 ± 3.31 |

Discussion

An anionic dendrimer-NAC conjugate was prepared with a high drug payload. The drug was linked to the dendrimer using a GSH sensitive linker, which released the drug at intracellular GSH concentrations. The cell uptake and the anti-oxidant and anti-inflammatory activity were evaluated in activated microglial cells, which are the target cells for the in vivo application in a rabbit model of cerebral palsy.

From the results of flow cytometry and confocal microscopy, it appears that PAMAM-(COOH)$_{62}$-(FITC)$_2$ dendrimer are transported inside the cells efficiently and relatively rapidly. BV-2 cells are known to possess anionic charge, which is the same as that of PAMAM-(COOH)$_{62}$-(FITC)$_2$ dendrimer at physiological pH. Therefore, it may be expected that the cellular entry of PAMAM-(COOH)$_{62}$-(FITC)$_2$ into BV-2 cells may be restricted. Despite this, the cell uptake is significant, perhaps suggesting an active endocytosis mechanism (Kannan et al., 2007; Perumal et al., 2008).

Cytotoxicity assay demonstrated that free NAC, free dendrimer, and the PAMAM-(COOH)$_{46}$-(NAC)$_{18}$ conjugate are relatively nontoxic. Previous work on the cytotoxicty of dendrimers has suggested that the toxicity depends on end functionality, concentration and the time of exposure (Malik et al., 2000). Typically, anionic dendrimers have found to be significantly less toxic than cationic dendrimers. For example, Malik et al. (2000) observed that the PAMAM-G2.5-COOH dendrimer did not exhibit any significant toxicity against B16F10 melanoma cells at 2 mg/mL. The fact that microglial cells do not show measurable cytotoxicity at these levels, allows researchers to assess the efficacy of the nanodevices at well-defined treatment conditions.

Inflammatory responses in the brain are now thought to be mainly associated with activity of microglial cells, the resident macrophages of CNS, serving the role of immune surveillance and host defense under normal condition. Under pathological conditions, microglial cells become activated and have been implicated as the predominant cell type governing inflammation-mediated neuronal damage. In particular, activated microglial cells exert cytotoxic effects by releasing inflammatory mediators, such as reactive oxygen species (ROS), nitric oxide (NO) and a variety of proinflammatory cytokines such as tumor necrosis factor alpha (TNF-α). In this study, LPS was used to activate BV-2 microglial cells in vitro. LPS, the cell wall component of Gram-negative bacteria, is known to activate nitrogen-activated protein kinases, nuclear factor kB (NF-kB), protein kinase C and tyrosine kinases, which have been implicated in the release of immune-related cytotoxic factors, such as ROS, NO and proinflammatory cytokines (Lu et al., 2007).

In the in vivo studies, N-acetyl-L-cysteine (NAC) was used to address neuroinflammation in perinatal brain injury (Makki et al., 2008). Therefore, the cellular efficacy of the conjugate in activated BV-2 microglial cells was evaluated. The anti-oxidative properties of the conjugate were tested by measuring the ROS and NO levels in cell culture medium, and nitrite was chosen as a marker of free radical NO. The anti-inflammatory activity was evaluated by measuring the TNF-α level in cell culture medium. The efficacy of PAMAM-(COOH)$_{46}$-(NAC)$_{18}$ conjugate on anti-oxidation and anti-inflammation between 24 hours or 72 hours stimulation of LPS following 3 hours pre-treatment were compared.

In the experiment, production of ROS by dysfunctional mitochondria or by xanthine oxidase may contribute to LPS-induced oxidative stress with microglial cells (Paintlia et al., 2007). Peroxisomes are important for detoxification of ROS, and LPS induced effects are known to cause peroxisomal dysfunction that has been linked with ROS generation in apoptosis (Paintlia et al., 2007). NAC can abolish LPS-induced ROS production. The PAMAM-(COOH)$_{46}$-(NAC)$_{18}$ conjugate (8 mM) showed significant therapeutic effect in reducing the ROS release compared to the same concentration of free NAC after 72 hours stimulation of LPS following 3 hours pre-treatment. Dendrimer did not show any effects on ROS release following short and long time treatment, suggesting that the conjugate is able to transport and release the drug inside the cells.

Nitric oxide (NO) is produced by most cells, and is cytotoxic at high concentration or in the presence of superoxide. The cytotoxic effects are due, at least in part, to the formation of peroxynitrite from NO and superoxide, which represents a strong oxidant and nitrating agent. On that other hand, NO itself can exert cytotoxic effects due to nitrosylation reaction and the inhibition of the mitochondrial respiration by binding to the mitochondrial cytochrome c oxidase (Noack et al., 2000). NAC can suppress LPS-induced NO production. The PAMAM-(COOH)$_{46}$-(NAC)$_{18}$ conjugate appears to show better therapeutic effect towards inhibiting activated microglial cells from releasing NO when compared to the same concentration of free NAC after 24 hours and 72 hours stimulation of LPS following 3 hours pre-treatment. High concentration of free PAMAM-COOH dendrimer significantly decrease the concentration of nitrite in medium. The mechanism is perhaps by the binding of the interior secondary amines between dendrimer and nitrite. Therefore, the PAMAM-(COOH)$_{46}$-(NAC)$_{18}$ conjugate may be decreasing the nitrite level in cell culture medium through the effects of both NAC and dendrimers.

LPS can also stimulate the secretion of pro-inflammatory cytokines TNF-α, IL-1β and IL-6 in maternal and fetal compartments including fetal brain. Pro-inflammatory cytokines induced severe peroxisomal dysfunction and increased oxidative stress. Anti-inflammatory effects of NAC are attributed to the suppression of pro-inflammatory cytokine expression and release, adhesion molecule expression and activation of NF-κB in cells (Paintlia et al., 2008). The PAMAM-(COOH)$_{46}$-(NAC)$_{18}$ conjugate showed more significant efficacy to inhibit activated microglial cells to release TNF-α when compared to the same concentration of free NAC after 24 hours and 72 hours stimulation of LPS following 3 hours pre-treatment. PAMAM-COOH dendrimer did not reduced TNF-α release.

From these results, it appears that high drug payload in the dendrimer conjugate produces a high local drug concentration inside the cells. The utilization of a GSH sensitive release mechanism is enabling faster drug release and higher pharmacological response compared to the same concentration of free drug. The improved in vitro efficacy of the conjugates is a significant result, since most polymer-drug conjugates show less efficacy in cells (partly attributed to slower, inefficient drug release from the conjugates), even though enhanced permeation and retention effect (EPR) and ligand-targeting produces better efficacy in vivo (references). Specific to dendrimers, recent studies have shown that the use of an anionic dendrimer and appropriate choice of linking chemistry can produce superior therapeutic efficacies, even in cells, without the use of any targeting moieties (Gurdag et al., 2005; Navath et al., 2008).

The PAMAM-(COOH)$_{46}$-(NAC)$_{18}$ conjugate can be a very good candidate for in vivo testing in neuroinflammation models (Makki et al., 2008). By achieving a high local drug concentration with conjugates at the target site one could overcome the systemic adverse effects of free drug and improve the therapeutic efficacy significantly with a reduced dose. Recent studies have shown that the PAMAM dendrimers may have an intrinsic ability to selectively accumulate in cells associated with neuroinflammation, upon local or intravenous delivery (Kannan et al., 2007). When this is combined with the lower cytotoxicity and improved efficacy in the target microglial cells, the potential for superior in vivo results could be enhanced. Relative to free drug, this conjugate shows better efficacy compared to ester-linked neutral PAMAM dendrimer-methyl prednisolone conjugate, perhaps due to better intracellular drug release enabled by the disulfide linker (Khandare et al., 2005).

Conclusions

A PAMAM-$(COOH)_{46}$-$(NAC)_{18}$ conjugate has been prepared using a disulfide linker, that enables relatively rapid intracellular release of the drug. The FITC-labeled anionic dendrimer is rapidly taken up by microglial cells, despite the anionic surface charge. PAMAM-$(COOH)_{46}$-$(NAC)_{18}$ conjugate is non-toxic even at the higher concentrations tested in vitro. PAMAM-$(COOH)_{46}$-$(NAC)_{18}$ conjugate is a more effective anti-oxidant and anti-inflammatory agent when compared to free NAC in vitro. The conjugate showed significant efficacy even at the lowest dose (0.5 mM NAC), where the activity was comparable or better than that of Eunice Kennedy Shriver free drug at 8 mM (16× higher dosage). This shows that dendrimer-NAC conjugates can be effective nanodevices in decreasing inflammation and injury, induced by activated microglial cells in disorders such as cerebral palsy. (Wang, B. et al., *Int. J. Pharm.* (2009), doi:10.1016/j.ijpharm.2009.04.050.)

Example 19

Poly(Amidoamine) Dendrimer-Drug Conjugates with Disulfide Linkages for Intracellular Drug Delivery Dendrimers offer well-defined nanoscale architecture, multivalency, and structural versatility, leading to their emergence as a promising class of nanobiomaterials. One class of the dendrimers that have been widely investigated is poly(amidoamine) (PAMAM) dendrimers. PAMAM dendrimers have been utilized as drug carriers for gene and drug delivery, as antiviral agents and as in vivo imaging agents. When PAMAM dendrimers are used as drug carriers, they can enhance the biodistribution of drugs and possibly take advantage of enhanced permeation and retention effect (EPR) for targeting tumors. Additionally, it was demonstrated that the dendrimer surfaces can be modified with ligands to target specific tissues and tumors, thus capable of active receptor targeting. For successful clinical applications of dendrimer-drug conjugates to emerge, the dendritic carriers should eventually release the drugs loaded on to them in a well-defined and favorable rate. The release rates are dependent on the type of linking chemistry used between the drug and its carriers as well as the nanoscale structure of the dendrimer conjugate and steric effects.

Several dendrimers have been investigated as drug carriers for various cancer drugs. The conjugates have shown the ability to target tumors and have led to improved in vivo efficacy. Recent work has shown that the efficacy of anionic PAMAM dendrimer-methotrexate conjugate is better than those of cationic conjugates in drug resistant cell lines, perhaps due to the differences in subcellular distribution and drug release. PAMAM dendrimers were also evaluated as carriers for anti-inflammatory agents, such as 5-aminosalicylic acid, ibuprofen, naproxen, and methylprednisolone. These ester or amide-linked conjugates showed improvements over the free drug and their release profiles were over times scales of days to weeks. The intended application in this study requires faster release within hours to days based on neonatal rabbit models. Recent work on dendrimer-N-acetyl cysteine (NAC) conjugates showed significant enhancement in activity over the free drug and disulfide linkages used have great prospect for delivery of small drugs. Consequently, objective of the work presented here is to determine the release mechanism and rates of PAMAM-S—S-NAC conjugates in the presence of various thiol containing species.

NAC is a potent antioxidant as well as mucolytic agent and a precursor of L-cysteine (Cys) and reduced glutathione (GSH). NAC is clinically used for reducing neuroinflammation, endothelial dysfunction, fibrosis, invasion, cartilage erosion, acetaminophen detoxification and transplant prolongation. In addition, NAC reduces cellular production of pro-inflammatory cytokines such as TNF-α and IL-1β. NAC has a low oral bioavailability requiring high doses. When administered intravenously, NAC binds to plasma proteins via covalent disulfide bonds and can also cause allergic reactions in some patients complicating its use. By using drug delivery vehicles such as PAMAM dendrimers, NAC can be protected from protein binding and can be targeted to specific tissues. The intrinsic ability of PAMAM dendrimers to target neuroinflammation has been shown previously. Therefore, the PAMAM-S—S-NAC dendrimer conjugates can facilitate in vivo neuroinflammation targeting, combined with enhanced anti-inflammatory and antioxidant effects of NAC, and through tailored intracellular release.

A key challenge in dendritic drug delivery is release kinetics. Dendrimer drug complexes are shown to be unstable in plasma and buffers. Conjugates with pH responsive linkages are widely investigated but the difference in pH of biological fluids is usually not very significant especially through intravenous route. Amide linkages are typically very stable, whereas ester linkages are cleaved faster compared to amides by pH dependent hydrolysis. Hydrazone linkages are more sensitive to changes in pH compared to ester linkages but the drug and the carriers need appropriate functional groups to form a hydrazone linkage. Enzymatic release of drugs from higher generation dendrimers has shown to be problematic due to the steric effects and variable enzyme levels in tissue. Therefore, development of systems that are stable in circulation but rapidly respond to small intracellular molecules for drug release would make dendrimer conjugates more versatile. One such candidate for initiating release of drugs from dendrimers effectively is Glutathione (GSH).

GSH is the most abundant thiol species in the cytoplasm, functioning as a natural oxidant scavenger and the major reducing agent in biochemical processes. The intracellular GSH concentration (2-10 mM) is substantially higher than extracellular levels (2 mM in plasma), which provides opportunities for intracellular delivery of therapeutic agents by disulfide-linked carriers. Disulfide linkages were utilized on melamine based dendrimers to incorporate dansyl groups into dendrimer structure and investigate the disulfide exchange kinetics. More recently, photosensitizer mesochlorin ($Mce_6$) conjugates of linear N-(2-hydroxypropyl) methacrylamide (HPMA) copolymer, linked by disulfide linkage for photodynamic therapy of cancer treatment was investigated. Various thiol containing species exist (i.e. plasma proteins such as albumin, lysosomal proteins, etc.) that can induce disulfide exchange reactions. For these purposes, the use of GSH was investigated as well as other thiol containing species such as albumin (BSA) and cysteine (Cys), for their kinetics of releasing disulfide linked NAC from PAMAM dendrimer conjugates.

Synthesis of PAMAM-S—S-NAC

Figure 57:
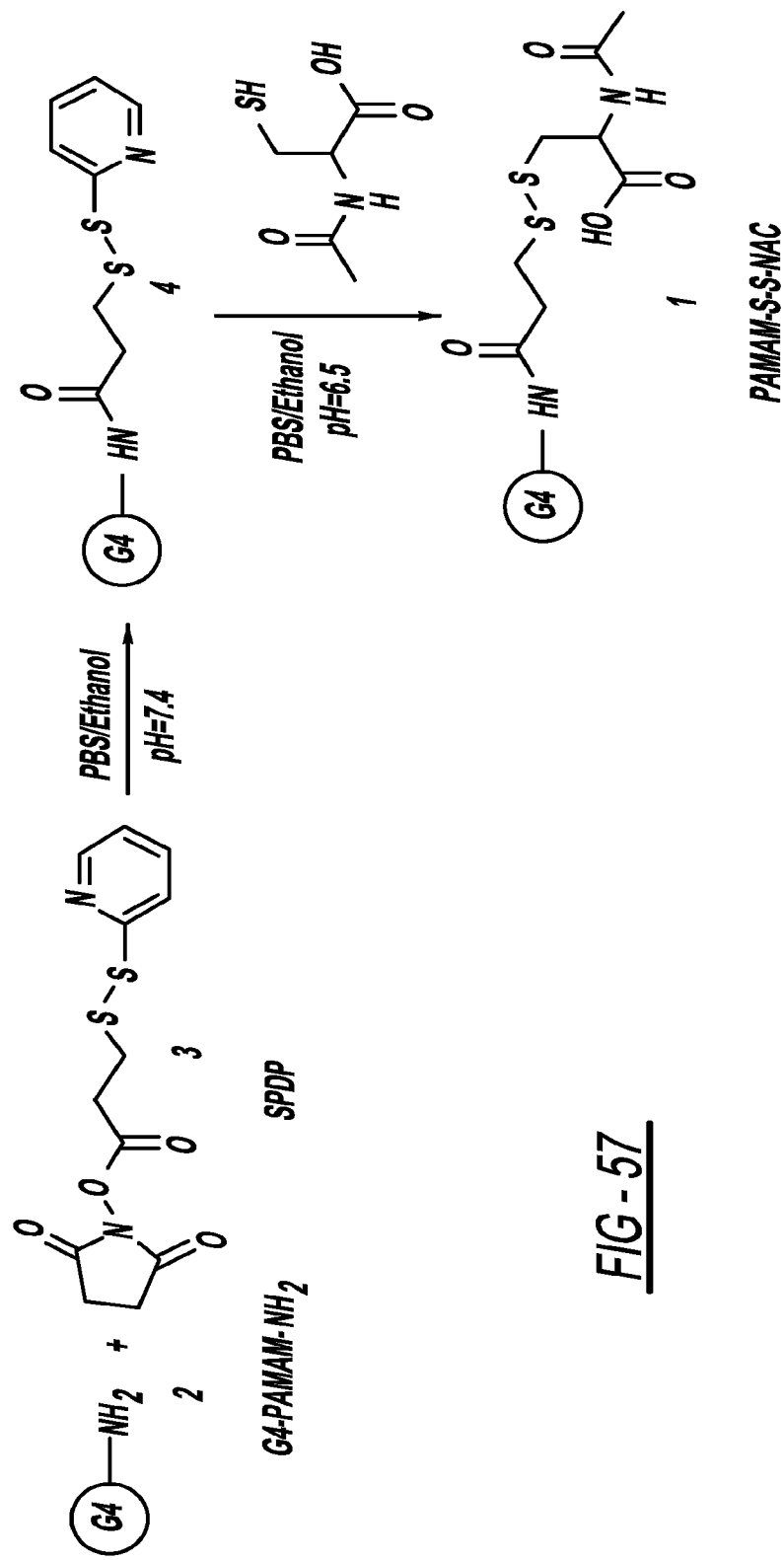
FIG. 57 shows the synthesis of PAMAM-S—S-NAC (1).

The scheme for the preparation of the conjugate is outlined in FIG. 57. Briefly, a solution of SPDP in ethanol was added to a solution of PAMAM-NH$_2$ dendrimer in PBS (pH 7.4). The reaction mixture was stirred at room temperature for 2 hours. N-Acetyl cysteine was added to this solution at once and the reaction mixture was stirred at room temperature for 4 hours. The reaction products were diluted with DMSO and dialyzed, first against DMSO followed by PBS, to remove by products and excess of reactants. The dialysis was then repeated three times (12 hours each) with deionized water to remove any salts remaining. The final solution was lyophilized and the purified product was weighted. The overall reaction yield was 71%. The attachment of 16 copies of NAC to PAMAM-NH$_2$-PDP dendrimers was determined by MALDI-TOF and $^1$H NMR. From $^1$H NMR analysis, methyl protons of N-acetyl cysteine are used as characteristic peaks. The attachment of NAC to PAMAM-NH$_2$-PDP dendrimers was determined by appearance of methyl protons as singlet at 1.94 ppm whereas attachment of PDP to PAMAM-NH$_2$ was confirmed by amide protons as multiplet at 8.40-8.75 ppm. The payload of NAC was calculated by proton integration method using the amide protons in PAMAM-NH$_2$ and methyl protons in PAMAM-S—S-NAC. The conjugate payload was confirmed further by the MALDI peak at 18.3 kDa, that agrees well with molecular mass calculated by $^1$H NMR analysis.

Drug Release Studies

Appropriate amounts of PAMAM-S—S-NAC conjugate were dissolved in release media (Citrate or PBS buffers) to form a solution of 1 mg/ml PAMAM-S—S-NAC. One of the thiol containing molecules (GSH, Cys or BSA) was added to the conjugates to form 10 mM, 2 mM, 0.5 mM 0.1 mM or 2 µM overall thiol group concentrations and to initiate the release of NAC. All samples were run as triplicates for statistical analysis.

As control samples, conjugates were analyzed in both release media in the absence of reducing agents. The solutions were kept at 37° C. and stirred continuously. At predetermined time intervals, 10 ml of samples were withdrawn and immediatelyanalyzed with RP-HPLC and the concentrations of analytes were determined by using appropriate calibrations prepared under same conditions.

In Vitro Cytotoxicity Studies

In vitro cytotoxicity of the conjugate, dendrimer and NAC, at conditions similar to that used in the efficacy assays, was investigated by MTT assay. Mouse microglial cell line (BV-2) was obtained from Children's Hospital of Michigan Cell Culture Facility. These cells were used because the eventual in vivo applications seek to target microglial cells that become activated as a result of neuroinflammation [33].

To investigate the cytotoxicity of the compounds, the cells were treated with the active compound (free drug, dendrimer, or the conjugate) for 3 hours. The lipopolysaccharide (LPS) was used to activate the cells for the ROS assay. For the cytotoxicity study, the LPS treatment was continuous for 24 hours. For both groups, the LPS concentration used was 100 ng/ml. Three concentrations of NAC were studied: 0.5 mM, 2 mM and 8 mM. For the conjugate assays, the concentrations used corresponded to equivalent NAC doses of the free drug treatment groups. Similarly, the dendrimer assays were run by using dendrimer concentrations that were equivalent to conjugate treatments. Control groups included cells receiving only LPS and no other treatment and cells with no LPS or other treatment. The proportion of viable cells in the treated group was compared to that of negative control. The cell viability is expressed as mean±SD of three samples per group, and assessed by t-test.

Reactive Oxygen Species (ROS) Assay

Cells were treated with lipopolysaccharide (LPS) to induce the production of ROS. The cells were treated with LPS (100 ng/ml) and either NAC, PAMAM-S—S-NAC, or free PAMAM-NH$_2$ dendrimers at appropriate concentrations to study the efficacy of the conjugates for reducing the ROS concentrations. In order to quantify the efficacy of conjugates, H$_2$O$_2$ released from BV-2 cells (ROS) was measured using the Amplex Red Hydrogen Peroxide/Peroxidase Assay Kit using previously established procedures [34]. The data is presented as percent reduction in H$_2$O$_2$ concentrations in cells treated with the active compound, compared to cells stimulated by LPS but did not receive any treatment. To investigate the effect of treatment time on the efficacy of the conjugates, two sets of experiments were performed: (1) In Group #1, the LPS and the active compounds (free drug, dendrimer, or the conjugate) were added to the cells at t=0, and the efficacy was followed after 24 and 72 hours; (2) In Group #2, the cells were treated with the active compound (free drug, dendrimer, or the conjugate) for just 3 hours, whereas the LPS treatment was continuous for 24 or 72 hours.

Results and Discussions

Synthesis of Conjugates

To facilitate the linking of NAC to dendrimers via disulfide bond a spacer group 3-(2-pyridyldithio)-propanoic acid (PDP) was used. To introduce sulfhydryl-reactive groups, PAMAM-NH$_2$ dendrimers were reacted with the heterobifunctional cross-linker SPDP. The N-succinimidyl activated ester of SPDP couples to the PAMAM terminal primary amines to yield amide-linked 2-pyridyldithiopropanoyl (PDP) groups. The PAMAM-NH-PDP synthesized was than reacted with water soluble NAC to get desired conjugate PAMAM-S—S-NAC. The attachment of NAC to PAMAM-NH-PDP was determined by the appearance of methyl protons as singlet at 1.94 ppm and amide protons as multiplet at 8.40-8.75 in $^1$H NMR. The attachment of multiple copies of NAC to PAMAM-NH-PDP dendrimers was further determined by MALDI-TOF. MALDI-TOF analysis of the unmodified PAMAM-G4 dendrimers gave a broad peak at 14.1 kDa, which closely agrees to the theoretical molecular mass of the dendrimers 14.2 kDa. Conjugation of the PAMAM-G4 terminal amine groups to NAC by the linker resulted in a shift in the mass peak to 18.3 kDa. Each thiopropanoyl-NAC group has a molecular mass of 250 Da. Therefore, the MALDI data indicate an average of 16 NAC molecules per dendrimer molecule.

TABLE 3

HPLC analysis summary
RP-HPLC retention time summary of analytes (min)

| GSH | GSSH | NAC | GSH-NAC | NAC-NAC | PAMAM-S-S-NAC |
|-----|------|-----|---------|---------|---------------|
| 3.8 | 3.9  | 4.7 | 5.3     | 8.2     | 17.4          |

Release Studies

Dendrimer NAC conjugates were analyzed for their drug release mechanism and kinetics in the presence of GSH, Cys and BSA. Buffer solutions with pH 5 (Citrate Buffer) and pH 7.4 (Phosphate Buffered Saline) containing various concentrations of these thiol containing moieties were used in release studies.

GSH Triggered Release Mechanism and Rates

Figure 58:
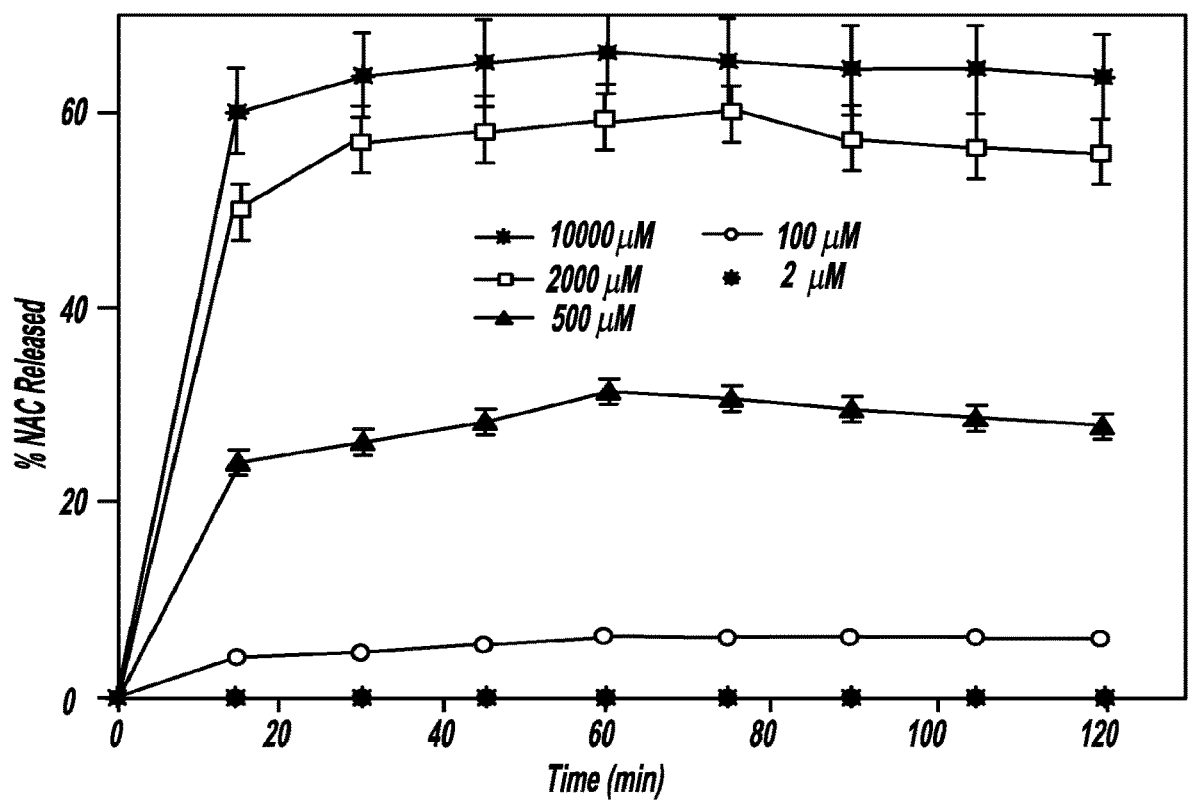
FIG. 58 shows the percent total NAC released at pH 7.4 at various GSH concentrations shown in the graph legend.

All GSH concentrations studied were between average plasma (2 µM) and intracellular (2-10 mM) GSH levels. Various GSH concentrations were used in order to determine the GSH dependent release kinetics of the conjugate. The conjugate solutions contained 730 µM NAC in the conjugated form (1 mg/ml PAMAM-S—S-NAC) at the beginning of the release studies. GSH concentration in the release media was compared to the conjugated NAC concentrations in the release solutions for analysis of the release kinetics and mechanism. PBS buffer (pH=7.4) was used in order to demonstrate the GSH dependent release kinetics in intracellular environment and in blood. NAC release profile of the conjugate is shown in FIG. 58. In the absence of GSH, the conjugate was stable, and did not release any NAC within 3 days.

GSH can reduce the disulfide linkage in the conjugates in two possible ways. The conjugates may release NAC in free form while a GSH attaches onto the dendrimers forming the disulfide bond. The other pathway may release NAC-GSH, leaving the dendrimer with a free thiol group. The NAC-GSH released can be exchanged again with another GSH molecule and liberate NAC while forming a dimer of glutathione (GSSG). Even though disulfide exchange reactions only transfer the disulfide bond from the conjugate to its dimer form GSSG, slow oxidation reactions can also take place forming new disulfide bonds over longer periods of time. For this reason, NAC-GSH and NAC-NAC was also monitored during the release studies.

Figure 59:
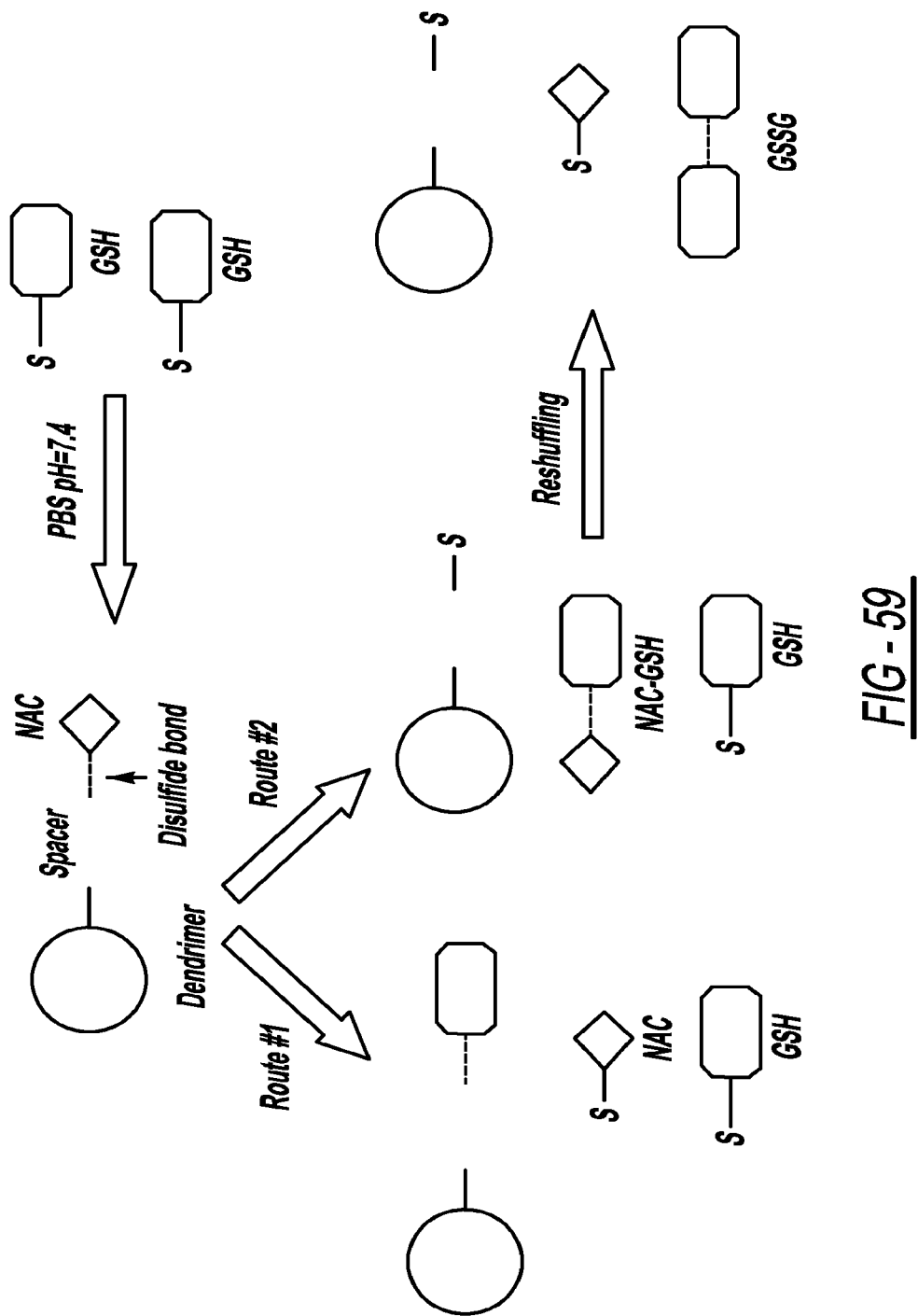
FIG. 59 shows the NAC release mechanism of PAMAM-S—S-NAC in the presence of excess GSH.

The results show that the conjugates released significant amounts of NAC within 1 hour at intracellular GSH concentrations. The release of NAC from the conjugate in the presence of GSH was fast and near completion within 1 hour. PAMAM-S—S-NAC conjugate released 47% of NAC payload in free form and 19% NAC payload in NAC-GSH form, at 1 hour. At high intracellular GSH concentrations NAC-GSH was gradually reduced to free NAC form at longer times but the overall percentage of NAC released did change notably. Similar trends were also observed in lower GSH concentrations. The amount of NAC released from the conjugate did not change significantly during the time period of 2 hours up to 17 hours (data not shown). This was in agreement with the expected fast disulfide exchange release mechanism. Release mechanism for PAMAM-S—S-NAC in the presence of GSH is shown in FIG. 59. When the GSH-induced exchange reaction cleaves the disulfide bond on the dendrimer conjugate, NAC can be released in the free form, with the dendrimer binding the GSH (Route #1). Alternately, NAC can bind GSH to form NAC-GSH (Route 2). Eventually, the presence of the excess GSH allows for the free NAC to be released, through subsequent reshuffling reactions.

At intracellular GSH concentrations, the conjugate released 66% and 60% (at 10,000 µM and 2000 µM GSH respectively) of its payload. The extent of release at 10,000 µM GSH solution was only 6% more than the release at 2000 µM. The amount of GSH at 10,000 µM and 2000 µM solutions exceeds the amount of NAC (730 µM) in conjugated form in the release media; therefore the amount released was not affected significantly. On the other hand, when the amount of GSH was limiting (at 500 µM and 100 µM GSH), the NAC release was reduced and was proportional to the GSH available; 31% and 6% respectively. When the release studies were carried out at 2 µM GSH solution, there was no detectable level of NAC released. The results of release studies at pH 7.4 indicate that the conjugates prepared can release their payload in a very rapid manner in the presence of GSH. The extent of NAC release will depend on the amount of GSH available, compared to the number of disulfide linkages.

Reducing activity of GSH is attributable to its thiol group. GSH thiol group has a $pK_a$ of ~8.8 and its thiolate form is more reactive than the thiol form. Therefore pH is an important parameter for reducing activity of GSH. In order to study the effect of pH on the reducing activity of GSH, the release studies were repeated at pH 5 (Citrate Buffer). The release at pH 5 was expected to be much slower due to the difference in thiolate/thiol ratios. The release studies at pH 5 are also relevant since the dendrimer conjugates are significantly taken up by the cells via endocytosis mechanism and reach the lysosomes where pH is 5. While GSH is not existent in the lysosomes and disulfide exchange reactions are disputed in lysosomes it is believed that other thiol containing molecules can carry on the task and take part in disulfide exchange reactions.

Figure 60:
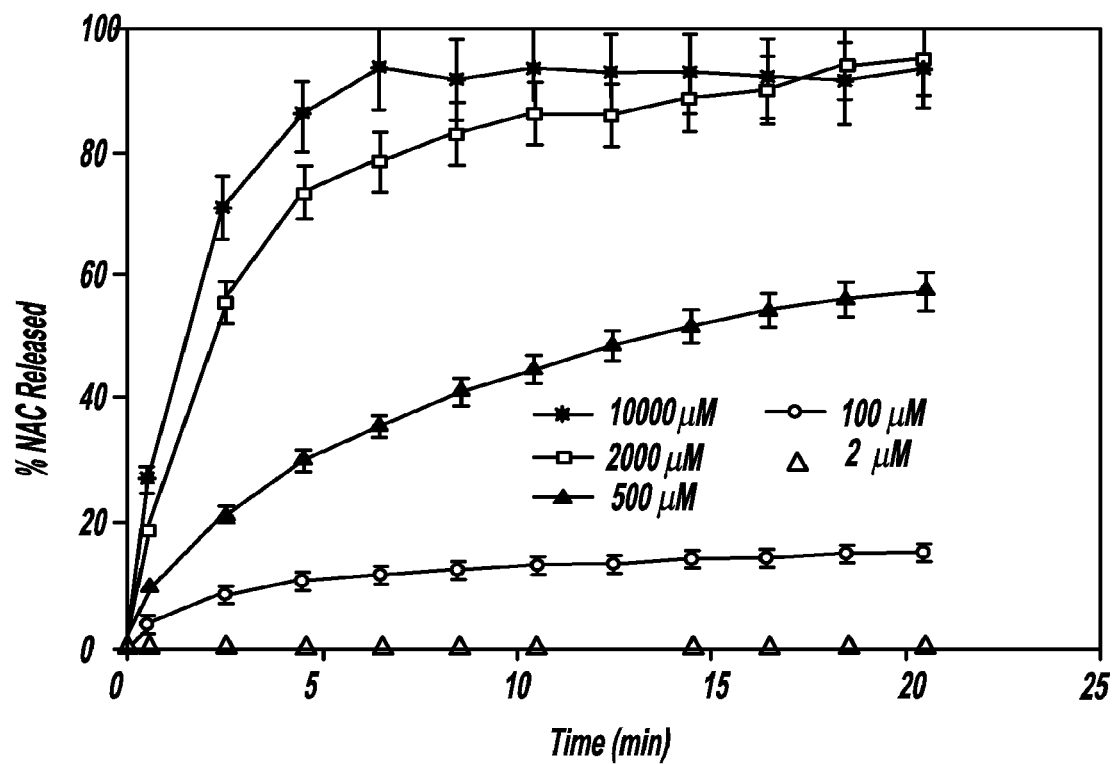
FIG. 60 shows a NAC release profile at pH=5 and various GSH concentrations shown in the graph legend.

The results of release studies with GSH at pH 5 are shown in FIG. 60. The same GSH concentrations were used as the studies at pH 7.4. The release profiles clearly indicate that the disulfide exchange reaction was significantly slowed due to reduced pH. The conjugates released their NAC payload for extended periods of time up to 20 hours. When the GSH was at intracellular concentrations and in excess of NAC in conjugated form, 95% of NAC payload was released within 20 hours. The release rates were slightly faster (nearly completed within 7 hours) at 10,000 µM GSH concentration compared to 2000 µM GSH concentration (nearly completed within 20 hours). The completion of NAC release was apparent from the flattening of the curve on released graph (FIG. 60). The release rates were significantly faster at these intracellular concentrations compared to lower GSH concentrations studied. At limiting GSH concentrations of 500 µM and 100 µM, the amounts released over 20 hours were 58% and 15% respectively. At 2 µM GSH concentration no significant amount NAC was released within 20 hours. The conjugate solutions containing no GSH did not release any NAC within the time period studied. Release studies at pH 5 indicate that, even though the disulfide exchange reactions are significantly slowed, the conjugates prepared can provide sustained release of their payload in the presence of GSH over a period of 20 hours.

It should be noted that the maximum extent of release achieved at intracellular GSH concentrations for the two different pH buffers studied were slightly different. The conjugate released about 90% of its payload at pH 5.0 whereas approximately 65% at pH 7.4. This difference may be caused by free NAC possibly attaching back to its carrier via an oxidation reaction. The oxidation reaction is faster at pH 7.4 compared to pH 5, therefore possible NAC reattachment may be more significant at pH 7.4. This can limit the equilibrium NAC concentrations to a lower value within the release media compared to pH 5. On the other hand, this should not be an issue inside the cell, since the reductive environment is constantly replenished by glutathione reductase enzyme that should shift the equilibrium conditions to complete the release process.

Cysteine Triggered Release

The release studies with GSH were repeated with Cys to investigate the ability of the amino acid to reduce the conjugate and to compare the rates of release to GSH.

Figure 61:
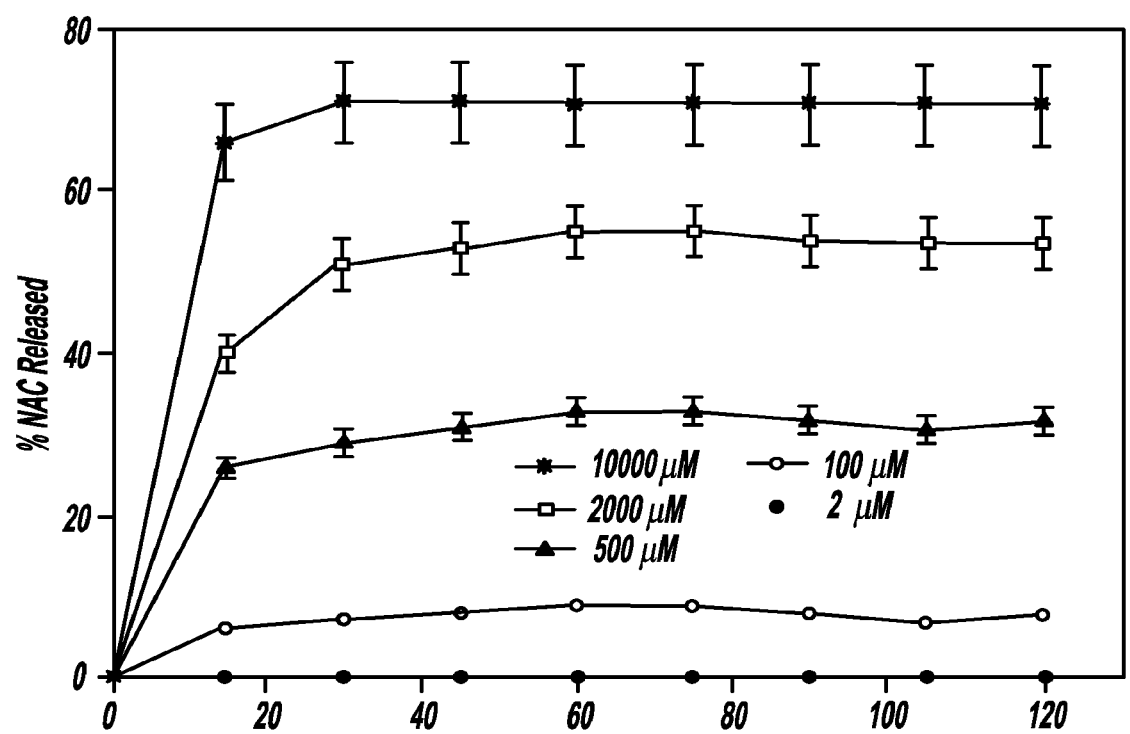
FIG. 61 depicts a percent total NAC released at pH 7.4 at various Cys concentrations shown in the graph legend.

The studies were carried out at same thiol group concentrations and in the same two buffers for investigation of pH effects, discussed earlier for GSH. The results of NAC release from the conjugate at pH=7.4 and in the presence of Cys are shown in FIG. 61. The results indicate that Cys was able to reduce the conjugate and release NAC at slightly faster rates compared to GSH. The slightly faster release rates can be explained by lower $pK_a$ value of Cys ($pK_a$=8.3) compared to GSH ($pK_a$=8.8).

The extent of release at all Cys concentrations was very similar to the extent of release of the corresponding GSH release studies. The similarity in extent of release combined with the release rates suggests that GSH and Cys are not affected by steric hindrance at the dendrimer surface when cleaving the drug from the dendrimer conjugate. While this should be obvious when the small size of Cys is considered, it is a quantitative proof that even though GSH is significantly larger compared to Cys, it is as effective in reducing the conjugate. Thus, GSH can be used as a drug-releasing agent from PAMAM dendrimer conjugates without steric problems most enzymes can face.

Figure 62:
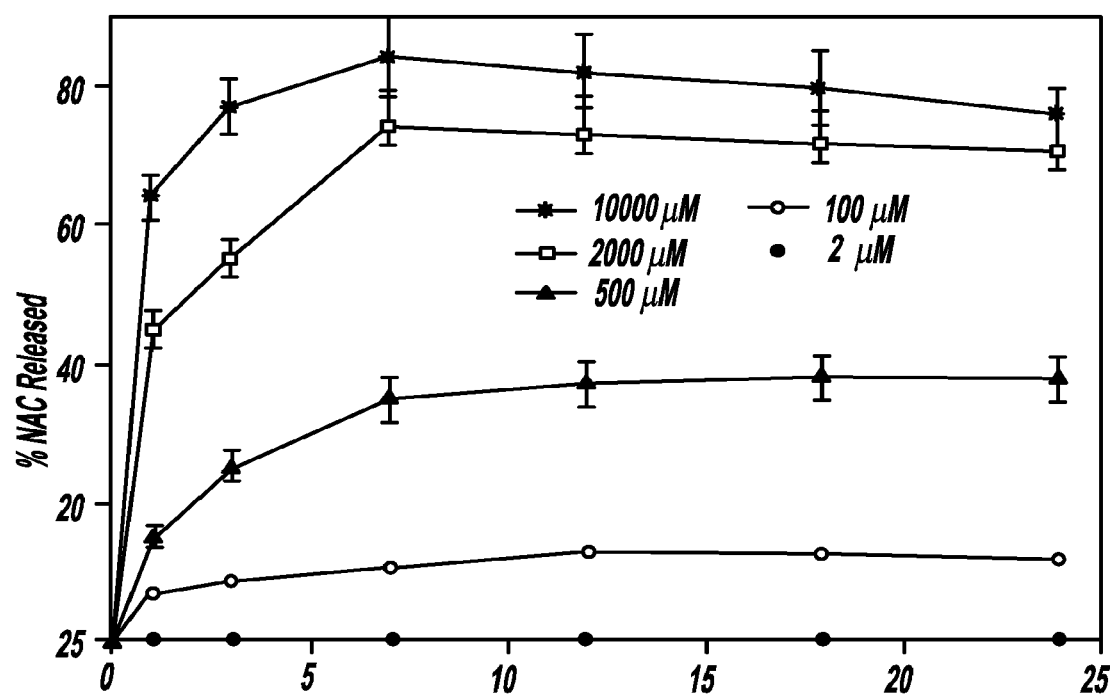
FIG. 62 depicts a percent total NAC released at pH 5 at various Cys concentrations shown in the graph legend.

The release profile of the conjugate was also determined at pH 5 using Cys as releasing agent as shown in FIG. 62. The rate of release was significantly reduced at this pH compared to pH 7.4, consistent with the result of GSH release studies. The extent of release was limited by the amount of available Cys for reducing the conjugate. The maximum extent of NAC release achieved with Cys for the two pH buffers studied agreed very well with GSH release studies. At pH 7.4, the release rate was much faster but the extent of release was less than the extent of release at pH 5. This suggests that pH of the media not only has direct implications on the rate of drug release, but also on its extent by governing the equilibrium concentrations of the thiol species. Cysteine is the most abundant thiol containing moiety in the body and also a part of GSH structure. The release studies with cysteine thus confirm that Cys can also function as a reducing agent for PAMAM-S—S-NAC as well as GSH.

Stability of Conjugates in Bovine Serum Albumin (BSA) Solution

Since the cysteine thiols are active reducing agents like GSH, and they do release the drug from the conjugate, it may be possible that cysteine residues on proteins can reduce the disulfide linkages on the conjugates if they are not sterically blocked. To investigate the reducing activity of Cys in protein structures, bovine serum albumin (BSA) was chosen for release studies since it is the most abundant protein in plasma. Additionally, for intravenous administration of conjugates, it is important for the drug to stay intact with the carrier until the conjugate reaches its final destination within the body. Thus the release characteristic in the presence of albumin is crucial for intravenous applications. The release studies in the presence of BSA were carried out at pH 7.4 and pH 5 as well. The BSA concentrations used for the studies were adjusted so that the overall Cys concentrations in BSA release media were the same as the GSH and Cys release studies, discussed earlier. In addition to the five thiol concentrations studied, the stability of the conjugate at plasma BSA concentration was also analyzed.

All of the release studies performed with BSA resulted in no NAC being released from the conjugates over 24 hours. BSA, with ~67 kDa molecular weight, is much bigger than the conjugate (~18 kDa). It was evident that BSA was not effective in reducing the disulfide linkages on the conjugates in any of the concentrations studied, most probably due to steric effects. This is not surprising since it was previously demonstrated that large proteins may have problems as releasing agents for dendrimer conjugates. On the other hand, the stability of PAMAM-S—S-NAC in the presence of BSA solution suggests that the conjugate can protect its payload from premature release while in blood circulation.

In Vitro Cytotoxicity

The induction of reactive oxygen species (ROS) production by LPS did not have significant cytotoxicity compared to control group that did not receive LPS treatment. The results indicate that there was no cytotoxicity associated with treatment by NAC in any of the MTT assays. When the cells were treated with the mentioned doses of free dendrimer or the PAMAM-S—S-NAC conjugate, the microglial cell viability was better than 80% at all doses of the dendrimer and the conjugate. The cells that received 24 hours continuous treatment with dendrimers or the conjugates showed some cytotoxicity at the highest dose, whereas the lower doses did not produce significant cytotoxicity. For this reason, only the lowest concentration treatment was considered for continuous treatment efficacy studies. The conjugate was not cytotoxic at the two lower concentrations whereas the highest dose generated some cytotoxicity with 84% cell survival rate. Similarly, some cytotoxicity associated with free dendrimer treatment at higher concentrations was observed. The cytotoxicity of the PAMAM-NH2 dendrimers could be associated to their cationic polyvalent structure. On the other hand, it was apparent that the cytotoxicity of the free dendrimers was reduced upon conjugation with NAC. This is probably due to occupation of the charged surface groups of the dendrimer by NAC. It should be pointed out that the efficacy of the conjugate is evaluated only at the lowest concentration of the conjugate, where the cell survival rate was greater than 95%.

Efficacy Assay (ROS) in Activated Microglial Cells

Reactive oxygen species (ROS) are important oxidative stress markers, and the oxidative stress is usually assessed by measuring ROS levels. Lipopolysaccharide (LPS) treatment is commonly used for activating microglia, resulting in ROS production. NAC reduces the ROS levels due to its ability to interact with ROS and also its ability to stimulate endogenous GSH synthesis. Suppression of ROS has been used widely to assess the in vivo efficacy of NAC in tissues undergoing neuroinflammatory processes. The reactive oxygen species formed by hydrogen peroxide ($H_2O_2$) are major contributors to oxidative damage of neuronal cells and oligodendrocytes in the brain leading to cell death and brain injury caused by activated microglial cells. Therefore the ability of the PAMAM-S—S-NAC conjugate to reduce $H_2O_2$ levels indicates the efficacy of conjugates in the activated microglial cells, which are the eventual target cells in vivo. Additionally, since the antioxidant effect of NAC is associated with its thiol group, which is occupied when in conjugated form, the conjugate would have to release the NAC to have antioxidant effects. The efficacy of the conjugates is dependent on entry of conjugates into cells and the subsequent release of free NAC.

Figure 63:
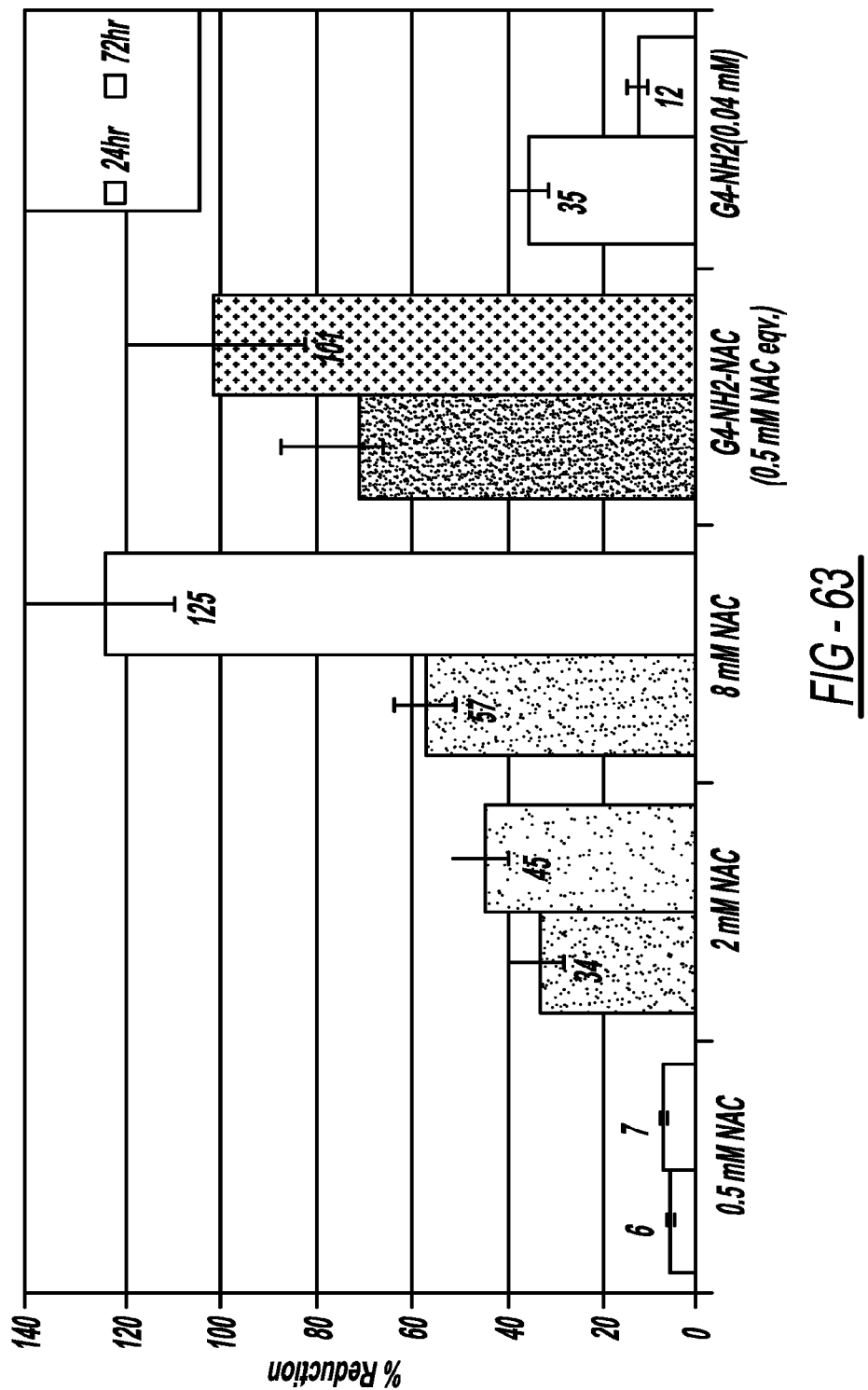
FIG. 63 shows a ROS assay, percent reduction in $H_2O_2$ levels with 24 hours NAC, PAMAM-S—S-NAC or dendrimer treatment with simultaneous induction by LPS stimulation. 100% reduction denotes $H_2O_2$ concentration of cells with no induction by LPS (control group). The amount of ROS released into the media was measured using Amplex Red. Data are mean±SD of three samples per group, and assessed by t-test. For the free dendrimer, equivalent concentrations of the dendrimer that correspond to the amount present in the conjugate at the given NAC concentration are shown in bracket.

BV-2 microglial cells were treated with LPS to stimulate ROS production and increase $H_2O_2$ concentration. The LPS exposed cells were co-treated with saline, NAC, dendrimer or the conjugate simultaneously for 24 hours. The results of reduction in $H_2O_2$ levels when compared to the untreated control are shown in FIG. 63. NAC treatment resulted in a dose dependant reduction in $H_2O_2$ concentrations with the lowest dose of 0.5 mM showing only 6% reduction in 24 hours and 7% in 72 hours. The highest dose of 8 mM resulted in 57% reduction in 24 hours and 125% reduction in 72 hours. When the cells were treated with free dendrimer at concentrations corresponding to that in the conjugates, there was a small reduction in $H_2O_2$ levels, but this effect seemed to diminish over time as suggested by 35% reduction in 24 hours which decreased to just 12% at 72 hours. It is possible that this reduction in $H_2O_2$ by the free dendrimer may be due to the cationic amine groups on the surface that may interact with the peroxide free radicals. The 'short term' nature of the effect suggests that the charge-balancing mechanism within the cell may reduce this effect eventually, or it may be possible that at longer time there is not enough dendrimer to 'reduce' intracellular $H_2O_2$ that is being produced continuously by the cells exposed to LPS. On the other hand, by conjugation of the linker and the drug, this cationic nature of the dendrimer is altered; therefore this effect should be even less significant for the conjugated form of the dendrimer.

When treated with the lowest dose of NAC in the form of a dendrimer conjugate, the efficacy was increased by more than an order of magnitude compared to free NAC treatment, with 72% reduction in 24 hours and 101% reduction in 72 hours. The efficacy of 0.5 mM NAC equivalent of conjugate was comparable in efficacy to 8 mM free NAC treatment, which suggests that the effective dose of NAC is reduced by about 16 times by administration in PAMAM-S—S-NAC form. At the 72-hours time point, the corresponding combined doses of free drug and free dendrimer have a significantly lower efficacy than the conjugate.

In order to understand the kinetics of dendrimer uptake and the subsequent intracellular drug release from the conjugates, the LPS treated BV-2 microglial cells were co-treated with NAC, dendrimer or conjugate for only 3 hours, followed by removal and refreshment of cell media containing LPS. The cells were then monitored for $H_2O_2$ concentrations for another 72 hours. The reduction of $H_2O_2$ levels at 24 hours and 72 hours after treatment is shown in FIG. 64. Dose dependent efficacy of NAC is observed for the concentration range studied (0.5-8 mM). When the cells were treated with equivalent concentrations of NAC in conjugated form, there was a significant enhancement in efficacy both at 24 hours and at 72 hours. Conjugation of NAC to G4-NH$_2$ dendrimer through a fast releasing disulfide linkage has clearly enhanced the cellular entry and activity of NAC. The reduction in effective dose by conjugate treatment is as much as 4-fold at lower drug doses (0.5 mM and 2 mM), even with only 3 hours of treatment. While the treatment with free dendrimers showed some reduction in $H_2O_2$ levels at 24 hours, this effect faded in 72 hours similar to the earlier ROS assay with continuous treatment (FIG. 63). Therefore effective intracellular delivery of NAC by conjugation to G4-NH$_2$ PAMAM dendrimer is responsible for the enhancement in efficacy, especially in the longer time scales.

For both 3-hours and 24-hours treatments, the dendrimer-conjugated NAC shows superior efficacy compared to free NAC. The high efficacy of conjugates even at the lowest dose indicates that the conjugate is able to release significant amount of its payload intracellularly. This could be explained by the fact that the dendrimer may be transporting more of the NAC inside the cells, and that the dendrimer conjugate enables a sustained delivery of NAC into the activated microglial cells effectively over several days. After the conjugates are taken up by the cells via endocytosis, they will reside in the lysosomes for a period of time where the release of NAC may be relatively slow, because of the lower thiol content in the lysosomes. As the conjugate escapes the lysosomal compartment, more NAC will be released at rates determined in the release studies. The combination of slower intracellular release, and higher NAC uptake enabled by the dendrimer, may be producing a longer therapeutic effect. Therefore, the lysosomal residence times of the conjugates may also play a role in determining the time period that the conjugate treatment will have efficacy.

For the free drug and the free dendrimer, at the three doses studied, there is a relatively minor difference in the efficacy between 24-hours continuous treatment and 3 hours treatment. However, there is a significant difference in the efficacy of the 0.5 mM conjugate between continuous and 3-hours treatment. This may be explained by an increase in endocytotic uptake due to the 'activation' of the microglial cells by sustained LPS treatment. Therefore, as more treatment time is allowed, more conjugate is transported inside the cell, perhaps releasing a factor of 5 or 6 times more drug intracellularly and providing even higher efficacy.

Conclusions

A PAMAM dendrimer NAC conjugate which uses a glutathione-sensitive disulfide linker for intracellular delivery of NAC in neuroinflammation treatment has been described. The conjugate prepared was characterized by NMR, MALDI, and HPLC analysis and the NAC payload was found to be 14%. Drug release characteristics and mechanism of the conjugate in the presence of Cys, GSH and BSA in a concentration and pH dependent manner has been investigated. The conjugate released significant amounts of NAC within 1 hour when present at intracellular GSH concentrations and pH. At lysosomal pH, drug release was sustained for about 8 hours. At both pH buffers, the extent of release was directly proportional to amount of free thiol present. The stability of conjugates against release by large proteins such as albumin has been demonstrated, which has implications for intravenous conjugate therapies. The cytotoxicity, cellular uptake, and efficacy of the delivery system were investigated in activated microglial cells. The cellular uptake of the dendrimers was relatively rapid, with significant uptake in the first 4 hours. The conjugate showed up to an order of magnitude improvement in efficacy of NAC, in vitro. The significant improvement in efficacy demonstrates that NAC is being effectively transported into the cells and released from its dendritic carrier in agreement with the release kinetics determined.

PAMAM dendrimer NAC conjugate reported here is a promising delivery vehicle for NAC, especially when inherent characteristic of PAMAM dendrimers to target neuroinflammation as well as their active and passive targeting capabilities are considered. This example establishes that PAMAM dendrimers can release high drug payloads in a short time intracellularly, through the use of a 'small', natural biomolecule GSH. (Kuroglu, Y. E. et al., *Biomaterials* 30:2112-2121, 2009.)

Example 20

Dendrimer-Drug Conjugates for Tailored Intracellular Drug Release Based on Glutathione Levels N-Acetyl cysteine (NAC) is a clinically important antioxidant, antiapoptotic, and anti-inflammatory drug used in the treatment of neuroinflammation, AIDS, colon cancer, and detoxification of heavy metals (e.g., lead, mercury, arsenic). NAC has been extensively studied as both a therapeutic agent and direct cysteine precursor. In the treatment of neuroinflammation, it acts at multiple neuroprotective sites and has recently been demonstrated to attenuate amniotic and placental cytokine responses after maternal infection induced by lipopolysaccharide (LPS) and to restore the maternal fetal oxidative balance and reduce fetal death and preterm birth. Further, a higher dose of NAC remains a primary treatment for acetaminophen overdose and exposure to toxic chemicals and is routinely used in hospitals. However, the use of NAC requires higher and repeated dosing. This is due to the poor bioavailability and blood stability, caused by the presence of free sulfhydryl groups in NAC, which are capable of spontaneous oxidation and forming disulfide bonds with plasma proteins. Early pharmacokinetic studies have demonstrated low oral bioavailability of NAC (between 6% and 10%), which were attributed to low blood concentrations of NAC. The need for high doses can lead to cytotoxicity and side effects, including increased blood pressure. NAC is one of the very few drugs being explored for treating neuroinflammation in perinatal applications, where side effects can be very critical.

The design of appropriate dendrimer-NAC conjugates can improve the stability and bioavailability, and at the same time enable intracellular release. These are especially important in the eventual interest in perinatal and neonatal applications of dendrimers and NAC. The unique design of conjugates involves linking of the NAC via disulfide bonds to spacer molecules attached to dendrimers. The resulting structure of the conjugates described here achieves two major objectives to ensure efficacy: (a) it may restrict the protein binding of NAC, as the free sulfydryl groups are involved in disulfide linkages; (b) it may enable higher intracellular levels of NAC and better release of NAC from the conjugate, resulting from disulfide linkages that are cleaved in the presence of intracellular glutathione (GSH). The results on in vitro release and the cellular efficacy toward reducing neuroinflammation in activated microglial cells shows the improved efficacy of the conjugates.

Over the past few decades, polymeric carriers have been extensively explored for controlled delivery of drugs intracellularly and to targeted tissues. Dendrimers are emerging as a viable class of polymeric vehicles (~5-15 nm) because of the large density of reactive functional groups and well-defined structure and monodispersity. This enables a high drug payload, but the steric hindrance at the dendrimer surface can make drug release a challenge when ester or amide linkers are used, especially at higher generations. Active molecules could be encapsulated, complexed, or covalently linked to the polymeric carrier. The polymer can improve the solubility, stability, and blood circulation times. Despite several significant achievements of the polymeric conjugates, clinical applications still remain elusive, partly due to the issues of drug release over an appropriate time interval. Common approaches in conjugate design involve the use of ester or amide linkers, which are cleaved hydrolytically or enzymatically. For practical applications in drug delivery, increasing the drug payload and engineering the drug release at the appropriate tissue are two key aspects in the design of polymer conjugates. For intravenous applications, it is highly desirable to design a linker that is stable during circulation but enables drug release when it reaches the target site. There is a need to design efficient polymer conjugates having cleavable bonds or linkers, with high drug payloads and appropriate release profiles.

Recently, specific chemical reactions, such as the disulfide reduction, have emerged as alternative mechanisms for drug release. Polymeric delivery systems offer an avenue for GSH responsive targeted delivery of drugs to tumor tissue. Various carriers such as gold nanoparticles, gold nanorods, mesoporous silica nanorods, nanoparticle inhibited β-galactosidase, poly (2-dimethylaminoethyl methacrylate) (PD-MAEMA), carbon nanotubes for siRNA delivery, poly (β-amino ester), gelatin nanoparticles, methyl acryloylglycylglycine 4-nitrophenyl ester for DNA delivery have been used in this regard with reductively cleavable disulfide spacers. Furthermore disulfide bonds have been incorporated in the synthesis of cleavable delivery systems for plasmid DNA, antisense oligonucleotides, peptide nucleic acids, toxins, and anticancer drugs. Therefore, a dendrimer-based delivery system was combined with disulfide chemistry, to develop a GSH-responsive release system with a high drug payload. The disulfide bonds are easily cleavable, and hence the drug release is not compromised. The gluta-thione (GSH)-mediated release of biomolecules from mono-layer-protected gold nanoparticle surfaces and manipulation of their bioactivity in vitro has been demonstrated. GSH is the most abundant thiol species in the cytoplasm and the major reducing agent in biochemical processes, providing a potential in situ releasing source in living cells. The intracellular GSH concentration (1-10 mM) is substantially higher than extracellular levels (0.002 mM in plasma). More importantly, the GSH levels in cancer tissues can be many-fold higher than those in normal tissues. Therefore, a GSH responsive linker will limit plasma release and can promote targeted release.

Experimental Procedure

Detection of Nitrite Production.

The presence of L-PS induces nitrite production, and the subsequent suppression of this by the dendrimer conjugates is used to assess the efficacy. BV-2 cells (passage 16) were seeded in 24-well plates at $10^5$/ml/well and incubated for 24 hours. The medium was removed and 500 μL of fresh serum-free medium was added. The cells were exposed to 100 ng/mL of lipopolysaccharide (LPS) and various concentrations of dendrimer conjugates for 3 hours. The medium was removed again, and 500 μL of fresh, serum-free medium containing 100 ng/mL of LPS was added. The cells were incubated for 24 and 72 hours, and the culture medium was removed for analysis. Control treatments with various concentrations of free NAC, positive controls with LPS induction and no treatment, and negative controls without any LPS induction were also studied. Accumulation of nitrite in the culture medium was used as a measure of NO formation. The nitrite concentration was determined by using the Griess reagent system (Cayman) that uses sulfanilamide and N-(1-naphthyl)ethylene diamine. In brief, 100 μL of supernatant from BV-2 cells exposed to different treatments was incubated with 50 μL of Griess reagent 1 (sulfanilamide) and 50 μL of Griess reagent 2 (N-(1-naphthyl)-ethylenediamine) for 10 min at room temperature. The absorbance at 540 nm was then measured, and nitrite concentration was determined using a curve calibrated with nitrite standards.

Intracellular GSH Measurement.

Levels of intracellular reduced glutathione (GSH) was assessed spectrofluorimetrically by monochlobimane staining (13). Briefly, the procedure for culture and drug treatment was the same as described in the previous section. Cells seeded in collagen I coated 96-well plates were washed once with PBS and incubated with 50 uM monochlobimane diluted in phenol red free medium. The fluorescence intensity was measured after 15 min at 37° C. Excitation and emission wavelengths were 380 and 485 nm, respectively. Intracellular GSH reduced rate was calculated according to the following formula: [reduced rate (%)= (fluorescence intensity of EMEM control−fluorescence intensity of treatment group)/fluorescence intensity of EMEM control×100%].

Results and Discussion

This therapeutic efficacy of polymer conjugates can be enhanced, and side effects reduced, if intracellular drug release can be enhanced. This is especially true in neonatal applications of NAC, where high doses of NAC are used. To attain this objective, there were developed GSH-responsive dendrimer NAC conjugates incorporating a connecting disulfide spacer. Use of the disulfide spacer can provide extracellular stability with rapid degradation once internalized in cells, releasing the free NAC. In the present investigation, there were synthesized and evaluated two dendrimer conjugates, a cationic PAMAM-NH—CO—Pr—S—S-NAC and an anionic G3.5-CO-Glutathione-S—S-NAC (G3.5-CO-GS-S-NAC) conjugate, for the first time in dendrimers with a disulfide bond between the drug and the dendrimer through a different spacer. The drug will be released at a rate dependent on GSH concentration.

PAMAM-NH—CO—Pr—S—S-NAC Conjugate Synthesis (1).

Figure 102:
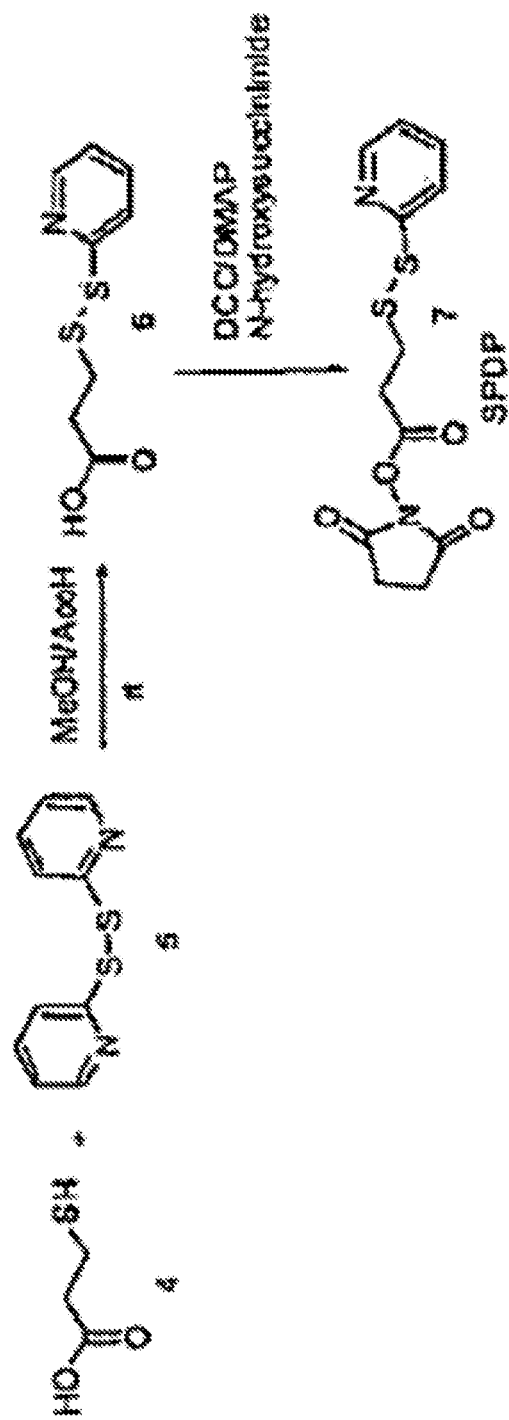
FIG. 102 shows a schematic representation for the synthesis of N-succinimidyl 3-(2-pyridyldithio)propionate (SPDP).
Figure 103:
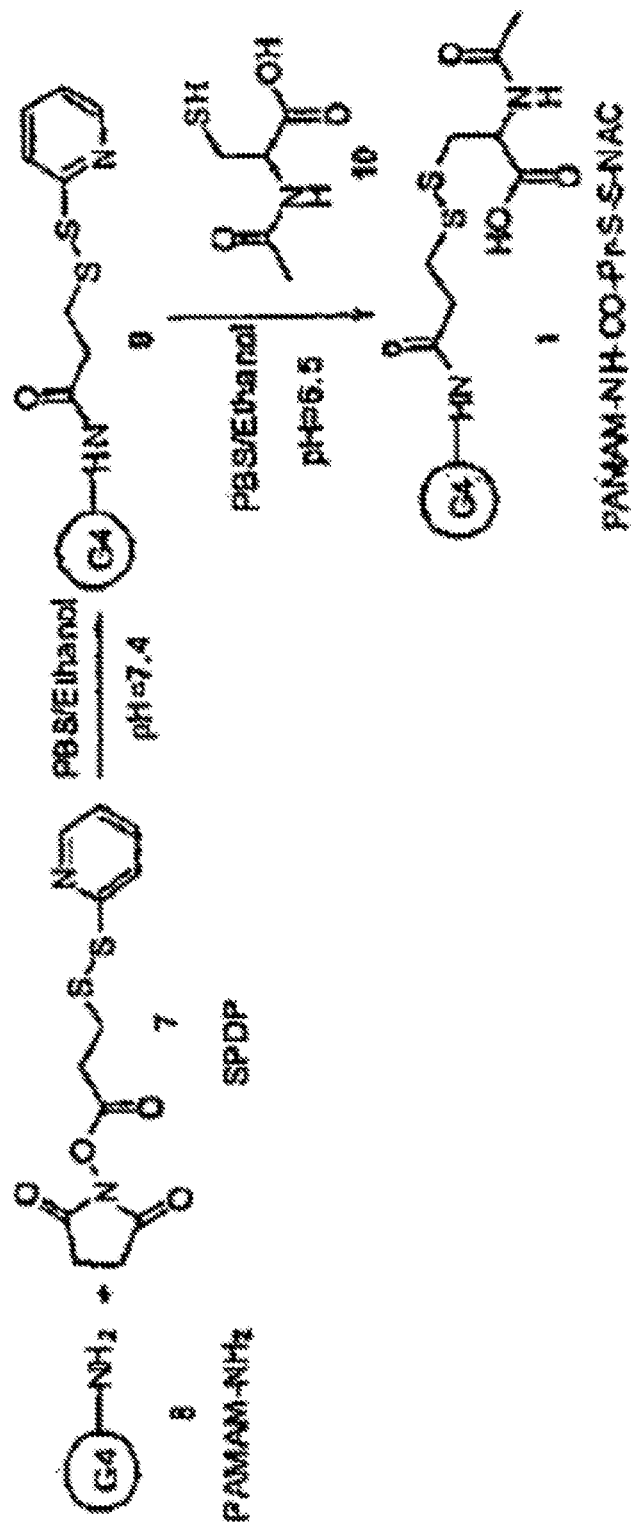
FIG. 103 shows a schematic representation for the synthesis of PAMAM-NH—CO—Pr—S—S-NAC.

To conjugate the NAC to dendrimers, the linker SPDP was appended to the dendrimer with the thiopyridine termination. The NAC was covalently attached to the PDP linked dendrimer by the formation of disulfide bonds. Synthesis of N-succinimidyl 3-(2-pyridyldithio)propionate (SPDP) was performed by a two step procedure (FIG. 102). First, 3-mercaptopropionic acid was reacted by thiol-disulfide exchange with 2,2'-dipyridyl disulfide to give 2-carboxyethyl 2-pyridyl disulfide (FIG. 102, Supporting Information R-V). To facilitate linking of amine-terminated dendrimers to SPDP, the succinimide group was appended on SPDP to obtain N-succinimidyl 3-(2-pyridyldithio)propionate (FIG. 103, Supporting Information R-VI), by esterification with N-hydroxysuccinimide by using N,N'-dicyclohexylcarbodiimide. To introduce sulfhydryl-reactive groups, PAMAM-NH$_2$ dendrimers were reacted with the heterobifunctional cross-linker SPDP (FIG. 103, Supporting Information R-VI). The N-succinimidyl activated ester of SPDP couples to the terminal primary amines to yield amide-linked 2-pyridyldithiopropanoyl (PDP) groups (FIG. 103). After reaction with SPDP, PAMAM-NH-PDP was analyzed using RP-HPLC to determine the extent to which SPDP had reacted with dendrimers.

Figures 66A, 66B:
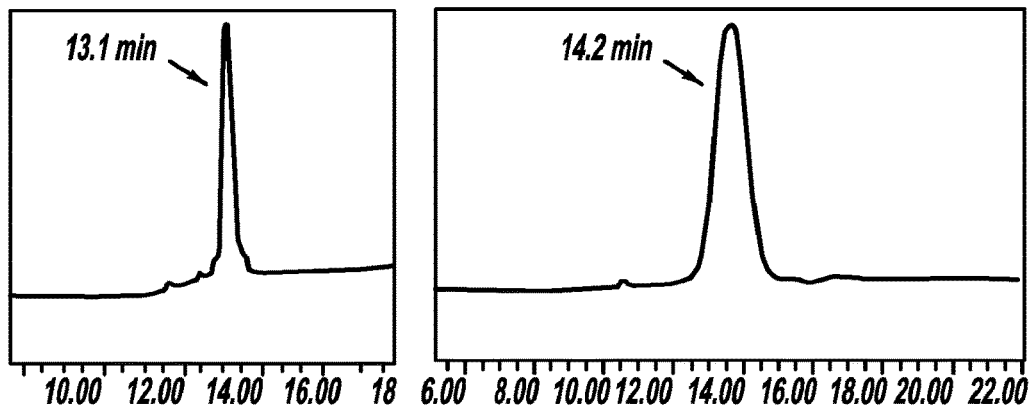
FIG. 66 shows an RP-HPLC analysis of the derivatization of PAMAM-NH2 dendrimer with the heterobifunctional cross-linker SPDP and followed by NAC reaction. PAMAM-NH$_2$ (A); PAMAM-NH—CO-Ethyl-S—S-NAC (B).

The samples were compared to unmodified PAMAM-NH$_2$ dendrimers. Samples were initially run on a linear gradient from 100:0H$_2$O (0.1 wt % TFA)/acetonitrile to 10:90H$_2$O (0.1 wt % TFA)/acetonitrile over 32 min. During this gradient, PAMAM-NH$_2$ was eluted after (13.1) compared to the modified PAMAM-NH-PDP dendrimer. The increased retention time is in line with the addition of hydrophobic PDP groups. The slight broadening of the peaks and appearance of shoulder peaks for both PAMAM dendrimers and PAMAM-NH-PDP might reflect structural defects that occurred during synthesis of the dendrimer, for example, by incomplete alkylation of the primary amines or intramolecular cyclization. The absence of amine-terminated dendrimer in the pyridyl disulfide-modified dendrimers indicates the completion of the reaction as reflected from the HPLC analysis. The PAMAM-NH-PDP so obtained was reacted with water soluble NAC to get the desired conjugate. The linking of NAC to dendrimer via the formation of a disulfide bond was confirmed by HPLC, NMR, and MALDI-TOF (Table 4, Supporting Information R-VII). The NMR and the MALDI data for the drug payload agree very well with each other, as summarized in Table 4. The HPLC chromatogram reflected decreased retention time (FIG. 66B) (15.0 min) with the addition of hydrophilic groups. The shift in retention times for the dendrimer conjugates confirms the conjugation with NAC; further, the shift to higher retention times indicates the hydrophobic nature imparted due to the spacer molecules and the NAC. The absence of the peaks corresponding to NAC and NAC-NAC and SPDP in the chromatogram for the conjugates confirms the purity of the compound synthesized.

TABLE 4

Molecular weight estimation (by $^1$H-NMR, MALDI-TOF, and ESI-MS) of NAC and PAMAM-NAC conjugates.

| | Generation no. | Molecular weight by (NMR/MALDI-TOF/ESI-MS) | Pay load | Purity of conjugate | HPLC elution time | Solubility in PBS/H$_2$O |
|---|---|---|---|---|---|---|
| G4-NH$_2$ | 4 | 14.1 kDa | — | 100% | 14.2 | Highly soluble |
| Pr-NAC | — | 250 Da | — | — | — | — |
| G4-NH-CO-PR-SS-NAC | 4 | 18.3 kDa | 16 | 99.2% | 15.0 | Highly soluble |
| FITC | — | 389 Da | — | 99.5% | — | Not soluble |
| FITC-G4-NH-CO-PR-S-S-NAC- | 4 | 19.0 kDa | 18 | 99.5% | 16.0 | Highly soluble |
| G3.5-COOH | 3.5 | 11.1 kDa | — | 100% | 8.25 | Highly soluble |
| GS-S-NAC | — | 468 kDa | — | 99.1% | — | Soluble |
| G3.5-CO-GS-S-NAC | 3.5 | 19.7 kDa | 18 | 99.5% | 12.5 | Highly soluble |

Figure 99:
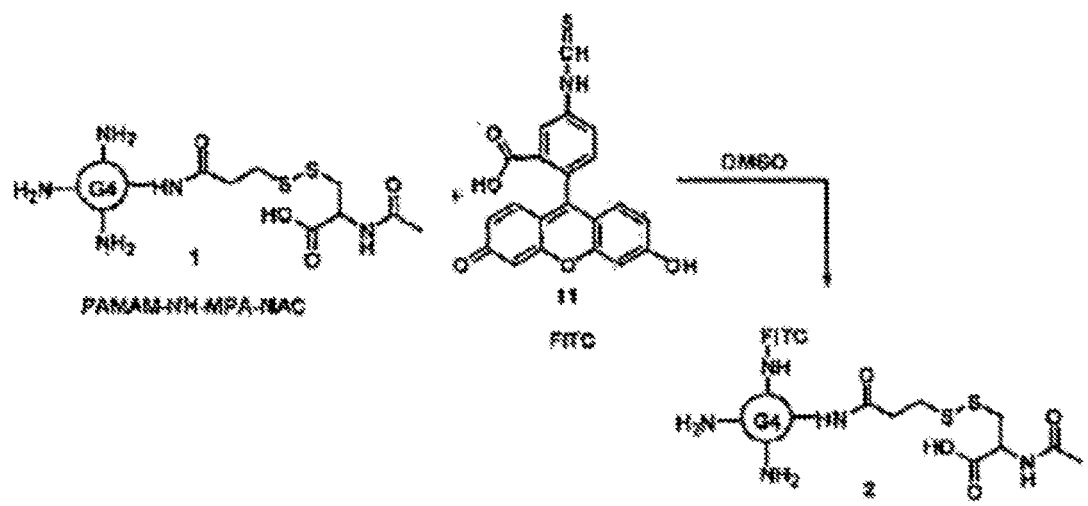
FIG. 99 shows a scheme of the PAMAM-NH—CO—Pr—S—S-NAC conjugate tagged with fluorescent dye FITC for a cell uptake study.

The chromatogram of the PAMAM-NH—CO—Pr—S—S-NAC conjugate showed the presence of a very small fraction of NAC-NAC as indicated by the slight hump at 8.2 min. Further, the appearance of methyl groups in NMR at 1.94 ppm confirms the formation of disulfide bonds between the PAMAM-NHPDP and NAC. The attachment of multiple copies of NAC to PAMAM-NH-PDP dendrimers was determined by MALDI-TOF. Analysis of the unmodified G4 dendrimer gave a broad M+ peak at 14.1 kDa (FIG. 65A), which closely corresponds to the theoretical molecular mass of the dendrimer 14.2 kDa. Coupling of the G4 terminal amine groups with NAC resulted in a shift in the major peak to 18.3 kDa (FIG. 65B, Table 4, Supporting Information R-VII). Each thiopropanoyl NAC group has a molecular mass of 250 Da. Therefore, these data indicate an average of 16 NAC molecules per dendrimer molecule (16 thiopropanoyl NAC groups per dendrimer molecule containing 64 amine terminal groups, n=3; number of independent experiments, Table 4, Supporting Information R-VII). The PAMAM-NH—CO—Pr—S—S-NAC conjugate was tagged with fluorescent dye FITC (FIG. 99) for a cell uptake study. The drug payloads in the conjugates have been kept moderate, in order to enable high solubilities of the conjugate for in vivo experiments.

PAMAM-CO-GS-S-NAC Conjugate Synthesis.

Figures 67A, 67B:
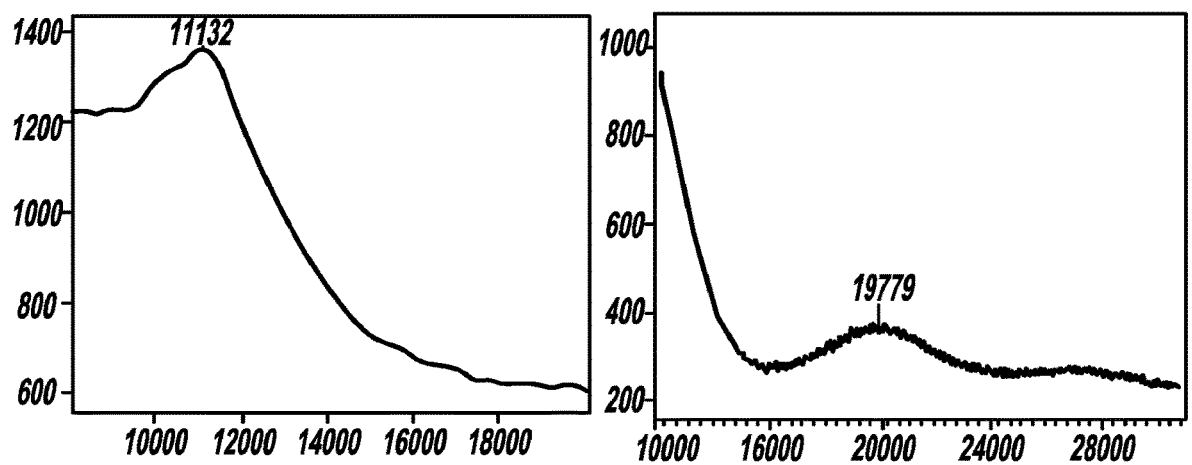
FIG. 67 shows a MALDI-TOF analysis of modified PAMAM-COOH dendrimers to determine the average number of coupled GS—S-NAC groups. PAMAM-COOH (A) and PAMAM-CO-GS-S-NAC (B).
Figure 68A:
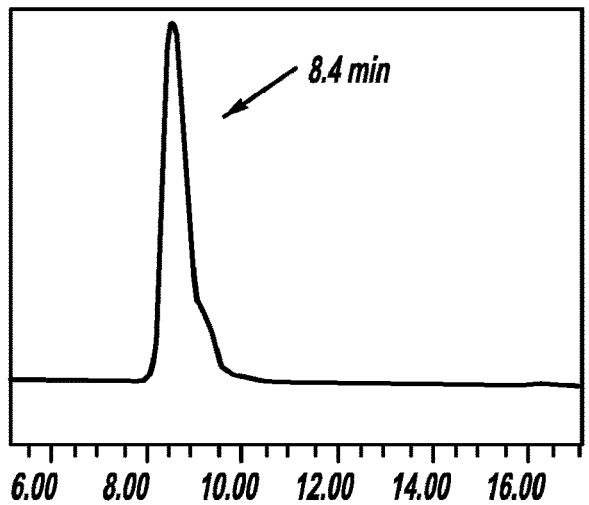
FIG. 68 shows an RP-HPLC analysis of the derivatization of PAMAM dendrimer with the GS-S-NAC. PAMAM-COOH (A), PAMAM-CO-GS-S-NAC (B).
Figure 68B:
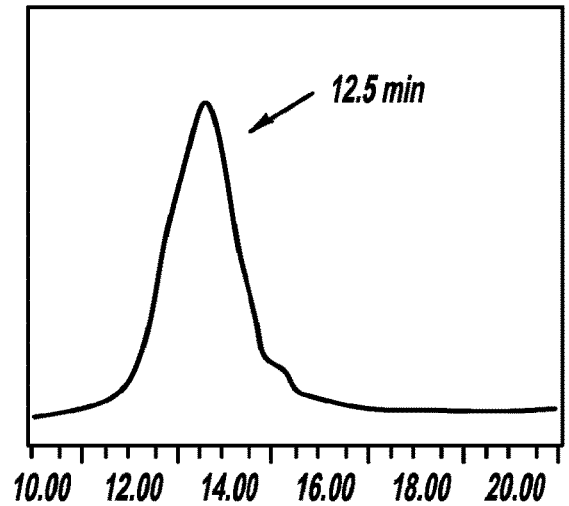
Figure 100:
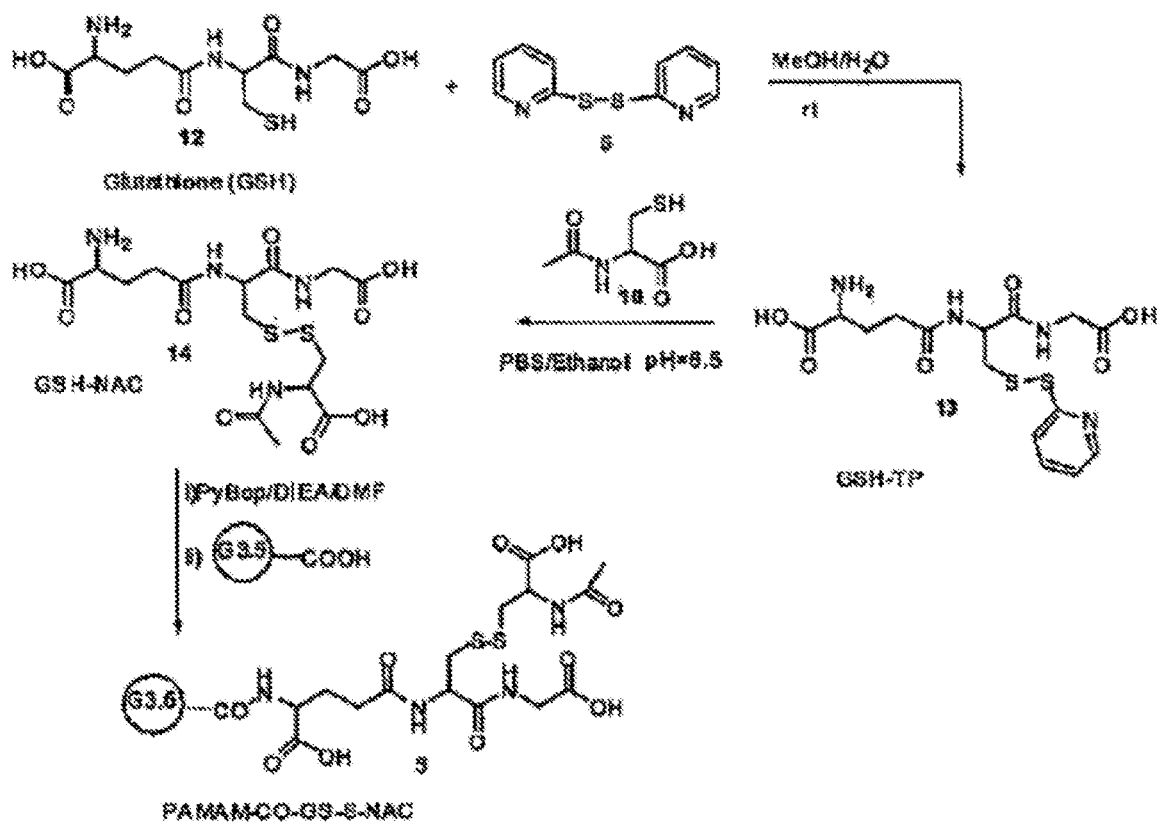
FIG. 100 shows a scheme of S-(2-Thiopyridyl) glutathione prepared from the reaction of 2,2'-dithiodipyridine in excess and the corresponding peptide in a mixture of methanol and water at room temperature.

S-(2-Thiopyridyl) glutathione, was prepared from the reaction of 2,2'-dithiodipyridine in excess and the corresponding peptide in a mixture of methanol and water at room temperature (FIG. 100). Upon completion of the reaction, methanol was removed in vacuo and the residue was washed with dichloromethane. The aqueous solution was subjected to reverse phase (RP) HPLC purification, and lyophilization of the eluent gave the pure product as a white solid (Supporting Information R-IX). This compound was reacted with NAC in PBS in pH=7.4 to get the desired glutathione-N-acetyl cysteine (GS-S-NAC) (FIG. 100) intermediate and purified. The formation of a disulfide bond was confirmed by NMR and ESI-MS (Table 4). The appearance of methyl groups in NMR at 1.90 ppm indicates the formation of disulfide bond between the GSH and NAC. To introduce the GS-S-NAC, PAMAM-COOH was reacted with GS-S-NAC in the presence of PyBop/DIEA to give the desired PAMAM-CO-GS-S-NAC conjugate (FIG. 100, Supporting Information R-XI). Introduction of S-NAC was confirmed HPLC, NMR, and MALDI. The same type of MALDI analysis yielded approximately 19.7 kDa (FIG. 67B, Supporting Information R-X) (18 GS-S-NAC groups for the PAMAM-COOH dendrimers). The number of GS-S-NAC groups was also determined via NMR analysis and the appearance of methyl protons at 1.70 and 1.92 ppm (Supporting Information R-XI) indicates the formation of GS-NAC conjugate with dendrimer. The NMR and MALDI data for the drug payload agree very well with each other, as summarized in Table 4. The yields of PAMAM-conjugates are high and reproducible.

Release Studies.

The release of NAC from the conjugates was investigated in the presence of GSH at intracellular and extracellular concentrations. It was assumed that the release of NAC would occur by the disulfide exchange reaction. GSH and its oxidized form (GSSG) are responsible for forming the intracellular redox buffer. Intracellularly, GSH takes the role of attacking thiolate moiety and gets oxidized in the process while cleaving the existing disulfide bonds. Disulfide exchange reactions do not change the total number of disulfide bonds but rather shuffle the species forming them. In the present study, the release of NAC from the conjugates by disulfide exchange reaction was confirmed by the HPLC analysis and is discussed in detail in the following sections.

Figure 69:
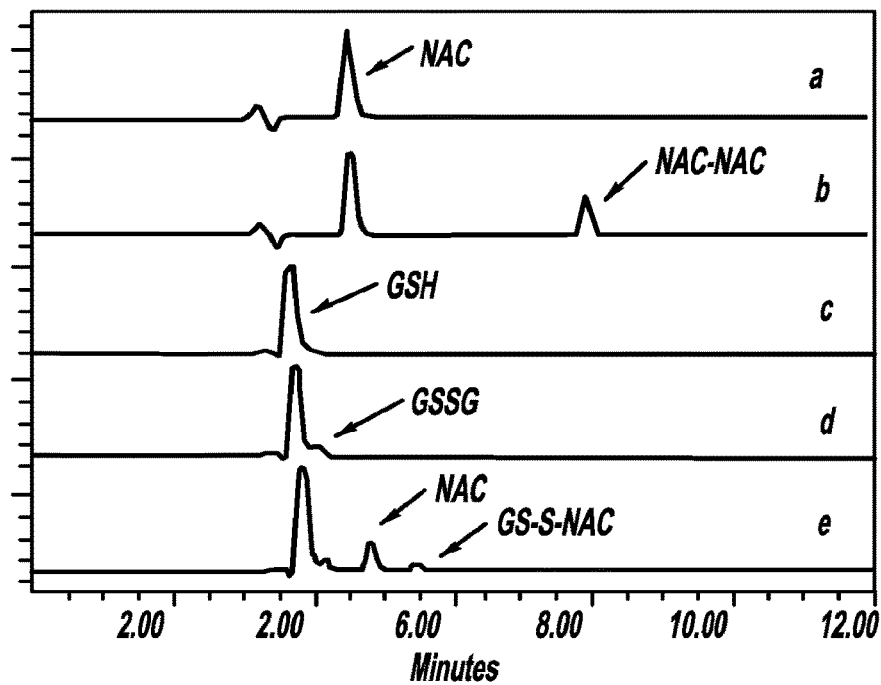
FIG. 69. RP-HPLC UV absorbance chromatograms at 210 nm (arbitrary AU units) (a) NAC; (b) NAC and NAC-NAC; (c) GSH; (d) GSH and GSSG; (e) GSH, GSSG, NAC, and GS-S-NAC.

Free NAC had an elution time of 4.7 min (FIG. 69a), whereas GSH eluted at 3.8 min (FIG. 69c). Oxidized forms of NAC and GSH were also analyzed by HPLC and the oxidized form of NAC eluted (NAC-NAC) at 8.2 min (FIG. 69b), while oxidized GSH (GSSG) eluted at 3.9 min (FIG. 69d). The GSSG peak was very close to the GSH peak, and when both were injected together, GSSG appeared as a shoulder on the GSH peak (FIG. 69d). On the other hand, NAC-NAC is more hydrophobic than NAC, as indicated by the higher elution times for the former than NAC in the chromatogram (FIG. 69b). Hydrophilicity of NAC can be associated with its thiol group, and when this group is occupied, the molecule is rendered more hydrophobic, as suggested by the significant increase in its retention time when NAC-NAC (FIG. 69b) was formed. A similar shift to higher retention was observed for GSSG, as indicated by the appearance of a shoulder on the peak seen for retention of GSH (FIG. 69d). However, this shift in retention time of GSSG is not as significant (FIG. 69d) as that seen for NAC-NAC (FIG. 69b). The retention time of GS-S-NAC (FIG. 69e) was 5.3 min, which was longer than both GSH (3.8 min) and NAC (4.7 min). This suggests that occupation of thiol groups reduces the hydrophilicity of both NAC and GSH.

Stability analysis of free NAC and free GSH suggests that both GSH and NAC go through slow oxidation and form their dimers (NAC-NAC and GSSG) by disulfide bond formation when dissolved in PBS. The rate of disulfide bond formation was relatively slow at 25% of NAC and GSH being converted to their oxidized form over 17 hours. It was determined that, in addition to their dimers, when NAC and GSH were present together, they formed GS-S-NAC as well. The formation rates of GS-S-NAC were in agreement with the oxidation rates determined for both NAC and GSH separately. When NAC and GSH were present together where GSH was in excess, no detectable NAC-NAC was formed. The conjugates were also analyzed in the absence of GSH to verify the stability of the disulfide linkage at physiological pH. When the conjugates were placed in PBS buffer and analyzed for 17 hours, both conjugates were stable and did not release any of the NAC they carried. The stability of the disulfide linkage shows that they are capable of carrying their payload without any release due to instability in aqueous media at physiological pH. The extent of the release of drug from both dendrimer-NAC conjugates was also analyzed at plasma and intracellular GSH concentrations. The conjugates and the GSH in required amounts were added to PBS solution, and the solution was analyzed at various time intervals by HPLC for up to 17 hours. UV absorbance peak areas were used to determine the concentrations of each of the species in the solution, based on appropriate calibration curves. At plasma GSH concentration (2 µM), both G3.5-CO-GS-S-NAC and G4-NH—CO—Pr—S—S-NAC conjugates were very stable and they did not release any detectable levels of free NAC within a 17 hours period. For both conjugates, 1% of the NAC payload was found in the release medium in reduced GS-S-NAC or NAC-NAC forms. The limited release of NAC in reduced GS-S-NAC or NAC-NAC forms was very rapid and competed within 1 hour. The remaining NAC stayed intact throughout the release study due to depletion of the reduced GSH in the media. This suggests that NAC releases from the conjugate rapidly but the amount of NAC released will be governed by the amount of reduced GSH available.

The expected release mechanisms of both PAMAM-NH—CO—Pr—S—S-NAC and PAMAM-CO-GS-S-NAC conjugates should be similar, with the only difference being the linker used. In the presence of excess GSH, the conjugates containing disulfide bonds can get shuffled by GSH in two possible ways. The conjugates may release NAC in the free form, while a GSH will attach onto the dendrimers forming the disulfide bond. The other possible way includes releasing of GS-S-NAC while the dendrimers have a free thiol group. The GS-S-NAC formed can be further shuffled by excess GSH present and can yield GSSG and NAC. The shuffling reactions will reach equilibrium where the concentration of each species is stabilized. These fast shuffling reactions will not change the total number of disulfide linkages, while slow oxidation reactions can also take place forming new disulfide bonds.

Figure 70:
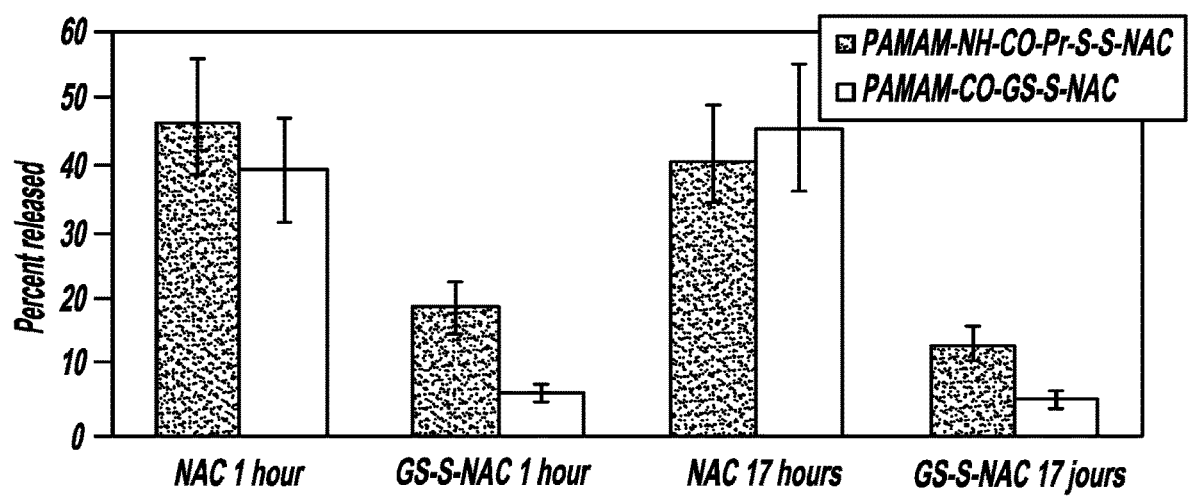
FIG. 70 depicts the release of NAC and GS-S-NAC from conjugates (in PBS with 10 mM GSH).

Both conjugates were analyzed for their release characteristics at intracellular GSH concentration (10 mM). The results suggest that both conjugates were able to release significant amounts of free NAC within an hour (FIG. 70). PAMAM-NH—CO—Pr—S—S-NAC conjugate released 47% of the NAC payload in free form within 1 hour. Additionally, 19% of NAC payload was found in GS-S-NAC oxidized form. The total NAC that was detached from the dendrimers within 1 hour was 66%. The extent of NAC released did not change significantly after the initial release within 1 hour; 41% of NAC payload was found in the free form and 14% was found as GS-S-NAC. The slight decrease in NAC content was most likely due to the error in concentration determination, and it was within standard error limits. Similarly, PAMAM-CO-GS-S-NAC conjugate released 39% of NAC in free form and another 6% in GS-S-NAC form within 1 hour, yielding a 45% total NAC release. At 17 hours, the free NAC content was determined as 46%, and 6% of NAC payload was in the GS-S-NAC form. At intracellular GSH concentration, no NACNAC was formed throughout the release studies. Absence of NAC-NAC can be explained by the excess amount of GSH present in the media, which can transfer the disulfide linkage onto either GSSG or GS-S-NAC by disulfide exchange reactions. After the initial rapid release of NAC, the concentrations the cleavage is by fast exchange reactions that reach equilibrium within 1 hour. The difference in drug release of the two conjugates may be explained by the different types of linkers used for attachment of NAC.

The study shows fast release of NAC from the conjugates in intracellular GSH levels and the stability at plasma GSH levels; these results suggest the similar release mechanism for NAC from the conjugates. This study demonstrates that PAMAM dendrimer-based NAC delivery systems can be developed for various applications. The above results have significant implications in designing dendrimer-based drug delivery systems. Enzymatic release of drugs from dendritic delivery systems is challenging. Smaller generations were shown to be capable of enzymatic cleavage, but lower generations lack the enhancements higher generations have to offer, whereas higher generations face steric hindrance issues. Commonly used pH-responsive release systems usually provide slower drug release over longer time periods unless the release takes place at a very low pH. The two GSH-responsive delivery systems described here have very fast release kinetics at intracellular conditions and demonstrate that GSH can be used as a reliable releasing agent in dendrimer-based delivery systems. Interestingly, the thiol-containing drugs are capable of forming disulfide bonds, and this is one major contributing factor for their enhanced protein binding and reduced bioavailability. Further, this study shows that the covalent linking of the thiol-containing drugs by disulfide bonds would provide a means of releasing these drugs from the carrier systems at the targeted sites.

Efficacy Assay of Conjugates.

Figure 71:
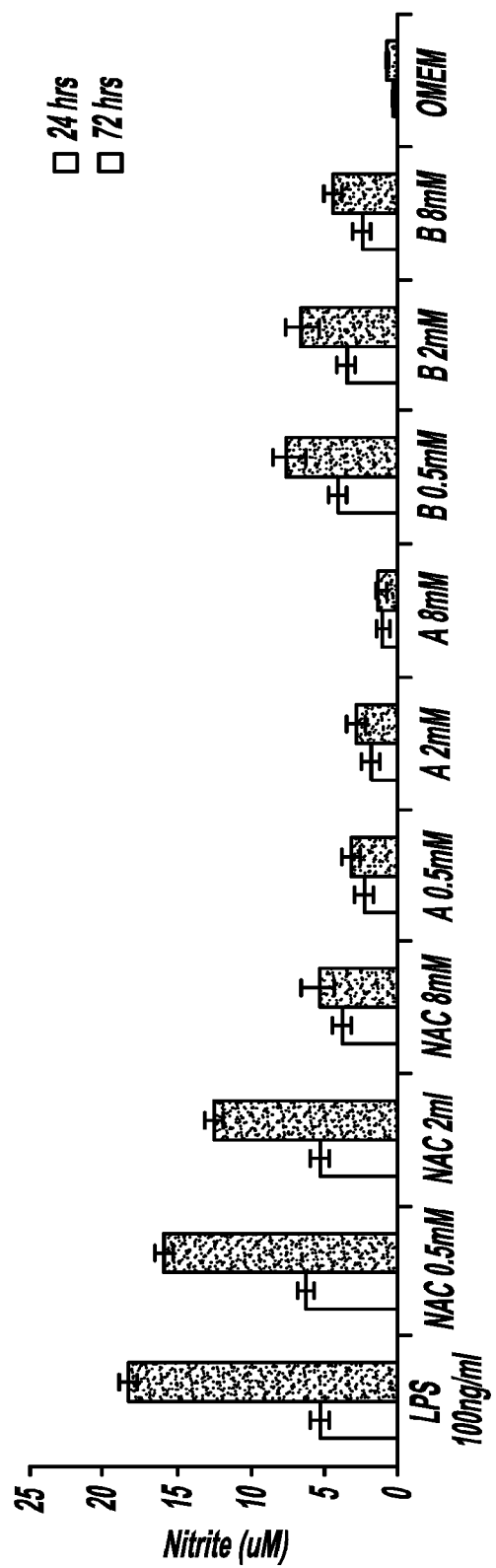
FIG. 71 shows an efficacy assay of dendrimer-NAC conjugates. BV-2 cells were treated with 100 ng/mL of LPS and the indicated concentration of NAC, PAMAM-NH—CO-Ethyl-S—S-NAC (abbreviated as A) conjugate and PAMAM-CO-GS-S-NAC (abbreviated as B) conjugate for 3 hours, and then incubated with 100 ng/mL of LPS for 24 and 72 hours. Nitrite in culture medium was measured using Griess reagent system. Data are mean (SD of three samples per group, and assessed by t test.

NAC exerts its therapeutic effects by decreasing the production of pro-inflammatory cytokines and reactive oxygen and nitrogen species. In the in vivo studies, NAC is used to treat neuroinflammation induced by activated microglial cells in perinatal brain injury. Therefore, the cellular efficacy of these conjugates was evaluated in the BV-2 mouse microglial cell line that is activated by LPS. Microglial cells activated by LPS release the free radical NO that can result in damage to membranes and DNA of the surrounding cells leading to cell death. The antioxidative properties of the conjugates were tested by measuring the nitrite levels as a marker of free radical NO production in the cell supernatant. Free NAC inhibited nitrite production in a dose dependent manner after 72 hours of incubation. At 24 hours, a time point at which a relatively lower amount of NO is produced, only the highest concentration of free NAC (8 mM) inhibited nitrite release. Both PAMAM-NH—CO—Pr—S—S-NAC and PAMAM-CO-GS-S-NAC conjugates showed significant inhibition of nitrite production even at the lowest equivalent dose of NAC (0.5 mM). In fact, in both conjugates, with anionic and cationic terminal groups, 0.5 mM NAC in the conjugated form showed equivalent efficacy to 8 mM of free NAC. The conjugates did not show a significant dose dependence, at the three concentrations equivalent to free NAC, perhaps because significant suppression (>60%-80%) was seen even at the lowest concentrations (FIG. 71) for both conjugates. Perhaps, the use of even lower concentration of conjugates may enable us to find dose dependence, but detailed dose dependence is beyond the scope of this study. At equivalent concentrations, the cationic PAMAM-NH2-NAC conjugate showed slightly better efficacy than the anionic PAMAM-COOH-NAC conjugate. From these results, it appears that improved intracellular uptake and high drug payload in the dendrimer conjugate may be producing a high local drug concentration inside the cell to elicit a significant therapeutic response. It also suggests that an appreciable amount of the drug is released intracellularly even at these relatively short time intervals (especially for polymer conjugates).

The above results have significant implications in both understanding and manipulating drug release mechanisms and achieving controlled intracellular drug release in dendrimer-based delivery systems. The results suggest that GSH can be used as a reliable in vivo releasing agent in dendrimer-based delivery systems. As the most abundant thiol species in living cells, GSH is the most likely candidate for the disulfide reduction in previously reported drug delivery systems. The relatively rapid drug release at intracellular GSH levels is key in dendrimer-based conjugates where drug release is typically much slower. The manipulation of GSH concentration in living cells as demonstrated here conclusively proves that GSH-mediated release is a viable mechanism for releasing payloads from dendrimer conjugates.

Conclusions

Dendrimer-NAC conjugates were developed as drug delivery systems for the treatment of neuroinflammation associated with cerebral palsy in perinatal applications. The PAMAM dendrimer-based intracellular drug delivery system uses a linker that uses GSH as the releasing agent. Two conjugates were prepared, one based on an anionic PAMAM G3.5-COOH dendrimer and one based on a cationic PAMAM-G4-$NH_2$ dendrimer. NMR, MALDI, and HPLC showed that the conjugate synthesis was effective and successful. In vitro release studies at different GSH levels have shown that GSH is responsible for releasing payloads from a dendrimer carrier in buffer. Flow cytometry and confocal microscopy revealed that the conjugates enter the cells rapidly and localize in the cytoplasm. The efficacy was assessed in activated microglial cells using nitrite inhibition. Both conjugates showed significant efficacy even at drug levels 16 times lower than that of the free drug. These studies address a key challenge that relates to drug release from polymer in general, and dendrimers in particular. The intrinsic ability of PAMAM dendrimers to target activated microglial cells in animal models of neuroinflammation. Combined with the findings of these studies, which allow tailoring of the intracellular release based on glutathione levels, thus enabling the design of dendrimer-drug conjugates with increased in vivo efficacy.

Example 21

PAMAM Dendrimers for Brain Delivery of Therapeutics for the Treatment of Cerebral Palsy Maternal intrauterine inflammation resulting in microglial activation has been implicated in the development of periventricular leukomalacia and cerebral palsy. N-acetyl cysteine (NAC) is a drug that is currently being explored for the treatment of neuroinflammation in neonatal and perinatal applications. However, plasma binding of NAC significantly reduces the bioavailability requiring very high doses (100-300 mg/kg in animal models). Neutral PAMAM dendrimer-based nanodevices where a disulfide linker is used to link the drug to the dendrimer were developed. This enables tailored intracellular release of the drug in a manner sensitive to the glutathione levels (low in blood circulation, high inside the cells). When this is combined with the ability of dendrimers to selectively localize in activated microglial cells, significant improvements in vivo performance is achieved. The nanodevices are evaluated extensively in a rabbit model of cerebral palsy. The biodistribution and efficacy of intravenously administered dendrimer-drug conjugates are compared with those of the free drug using a combination of tools. The biodistribution is studied using microPET imaging and tissue confocal microscopy. The efficacy is evaluated using a combination of neurobehavioral analysis, assessment of brain tissue level inflammatory cytokine analysis. The studies show that dendrimer-drug conjugates are 10-100 times more efficacious that free drug, suggesting that these conjugates (~18000 Da) are able to cross the blood brain barrier and deliver the drug significantly better than free drug.

Example 22

Dendrimer Applications in Maternal-Fetal Medicine

This Example discloses methods and compositions for delivering therapeutics to the mother, without affecting the baby, through the use of placental and amniotic sac barrier. The infection can be treated in the mother, and neuroinflammation treated in the fetus/baby. The Example also provides improved detection of cytokines in the amniotic sac, and multimodal imaging/targeting.

Treatment of neurological disorders historically has been a challenge due to the blood brain barrier (BBB). More than 98% of all small-molecule drugs do not cross the BBB. The typical small molecule threshold is 500 Da. Typical nanoplatforms, such as nanoparticles (100 nm), liposomes (~100 nm), are not expected to cross the BBB.

Biodistribution Results.

Dendrimers preferentially localize in the periventricular region, where activated microglia and astrocytes are present, allowing targeting of neuroinflammatory processes in the brain. Central nervous system (CNS) infections are diseases with high rates of morbidity and mortality. Since the majority of antimicrobial agents discovered so far do not cross the BBB, the treatment of CNS infections is a major binding of NAC to plasma proteins reduces the bioavailability significantly (to less than 8%). It is highly desirable to have fast intracellular drug release from the dendrimer, since the treatment has to be effective over the first few days. If administered IV, the drug has to reach the brain and be targeted to neuroinflammatory cells. The results disclosed herein show that dendrimers can target neuroinflammation. The thiol functional group in NAC is used to create disulfide links that release the drug based on glutathione levels (intracellular GSH levels are 1000-fold higher, so minimal release in circulation is expected). Since NAC is conjugated to dendrimers, plasma binding will be minimal.

Dendrimers, for example 5 nm objects, have unique in vivo properties, including targeting neuroinflammation both in the retina and the brain. Taking advantage of the structural and functional aspects of dendrimers can lead to improved diagnostics and therapeutic applications (nanoscale effects in medicine). Upon intravenous administration, dendrimer-NAC nanodevices can improve the efficacy by as much as a factor of 100, based on in vivo testing in rabbit models. This is achieved even without any targeting moieties on the dendrimers. Dendrimers can therefore function as a platform technology (theranostics: therapy and diagnostics).

N-Acetyl Cysteine (NAC) is a potent antioxidant and anti-inflammatory agent. NAC is a precursor of L-cysteine (Cys) and glutathione (GSH). NAC is used to treat conditions associated with cytoplasmic oxidative stress, such as during inflammation. NAC acts by binding Reactive Oxygen Species (ROS) and suppresses the production of cytokines such as TNF-$\alpha$ and IL1-$\beta$. Clinical uses of NAC include acetaminophen detoxification, stroke, detoxification of heavy metals (e.g. lead, mercury, arsenic), as an antioxidant, and now maternal-fetal applications.

Example 23

Understanding and manipulating the tissue localization and targeting of nanomaterials in different disease processes is key to improving their efficacy for specific applications. For example, therapy of several debilitating neurodegenerative and neuroinflammatory conditions of the central nervous system (CNS) such as hypoxic-ischemic injury, cerebral palsy, Alzheimer's, multiple sclerosis, and Huntington's disease have not been feasible due to the inability to deliver adequate concentrations of the drug into the CNS. Even though intraventricular delivery of drugs into the cerebrospinal fluid (CSF) results in greater drug concentration with a longer half-life in the cerebrospinal fluid (CSF), drug penetration in the parenchyma is limited, with most of the drug being taken up by the ependymal cells lining the ventricles, rather than the target cells. Implants or injections of drugs or convection-enhanced delivery (CED) into the brain interstitium are other methods that have been attempted in delivering drugs or nanoparticles/microsomes loaded with drugs into the brain. These methods are useful for localized areas of injury or disease where diffusion of the drug occurs in the area surrounding the site of insertion or delivery. The drug concentration decreases with increase in the distance from the site of injection. Hence these techniques of drug delivery would be unsuitable for diffuse neuroinflammatory or neurodegenerative disorders where multiple regions in the brain may be affected. Drug delivery vehicles that can target the inflammatory cells in targeted areas of the brain.

The unique interactions between dendrimers (with no targeting moieties) and in vivo neuroinflammatory processes are investigated in this study. Inflammatory responses in the brain are associated with the activation of microglial cells, the resident macrophages of CNS that serve the role of immune surveillance and host defense under normal conditions. Microglial cells are known to be activated by stimuli such as trauma, infection, inflammation and ischemia resulting in the secretion of pro-inflammatory mediators, generation of reactive oxygen species (ROS) and peroxynitrites that may lead to further neuronal damage. The distribution of dendrimers in the presence and absence of neuroinflammation was studied using a newborn rabbit model of maternal inflammation induced cerebral palsy. There is shown that intrauterine injection of endotoxin near-term, in pregnant rabbits leads to neuroinflammation as indicated by a robust microglial activation in the periventricular regions of the brain. This was associated with a phenotype and histologic changes indicating cerebral palsy in the newborn rabbits.

Consequently, delivering anti-inflammatory agents in a targeted manner to activated microglial cells in the central nervous system may result in attenuation of the motor deficits and brain injury seen in cerebral palsy. This strategy will also have broad applications in decreasing microglial activation in other neuroinflammatory disorders such as Alzheimer's disease, multiple sclerosis and Parkinson's disease. Although in vivo studies have shown that there is very low accumulation of dendrimers in the brain, most of these studies have used normal animals. The biodistribution of dendrimers appears to be closely related not only to its surface moieties which would dictate the interactions of the dendrimers with various cells, but also the disease state and in vivo conditions that may influence the extent of uptake of the dendrimers by various cells.

The cellular uptake and distribution of fluorescein-labeled neutral polyamidoamine dendrimers (FITC-G4-OH) was imaged following subdural injection, in the neonatal rabbit brain with and without neuroinflammation. Neutral dendrimers were chosen because of their improved biocompatibility, reduced cytotoxicity, and reduced protein interactions. Moreover, neutral and cationic nanoparticles have been shown to have the greatest diffusivity in the brain parenchyma when administrated by convection-enhanced delivery (CED). In newborns, the cerebrospinal fluid is easily accessible by injection into the subdural/subarachnoid space through the bregma, which corresponds to the anterior fontanelle or the "soft spot" in human, since the cranial sutures are not completely fused. Local delivery of drugs into the CSF in newborns can be achieved without any more invasive mechanism of injection into the interventricular space. The subarachnoid injection of FITC-G4-OH into the CSF in the newborn rabbit, the tissue images were taken by fluorescence and confocal microscopy. HPLC analyses of homogenized tissue from specific areas of the brain allowed for estimation of dendrimer uptake in the targeted region.

Preparation of FITC-G4-OH Dendrimers

To a solution of fluorescein isothiocyanate (FITC) (80 mg) in anhydrous DMSO, 1-ethyl-3-(3-dimethylaminopropyl) carbodiimide hydrochloride (EDC) (60 mg) and catalytic amount of N-dimethyl amino pyridine (DMAP) was added. [28] The reaction was stirred for 20 min and G4-OH (250 mg) was added to it, the reaction was allowed to proceed further for 18 hours at room temperature in dark. To remove unreacted FITC and EDC the reaction mixture was dialyzed (molecular cut off of membrane 1000 Da) in DMSO for 24 hours (by changing the DMSO 3 times). The DMSO solvent was lyophilization to get FITC-G4-OH. The FITC-G4-OH compound was reconstituted into methanol and precipitation in acetone. The product was dried by lyophilization to obtain FITC-G4-OH (1) conjugates. Absence of free FITC in the conjugate was verified by TLC using chloroform and methanol (ratio 1:1) as mobile phase and further by $^1$H-NMR and HPLC analysis. $^1$H NMR (DMSO-$d_6$), δ ppm 2.18 (m, G4-OH protons), 2.39-2.70 (m, G4-OH protons), 3.0-3.16 (m, G4-OH protons), 3.22-3.41 (m, G4-OH) 4.65-4.78 (bs, OH protons of G4-OH), 6.56-6.68 (m, aromatic protons of FITC), 7.76-7.91 (m, amide protons of G4-OH), 6.47-6.59 (d, 6H, Ar, FITC), 6.61-6.72 (s, 3H Ar, FITC) corresponding to the FITC protons and interior dendrimer amide protons at 7.793-7.63 (br. d, 1H, NH, interior dendrimer amide amide).

Animal Model of Cerebral Palsy

New Zealand White rabbits (Covance Research Products Inc., Kalamazoo, Mich.) with timed pregnancies that were confirmed breeders with a history of delivering 7-11 kits per litter, underwent laparotomy under general anesthesia (2-3% isoflurane by mask) on gestational day 28 (E28, term pregnancy is 31-32 days). One mL of saline for the control group (n=3) or 1 mL of saline containing 20 μg/kg of LPS (*Escherichia coli* serotype O127:B8) (Sigma-Aldrich, St Louis, Mo.) for the endotoxin group (n=3), was equally divided and injected into the uterine wall using a 27 gauge needle between the fetuses taking care not to enter the amniotic sac. This ensured that all the kits were exposed to the same amount of endotoxin. Normothermia was maintained using a water circulating blanket, and heart rate, oxygen saturations, and arterial blood pressure measured through a 20 G arterial catheter placed in the marginal ear artery, were monitored continuously during the procedure. Maternal serum was collected before laparotomy (0 hours) and at 6, 24 hours following endotoxin injection. The dams were monitored daily for changes in activity, feeding and fever. A surveillance camera was placed in the rabbit room and the dams monitored remotely to determine the time of delivery. The kits were born spontaneously at 31 or 32 days gestational age and the litter size ranged from 7-12 kits, live kits were weighed and recorded.

Tissue Processing

Animals in each group were euthanized 24 hours after subarachnoid administration of FITC-G4-OH with an overdose of pentobarbital (120 mg/kg administered intra-peritoneal). Following administration of the drug, animals were secured to a stainless steel surgical apparatus, the heart was exposed rapidly and a butterfly needle was inserted and secured in the left apex of the heart, the vena cava was incised and perfusion was initiated. Animals were perfused under pressure with 30 mL chilled physiological saline (0.9%) and 120 mL of 4% paraformaldehyde in phosphate buffer (0.1 M, pH 7.4) at a constant rate of 5 ml/min using a constant pressure pump, brains were removed and immersed in the same fixative for 48 hours, cryoprotected using graded solutions of sucrose and frozen at −80° C. until they were sectioned. Brains were embedded in 100% OCT media (Tissue-Tek®) and twenty-micron thick coronal brain sections were cut using a cryostat (Leica Microsystems; Nuchloss, Germany) and mounted on poly-L-lysine coated slides (Sigma-Aldrich, St Louis, Mo.).

Lectin, GFAP&MBP Fluorescent-Histochemistry Staining

Brain sections were washed with PBS followed by incubation in 1% hydrogen peroxide for 30 minutes in order to inactivate the endogenous peroxidase, and then in PBS solution containing 0.3% triton X-100 (PBST) and 0.5% bovine serum albumin (BSA) for 1 hours following which slides were washed thrice with PBS for 5 minutes each. For microglial staining, the slides were covered with Texas red labeled tomato lectin (1:100) (Vector Laboratories, Burlingame, Calif.) overnight. For glial fibrillary acidic protein (GFAP) immunolabeling, brain sections were incubated with mouse polyclonal GFAP to detect astrocytes (diluted 1/500; Dako Cytomation, Glostrup, Denmark). For myelin basic protein (MBP) immunolabeling, brain sections were incubated with rat monoclonal MBP to detect oligodendrocyte (diluted 1/100; Abcam). After over night incubation, slices were washed with PBS thrice for 5 minutes each and then incubated with the secondary antibody which was rhodamine-conjugated goat anti-mouse for GFAP immunostaining (diluted 1/500; Abcam.) or rhodamine-conjugated goat anti-rat for MBP immunostaining (diluted 1/200; Abcam.) for 2 hours. All slides were stained for nuclei using DAPI stain at a concentration of 1 μg/ml for 10 mins at room temperature. Slides were then rinsed in PBS, dehydrated in graded ethanol and cleared in xylene. The slides were then mounted with mounting medium (Sigma-Aldrich) and images obtained using a Leica DM2500 microscope (Leica Microsystems; Nuchloss, Germany) equipped with a camera or a confocal microscope (Zeiss LSM 310). The $\lambda$ex=495 nm, $\lambda$em=521 nm for FITC. Injection of equivalent amount of free FITC served as control.

Estimation of FITC-G4-OH in Rabbit Brain Using HPLC.

Brain tissue samples weighing approximately 1 mg were collected from healthy pups and CP pups and used for analysis. The tissue sections were homoginized in 1× ice cold cytoplasmic lysis buffer with manual agitation and repeated for 5 times. The samples were centrifuged at 8,000×g for 20 minutes and the supernatant containing the cytosolic portion of the cell lysate were obtained. The samples were analyzed by HPLC and the amount of dendrimer-FITC quantified using the standard calibration curve for FITC-G4-OH. To estimate the fluorescence as a measure of concentration of FITC-G4-OH localized in hippocampus or cortex, the samples were analyzed by reverse phase-HPLC and the amount was quantified using the standard calibration curve for FITC-G4-OH. All measurement were performed in triplicate for statistical analysis.

Results and Discussion

Preparation of FITC-Labeled G4-OH (FITC-G4-OH) Dendrimers

Figure 72:
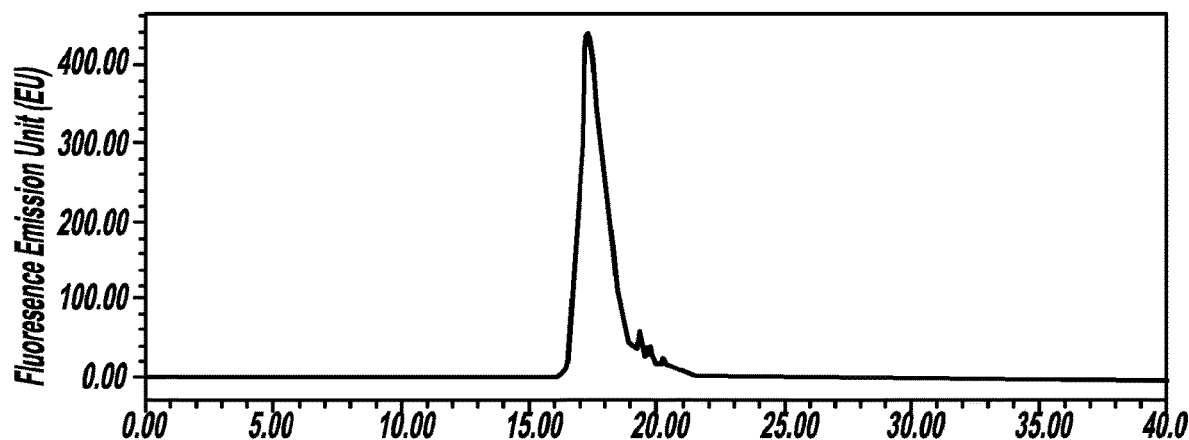
FIG. 72 is an HPLC chromatogram that shows the FITC-G4-OH (1) conjugate. The FITC-G4-OH (1) conjugate showed a single peak at 17.5 in the HPLC chromatogram indicating absence of free FITC using florescent detector ($\lambda$ex=495 nm, $\lambda$em=521 nm).
Figure 73:
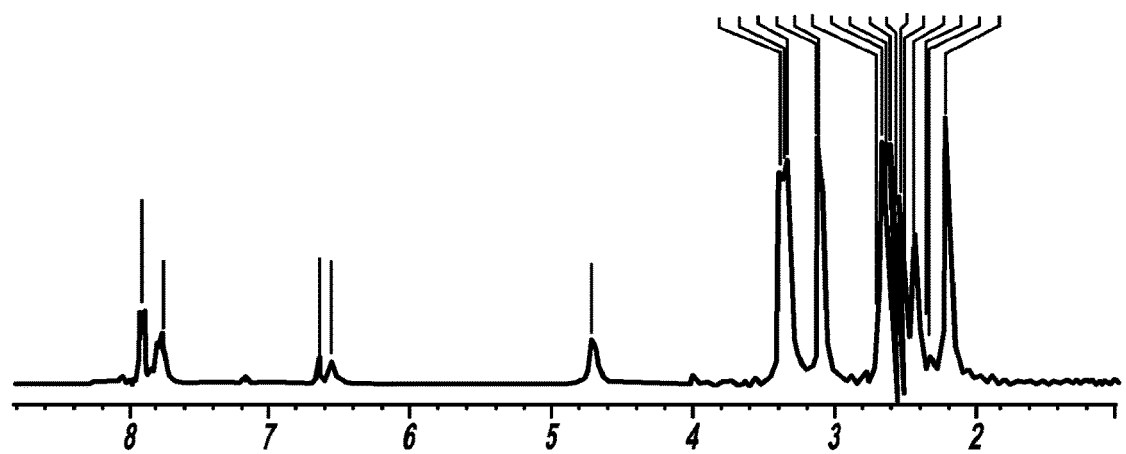
FIG. 73 is an $^1$H-NMR spectrum of FITC-G4-OH conjugate in DMSO-d6. FITC-G4-OH conjugate was obtained by the reaction of FITC with G4-OH. The integration ratio for FITC and dendrimer corresponds to 2 molecules of FITC per dendrimer.
Figure 101:
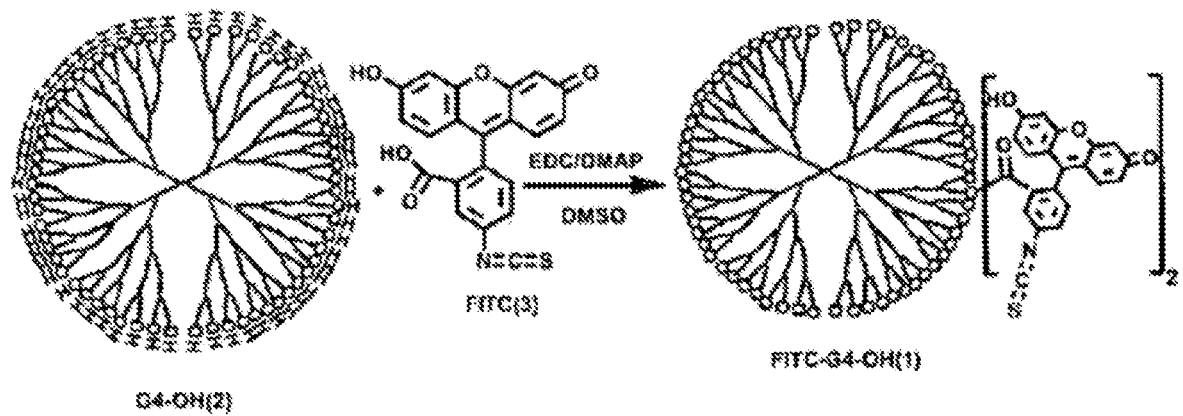
FIG. 101 shows a scheme of the carboxylic acid group of FITC, conjugated with —OH groups of PG4-OH dendrimer using 1-ethyl-3-(3-dimethylaminopropyl) carbodiimide hydrochloride (EDC) as a coupling agent.

The dendrimer (2) was covalently conjugated to FITC (3) by one-step synthesis reaction, through the formation of an ester bond. For this, the selection of an appropriate dendrimer candidate for FITC conjugation is crucial. The higher generation cationic amine-terminated dendrimers are sometimes cytotoxic when compared to the neutral hydroxyl terminated dendrimers. The appropriate dendrimers should have an adequate number of reactive, surface end groups to conjugate the FITC ensuring optimal payload. G4-OH dendrimer, which contains 64 hydroxyl groups and is non toxic within the concentration range used in the present study, was used. The carboxylic acid group of FITC was conjugated with —OH groups of PG4-OH dendrimer by using 1-ethyl-3-(3-dimethylaminopropyl) carbodiimide hydrochloride (EDC) as coupling agent (FIG. 101). With one-step reaction scheme, reasonable payload of FITC was expected because of the multiple free surface functional groups that are available on the periphery of the dendrimer, and the high reactivity of the acid group of FITC. The FITC-labeled compound (FITC-G4-OH) (1) was purified on dialysis using dialysis membrane (cutoff 1000 Da) against DMSO in dark by replacing DMSO, to remove unreacted compounds. Purity of FITC-G4-OH conjugate was confirmed by HPLC (FIG. 72) using a florescent detector ($\lambda$ex=495 nm, $\lambda$em=521 nm). The FITC-G4-OH conjugate showed a single peak at 17.5 in the reverse phase HPLC chromatogram indicating absence of free FITC which was further confirmed by the comparison of the retention times for conjugate and free FITC which were distinct. The conjugates formed through this condensation reaction were characterized using $^1$H NMR spectroscopy $^1$H-NMR was used to characterize the conjugate based on the appearance of dendrimer protons at 2.18 (m, G4-OH protons), 2.39-2.70 (m, G4-OH protons), 3.0-3.16 (m, G4-OH protons), 3.22-3.41 (m, G4-OH) 4.65-4.78 (bs, OH protons of G4-OH), and aromatic protons at 6.47-6.59 (br.d, 6H, Ar), 6.61-6.72 (s, 3H Ar) corresponding to the FITC protons and interior dendrimer amide protons at 7.793-7.63 (br. d, 1H, NH amide) respectively (FIG. 73). Further $^1$H-NMR analysis confirmed attachment of 2 molecules of FITC per dendrimer molecule in FITC-G4-OH conjugate (1).

Subdural Administration of FITC-G4-OH Leads to Localization in Activated Microglia and Astrocytes in Endotoxin Kits with Neuroinflammation.

Figure 74:
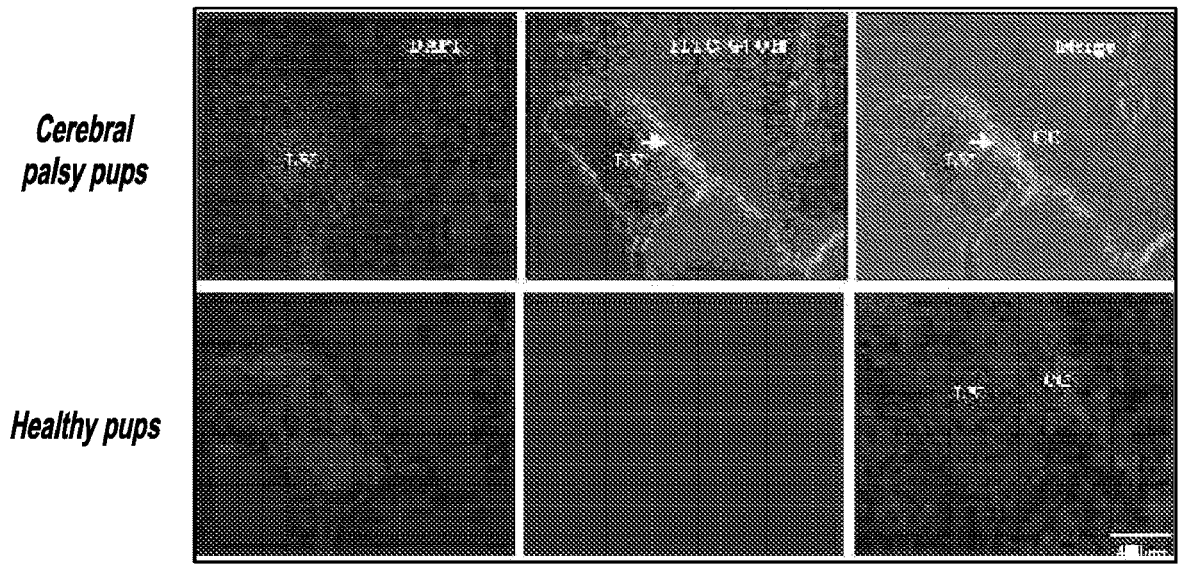
FIG. 74 shows the biodistribution of FITC-G4-OH in the brain after injection into the subarachnoid space in postnatal day 1 endotoxin and control pups. Increased uptake of FITC-G4-OH was seen in the periventricular regions in the endotoxin kits (top panel), and with no obvious uptake in the controls (bottom panel) at 24 hours post-injection, scale bar is 400 µm for lateral ventricle (LV) and for corpus callosum (CC) the scale bar is 400 µm.

Pregnant New Zealand White rabbits were injected with endotoxin lipopolysaccharide (LPS) or saline along the length of the uterus at 28 days gestation (term gestation=31 days). Rabbit pups that were exposed to maternal endotoxin in utero were born at term spontaneously with cerebral palsy while those that were exposed to maternal saline injection had a normal phenotype as previously described by the group. The full term pups were born with cerebral palsy (referred to as 'cerebral palsy pups', n=3) or those born to healthy pregnant rabbits that were administered saline (referred to as 'healthy pups', controls, n=3) were injected with 2.5 µg of dendrimer-FITC (FITC-G4-OH) in 5 µL PBS into the CSF in the subarachniod space through the skin and dura at the bregma and sacrificed 24 hours later. Brains were fixed with paraformaldehyde, frozen and sectioned into 20 □m sections, and all sections were examined under fluorescence microscopy for the presence of FITC-G4-OH. Alternating sections from the para formaldehyde-fixed and frozen brains were stained for microglia (Texas-red tagged lectin), and for astrocytes (Rhodamine-labeled Glial fibrillary acidic protein (GFAP)) to determine specific cellular co-localization of dendrimer-FITC. In the healthy pups (control), very little FITC-G4-OH was noted in the brain parenchyma (FIG. 74, healthy pups). Surprisingly, in the pups with cerebral palsy, the distribution of dendrimer-FITC in the brain parenchyma was found to be far-removed from the site of injection and localized to the periventricular white matter regions involving the corpus callosum, internal capsule, along the lateral ventricle and hippocampus, without any uptake noted in the cortex even near the site of injection (FIG. 74, CP pups). The presence of FITC-labeled dendrimer in these regions was significantly greater in the CP pups with neuroinflammation than in the healthy pups. Based on previous studies, these were the regions that were known to have an increased density of microglia and astrocytes in this rabbit model of CP.

Figure 75A:
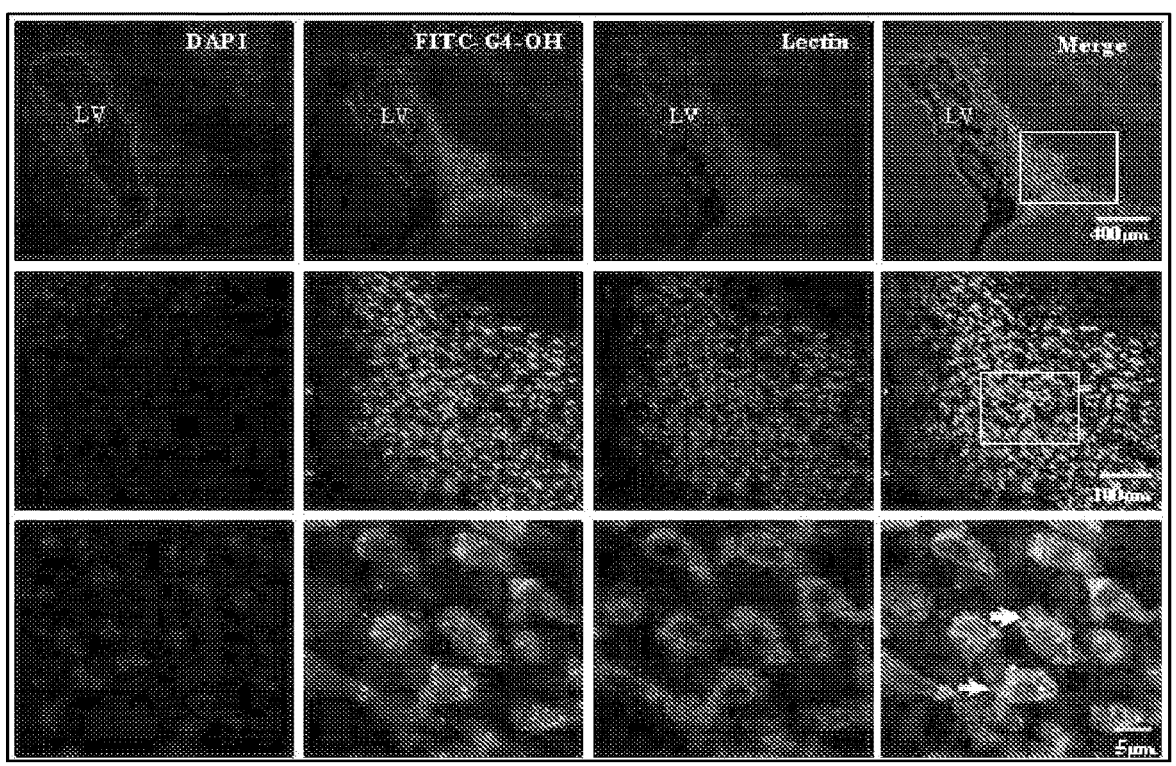
FIG. 75A shows the lectin staining of microglia for cellular distribution of FITC-G4-OH in the brain following the subarachnoid injection in postnatal day 1 CP pups. Images show uptake of FITC-G4-OH (Green) in activated microglial cells (Red, Texas-red tagged lectin staining for microglia), seen as co-localization of staining in cells (arrow) around the lateral ventricle & in the corpus callosum of the newborn rabbit brain 24 hours post-injection. DAPI staining of nuclei is seen in left hand side of each panel, scale bar is 400 µm for lateral ventricle (LV) (top panel); 100 µm (middle panel); 5 µm (bottom panel).
Figure 75B:
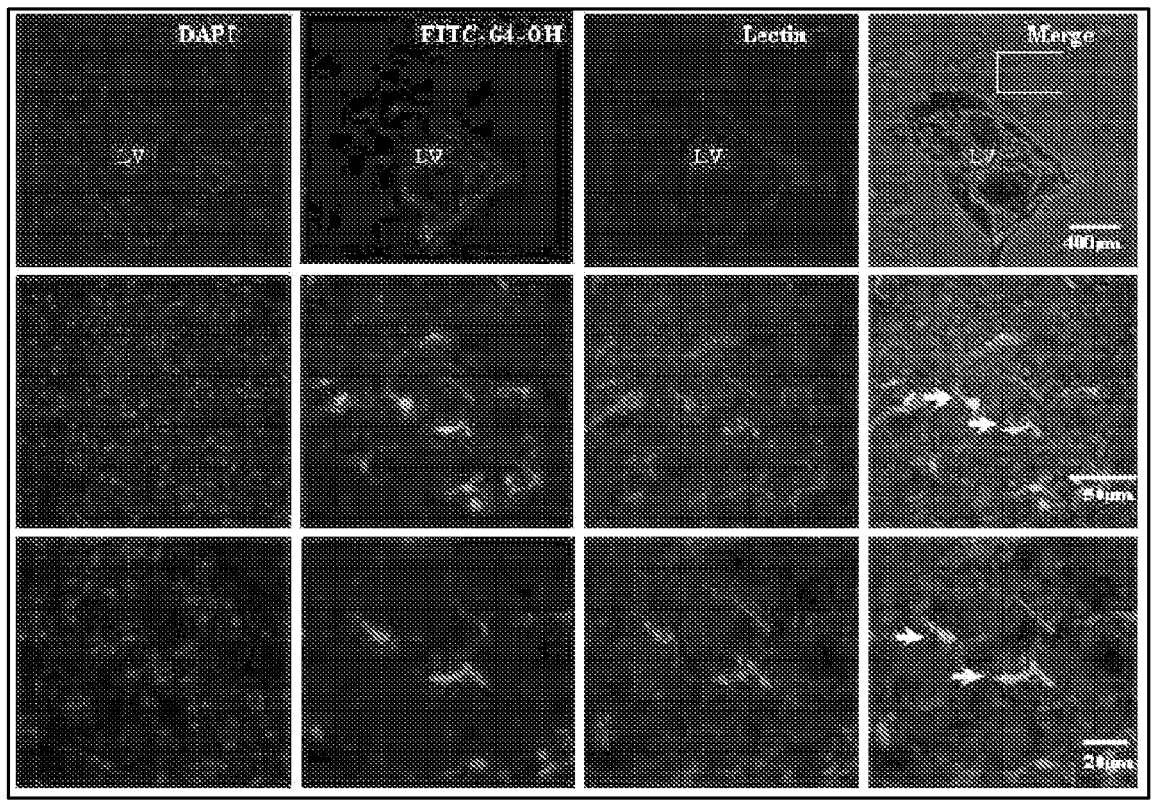
FIG. 75B shows the cellular distribution of FITC-G4-OH in the brain following subarachnoid injection in healthy pups (Lectin staining for microglia). Images show a few microglial cells (Red, Texas-red tagged lectin staining for microglia) in healthy animals that co-localize with green FITC-G4-OH (indicated by arrows), in the periventricular region of the newborn rabbit brain at 24 hours post-injection. Nuclei are identified by DAPI staining. Scale bar is 200 µm for lateral ventricle (LV) (top panel); 50 µm (middle panel) 20 µm (bottom panel).
Figure 76A:
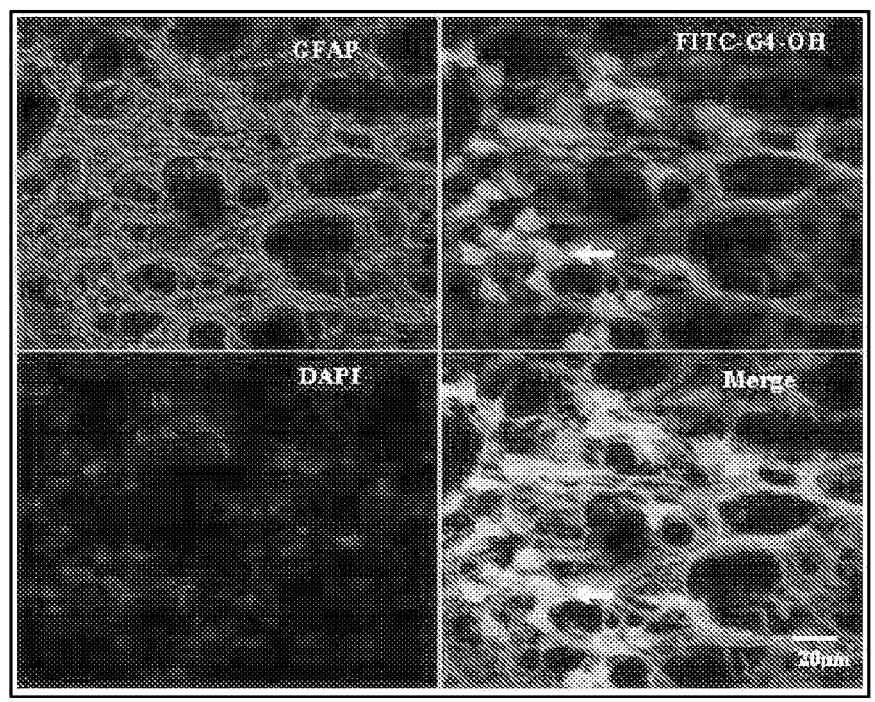
FIG. 76A shows the cellular distribution of FITC-G4-OH in the brain following subarachnoid injection in CP pups (GFAP staining for astrocytes cells). Images show significant uptake of FITC-G4-OH (Green) in activated astrocytes (Red, Rhodamine labeled GFAP staining for astrocytes), seen as co-localization of staining in the periventricular region of the newborn rabbit brain at 24 hours post-injection. Nuclei are stained blue with DAPI. Arrow indicates FITC-G4-OH co-localizing with GFAP staining in activated astrocytes. Scale bar: 20 µm.
Figure 76B:
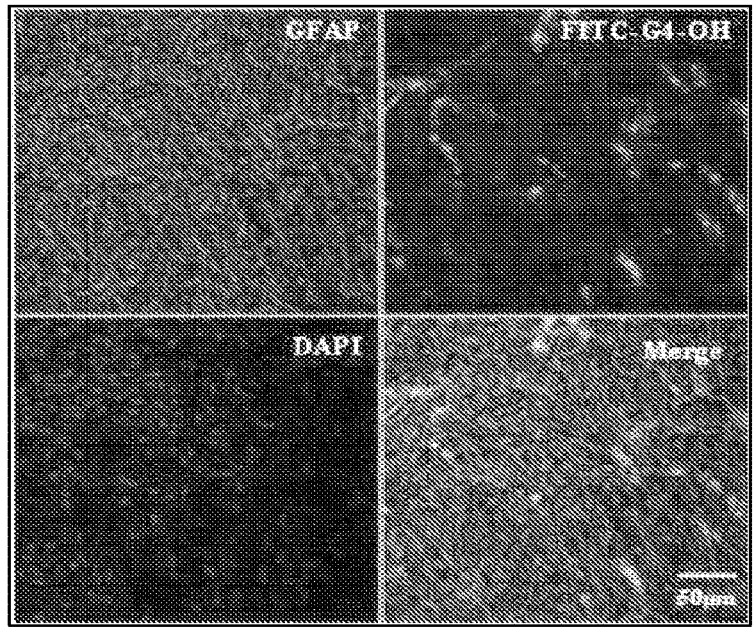
FIG. 76B shows the cellular distribution of FITC-G4-OH in the brain following subarachnoid injection in healthy pups (GFAP staining for astrocytes cells). Images show no co-localization of FITC-G4-OH (Green) with astrocytes (Red, Rhodamine labeled GFAP staining for astrocytes) 24 hours after subdural injection. The astrocytes are thinner and are not activated in the healthy animals. A few microglial cells appear to take up the FITC-G4-OH in the normal newborn rabbit. DAPI is staining nuclei. Scale bar: 50 µm.

When the microglia were stained with Texas-red tagged lectin, FITC-G4-OH was found to localize largely in the cytoplasm of activated microglial cells in both CP and healthy kits (FIGS. 75a and 75b). The activated microglia are recognized by their amoeboid cell body with short and thick processes. Since the CP pups had a significantly greater expression of activated microglial cells, there was increased dendrimer uptake noted in these animals. The co-localization of dendrimers and astrocytes were investigated by labeling astrocytes with rhodamine-tagged GFAP. In CP pups, there is significant activation of astrocytes, indicated by an increase in number, along with the enlargement of the cell bodies and thickening of the processes. In contrast, in the healthy pups, the astrocytes have thin processes and extensive branching with very small cell bodies. Dendrimer-FITC was found to co-localize significantly in activated astrocytes in CP pups (FIG. 76a), with no co-localization in astrocytes noted in the healthy pups (FIG. 76b).

Figure 77:
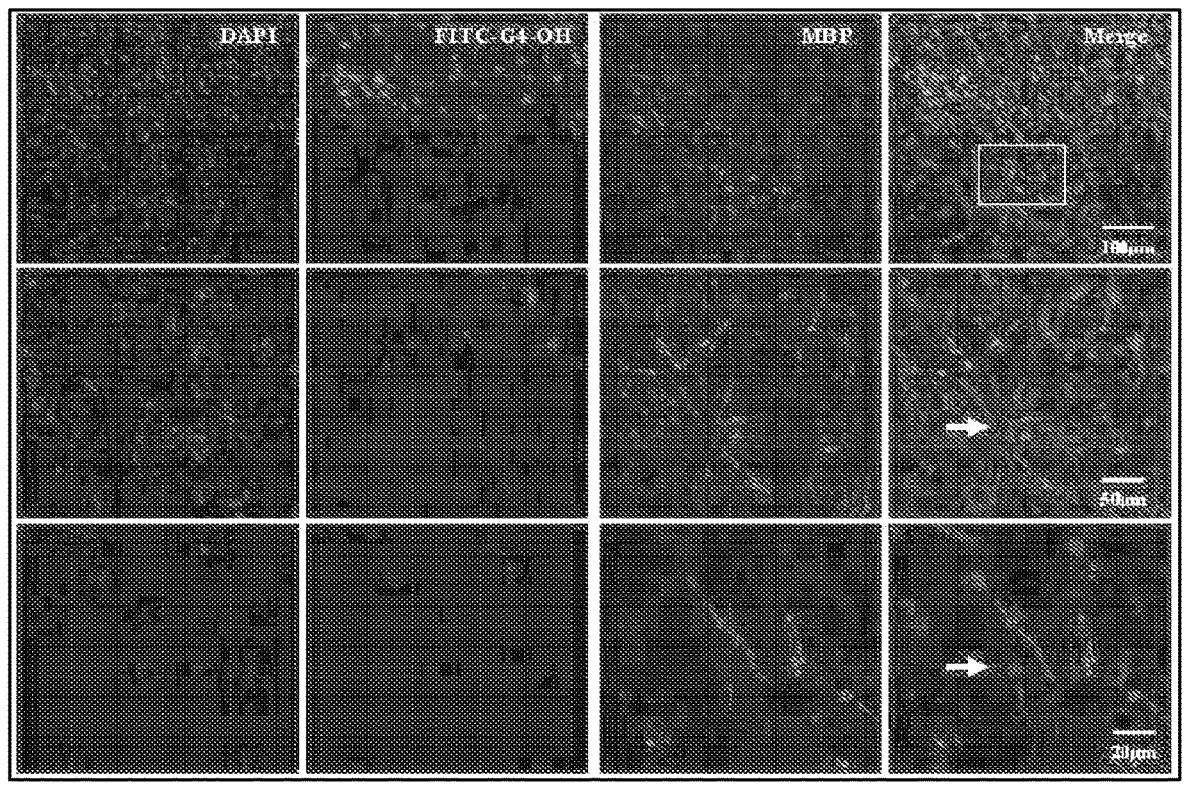
FIG. 77 show the cellular distribution of FITC-G4-OH in the brain following subarachnoid injection in postnatal day 1 control kits (MBP staining for oligodendrocytes cells). Images show no co-localization of FITC-G4OH(Green) in oligodendrocytes (Red, MBP staining for oligodendrocytes), DAPI for nuclear staining. Scale bar: 100 µm (top panel); 50 µm (middle panel) 20 µm (bottom panel). Arrow indicates oligodendrocytes.
Figure 78:
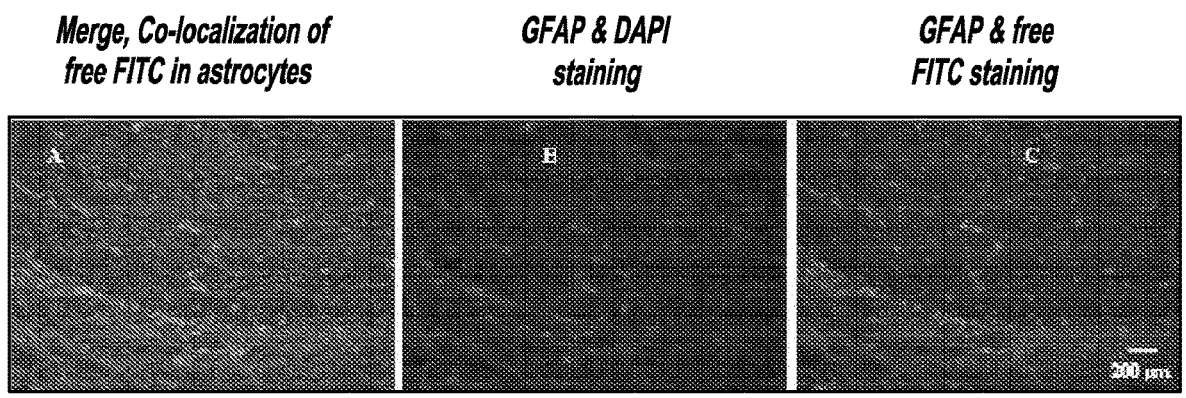
FIGS. 78A and B are images following subarachnoid injection of free FITC in the newborn rabbit. Equivalent amount of free FITC was injected and the animal was euthanized after 24 hours. Astrocytes are stained with rhodamine labeled GFAP (red). Non-specific background staining is noted throughout the tissue. No co-localization of FITC is seen with astrocytes (A). GFAP and DAPI staining in B; Free-FITC & DAPI staining in C. DAPI staining of nuclei seen in all slides. Scale bar is 200 µm.

The increased uptake and specific distribution in the periventricular regions in the CP pups is related to the presence of activated microglia and astrocytes in these areas. This may be because of the increased endocytotic ability of activated microglial cells and astrocytes in CP pups with neuroinflammation. Interestingly, cells such as oligodendrocytes and neurons that are typically not involved in causing inflammation do not appear to take up the dendrimers to an appreciable extent (FIG. 77). When equivalent amount of FITC alone was injected into the CSF, both the CP and healthy pups showed non-specific uptake in all layers of the cortex and ventricular region (FIG. 78) with relatively minimal fluorescence seen in the regions associated with inflammatory activity where an increased density of activated microglial cells and astrocytes are noted. This suggests that the unique uptake profile described is related to the properties of the dendrimer, rather than FITC.

Activated microglia and astrocytes, which are the neuroinflammatory cells, are typically found in the periventricular white matter tracts and the hippocampus in the CP pups, with the cortex being relatively spared of these cells. Localization of dendrimer-FITC in the activated neuroinflammatory cells would be further confirmed by increased presence of the dendrimer-FITC in the periventricular regions and the hippocampus with it being absent in the cortex in CP pups. In order to get a semi-quantitative measurement of the amount of dendrimer-FITC in the different regions of the neonatal rabbit brain, the hippocampus (that would be expected to localize dendrimer-FITC in the neuroinflammatory cells) and part of the frontal cortex (that would lack dendrimer-FITC due to lack of neuroinflammatory cells) were dissected from five adjacent 20 μm sections of the brain starting from the level of the bregma in both healthy and CP pups. In both groups there was no fluorescence detected in the cortex indicating that there was no detectable uptake by cells in the cortex. In the hippocampus, there are normally a small amount of microglial cells in the control and an abundance of activated microglia and astrocytes in the CP pups. A 13-fold greater fluorescence was noted in the CP pups indicating increased uptake by neuroinflammatory cells in this region, compared to control (0.0297 μg/mg±0.0044 of FITC-G4-OH in CP pups vs 0.0022 μg/mg±0.00095 in healthy pups as detected by HPLC analysis (Table 5). This corresponds well with the histological data where co-localization of dendrimer-FITC is seen with activated microglia and astrocytes that are confined to the periventricular white matter regions and the hippocampus with relative sparing of the cortex in the endotoxin animals. Table 5 summarizes (qualitatively) the regional and cellular differences in the biodistribution of the dendrimer in the brain of healthy and CP pups.

TABLE 5

Subdural Injection of FITC-G4-OH in Rabbit Model of Cerebral Palsy

| | Endotoxin animal | | Control animal | |
|---|---|---|---|---|
| | PVR | CORTEX | PVR | CORTEX |
| S. No | μg/mg tissue ± SD | | μg/mg tissue ± SD | |
| Pup 1 | 0.0321 ± 0.0041 | Not | 0.0015 ± 0.00091 | Not |
| Pup 2 | 0.0277 ± 0.0044 | detectable | 0.0024 ± 0.00098 | detectable |
| Pup 3 | 0.0292 ± 0.0045 | | 0.0028 ± 0.00096 | |
| Average | 0.0297 ± 0.0044 | | 0.0022 ± 0.00095 | |

Figure 79:
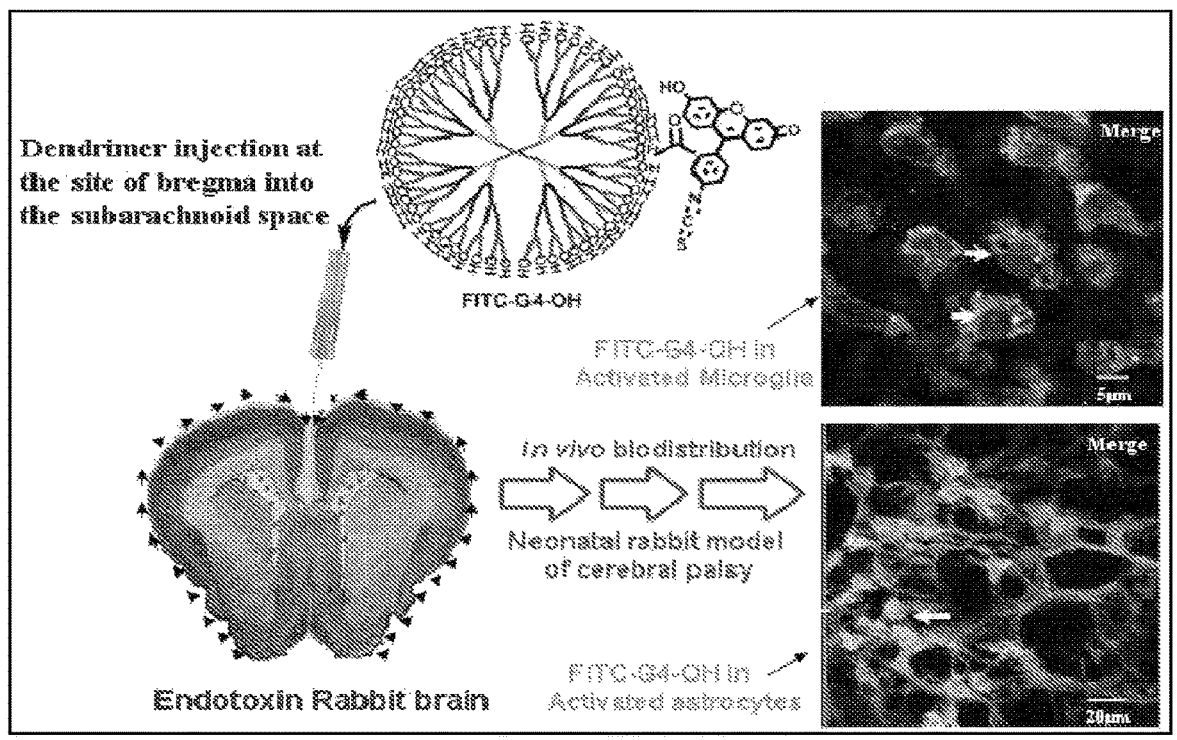
FIG. 79 is a schematic representation of dendrimer nanodevice injection and biodistribution of FITC-G4-OH in activated microglial and astrocytes its co-localization in the process occurred in cerebral palsy rabbit model.

When activated with lipopolysaccharide (LPS), microglial cells actively take up dendrimers with peak intracellular concentrations being achieved within 1-2 hours after exposure. Injection of dendrimers into the CSF in the subarachnoid space (FIG. 79) results in maximal uptake by the meninges and the cells in the cortex since they are most in contact with the CSF. Instead, it was determined that the dendrimers predominantly localize in cells in the periventricular regions and deep within the white matter and grey matter regions which are infiltrated with activated microglia and astrocytes in the newborn rabbits with neuroinflammation. The microglial cells endocytose the FITC-G4-OH from the site of injection and migrates to the periventricular region. Microglia constitutes 10% of the total cells in the brain and plays a pivotal role in immune surveillance function. Microglia constantly survey their local surrounding with their highly motile processes by endocytosing of nutrients and clearing cellular debris. Under pathological condition ramified microglia rapidly transforms into amoeboid morphology and migrates to the site of injury following a chemotaxis signal. In vivo two-photon microscopy demonstrated that microglial cells are capable to migrate within 1-2 days to newly formed amyloid plaques in an animal model of Alzheimer disease (AD). It is plausible that following subdural injection of FITC-G4-OH, microglia migrates to the site of injection, endocytose FITC-G4-OH and further migrates to the periventricular regions. Owing to the highly efficient endocytosis function of microglia, it may be presumed that in the presence of microglia there may be a limited uptake of FITC-G4-OH by oligodendrocytes or other neuronal cells. Hence, CP pups show higher uptake of FITC-G4-OH into astrocytes and microglia cells compared to healthy ones indicating a differential uptake of FITC-G4-OH by activated cells, which is expected due to inflammation.

Conclusion

Understanding the intrinsic targeting potential of nanomaterials (in vivo) has a significant impact on the design of targeting nanotherapeutic approaches. Current study suggests endocytosis of neutral PAMAM-G4 dendrimers in activated microglia and astrocytes that subsequently migrate to the location of persistent inflammation (like the periventricular region) in a rabbit model of cerebral palsy. These results indicate the prospective use of dendrimers as effective drug and gene delivery vehicles, with a potential for targeted therapy for neuroinflammatory conditions such as Alzheimer's, multiple sclerosis, Parkinson's disease and cerebral palsy. The in-vivo results of the selective uptake of PAMAM dendrimer by microgial cells in the rabbit cerebral palsy are further corroborated by the in-vitro results showing uptake of the PAMAM dendrimer in microgial cells.

This shows that nanomaterials injected into the brain can be endocytosed by activated microglial cells and astrocytes and migrate to the persistent inflammatory region, and may have broad implications in the treatment of several neuroinflammation-associated diseases, such as cerebral palsy, Alzheimer's, Multiple sclerosis, Parkinson's disease and cerebral palsy in the future.

The most significant finding of the present study is the endocytosis of PAMAM dendrimer (without a targeting ligand) into the activated microglia and astrocytes. Interestingly, these cells migrate to the persistent inflammatory region associated with neuroinflammation as seen from the immunofluorescence histological evaluation. This shows that these dendrimers can be effective drug delivery vehicles to target drugs to CNS for neurodegenerative diseases this study, by establishing that a PAMAM dendrimer (without a targeting ligand) is endocytosed by activated microglia and astrocytes and migrates to the persistent inflammatory region associated with neuroinflammation. Thus these dendrimers will be effective drug delivery vehicles to target drugs to CNS for neurodegenerative diseases.

Example 24

In Vivo Efficacy and Biodistribution of Dendrimer-NAC Conjugates

Results:

5.5 mg/kg of dendrimer-alexa was injected intravenously to both control and endotoxin-administered mothers in the rabbit model. The animals were sacrificed 24 hours later, by administering a cocktail of ketamine and xylazine (IM; 45-75 mg/kg and 5-10 mg/kg respectively). Anesthetized animals were secured to a stainless steel surgical apparatus, the heart was exposed and a butterfly needle was inserted and secured in the left apex of the heart, the vena cava was incised and perfusion was initiated. After blood collection, animals were perfused under pressure with 30 mL chilled physiological saline (0.9%). After the rabbits were sacrificed, liver, lung, kidneys, large and small intestine, heart, spleen, placenta samples were removed and stored at −80 C until analyses were performed. The dendrimer was extracted from the thawed samples according to Whelpton's protocol. The extracting solution consisted of methanol-dimethyl sulfoxide-water (32:8:1 v/v/v). Tissues were rinsed in cold saline, blotted dry on filter paper and weighed. Tissue samples (40 mg, depending on the organs) were homogenized 10-20 seconds in 0.1 mL ice-cold extracting solution with a homogenizer, repeat this procedure 5-8 times. The sample was kept on ice during homogenization. The homogenate was then centrifuged (10 min, 600 g) and supernatants were kept for further HPLC analysis. Results on amniotic fluid and placental samples collected from an endotoxin-administered rabbit pup and mother respectively, are shown for the HPLC quantification of dendrimer-alexa uptake.

In Vivo Evaluation of Free n-Acetyl Cysteine and Dendrimer-n-Acetyl Cysteine for the Treatment of Neuroinflammation in a Newborn Rabbit Pup with Cerebral Palsy Based on the results that showed that dendrimers can target neuroinflammation even upon intravenous administration to newborn pups with CP, the efficacy of dendrimer-NAC in suppression of neuroinflammation and oxidative stress along with attenuation of motor deficits was evaluated. The neutral dendrimer-NAC conjugate (D-NAC) was used in this study. Newborn littermate rabbits born with motor deficits secondary to maternal endotoxin administration were treated with a single dose of either PBS, NAC 100 mg/kg, D-NAC 1 mg/kg or 10 mg/kg, or dendrimer alone on day 1 of life (31 days post-conception). Newborn rabbits were then subjected to neurobehavioral testing on day 5 of life. Animals were video-taped for 10 minutes and were scored by two observers in a blinded manner. Scores were based on the maximum number of steps taken without falls (scored from 0-4) and number of hops without falls (scored from 0-4) in one minute of continuous activity. Both scores were averaged for obtaining the final score. Since the newborn rabbits are not able to hop on day 1, the maximum score that can be obtained is 4 for day 1 of life and 8 for day 5 of life.

Experimental Design:

Pregnant New Zealand white rabbits at 28 days gestation underwent laparotomy and endotoxin injections. Controls had no intervention. Littermates were treated at birth with PBS, NAC 100 mg/kg, Dendrimer-NAC(D-NAC) 1 mg/kg, Dendrimer-NAC 10 mg/kg, or Dendrimer linker.

Significance:

The in vivo results suggest that attenuation of neuroinflammation using dendrimer-NAC in the newborn leads to significant improvements in the motor deficits, and myelination. When conjugated to the dendrimer, NAC is significantly more effective than NAC (by as much as a factor of 100. This is despite the fact that the conjugate (~18 kDa) was injected IV, and that the dendrimer had no targeting ligands. This validates the dendrimer-based therapeutic approach for neuroinflammation in this model, and provides impetus for the proposed future research.

Example 25

Antimicrobial Properties of Neutral PAMAM Dendrimers

Intrauterine infection is usually caused by microorganisms ascending from vaginal and affecting the fetus and amniotic fluid leading to chorioamnionitis, cerebral palsy, increased efficiency of HIV seroconversion, miscarriage, and spontaneous preterm birth (Chaim et al., 1997), (Romero, 2003; Ugwumadu, 2007). Chorioamnionitis is known to cause fetal brain injury (Patrick et al., 2004) due to the generation of pro-inflammatory cytokines (Dickinson et al., 2009; Harnett et al., 2007). Antibacterial and antifungal agents are applied to vagina and cervix to treat intrauterine infections in the pregnant women (Chaim et al., 1997; Ugwumadu, 2007). E. coli infection in pregnant guinea pig can be treated by topical vaginal and cervical application of $G_4$-PAMAM-OH dendrimer. This is the first report using the guinea pig model of chorioamnionitis to induce E. coli infections and show the effective inhibition of bacterial growth by treatment with $G_4$-PAMAM-OH. Cytokine levels in placenta of the $G_4$-PAMAM-OH treated animals were comparable to those in healthy animals and significantly less than infected animals. Although PAMAM dendrimers are the most extensively studied dendrimers the antimicrobial activity of unmodified $G_4$-PAMAM-OH and $G_{3.5}$-PAMAM-COOH has not been reported previously. Though $G_4$-PAMAM-$NH_2$ dendrimer shows strong antibacterial activity it shows high cytotoxicity to human cervical cell line and the antibacterial activity of G4-PAMAM-OH dendrimer is notable since it is non-cytotoxic at higher concentrations. $G_4$-PAMAM-OH has a potential as antibacterial agent.

Experimental Section

Materials

The PAMAM dendrimers (generation 4, with end groups OH, $NH_2$ and generation 3.5 COOH 14.93% w/w in methanol) were purchased from Dendritech. 3-(4, 5-dimethylthiazol-2-yl)-2, 5-diphenyltetrazolium bromide (MTT), 2-Nitrophenyl-β-D-galactopyranoside (ONPG), Osmium tetrozxide N-Phenyl-1-naphthylamine (NPN), Glutaraldehyde and Hexamethyldisilazane were purchased from Invitrogen. Nutrient broth and nutrient agar were purchased from BD Biosciences. Mouse TNFα, IL-6 and IL-1β ELISA kits were purchased from R&D Systems.

Preparation of Bacteria

Escherichia coli (ATCC 11775) isolated from human urine is the bacterial strain used in this study. Single colony on nutrient agar was used to inoculate 5 mL of nutrient broth at 37° C. overnight. A small volume (100 μL) of this growth was used to inoculate 20 mL of nutrient broth media at 37° C. for 6 hours. The bacteria were resuspended at $10^6$ colony forming units (CFU)/mL for the experiments.

Bacterial Growth Inhibition Assays

The inhibitory concentration ($IC_{50}$) of dendrimers was determined using the broth microdilution method (Lopez et al., 2009; Wiegand et al., 2008). Briefly, serial dilutions of dendrimers (0.76 g/mL to 200 mg/mL) were prepared in PBS and combined 1:1 v/v with bacteria at $10^6$ CFU/mL in a 96 well polypropylene plate. After incubation at 37° C. for 18 hours, the absorbance was measured at 650 nm using a microplate reader to assess the cell growth. The positive-control wells contained PBS and nutrient broth medium inoculated with bacteria ($5\times10^5$ CFU/mL), and the negative-control wells contained PBS and nutrient broth medium without bacteria. The $IC_{50}$ value was determined as the concentration of the dendrimers which inhibits 50% of microbial growth after 18-24 hours incubation (Lopez et al., 2009; Wiegand et al., 2008). The % survival of the bacteria was determined on the basis of the positive control which was considered as 100%.

Evaluation of Normal Cell Cytotoxicity

End1/E6E7 and BV-2 (passage 19) cells were seeded into a 96-well plate at $1.5\times10^4$/well, and $5\times10^3$/well, respectively. After 24 hours, cells were exposed to various concentrations of dendrimers (10 ng/mL to 1 mg/mL) in serum free medium for 24 hours. Controls were carried out with medium alone. Cytotoxic effect was determined using MTT assay. The proportion of viable cells in the treated group was compared to that of the control.

Evaluation the Antimicrobial Activity in Guinea Pig Model of Chorioamnionitis

All the animal experimental procedures were approved by the institutional animal care and use committee of Wayne State University. Intracervical bacterial inoculation was performed as previously reported (Patrick et al., 2004). Briefly, pregnant Dunkin-Hartley strain guinea pigs (Charles River) at 52 days of gestation were anesthetized with 1.5% isoflurane using the mask. An endoscope was used to visualize the cervix. Guinea pigs were inoculated intra-cervically with 150 CFU E. coli (n=11) to induce infection. Dendrimer $G_4$-PAMAM-OH 500 µg was injected into the cervix 5 min after E. coli inoculation in the treatment group 3 (n=4). The E. coli inoculated guinea pigs without treatment (group 2) were used as positive control (n=4). The guinea pigs without any treatment (group 1) and inoculation were used as negative controls (n=3). Forty eight hours after intervention, guinea pigs were euthanized with pentobarbital sodium (120 mg/kg) and midline laparotomy was performed to expose uterus. Amniotic fluid was collected from each gestational sac and 50 µL was plated on nutrient agar to determine the presence of microbiologic chorioamnionitis.

Cytokine Quantification in Placenta

The placental tissue (0.3 g) was homogenized in 1 mL RIPA lysis buffer. The homogenate was kept on ice for 30 min, centrifuged at 10,000 g for 25 min at 4° C. and the protein concentration of supernatant was determined. Cytokines; tumor necrosis factor (TNFα), interleukin (IL-6 and IL-1β) concentrations were measured in the total protein fraction using ELISA kits (Ethier-Chiasson, 2008).

Statistical Analysis

Data are presented as mean±SD. Specific comparisons between control and individual experiment were analyzed by ANOVA test with p-value less than 0.05 considered as statistically significant.

Results

Antimicrobial Assay

Figure 80A:
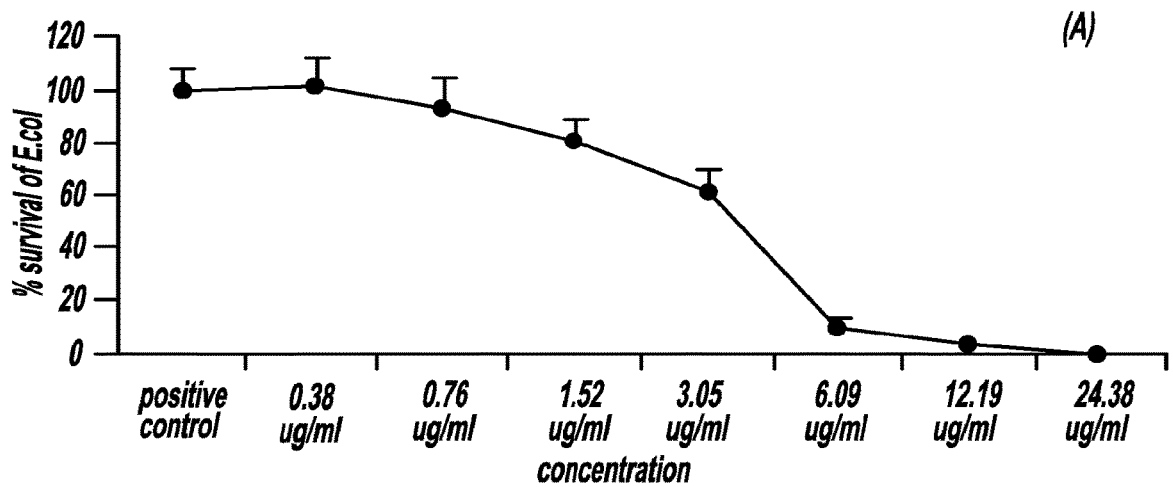
FIG. 80 depict bacterial growth inhibition assays. *E. coli* was treated with the indicated concentration of $G_4$-PAMAM-$NH_2$ (A) and (B), $G_4$-PAMAM-OH (C) and (D), $G_{3.5}$-PAMAM-COOH (E) and (F) dendrimers for 18 hours. The initial concentration used for bacterial seeding was $5 \times 10^5$ CFU/mL. Three samples were in each group. Bacterial growth was measured by turbidity as the optical density at 650 nm using a microplate reader. *P<0.05, P<0.01, *P<0.001 VS Positive control.
Figure 80B:
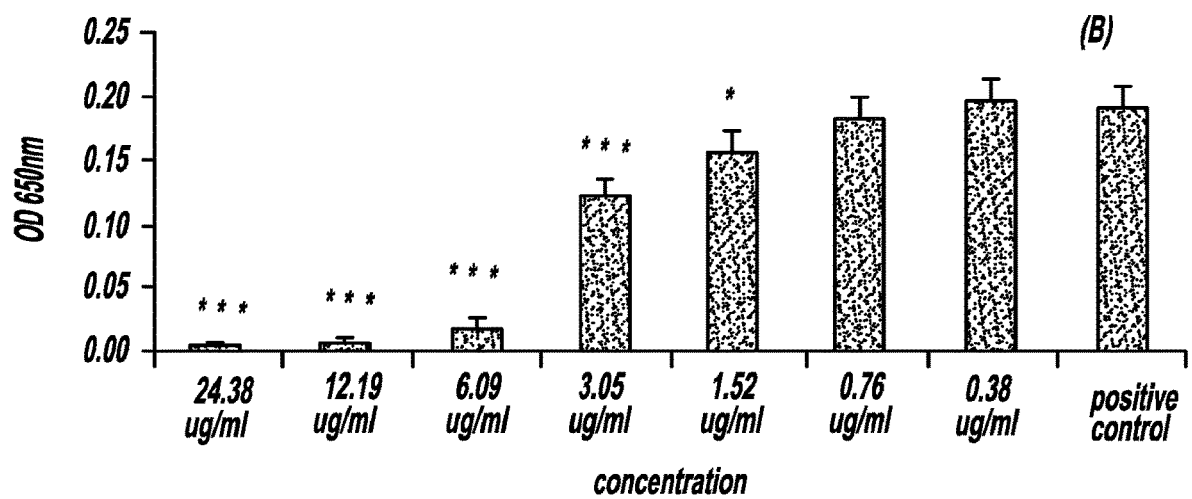
Figure 80C:
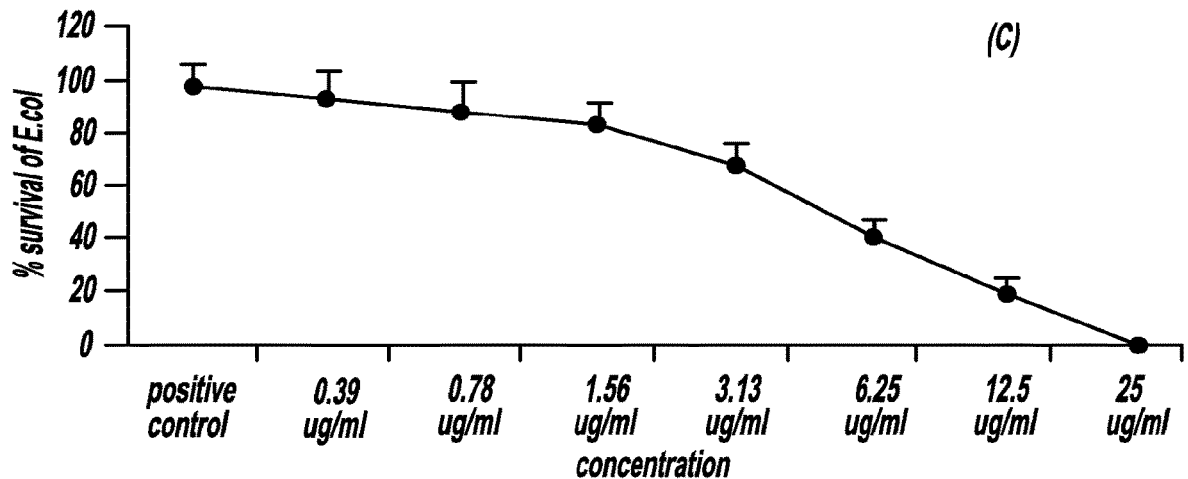
Figure 80D:
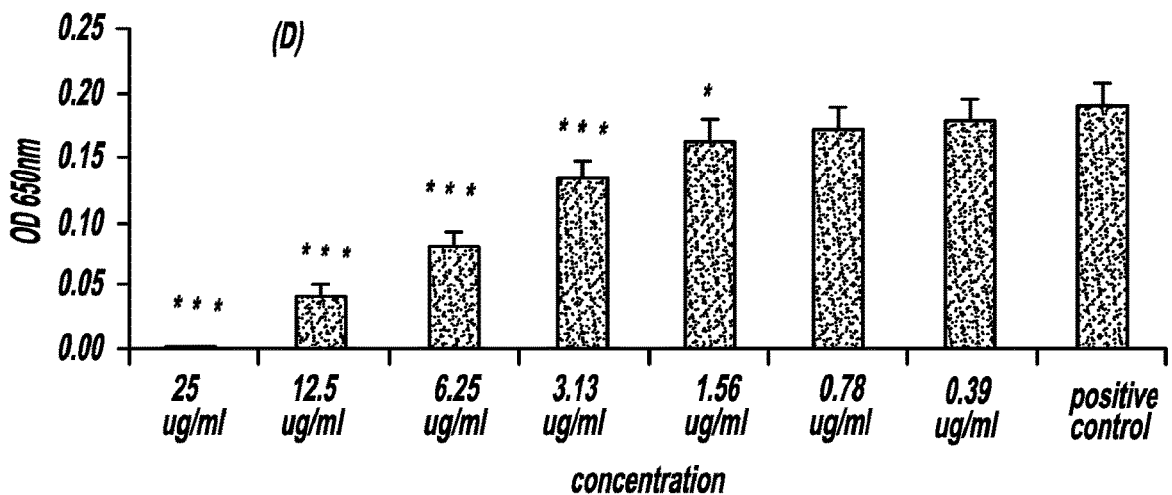
Figure 80E:
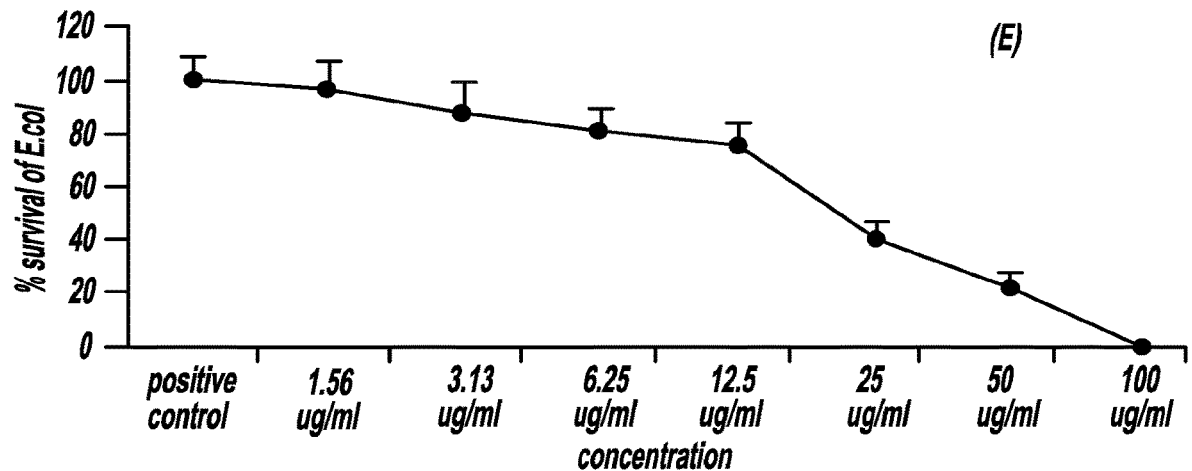
Figure 80F:
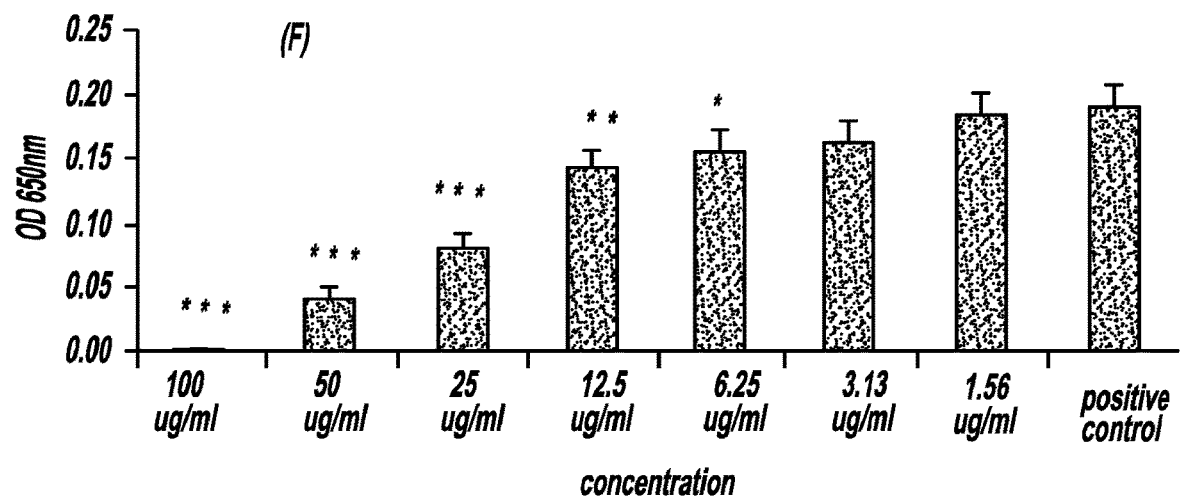
Figure 81A:
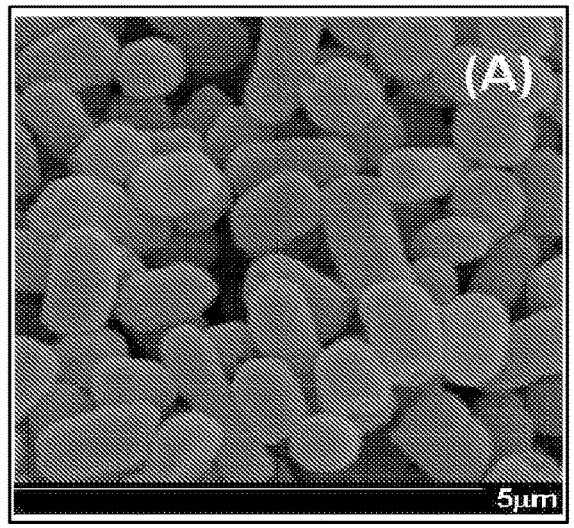
FIGS. 81A-D are SEM images of *E. coli*. (A) untreated *E. coli* (B) 8 hours treatment of $G_{3.5}$-PAMAM-COOH (C) 8 hours treatment of $G_4$-PAMAM-OH (D) 8 hours treatment of $G_4$-PAMAM-$NH_2$. Magnification 20000×. Scale bars indicate 5 μm. The treatment with dendrimers shows the damage to the bacterial cell wall.
Figure 81B:
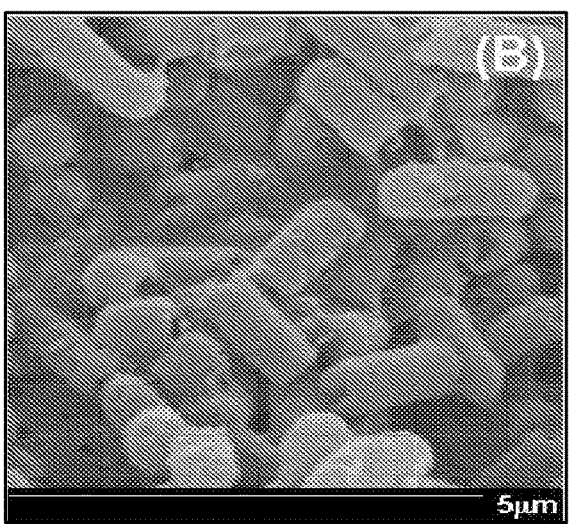
Figure 81C:
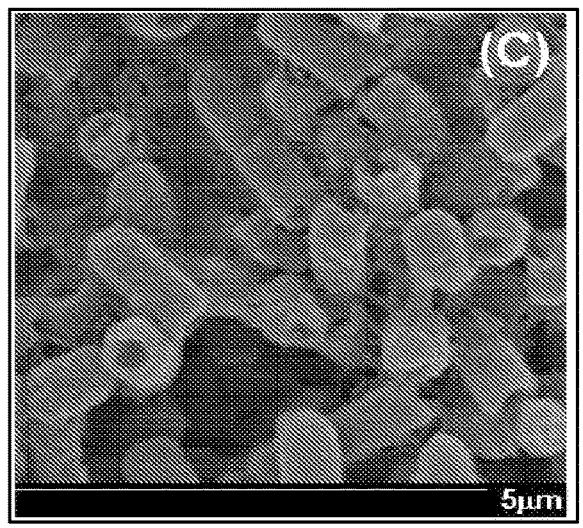
Figure 81D:
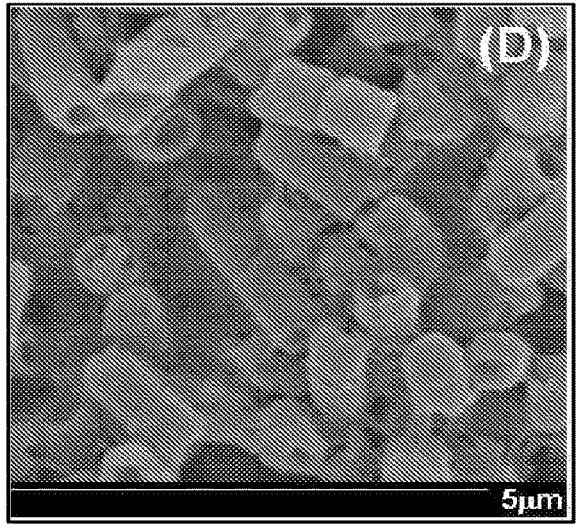

An antibacterial assay procedure reported previously (Lopez et al., 2009) was used to assess the antimicrobial activity of $G_4$-PAMAM-OH and $G_{3.5}$-PAMAM-COOH dendrimers towards the gram negative bacteria E. coli and compared it with the activity of $G_4$-PAMAM-NH$_2$. E. coli was used in this study since it is known to cause the choriomanionitis condition in pregnancy and there is an established guinea pig model based on E. coli infection (Patrick et al., 2004). E. coli was used for in-vitro and in-vivo evaluations to demonstrate the antibacterial activity of PAMAM dendrimers. In the present study the $IC_{50}$ values of PAMAM dendrimers were measured using a modified broth microdilution assay in a 96-well plate format. The optical density of the suspension of bacteria in different dendrimer solutions was measured at 650 nm. The $IC_{50}$ value of the dendrimer was then obtained from the plot of % survival of bacteria vs. the concentrations of the dendrimer and the plot of optical densities vs. the concentrations of the dendrimer. $G_4$-PAMAM-OH, $G_{3.5}$-PAMAM-COOH and $G_4$-PAMAM-NH$_2$, dendrimers inhibited the growth of E. coli in a concentration-dependent manner as seen from 18 hours treatment (FIG. 80B). The strong antimicrobial activity of $G_4$-PAMAM-NH$_2$ is consistent with that reported previously (Calabretta et al., 2007). It is interesting to note that $G_4$-PAMAM-OH markedly inhibited the growth of E. coli from 3.13 mg/mL to 25.0 mg/mL concentration. $G_{3.5}$-PAMAM-COOH also inhibited the growth of E. coli but at relatively higher concentrations 6.25 mg/mL to 100 mg/mL. The $IC_{50}$ values for $G_4$-PAMAM-OH, $G_{3.5}$-PAMAM-COOH and $G_4$-PAMAM-NH$_2$ were observed as 5.4 mg/mL, 22.0 mg/mL and 3.8 µg/mL respectively. Since $G_4$-PAMAM-NH$_2$ dendrimer exhibits high cytotoxicity, the $G_4$-PAMAM-OH was considered for in-vivo evaluations in guinea pigs.

For the amine terminated PAMAM dendrimers its proposed that the amino groups form nanoscale holes in supported lipid bilayers of bacterial membrane causing its rupture and cell lysis (Calabretta et al., 2007; Hong et al., 2006; Mecke et al., 2005; Milovic et al., 2005). The quaternary ammonium dendrimers adsorb onto negatively charged bacterial cell surfaces, diffuse through the cell wall, bind to cytoplasmic membrane, disrupt and disintegrate the cytoplasmic membrane, release of electrolytes such as potassium ions and phosphate from the cell and release nucleic materials such as DNA and RNA, all contributing to the death of the bacterial cell (Chen et al., 2000). These reports suggest that dendrimers mediate their antimicrobial activity by disrupting the bacterial outer and inner membrane. The antibiotic ampicillin is known to penetrate the outer membrane of gram negative bacteria and inhibits the bacterial cell wall synthesis. The antibacterial activity of dendrimers is limited to its effect on bacterial membrane permeabilities.

Cytotoxicity Assay

The cytotoxicity of PAMAM dendrimers was evaluated against human cervical epithelial (End1/E6E7) and immune cells; mouse microglial cells (BV-2). MTT assay showed that $G_4$-PAMAM-OH and $G_{3.5}$-PAMAM-COOH dendrimers were non cytotoxic to End1/E6E7 cells and BV-2 cells in 24 hours treatment at concentrations 10 ng/mL-1 mg/mL (FIG. 85). The $G_4$-PAMAM-NH$_2$ showed high cytotoxicity above 10 µg/mL concentration to human cervical epithelial End1/E6E7 cells. Also the $G_4$-PAMAM-NH$_2$ exhibited cytotoxicity at 1 mg/mL concentration to microglial cells. On the basis of the MTT assay, $G_4$-PAMAM-OH did not exhibit cytotoxicity upto 1 mg/mL concentration, while the $G_4$-PAMAM-NH$_2$ was found to be cytotoxic at higher concentrations. The indication chorioamnionitis is induced due to E. coli infections in the vagina. The experimental data shows that $G_4$-PAMAM-OH dendrimer is non cytotoxic to the human cervical cell line and also exhibits antibacterial activity towards E. coli, hence it was chosen as antibacterial agent to treat chorioamnionitis in pregnant guinea pigs. In the in-vivo experiments a total of 500 µg of $G_4$-PAMAM-OH were applied to the cervix of E. coli infected pregnant guinea pigs and at this concentration the dendrimer showed efficacy.

Antimicrobial Activity in Guinea Pig Model of Chorioamnionitis

The in-vitro studies brought out antibacterial potential of $G_4$-PAMAM-OH dendrimer as seen from the antibacterial assay, OM and IM permeabilization assays and bulk changes in morphology seen from SEM analysis. These interesting results coupled with its non cytotoxicity to human cervical epithelial cells encouraged the evaluation of $G_4$-PAMAM-OH as an antibacterial agent in-vivo using the guinea pig model of chorioamnionitis. Though this model is established for creating infection and assessing injury to the fetus, it has not been previously used to demonstrate the effective treatment. This shows the treatment of the pregnant guinea pig using the model of chorioamnionitis. The ascending E. coli infection causes chorioamnionitis which is associated with development of cerebral palsy, a motor disorder in children due to stimulation of proinflammatory cytokines causing white matter damage and fetal brain injury (Patrick et al., 2004). The dose of the E. coli inoculation in the guinea pigs (n=17) was optimized in the pilot experiments for the strain (ATCC 11775). 1000 CFU of E. coli effectively induced the infection causing extreme sickness in mother and further this dose lead to abortion of dead fetuses within 48 to 72 hours. The lower CFU of E. coli were subsequently inoculated to identify the optimum dose, which lead to infection and yet the guinea pigs did not abort upto 48 hours. Based on this evaluation a dose of 150 CFU of E. coli was found to effectively induce the infection in the pregnant guinea pigs without leading to abortion of fetuses.

Figure 87A:
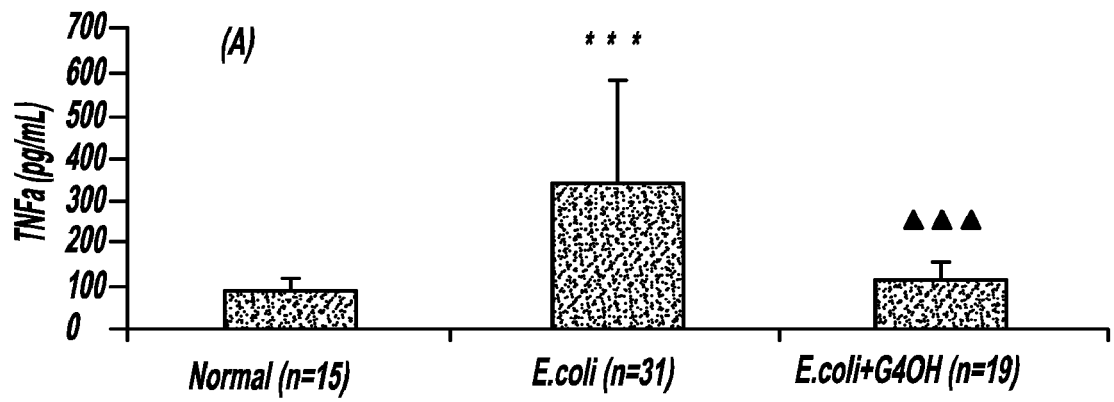
FIG. 87 show the placental tissue (0.3 g) was homogenized in 1 ml RIPA lysis buffer. The homogenate was kept on ice for 30 minutes and the protein concentration of supernatant was determined. Cytokines concentrations were measured in the total protein fraction using ELISA. *P<0.05, ***P<0.001 VS Normal control. ▲▲P<0.01, ▲▲▲P<0.001 VS *E.coli* group.
Figure 87B:
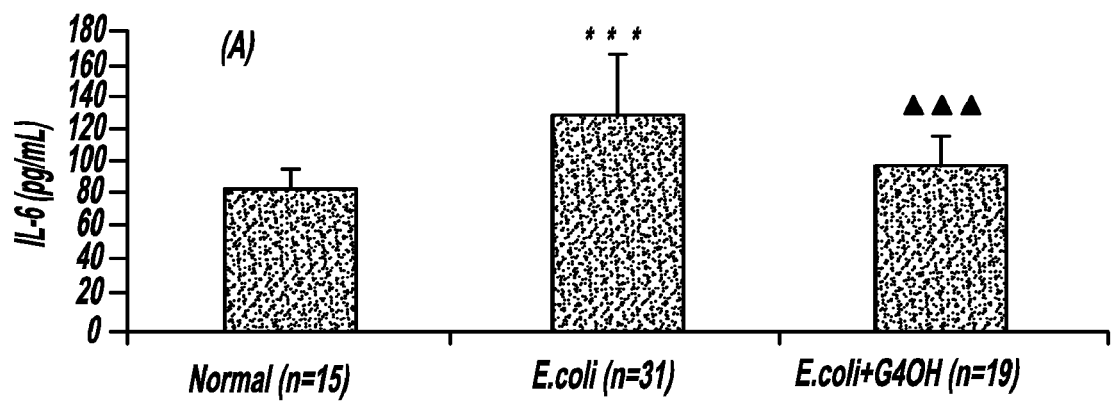
Figure 87C:
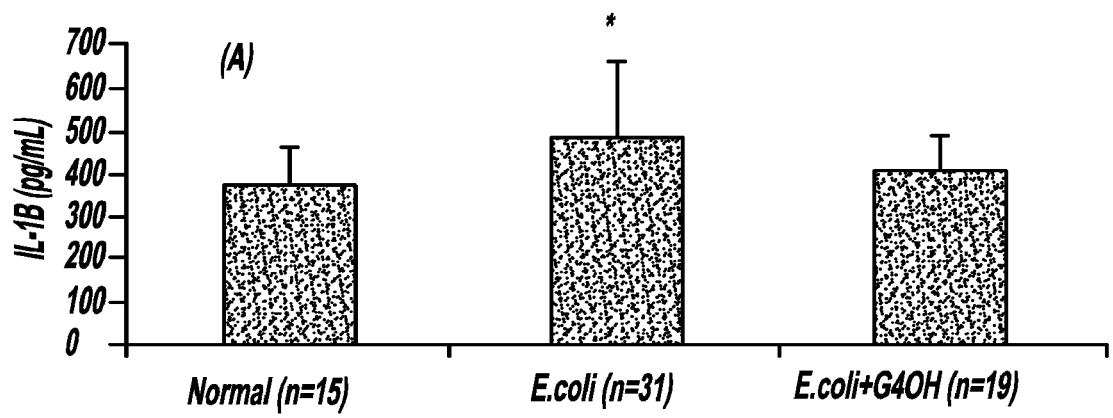
Figure 88A:
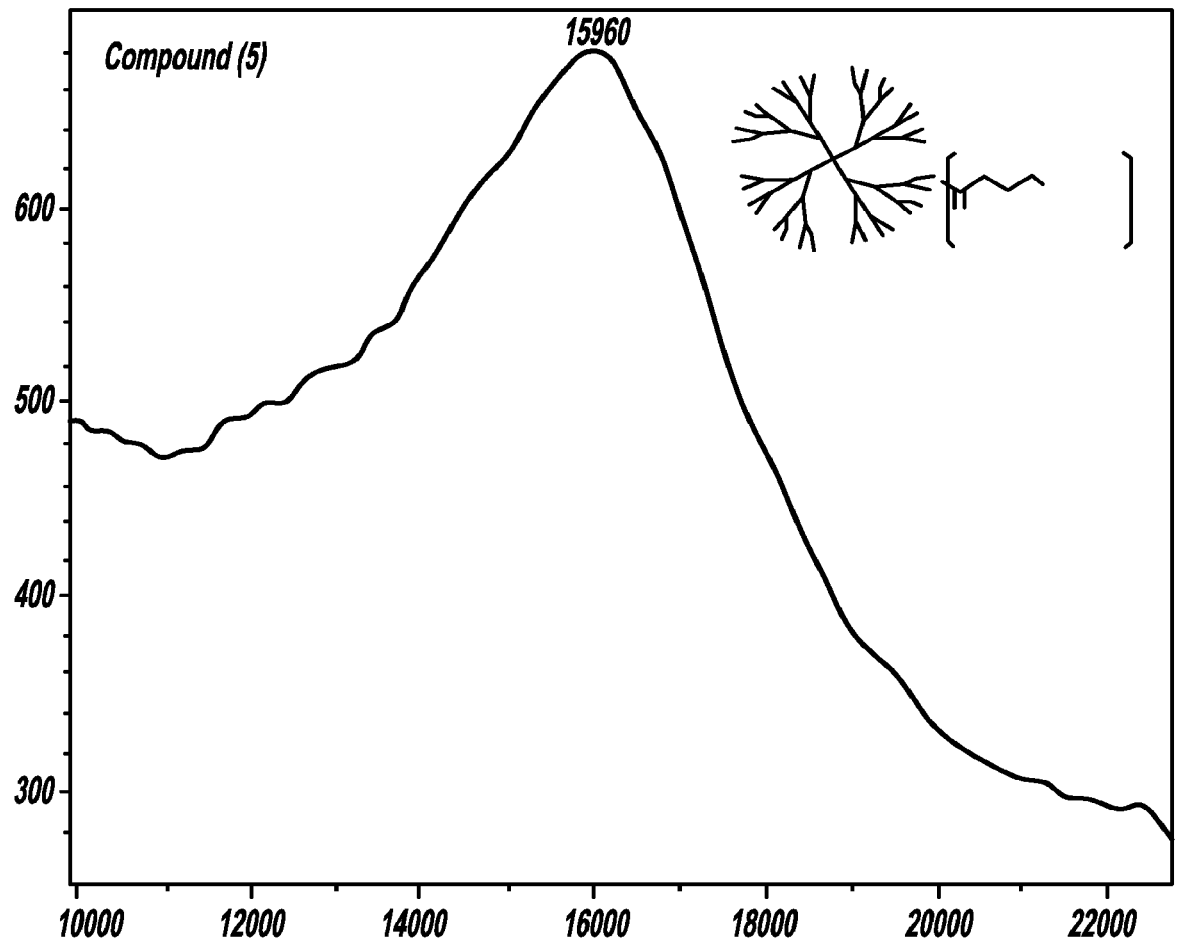
FIG. 88 are MALDI TOF MS spectra for G4-PAMAM-O-GABA-Boc (5) (Mw=15,960 Da), G4-PAMAM-O-GABA-$NH_2$ (6) (Mw=14,949 Da), G4-PAMAM-O-GABA-NH-FITC (1) (Mw=15,805 Da) and G4-PAMAM-O-GABA-NH-Alexa (2) (Mw=16065 Da) showing the corresponding mass.
Figure 88B:
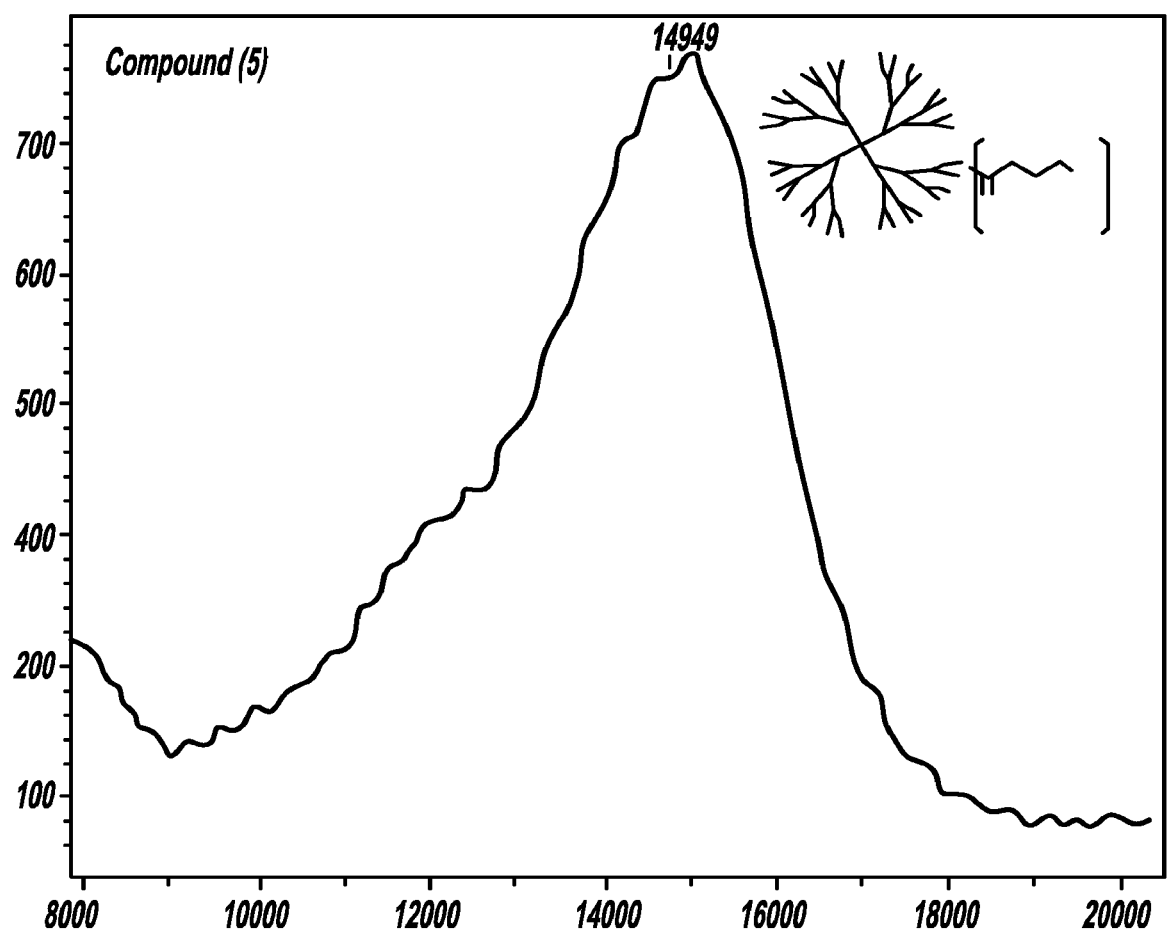
Figure 88C:
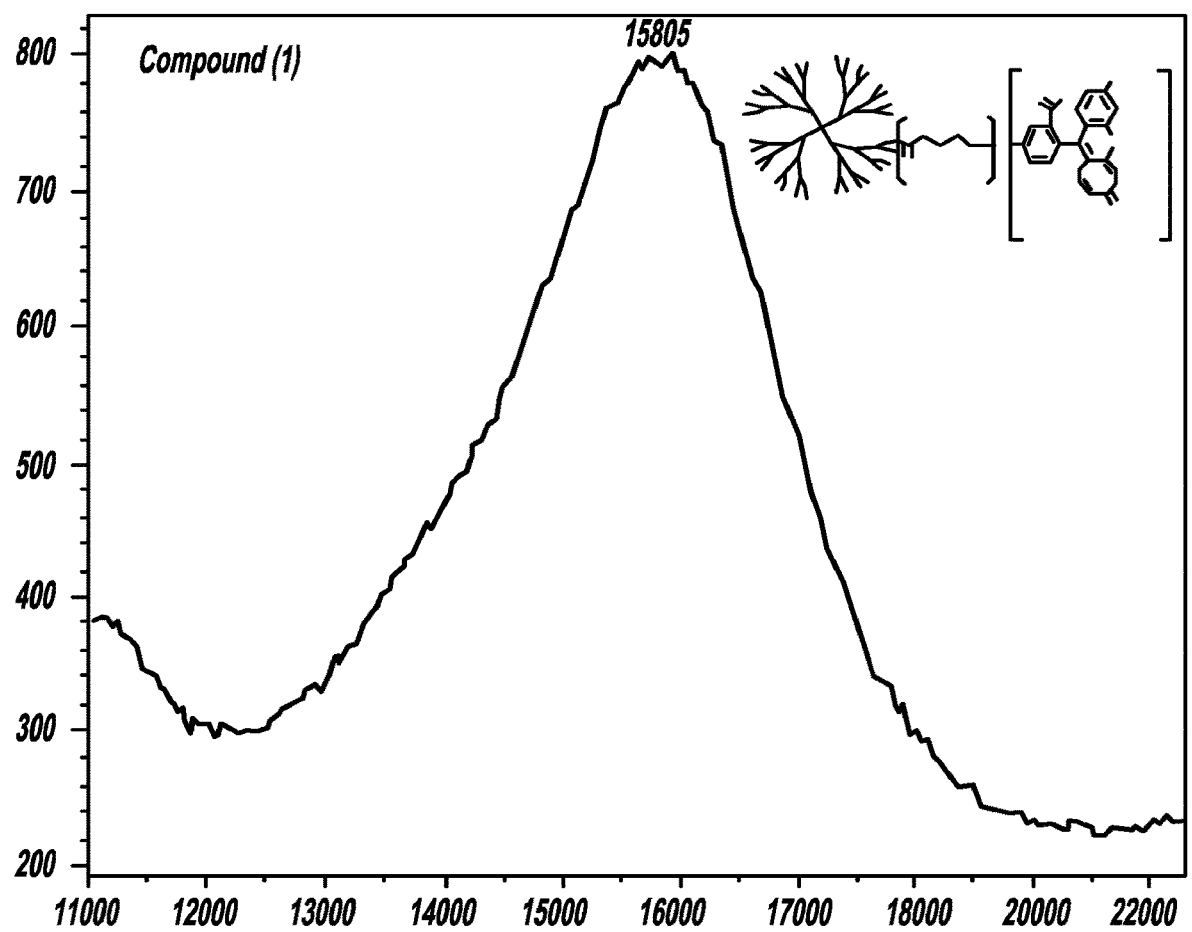
Figure 88D:
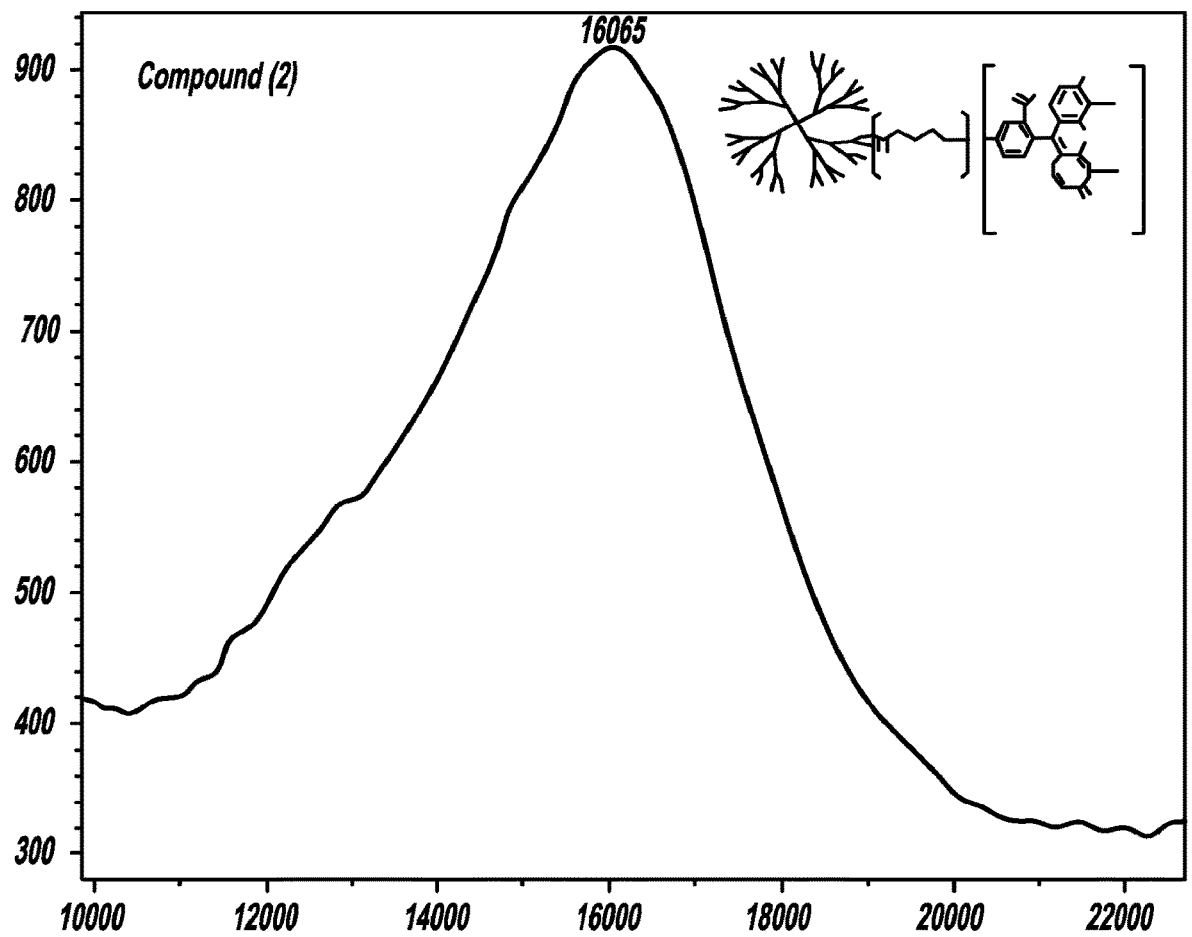

In the present study, chorioamnionitis was induced after intracervical inoculation with E. coli in 8 guinea pigs of which n=4 were considered as positive control (group 2) and n=4 were used for treatment with $G_4$-PAMAM-OH (group 3). None of the amniotic fluid samples plated from the negative control group-1 (n=3) showed evidence of microbiologic chorioamnionitis. Of the pregnant guinea pigs (group 2, n=4) that were inoculated with 150 CFU of E. coli, 57.1% of the amniotic fluid samples for different fetus were positive with bacterial growth (indicative of induced infection) as seen from the culture inoculated with it (see Table 6). Prenatal exposure to maternal infection alters cytokine expression in the placenta (Urakuboa, 2001). Abundance of cytokines in placental tissues is an indicator of activation of inflammatory response in gestational membranes with term and preterm parturition (Keelan et al., 1999). The cytokine IL-6 is known to peak after 48 hours of infection (Dickinson et al., 2009) and hence in present study animals were sacrificed after 48 hours to determine the cytokine level in positive and treated animals. When the expression of cytokine levels in negative control vs the positive controls were compared, the cytokines especially TNFα and IL-6 increased significantly in placenta of positive controls after 48 hours of inoculation with E. coli (FIG. 87). These results demonstrated that chorioamnionitis was successfully induced after 48 hours of cervical inoculation with 150 CFU of E. coli.

The $G_4$-PAMAM-OH dendrimer was applied topically at a dose of (625 µg/kg) on the cervical endometrium of guinea pigs (group-3, n=4) in form of aqueous solution in saline after E. coli inoculation. The total amount applied was 500 µg dissolved in saline based on the average weight of the guinea pigs (800 gm/animal). The amniotic fluid samples for different fetus were collected after 48 hours and were plated on the culture plates and evaluated for the bacterial growth. All these samples did not show any bacterial growth (0%) on the culture plates (Table 6). The study shows that the treatment with $G_4$-PAMAM-OH dendrimer completely eliminated the bacterial growth and prevented bacteria ascension into uterine cavity and amniotic fluid i.e. from 57.1 (positive control) to 0% (treatment group) bacterial growth. Earlier, the in-vitro data showed antibacterial nature of $G_4$-PAMAM-OH at higher concentration and the in-vivo results show that amniotic fluid samples for different fetus in treatment group-3 were found to be negative. The comparison of cytokine expression in placenta of the treatment group, negative and positive control groups shows that the cytokine levels (TNFα and IL-6) in treatment group are comparable to the negative control while they are overly expressed in positive controls (FIG. 87). These results indicate the potential of $G_4$-PAMAM-OH to effectively kill gram negative bacteria E. coli in cervix of guinea pig and prevent chorioamnionitis. This is a significant finding since the chorioamnionitis is known to cause fetal brain injury (Patrick et al., 2004) which could possibly be averted by treatment with $G_4$-PAMAM-OH as indicated from these findings.

Conclusion

The bactericidal activity of hydroxyl and carboxylic acid terminated PAMAM dendrimer was evaluated against gram negative E. coli and compared with amine terminated PAMAM dendrimers. The antimicrobial assay, SEM analysis, cell integrity, inner and outer membrane permeability assays showed that G4-PAMAM-OH and G3.5-PAMAM-COOH dendrimers affect the cell wall of E. coli, and were antibacterial at the concentrations evaluated. The major finding was the bactericidal effect of $G_4$-PAMAM-OH dendrimer and its ability to treat E. coli infections in-vivo in pregnant guinea pigs. Topical cervical application of 500 µg of $G_4$-PAMAM-OH treated the E. coli infections induced in guinea pig model of chorioamnionitis. The amniotic fluid collected from different fetus in the infected guinea pigs, post treatment showed absence of E. coli growth in the cultures plated with it. The cytokines levels were higher in the positive controls confirming presence of infection after inoculation with E. coli. The cytokine expression (TNFα and IL-6) in the treatment group was comparable to that in negative control showing the efficacy of $G_4$-PAMAM-OH to treat the E. coli infections. The G4-PAMAM-$NH_2$ dendrimer is known to be potent antibacterial agent, however, it was found to be highly cytotoxic to above 10 µg/mL to human cervical epithelial (End1/E6E7) cells and immune cells (BV-2) while the $G_4$-PAMAM-OH dendrimer was non cytotoxic upto 1 mg/mL concentrations to both cell lines. Each dendrimer appears to affect the bacterial cell wall in a different way. The possible mechanisms involve the $G_4$-PAMAM-$NH_2$ acting as polycation binding to the polyanionic lipopolysaccharide, the $G_4$-PAMAM-OH binding via hydrogen bonds to the hydrophilic O-antigens and the $G_{3.5}$-PAMAM-COOH acting as a polyanion chelating the divalent ions in outer cell membrane. The outer and inner membrane permeabilization assay shows that $G_4$-PAMAM-OH brings major structural changes to the outer membrane whereas $G_4$-PAMAM-$NH_2$ brings major changes to both outer and inner membrane.

TABLE 6

The inhibition of E. coli growth after treatment with G$_4$-PAMAM-OH dendrimer in guinea pig model of chorioamnionitis

| Inoculation with E. coli | | | Treatment: With G4-OH after E. coli inoculation | | |
|---|---|---|---|---|---|
| Guinea Pig | Amniotic fluid from different gestational sacs Bacterial growth | % | Guinea Pig | Amniotic fluid from different gestational sacs Bacterial growth | % |
| Mother 1 | Fetuses (4/5) | 80.0 | Mother 1 | Fetuses (0/5) | 0 |
| Mother 2 | Fetuses (5/6) | 83.3 | Mother 2 | Fetuses (0/6) | 0 |
| Mother 3 | Fetuses (1/4) | 25.0 | Mother 3 | Fetuses (0/5) | 0 |
| Mother 4 | Fetuses (2/5) | 40.0 | Mother 4 | Fetuses (0/3) | 0 |
| | Average | 57.1 | | Average | 0 |

Example 26

Dendrimers can Provide Selective Treatment to Pregnant Women, without Affecting the Fetus Synthesis of G$_4$-PAMAM-O-GABA-NHBoc The solution of Boc-GABA-OH (914 mg, 4.50 mmol) in DMSO/DMF (3:1) was cooled to 0° C. and then added to the solution of EDC (860 mg, 4.50 mmol), DMAP (549 mg, 4.5 mmol) and G$_4$-PAMAM-OH (1000 mg, 0.070 mmol) in DMSO/DMF (3:1). The reaction mixture was stirred at room temperature for 24 hours. The reaction mixture was purified by dialysis with DMSO (24 hours) to remove by-products and the excess of reactants. After dialysis the solvent was removed under lyophilization to get pure compound in 78% yield (889 mg, 0.055 mmol). $^1$H-NMR (DMSO-d$_6$, 400 MHz), δ (in ppm): 1.37 (s, 9H), 1.50-1.66 (m, 2H) 2.10-2.20 (m, 4H), 3.97-4.03 (br s, 1H), 6.77-6.85 (br s, NH amide from GABA-NH-Boc), 7.70-8.05 (3 br s, NH amide from interior of dendrimer).

Synthesis of G$_4$-PAMAM-O-GABA-NH$_2$

G$_4$-PAMAM-O-GABA-NHBoc (1.0 g, 0.062 mmol) was treated with trifloroacetic acid and dichloromethane (1:1, 10 mL). The reaction was stirred at room temperature for 10 min. After completion of the reaction, trifloroacetic acid/dichloromethane were removed under vacuum using rotavapor equipped with NaOH trap. Reaction mixture was neutralized with Na$_2$CO$_3$ and dialyzed with water (12 hours) and solvent was removed under lyophilization to get pure compound in 92% yield (861 mg, 0.057 mmol). $^1$H-NMR (DMSO-d$_6$, 400 MHz), δ (in ppm): 1.65-1.78 (m, 2H), 2.2-2.39 (m, 4H), 3.91-3.99 (br s, 1H), 7.8-7.98 (br d, NH amide from GABA-NH$_2$), 8.03-8.25 (br d, NH amide from interior of dendrimer)

Synthesis of G$_4$-PAMAM-O-GABA-NH-FITC

To a solution of G$_4$-PAMAM-O-GABA-NH$_2$ (2.50 g, 0.167 mmol) in anhydrous DMSO (50 mL) was added fluorescein isothiocynate (FITC) (800 mg, 2.05 mmol) and stirred. The reaction was allowed to proceed further for 18 hours at room temperature in dark. To remove unreacted FITC the reaction mixture was dialyzed (molecular cut off of the membrane is 1000 Da) in DMSO for 24 hours. The compound was dissolved in methanol and precipitated in acetone. The product was dried by lyophilization to obtain G$_4$-PAMAM-O-GABA-NH-FITC conjugate in the 75% yield (1.98 g, 0.125 mmol) and analyzed by $^1$H-NMR and MALDI TOF/MS. Absence of free FITC in the conjugate was verified by TLC using chloroform and methanol (ratio 1:1) as mobile phase and further by HPLC analysis.

Synthesis of G$_4$-PAMAM-O-GABA-NH-Alexa-488

Alexa Fluor 488 carboxylic acid, succinimidyl ester (2 mg, 0.0013 mmol) was added to a solution of G$_4$-PAMAM-O-GABA-NH$_2$ (17.5 mg) in PBS (pH=8) (3 mL) and the reaction was stirred at room temperature in dark for 15 hours. The reaction mixture was dialyzed in DMSO (molecular cut off of the membrane is 1000 Da) for 24 hours in dark. The product was dried by lyophilization to obtain G$_4$-PAMAM-O-GABA-NH-Alexa conjugate in the yield 78% (1.67 mg, 0.0001 mmol) and analyzed by MALDI TOF/MS. Absence of free Alexa in the conjugate was verified by TLC using chloroform and methanol (ratio 1:1) as mobile phase and further by HPLC analysis.

Dynamic Light Scattering Measurements

Dynamic light scattering (DLS) analyses were performed using a Malvern Instruments Zetasizer Nano ZEN3600 instrument (Westborough, Mass.) with reproducibility being verified by collection and comparison of sequential measurements. G4-PAMAM-O-GABA-NH-FITC and G4-PAMAM-O-GABA-NH-Alexa conjugate samples were prepared using PBS pH=7.4. DLS measurements were performed at a 90° scattering angle at 37° C. Z-average sizes of three sequential measurements were collected and analyzed.

Chorioamniotic Membrane Specimens

Study Design

All the human fetal (chorioamniotic) membrane samples were collected from women in uncomplicated normal pregnancies, immediately after elective caesarian section performed prior to the onset of labor. Fetal membrane samples were obtained from 21 normal pregnancies from the bank of biological samples of the Perinatology Research Branch.

Chorioamniotic Membrane Processing

All human fetal membrane specimens were obtained at the time of cesarean section for obstetrical indications. The fetal membrane comprising chorioamniotic membrane (intact membranous tissue containing both amnion and chorion together) (n=7) and amnion (n=7) and chorion (n=7) were separately procured (size 6×9"). Each membrane was cut into 9 pieces for the 9 sets of diffusion chamber. The fresh membranes were collected immediately after the delivery, washed with PBS to remove the blood and stored in PBS until (~1 h at 4° C.) it was mounted on the diffusion chamber (37±0.5° C.). Excess membranes were trimmed. The diffusion experiments were performed for 48 hours by mounting the membrane in the chamber to study the transport across the membranes. In all the experiments with chorioamniotic membrane the choriodecidua (maternal side) was placed facing the donor chamber and the amnionic epithelium (fetal side) was facing the receptor chamber. The chorion and amnion were mechanically separated by gently pulling the two membranes apart. For the chorion, the side attached to amnion was placed facing the receptor chamber and for the amnion the side attached to the chorion was placed facing the donor chamber in the diffusion apparatus. For histological evaluation, the tissue samples were collected at 0.5, 1, 2, 3 and 4 hours for and were fixed in 10% formalin overnight. Further, some sections were analyzed by hematoxylin and eosin (H & E) staining. The membrane thickness was measured using the Mitutoyo Super Caliper by placing the respective membranes between the two glass slides and subtracting the thickness of the glass slides without the membrane.

Immunofluorescence

An immunofluorescence study was performed to investigate biodistribution of the dendrimer through the different layers of the fetal membrane with progression of time. The fetal membrane tissues were removed from the side by side diffusion chambers at different time points and fixed in 10% formalin overnight. Double immunofluorescent staining was performed on 5 μm thick, paraffin sections of membranes placed on silanized slides. The different regions in the fetal membranes were identified based on the presence of trophoblast in the chorion as documented by staining with cytokeratin and the presence of the stromal cells as documented by staining with vimentin. The immunofluorescent staining was performed using Ventana Discovery autostainer for controlled and optimised reaction environment using the automation-optimized reagents from Ventana Medical Systems Inc. Briefly, paraffin wax sections were loaded onto the Ventana Discovery platform and following steps were completed automatically, these included dewaxing by EZ prep buffer (Ventana Medical Inc.), pre-treatment in Tris/EDTA pH 8.0 antigen retrieval solution (Ventana mCC1) or protease solution for 1 hour (Ventana protease 2). Endogenous peroxidase was inactivated using an enhanced inhibitor provided in the staining kit and nonspecific antibody binding was blocked by treatment with blocking solution for 10 min. The blocking solution was removed and the sections were washed three times with PBS/Tween solution incubated with primary antibodies for 1 hour using the liquid cover slip (Ventana Medical Inc). The primary antibodies used were monoclonal mouse anti-human cytokeratin (1:200, M7018, Dako Carpinteria, Calif., USA) and rabbit polyclonal IgG vimentin (H-84) (1:100, sc5565, Santa Cruz Biotechnology Inc). The sections were again washed three times with PBS/Tween solution incubated with secondary antibodies, Alexa Fluor®594 goat anti-mouse IgG (1:500, A11005, Invitrogen) and Alexa Fluor® 633 F(ab')$_2$ fragment of goat anti-rabbit IgG (1:500, A21072, Invitrogen) for 1 hours using the antibody diluent from Ventana. The sections were washed with PBS/Tween, counterstained and mounted with DAPI prolong Gold antifade and cover slipped. Negative controls replaced primary antibodies with rabbit isotype control and mouse isotype controls (Invitrogen) in PBS. Images were captured from Leica TCS SP5 Laser Scanning Confocal Microscope (Leica Microsystems GmbH, Wetzlar, Germany). All study specimens were analyzed by a pathologist blinded to the clinical information.

In Vitro Permeability Study

Permeation experiments were carried out using a two-chamber (donor and receptor) side-by-side Permegear diffusion cell with a chamber volume of 3 mL and with a diameter of 13 mm and a diffusional area of 1.32 cm$^2$. The fetal membranes (chorion and amnion together, amnion and chorion) each (n=9) were mounted between two halves of the donor and receptor cell (9 sets), which were further clamped together and sealed tightly with the rubber packing at the end of each glass chamber. The receptor cell (volume 3 mL) was filled with sterile PBS (pH 7.4). The donor cell (volume 3 mL) was filled with solution of compounds whose permeability was evaluated. The solutes chosen for the permeation study were FITC (MW=389 Da), G$_4$-PAMAM dendrimers (G$_4$-PAMAM-O-GABA-Alexa (2), Mw=~16 kDa and G$_4$-PAMAM-O-GABA-FITC (1), Mw=~15.8 kDa). The system was maintained at 37° C. by using a circulating water bath and a jacket surrounding each cell. The donor and receiving medium was continuously stirred (600 rpm) with a magnetic bar to avoid stagnant aqueous diffusion layer effects. Aliquots (200 μL) were collected from the receptor cell every 30 min till first 6 hours and at predetermined intervals thereafter and replaced with equal volume of PBS to maintain sink conditions throughout the study. The concentration of the solutes used were G$_4$-PAMAM-O-GABA-Alexa (0.6 mg/mL), G$_4$-PAMAM-O-GABA-FITC (3 mg/mL and 0.6 mg/mL), and FITC (0.3 mg/mL). The concentration of compound in the receptor medium was determined using a Molecular Devices SpectroMax M2, UV visible and Fluorescent plate reader at ex 495/em 521. The cumulative amount of compound transported across the membrane in the receptor cell was determined using a calibration curve (a transport of 50% corresponds equilibrium achieved). All the experiments were conducted in dark room. All experiments were done in triplicate and the results are reported as mean±STDev.

Results and Discussion

A variety of in-vitro approaches have been used to assess the transport and permeation characteristics of drugs administered by different routes, such as permeability across the skin for topical formulations and permeability across the intestine, colon and jejunum for orally administered drugs. Recently, dendrimers have been considered for topical applications to the vaginal and cervical mucosa as antimicrobicidal agents. The fetus is separated from the extra-amniotic space in the uterus by the fetal membranes and the ascending genital infections in pregnant women are treated by topical intravaginal application of antibacterial and antifungal drugs. Since the dendrimers are explored as topical antimicrobial agents themselves and also as components of topical gel formulations, the transport, permeation and biodistribution of dendrimer across the human fetal membranes was evaluated in the present study. The selective treatment for the mother without affecting the baby is always desired. The present study differs from the transplacental transport, where the transport of molecules or drugs across the placenta is evaluated and is relevant for substances present in systemic circulation of mother following administration by oral, parenteral or any other route. The purpose of the present study is to determine whether (a) dendrimers on topical application to vagina and extra-amniotic cavity in pregnant women cross the fetal membrane and (b) could the dendrimers be used for site specific (local) activity and as components of topical delivery systems in pregnant women without crossing the fetal membranes and affecting the fetus.

Preparation of FITC-Labeled G$_4$-PAMAM-O-GABA-NH$_2$ Dendrimer (1)

To conjugate FITC to G$_4$-PAMAM dendrimer with hydroxyl terminations, the linker GABA with the amine groups protected with Boc (tert-butoxycarbonyl) was appended to the dendrimer to yield G$_4$-PAMAM-O-GABA-NHBoc. First, 4-(tert-Butoxycarbonylamino) butyric acid was reacted with G$_4$-PAMAM-OH to give G$_4$-PAMAM-O-GABA-NHBoc (FIG. 104) and the product so obtained was purified by dialysis using DMSO (cutoff 1000 Da). The $^1$H NMR spectrum shows the appearance of characteristic signals of G$_4$-PAMAM-O-GABA-NHBoc at 1.37 (s, 9H), 1.50-1.66 (m, 2H) 2.10-2.20 (m, 4H), 3.97-4.03 (br s, 1H), 6.77-6.85 (br s, NH amide from GABA-NHBoc), 7.70-8.05 (3 br s, NH amide from interior of dendrimer). This confirms the formation of G$_4$-PAMAM-O-GABA-Boc product. It is evident from the integral ratio of the amide protons of G$_4$-PAMAM-O-GABA-NHBoc at 7.70-8.05 ppm to the four methylene protons of GABA at 2.10-2.20 (m, 4H), that each G$_4$-PAMAM-OH dendrimer contains approximately 10 copies of GABA-NHBoc molecules attached to it. The molecular weight of GABA-NHBoc is 203 Da and the increment in mass of G$_4$-PAMAM dendrimer (from ~14 kDa) to 15960 Da as observed from MALDI TOF MS analysis further confirms the attachment of approximately 10 copies of GABA-NHBoc to the dendrimer (FIG. 88). The product so obtained was deprotected to remove tert-butoxycarbonyl groups by treatment with trifloroacetic acid in dichloromethane to obtain the amine-terminated G$_4$-PAMAM-O-GABA-NH$_2$ dendrimer. $^1$H NMR spectrum shows the disappearance of characteristic signals at 1.37 ppm corresponding to tert-butoxycarbonyl after the deprotection step. Further, the spectrum shows presence of methylene protons at 1.65-1.78 (m, 2H) 2.2-2.39 (m, 4H) and amide protons at 7.8-7.98 (br d, NH amide from GABA-NH$_2$), 8.03-8.25 (br d, NH amide from interior of dendrimer) confirming the desired product G$_4$-PAMAM-O-GABA-NH$_2$. The MALDI-TOF/MS analysis of G$_4$-PAMAM-O-GABA-NH$_2$ shows mass corresponding to 14,949 Da (FIG. 88). The mass of GABA is 103 Da suggesting an attachment of 10 molecules of GABA on G$_4$-PAMAM-O-GABA-NH$_2$ (MALDI showed mass of G$_4$-PAMAM-OH as ~14 kDa).

Figure 104:
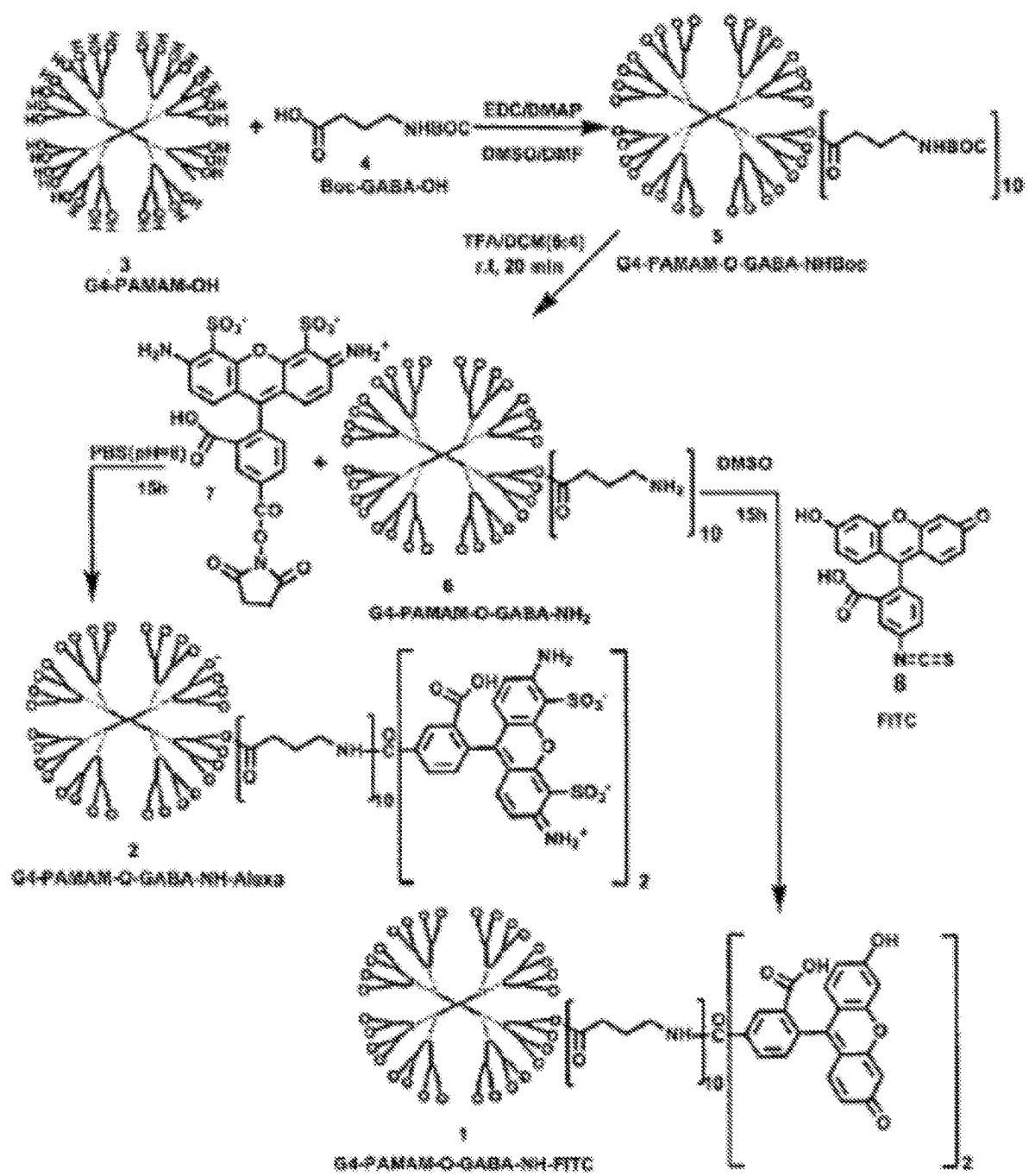
FIG. 104 shows a schematic representation for the synthesis of fluorescently labeled $G_4$-PAMAM-dendrimers; G4-PAMAM-O-GABA-NH-FITC (1) and G4-PAMAM-O-GABA-NH-Alexa (2).

The G$_4$-PAMAM-O-GABA-NH$_2$ dendrimer was tagged with fluorescent dye FITC as shown in FIG. 104. The FITC-labeled compound (G$_4$-PAMAM-O-GABA-NH-FITC) was purified by dialysis (membrane cutoff 1000 Da) against DMSO in dark by replacing DMSO, to remove un-reacted compounds. Purity of G$_4$-PAMAM-O-GABA-NH-FITC conjugate was confirmed by HPLC using fluorescent detector ($\lambda$ex=495 nm/$\lambda$em=521 nm). The G$_4$-PAMAM-O-GABA-NH-FITC conjugate showed a single peak at 17.5 min in the reverse phase HPLC chromatogram indicating absence of free FITC in the conjugate after dialysis (FIG. 89). The stability of the conjugate in PBS (pH 7.4) after 72 hours was evaluated by HPLC analysis which showed a single peak for the conjugate and FITC was not released from the conjugate. This observation is consistent with previous reports where drugs conjugated to dendrimers by amide linkage are not released by hydrolytic or enzymatic degradation. $^1$H-NMR was used to characterize the conjugate. $^1$H-NMR spectrum shows the appearance of aromatic protons at 6.47-6.59 (d, 6H, Ar) and 6.61-6.72 (s, 3H Ar) corresponding to the FITC protons confirming the tagging of FITC on G$_4$-PAMAM-O-GABA-NH$_2$. The MALDI TOF/MS spectrum showed that the mass of G$_4$-PAMAM-GABA-NH$_2$ increased from 14,949 Da to 15,805 Da suggesting the attachment of 2 molecules of FITC on G$_4$-PAMAM-O-GABA-NH-FITC (FIG. 88).

Synthesis of G$_4$-PAMAM-O-GABA-Alexa Conjugate

G$_4$-PAMAM-O-GABA-NH$_2$ dendrimer was reacted with the Alexa 488 carboxylic acid succinimidyl ester (FIG. 104). The N-succinimidyl activated ester of Alexa 488 couples to the terminal primary amines to yield amide-linked G$_4$-PAMAM-O-GABA-Alexa conjugate. The formation of conjugate was confirmed by HPLC (FIG. 89) using florescent detector ($\lambda$ex=495 nm/$\lambda$em=521 nm). The G$_4$-PAMAM-O-GABA-NH-Alexa conjugate showed a single peak at 15.5 min in the reverse phase HPLC chromatogram. The absence of any other peak in chromatogram after dialysis of product confirms the absence of free alexa. Further, the stability of the conjugate in PBS (pH 7.4) after 72 hours was evaluated by HPLC analysis, which showed a single peak for the conjugate and alexa was not released from the conjugate. The MALDI spectrum showed that the mass of G$_4$-PAMAM-GABA-NH$_2$ increased from 14,949 Da to 16065 Da confirming the attachment of 2 copies of alexa on G$_4$-PAMAM-O-GABA-NH-Alexa (FIG. 88). The dendrimer alexa conjugate was prepared for enhanced histological visualization of samples as confocal imaging causes quenching and also to match with the intensities of other alexa conjugated secondary antibodies.

Transmembrane Transport of G$_4$-PAMAM Dendrimer

The dendrimer transport and permeability was determined from chorioamnion i.e. the intact fetal membrane comprising the amnion and chorion together (n=7). The chorion was mechanically stripped off from the intact fetal membrane to study the permeability across the amnion (n=7) and the chorion (n=7) separately. The experiments were conducted in dark to avoid quenching of fluorescence. Individual membranes were used to determine which membrane acts as a rate limiting barrier for the permeability of molecules based on the size. Usually the permeability of a molecule directly reflects the interactions of the molecules with the tissue and physiological properties of the tissue. The G$_4$-PAMAM-GABA-NH-FITC used for transport and permeability study is hereafter referred to as dendrimer and the unconjugated or free FITC is referred as FITC.

PAMAM dendrimers are nanosized macromolecules and their size increases from 1.1-12.4 nm as they proliferate from generations 1-10. The Alexa and FITC labeled G$_4$-PAMAM dendrimers synthesized in the present study have a size of 5.6 and 5.4 nm respectively, as seen from the particle size analysis by DLS. In case of the biological compartments, the epithelium acts as a general barrier for the entry of nanosized materials into the body. The paracellular transport of nanomaterials across the epithelium is prevented by the presence of tight junctions and adherens which have a small gap <2 nm. So far there has been little or no information on the transmembrane transport of G$_4$-PAMAM dendrimers across the human chorioamniotic membrane. In the past, carboxyfluorescein encapsulated liposomes were used to study transplacental transport and fluorescein has been used to study transplacental transport in vitro using BeWo (chorionic) cell line. Carboxyfluorescein does not bind to the tissue proteins, it is inert and does not undergo biotransformation and its molecular weight is similar to the commonly used therapeutic agents therefore it is considered as suitable marker for transplacental transfer. Literature shows that fluorescein is established marker for transplacental transfer, hence the fluorophore (FITC and Alexa) tagged G$_4$-PAMAM dendrimers were used in the present study.

Figure 90A:
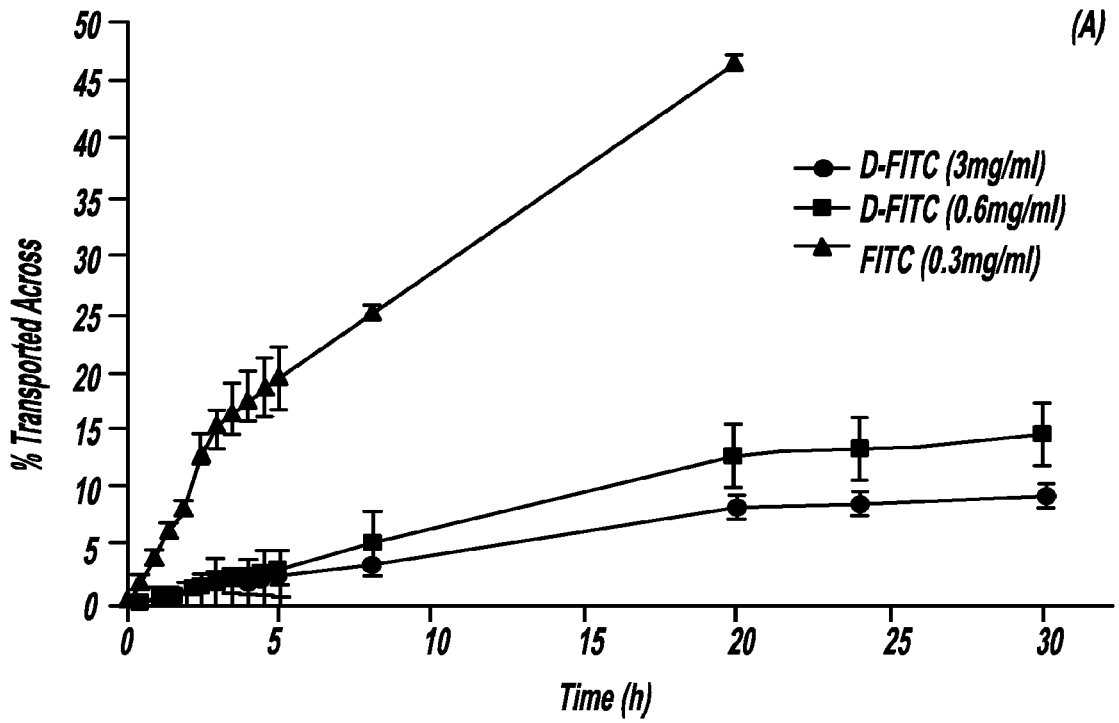
FIGS. 90 A and B show transport across membranes. (A) The transport of $G_4$-PAMAM-O-GABA-NH-FITC (D-FITC) and FITC (unconjugated) across the fetal membrane comprising amnion and chorion together over 30 hours in the side by side diffusion chamber. (B) The FITC shows a rapid transport across the membrane in 5 hours (~20%), while the dendrimers show negligible transport of ≤3% in 5 hours. The concentrations of D-FITC studied were 0.6 mg/mL and 3 mg/mL. The concentration of FITC was 0.3 mg/mL.
Figure 90B:
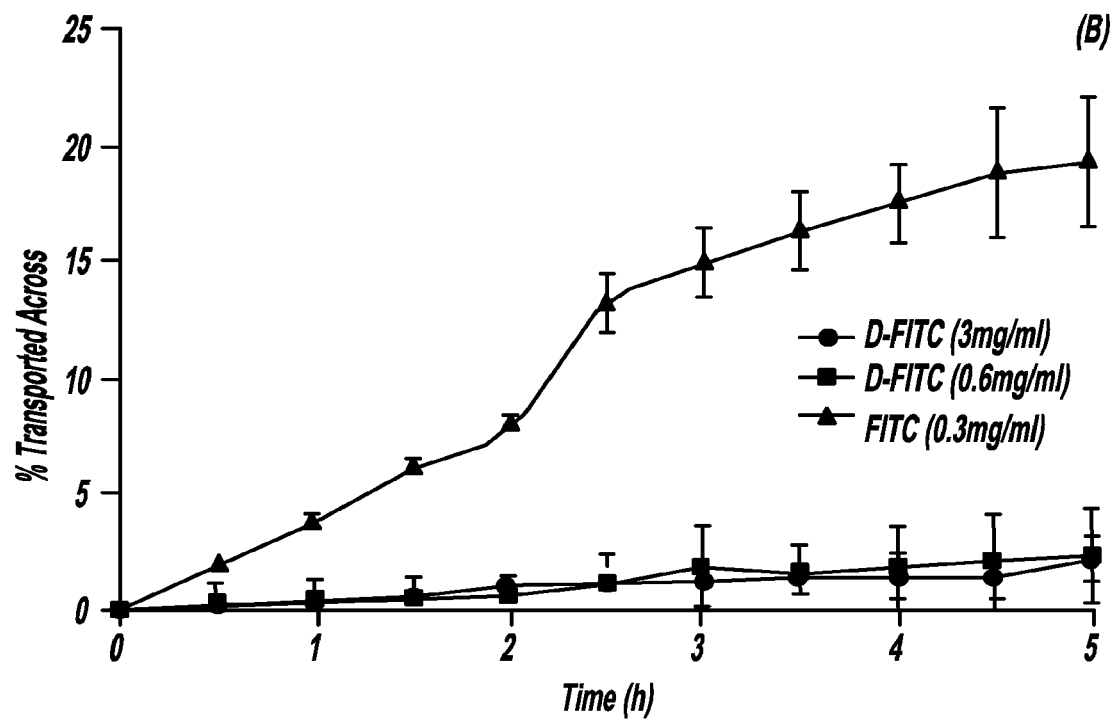
Figure 91A:
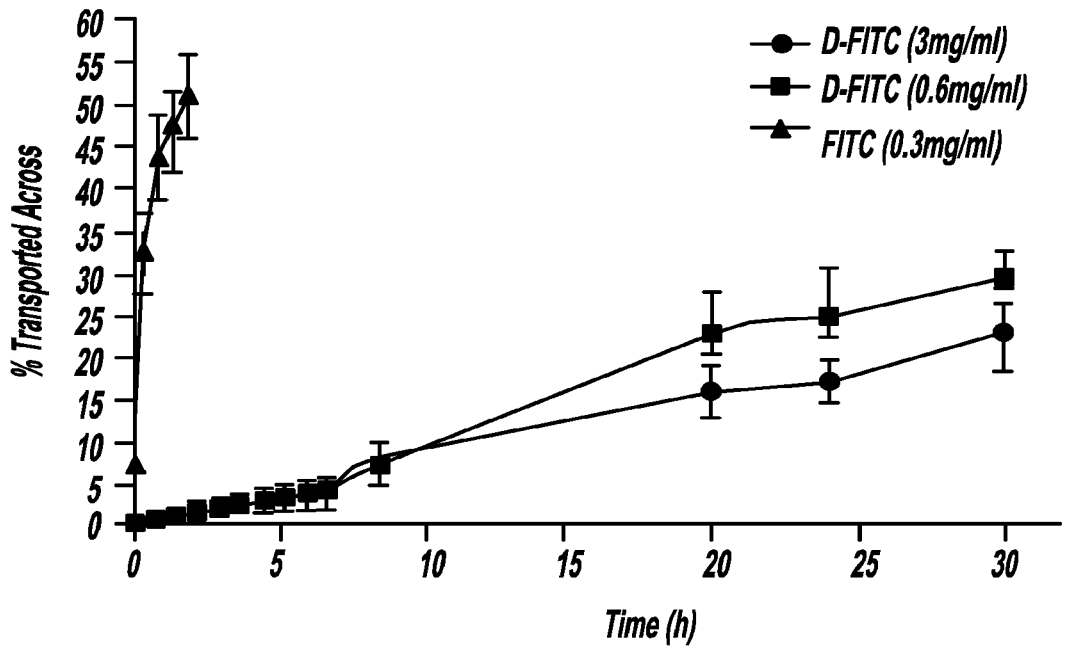
FIGS. 91A and B show transport across membranes.
Figure 91B:
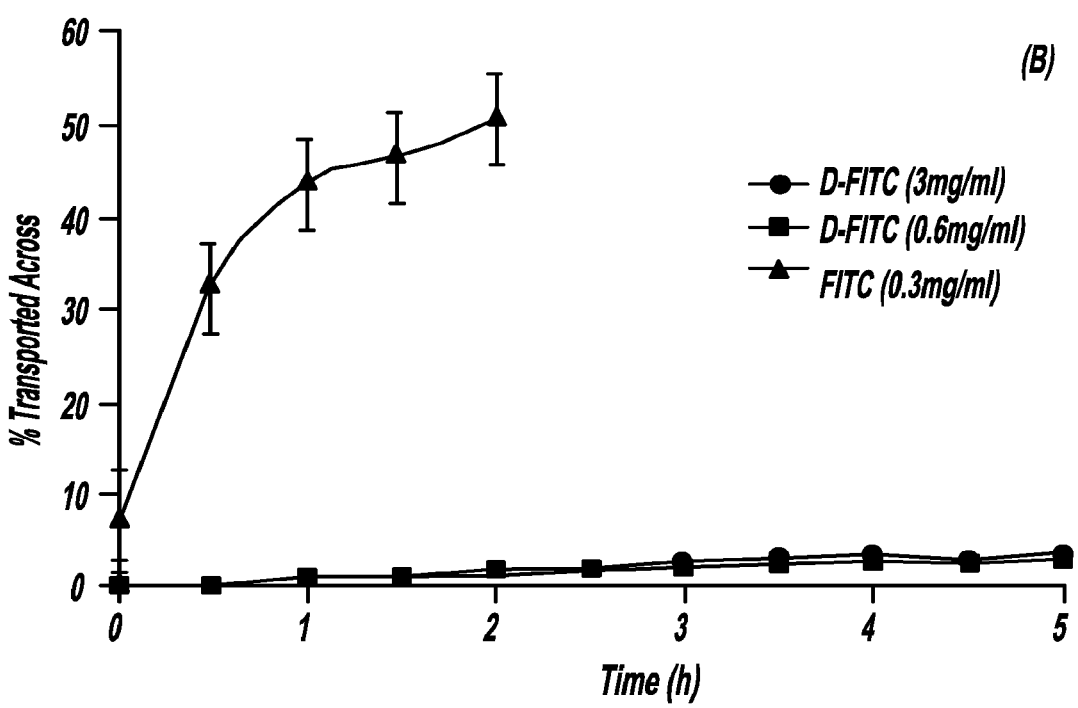
(FIG. 91B) The FITC shows a rapid transport across the membrane (50%) in 5 hours, while the dendrimers show negligible transport of ≤3% in 5 hours. The concentrations of D-FITC studied were 0.6 mg/mL and 3 mg/mL. The concentration of FITC was 0.3 mg/mL.
Figure 92A:
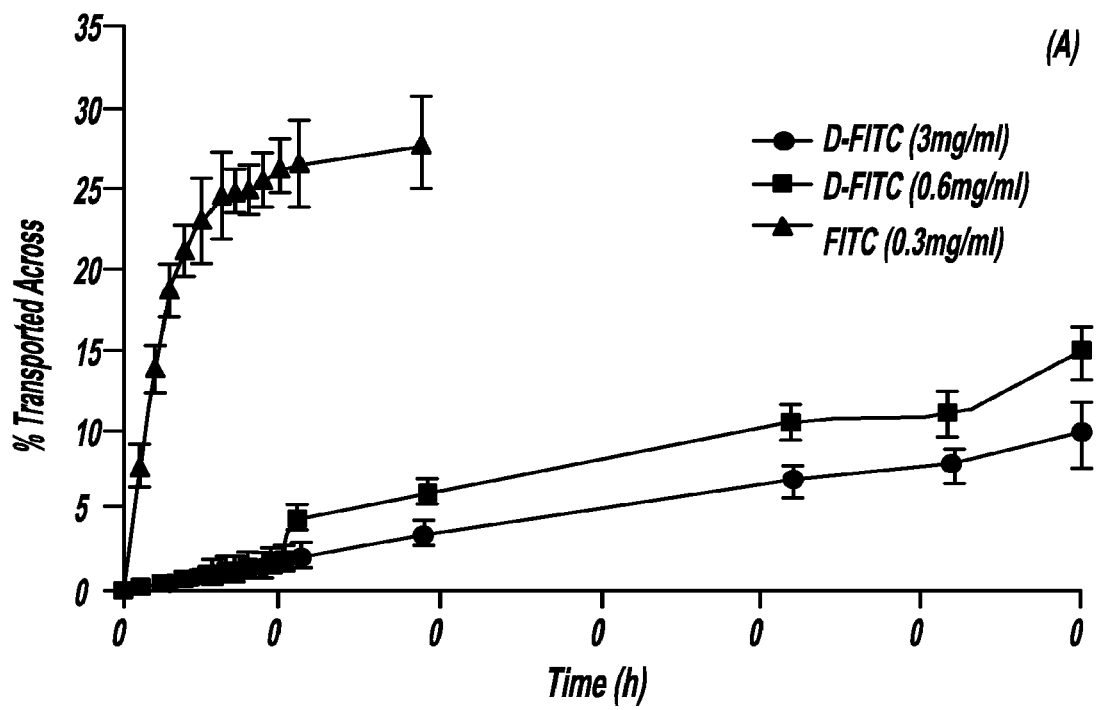
FIGS. 92A and B show transport across membranes.
Figure 92B:
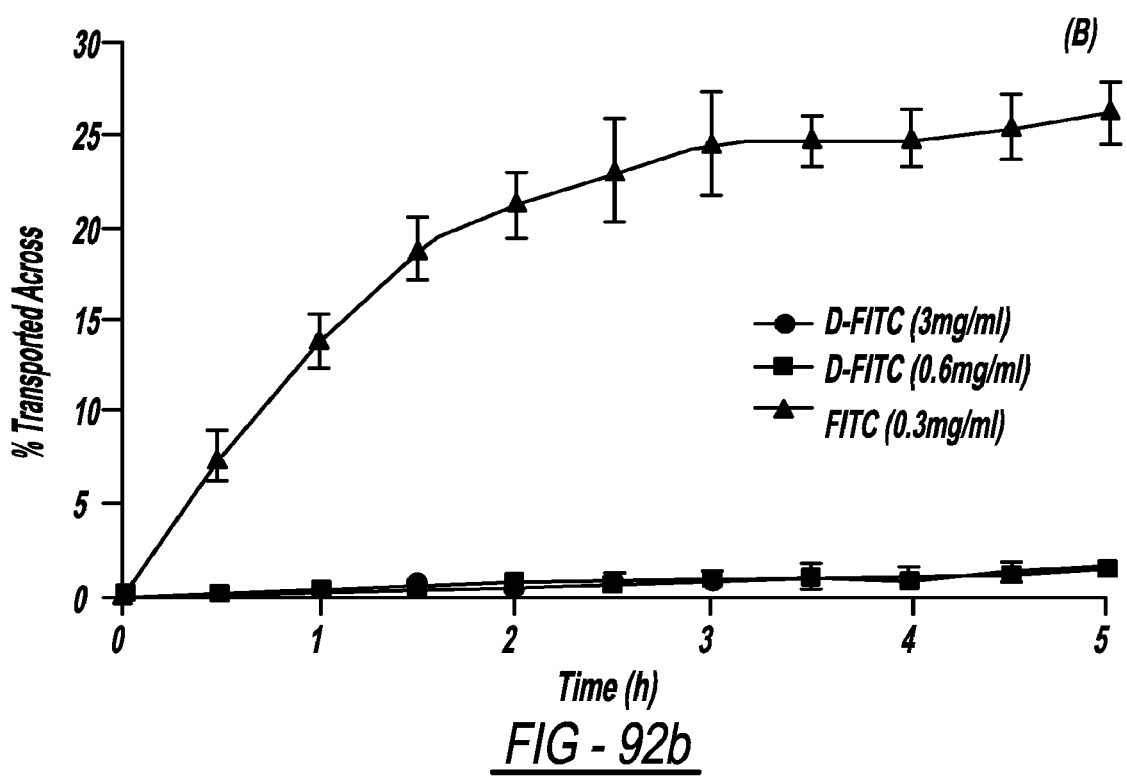
(FIG. 92B) The FITC shows a rapid transport across the membrane (~25%) in 5 hours, while the dendrimers show negligible transport of ≤3% in 5 hour. The concentrations of D-FITC studied were 0.6 mg/mL and 3 mg/mL. The concentration of FITC was 0.3 mg/mL.

As compared to the larger G$_4$-PAMAM dendrimer molecule, the small FITC molecule showed a rapid transport across all the three membranes (chorioamnion, amnion and chorion, respectively) in first few hours (in 2-3 hours) as seen from FIGS. 90, 91, and 92. The transport of FITC was fastest across the amnion and a near complete transport (49%)(concentration equilibration) of FITC on the receptor side seemed to occur in 2 hours (FIG. 91B). About 26% of FITC was transported across the chorion in 5 hours (FIG. 92B). The transport of FITC from chorioamnion was slower than that observed for amnion and chorion, and about 20% transmembrane transport was seen in first 5 hours (FIG. 90B), while a complete transport occurred after 20 h (FIG. 90A). The transport of G$_4$-PAMAM dendrimer from all the three membranes across to the receptor side was negligible (<3%) in the initial few hours (5 hours) (FIGS. 90-92B). The transport of dendrimer did not seem to change with respect to concentration (3 and 0.6 mg/mL) in first 5 hours and was significantly low when compared to FITC. The dendrimer transport for lower concentration (0.6 mg/mL) increased from ≤3% at 5 hours to 8.3% in 20 hours for chorioamnion, while for amnion it increased from ≤3% at 5 hours to 22% in 20 hours and for chorion in increased from 3% in 5 hours to 10% in 20 hours. The transport of dendrimer was slowest from chorioamnion followed by chorion and was relatively faster in amnion. To mimic the in vivo conditions the transport across chorioamnion is relevant. The transmembrane transport of the dendrimer seemed to increase slightly as time progressed (24-30 hours) but substantial amount of dendrimer was not found to transport when compared to FITC alone across all the three membranes as seen from FIGS. 90-92A. Previously, an inverse relation with the molecular weight and the transport across the BeWo (choriocarcinoma) cell line was observed for various markers such as fluorescein, sucrose, dextans and several amino acids of varying molecular weights. The molecular sieving of the BeWo monolayers seemed to restrict the transport of peptides >1033 Da and the paracellular route was major pathway for transport.

The solute membrane partition coefficient is another parameter that affects the transport across the biomembrane. The two possible pathways for the solutes to cross the fetal membrane barriers are (a) transcellular route and (b) water filled trans-trophoblastic channels. The hydrophilic molecules are mostly transported thorough the water filled channels with the exception of very few hydrophilic solutes which show transcellular transport across the human placenta. The Log P values for the $G_4$-PAMAM dendrimers are negative indicative of its hydrophilic nature, therefore the transcellular mechanism of transport seems unlikely and the major transport mechanism for these molecules could be through the water filled transmembrane channels or pores. The histological evaluation was carried out to further evaluate the mechanism of transport and biodistribution discussed in subsequent sections. The overall results show that the dendrimer in size range 5-6 nm do not cross the chorioamnion appreciably (<3%) in first 5 hours. This, combined with the fact that dendrimers biodistribute relatively rapidly (with ~2-3 hours), suggest that dendrimers could be candidates for selective topical delivery to the mother without affecting the fetus.

Permeation of $G_4$-PAMAM (1) and FITC

The transport of molecules across the membranes occurs as a result of passive diffusion or active transport. The passive diffusion differs from the active process such that the passive diffusion of the compound through the cell membrane is dependant on the concentration gradient with a constant permeability coefficient. Previously, it has been shown that the quantity of D-arabinose or carbohydrate transferred across 1 cm² of human chorion per unit gradient per unit time can be given by $$\frac{D}{\Delta x} = \frac{P}{A}$$

Where, D is Diffusion coefficient, $\Delta x$ is the thickness of the tissue studied, P is the permeability constant and A is the area. When the permeability coefficient is known it's often used to calculate the other unknown parameters such as diffusion coefficient (D) or partition coefficients (k) or the membrane thickness.

In the current study, the influence of dendrimer size vs the small of molecule (FITC) on permeability through the fetal membranes was evaluated. As per the Fick's law of diffusion, the permeability of the solute can be given by the equation, $$\frac{P}{\delta} = \frac{-V}{2At}\ln\frac{\Delta C_t}{C_0}$$

where $C_t$ is the solute concentration in the receptor cell; $C_0$ is the initial solute concentration in the donor cell; V is the volume of each half cell; A is the effective permeation area; P is the permeability coefficient; t is the time; and $\delta$ is the thickness of the membrane. The above equation can be rewritten as $$\ln\left(1 - 2\frac{C_t}{C_0}\right) = \frac{-2A}{V}Pt$$

To determine the permeability coefficient, P, a plot of $-V/2A$ ln $(1-2C_t/C_0)$ against t was constructed and linear fitting was performed. The slope of the linear portion of the graph yields a permeability coefficient. The thickness of the chorioamnion, chorion and amnion was 0.22 mm, 0.16 mm and 0.05 mm respectively (n=7), as measured with the help of Mitutoyo Super Caliper. Table 7 shows the permeability coefficients for $G_4$-PAMAM-dendrimer and free FITC through the different membranes. The FIGS. 93A-C and FIG. 94 show the plots used for calculation of the permeability and the correlation in all the cases ranged from 0.96 to 0.99.

The permeability of FITC (Mw=389 Da) was found to be $1.32\times10^{-6}$ ($r^2$=0.97) and $2.26\times10^{-6}$ cm²/s ($r^2$=0.99) for the chorion and amnion respectively. Previously, the in vitro permeability of cell free amnion was reported to be $1.5\times10^{-6}$ cm²/s for D-glucose and 2-aminoisobutyrate. Further, the in vitro permeability across chorion for meperidine (Mw=247.33 Da) and diazepam (Mw=284.7 Da) was reported to be $5.26\times10^{-6}$ and $4.51\times10^{-6}$ cm²/s respectively. The results for the FITC seem to be within the range to those reported comparing the molecular weights of these compounds to FITC. The permeability of FITC from chorioamnion was found to be $7.93\times10^{-7}$ cm²/s. These results show that amnion is more permeable to FITC than the chorion. The permeability of fetal membranes in rhesus monkey is similar to that of humans and the chorion and chorioamnion in the rhesus monkey were found to be less permeable than the amnion. Further, previous reports arranged the permeability for water, sodium ions, urea, D-arabiniose and sucrose in the order amnion>chorion=chorioamnion.

Figure 93A:
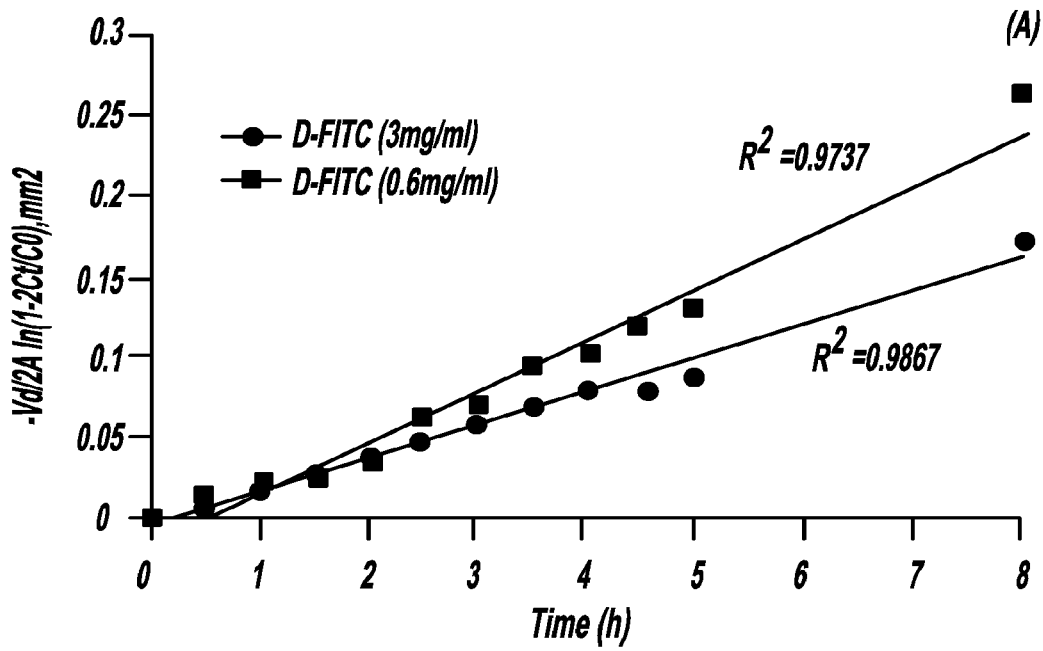
FIG. 93 depicts the Permeability coefficient for dendrimer measured across the (A) chorioamnion (B) amnion and (C) chorion. The concentrations of $G_4$-PAMAM-O-GABA-NH-FITC (D-FITC) studied were 0.6 mg/mL and 3 mg/mL. The permeability coefficient of 0.6 mg/mL and 3 mg/mL D-FITC through (A) chorioamnion was $7.5 \times 10^{-8}$ and $5.8 \times 10^{-8}$ respectively (B) amnion was $1.86 \times 10^{-8}$ and $2.08 \times 10^{-7}$ and (C) chorion was $2.94 \times 10^{-8}$ and $2.94 \times 10^{-8}$ cm$^2$/s
Figure 93B:
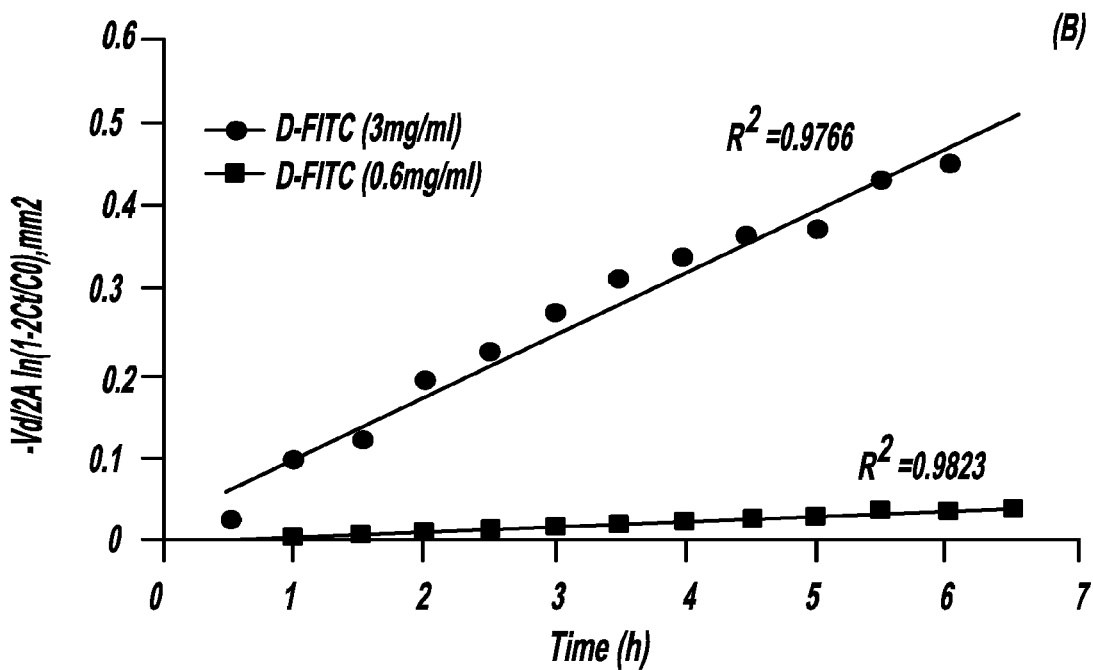
Figure 93C:
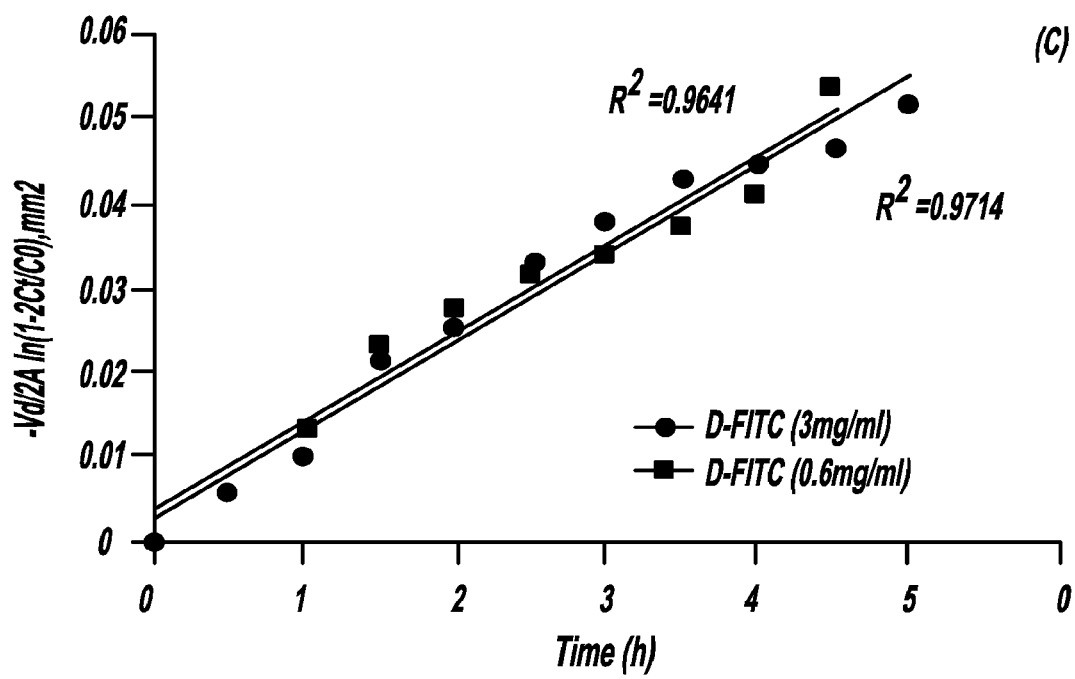
Figure 94:
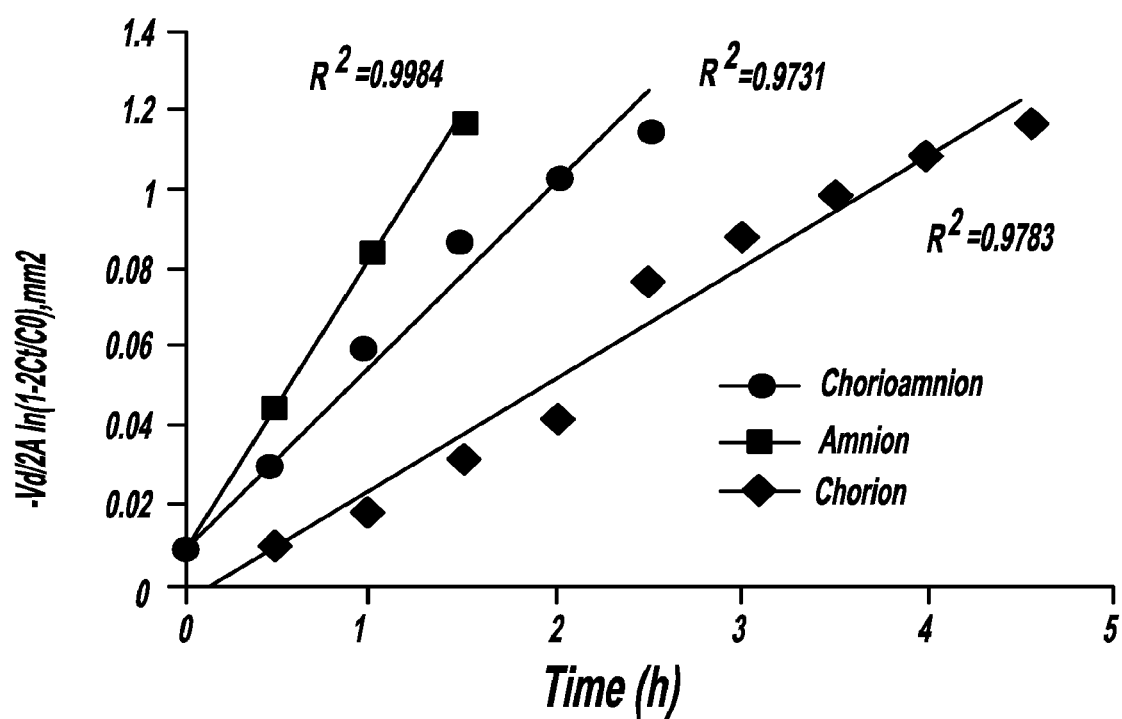
FIG. 94 depicts the permeability coefficient for FITC (unconjugated) measured across the chorioamnion, amnion and chorion. The concentration of FITC was 0.3 mg/mL. The permeability coefficient of FITC through chorioamnion was $7.93 \times 10^{-7}$, amnion was $2.26 \times 10^{-6}$ and chorion was $1.32 \times 10^{-6}$ cm$^2$/s.

The permeability of small molecule FITC is 100 folds higher from chorion and amnion alone when compared to the permeability of $G_4$-PAMAM-dendrimer. When permeability across chorioamnion (intact membrane) was compared, FITC was found to be 10-fold more permeable than the dendrimer (Table 7). The permeability of the compounds was inversely proportional to their molecular weights. The permeability of dendrimer in the amnion was concentration dependant with a value of $1.86\times10^{-8}$ cm²/s ($r^2$=0.98) for low concentration and $2.08\times10^{-7}$ cm²/s ($r^2$=0.97) for the higher concentration (Table 7). While in case of the chorioamnion the lower concentration (0.6 mg/mL) showed a slightly higher permeability ($7.5\times10^{-8}$ cm²/s) ($r^2$=0.97) than that exhibited by the higher (3 mg/mL) concentration ($5.8\times10^{-8}$ cm²/s) ($r^2$=0.98). On the other hand, the chorion alone did not show a concentration dependant permeability where both the high and low concentrations showed a permeability coefficient of $2.94\times10^{-8}$ cm²/s ($r^2$=0.96 and 0.97 respectively) (FIG. 93C)). In the present study, the amnion and the chorioamnion were able to differentiate between the high and low concentrations of the dendrimer unlike the chorion (FIG. 93A-B). Previous reports have shown that the human amnion has better ability to differentiate between different cations than the chorion, and also the amnion has better differentiating ability towards the transport of small non electrolytes and water than the chorion. The order of conductance of cations by different layers was reported to be amnion=chorioamnion>chorion. These differences are attributed to the larger intercellular sites in chorion when compared to amnion and hence the chorion cannot differentiate between the cations. The entrapped water in the amnion forms an unstirred water layer which itself acts as an effective diffusional barrier to transport of molecules in addition to the amniotic membrane structure and the human amnion cell layer is a more effective diffusion barrier than chorion.

The molecular weight of the $G_4$-PAMAM-O-GABA-NH-FITC is approximately 40 times higher (~16 kDa) than the molecular weight of FITC (389 Da) and based on the dendrimer size, its transport is hindered across the membranes. The fetal membranes allow the passage of small molecules (<600 Da) like sodium and glucose by simple diffusion but do not readily permit the passage of substances of molecular weight >1000 Da. The amnion and the chorioamnion, behave physicochemically as porous and partially semipermeable membranes and their cell junctions made of desmosomes, gap junctions and occasional tight junctions offering resistance for paracellular transport. The human chorion is sieve-like membrane with large water filled extracellular channels and also the intercellular spaces. The transfer by paracellular pathway is more important than the transcellular pathway in the fetal membranes. The paracellular transfer is dependant on the different pore sizes and the trophoblast in chorion region has limited number of dilated branching wide openings with a diameter of 15-25 nm which regulate the overall permeability. While the non dilated channels in chorion provide transport for the smaller substances having an effective molecular radius under 2 nm, the clefts at the intercellular junctions further have few tight regions of 4.1 nm in diameter restricting the passage of large molecules. The size of $G_4$-PAMAM-Alexa and $G_4$-PAMAM-FITC was found to be 5.6 nm and 5.4 nm respectively, and hence their passage could occur through the limited dilated openings in chorion.

There is a linear relationship between the rate of transport and the concentration of dendrimer till 5 hours, which shows that the transfer (<3%) occurs by passive diffusion for all the three membranes in this time frame. This observation was from both the permeability and transmembrane transport plots till 5 hours (FIGS. 90-92B and 93A-C). At later time points (5 to 30 hours), as seen from the plots of transmembrane transport (FIGS. 88-90A), the dendrimer with higher (3 mg/mL) concentration showed a lower transport as compared to the lower concentration (0.6 mg/mL). This suggests that the major pathway for transport in initial phase (up to 5-6 hours) is passive diffusion but at later times a saturable process for the transport of higher concentration is likely, suggesting an additional pathway for transport across the membrane. Valproic acid uptake (and transport) by the trophoblast cells is energy dependant (carrier mediated) and was saturable at higher concentration. Further, despite similar molecular weights, the transport of lipophilic compound was substantially higher than the hydrophilic compound. In this study, varying the donor concentration of dendrimer did not lead to a significant change in the permeability coefficient in the chorioamnion and the chorion (Table 7). However, the permeability through the amnion alone was found to differ with change in concentration of the dendrimer. These findings suggest that transmembrane transport of dendrimers occurs by paracellular and energy dependant pathways.

The previous reports on transplacental and transmembrane transport of macromolecules like thyrotropin stimulating hormone (TSH), with molecular weight 28 kDa using a dual chamber was found to be negligible across the placenta and fetal membranes. The results of present study show that fetal membranes exhibit barrier properties for transmembrane transport based on molecular weight. These results are consistent with those reported in past. The experimental observation and inferential evidence suggests that if the drugs are conjugated to the dendrimers or other polymers of large molecular weights, then their transport across the fetal membranes will be restricted due to the larger size in conjugated form and these agents could be used for the selective topical delivery in pregnant women without affecting the fetus. It must be pointed out the present measurements of diffusion from a high concentration water solution across the chorioamniotic membrane in a side-by-side chamber would overestimate the transport, when compared to a topical application, where volume of the body fluids will be present at relatively lower levels.

Biodistribution of Dendrimer in the Chorioamniotic Membrane

Figure 95A:
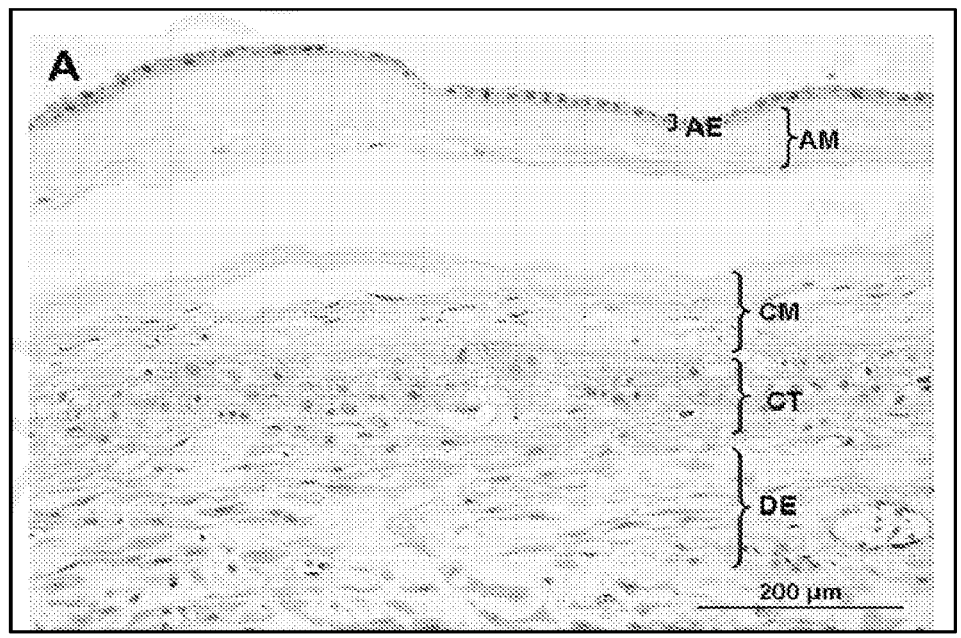
FIG. 95A shows the H and E stained human chorioamniotic (fetal) membrane. AE=amniotic epithelium, AM=amniotic mesoderm, CM=chorionic mesoderm, CT=chorionic trophoblast, DE=decidua comprising the stromal cells. For the transmembrane study the amniotic epithelium was placed facing the receptor cell to study the transport of dendrimer from maternal side (extra-amniotic cavity) to the fetal side.
Figure 95B:
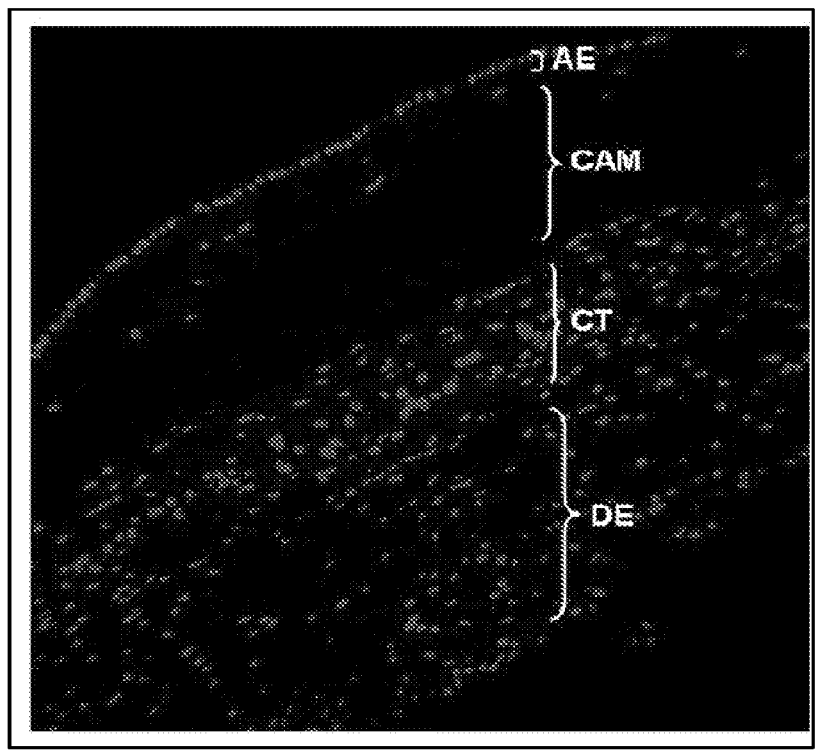
FIG. 95B shows the human chorioamniotic (fetal) membrane showing the nuclei stained blue with DAPI (control membrane without the treatment with $G_4$-PAMAM-O-GABA-NH-Alexa (D-alexa) (20×). The negative controls rabbit isotype and mouse isotype replaced the primary antibodies. AE=amniotic epithelium, CAM=chorioamniotic mesoderm, CT=chorionic trophoblast, DE=decidua comprising the stromal cells. For the transmembrane study the amniotic epithelium was placed facing the receptor cell to study the transport of dendrimer from maternal side (extra-amniotic cavity) to the fetal side.
Figure 96:
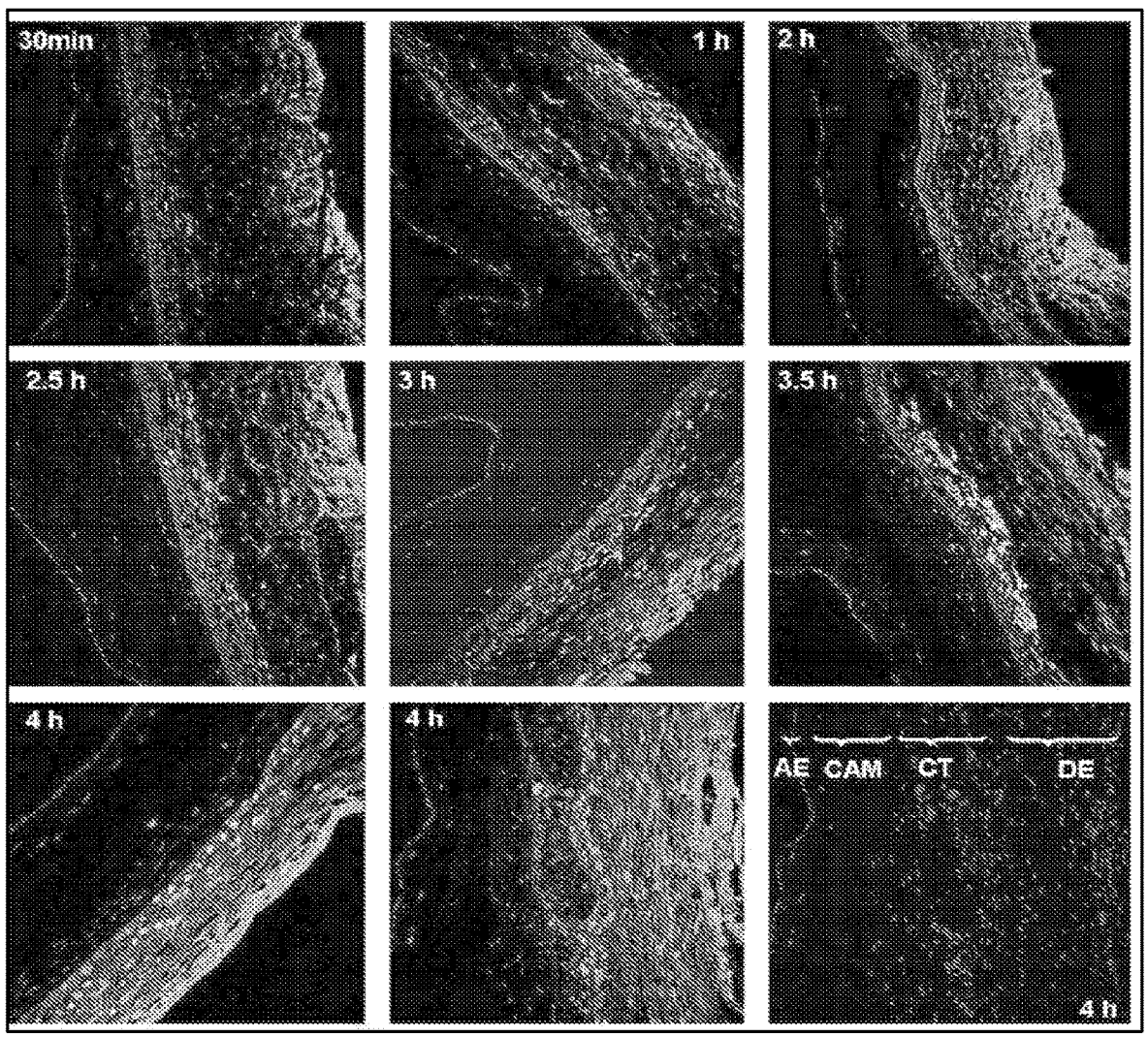
FIG. 96 shows the transmembrane transport of $G_4$-PAMAM-O-GABA-NH-Alexa (D-alexa) across the human fetal membrane at different time points (30 minutes, 1, 2, 2.5, 3, 3.5 and 4 hours respectively) (20×). The nuclei are stained as blue (DAPI), the trophoblast cells in the chorion region are stained cytokeratin positive (red) and the stromal cells in the decidua are stained vimentin positive (magenta). The D-alexa (green) can be seen advancing through the different regions (the different regions are marked in the control membrane shown in bottom panel). At initial time points (30 min to 2 hours) the dendrimer is seen in mostly in the decidua and stromal cells and at time points 3 to 4 hours the dendrimers seem to diffuse into the chorionic trophoblast region. The image without cytokeratin and vimentin shows the diffusion of dendrimer throughout the decidua and trophoblast cells (4 hours, bottom panel, center). AE=amniotic epithelium, CAM=chorioamniotic mesoderm, CT=chorionic trophoblast, DE=decidua comprising the stromal cells. For the transmembrane study the amniotic epithelium was placed facing the receptor cell to study the transport of dendrimer from maternal side (extra-amniotic cavity) to the fetal side.

Confocal microscopy was used for histological visualization of the transport and biodistribution of dendrimer (G4-PAMAM-GABA-NH-Alexa) across the chorioamniotic membrane. FIG. 95A shows the general morphology of the human chorioamniotic membrane. The FIG. 95B shows the control membrane (without the treatment with dendrimer) and with negative controls rabbit isotype and mouse isotype replacing the primary antibodies showing the nuclei stained blue with DAPI. To identify the different cells and regions in the chorioamniotic membranes they were stained with cytokeratin and vimentin positive. The transport of the dendrimer across the chorioamniotic membrane as a function of time was investigated and the histology data is shown in FIG. 96. The nuclei for all cells are stained blue (by DAPI), the trophoblast cells in the chorion region are stained cytokeratin positive (red) and the stromal cells in the decidua are stained vimentin positive (magenta). The progressive advancement of the dendrimer front across the membrane with respect to the time (30 min to 4 hours) can be visualized from FIG. 96. The dendrimer is mostly confined to the chorionic regions in the membrane as seen from the differential staining for the amnion and chorionic regions (FIG. 96). At early time points, 30 min to 2 hours (FIG. 96 top panel) the dendrimer is mostly seen in the decidual region and not much has traversed into the trophoblast region (stained red). While at 2.5 to 3.5 hour time points the dendrimer transport has progressed slightly further and sparsely the dendrimer can be visualized in the trophoblast cells in the chorionic region, though most of the dendrimer seems retained in the decidual region (FIG. 96, middle panel). After 4 hours the dendrimer seems to have traversed into the trophoblast regions as seen from the image (FIG. 96, bottom panel extreme left).

It is interesting to note that with the passage of time (30 min to 4 hours) the dendrimer progresses gradually across the decidua into the trophoblast region, however a corresponding increase of the dendrimer transport across the chorion mesoderm, spongy layer, reticular mesh of fibroblast layer, amniotic mesoderm or amniotic epithelium is not observed from the histological evaluation (FIG. 96). In general, the histology of membranes shows that the dendrimer is not seen in the chorioamniotic mesoderm and amniotic epithelium for the entire time frame (30 min-4 hours). Its is reported that the human amnion epithelial cells express the multidrug resistant associated proteins (MRPs) which are responsible for preventing the accumulation of xenobiotics and contribute for their efflux out of the amnion cells. A similar mechanism was speculated for the negligible transport of alkaline phosphatase (180 kDa) across the amniotic epithelial cells, while the small molecules (<600 Da) were reported to be largely transported by paracellular pathways. The transport experiments showed ≤3% transfer of dendrimer from the chorioamnion upto 5 hours. It appears from the immunofluorescence images that whatever dendrimer traverses across chorionic trophoblast region is also transported across the amnion without being retained by the amnion cell layer, while the dendrimer is mostly accumulated and retained by the chorionic trophoblast region.

Figure 97A:
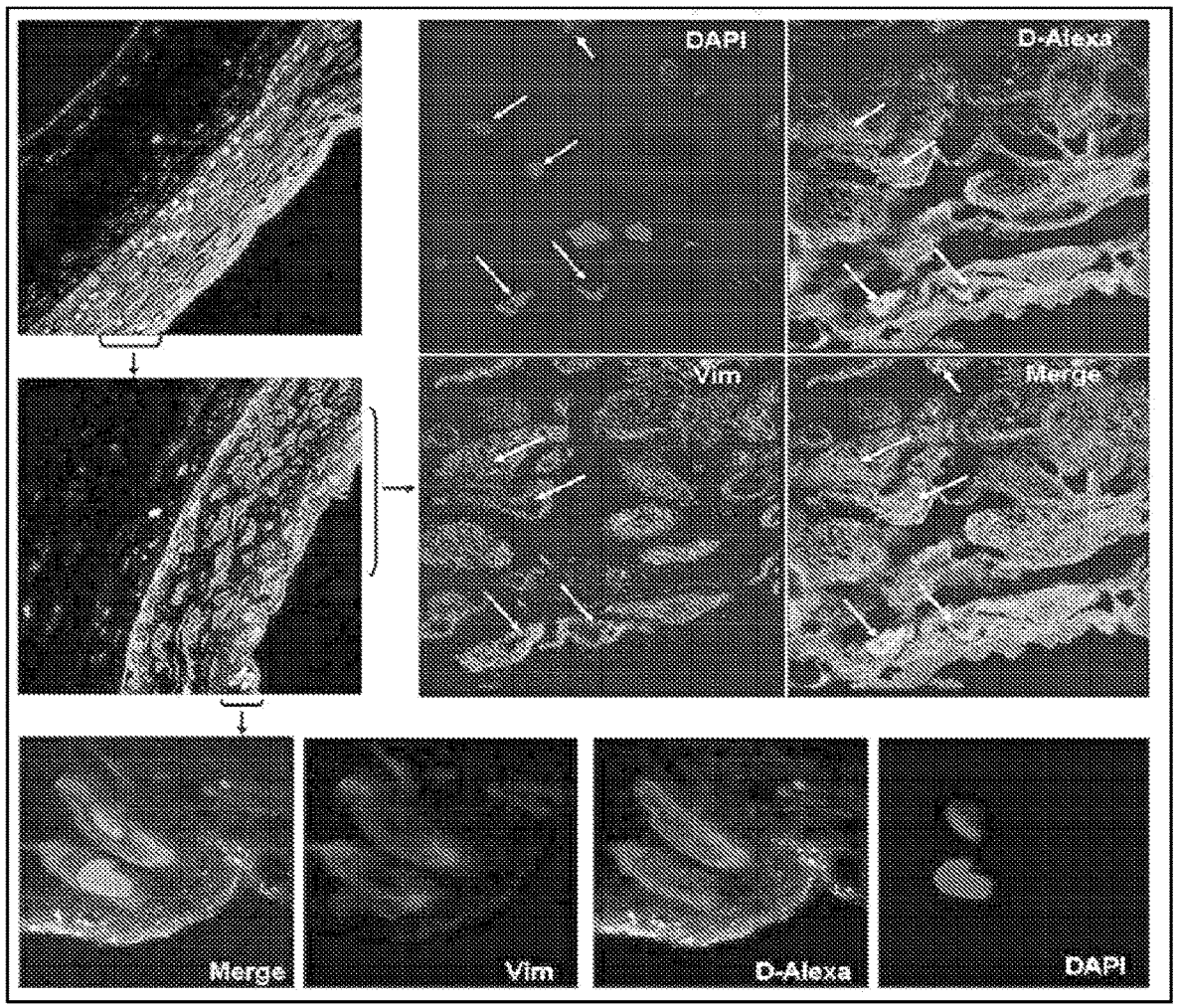
FIG. 97a shows colocalization images for the $G_4$-PAMAM-O-GABA-NH-Alexa (D-alexa) in the decidual stromal cells at 4 hours. The stromal cells are vimentin positive (magenta) and the nuclei of all the cells are stained blue. The D-alexa is seen in green. The internalization of D-alexa in the nuclei and cytoplasm of stromal cells can be seen from the merged composite image. The colocalized D-alexa with nuclei appears as cyan (63×). The arrows identify the cells showing cellular uptake of dendrimer (63×). Also the dendrimer seems largely in the interstitial regions.
Figure 97B:
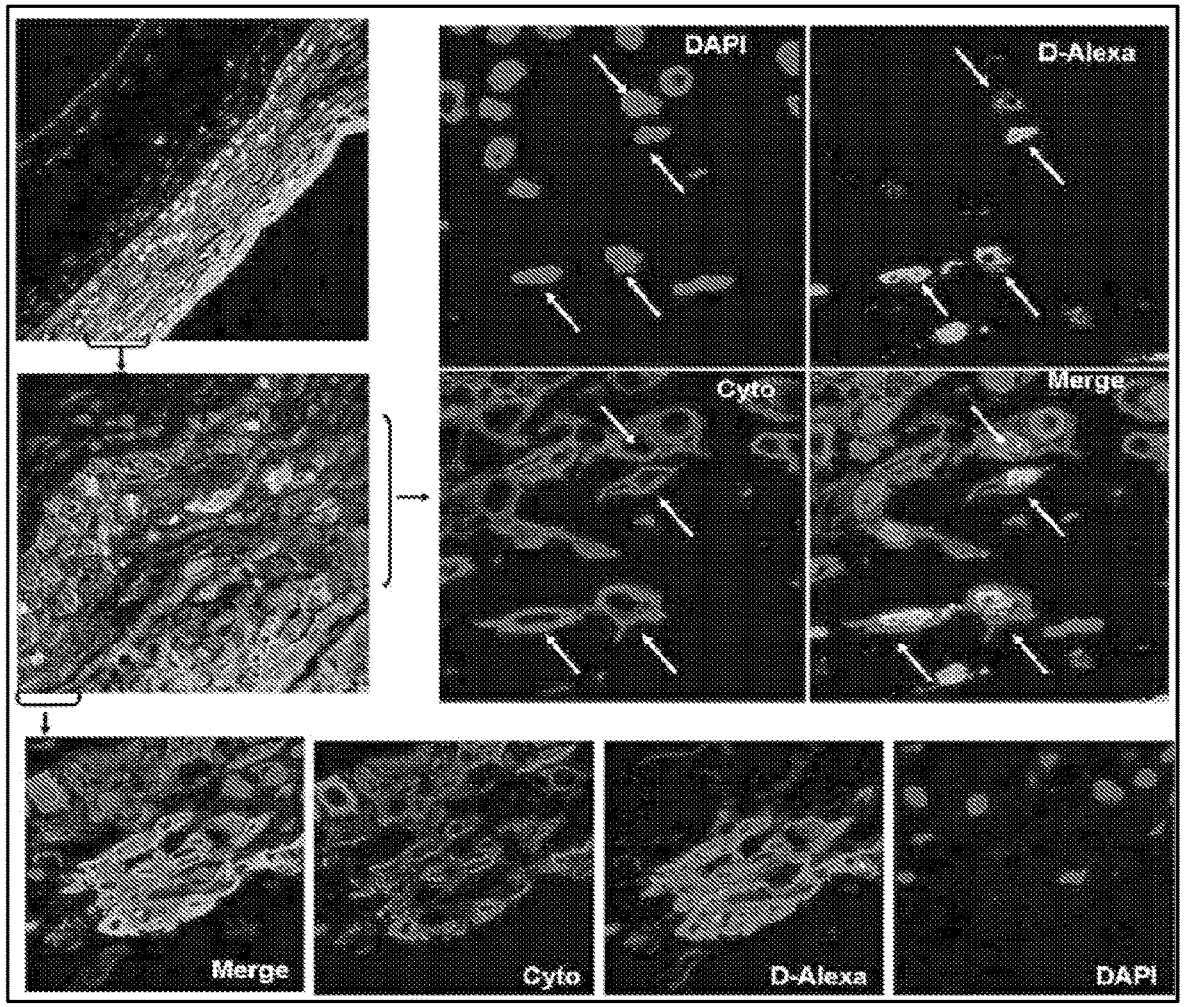
FIG. 97b shows colocalization images for the $G_4$-PAMAM-O-GABA-NH-Alexa (D-alexa) in the chorionic trophoblast region at 4 hours. The chorionic trophoblast cells are cytokeratin positive (red) and the nuclei of all the cells is stained blue. The D-alexa is seen in green. The internalization of D-alexa in the nuclei of trophoblast cells is seen from the merged composite image. The arrows identify the cells showing cellular uptake of dendrimer. The colocalized D-alexa with nuclei appears as cyan (63×). Also the bottom panel shows that dendrimer is largely in the interstitial regions (20×).
Figure 98:
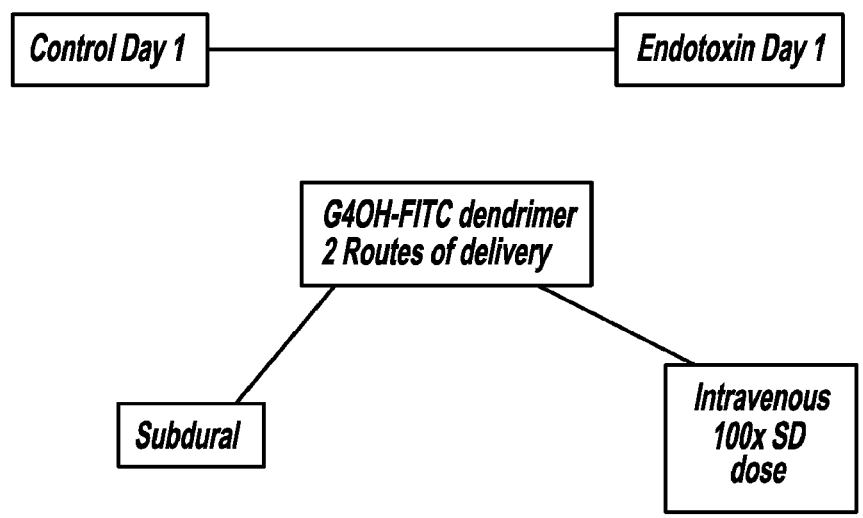
FIG. 98 shows the dendrimer biodistribution in the brain, wherein animals are sacrificed at 6 or 24 hours and brain sections are stained with Rhodamine labeled GFAP or tomato lectin for co-localization.

To further evaluate if the dendrimers were taken up by the cells in the chorionic region the histology of membranes was evaluated under higher magnification (63×). The colocalization images (FIG. 97A-B) with either cytokeratin or vimentin show the internalization of dendrimer in both cytokeratin positive trophoblast cells and vimentin positive stromal cells. The colocalization of the dendrimer is seen in the nuclei of the trophoblast cells in chorion (FIG. 97B) and the nuclei and cytoplasm of stromal cells in decidua (FIG. 97A). Further, the image (FIG. 97A) shows that the dendrimer surrounds these stromal cells suggesting that both paracellular and transcellular mechanisms could be responsible for transport, though passive diffusion seems to be dominant and only a small fraction of the dendrimer might be internalized in the cells. A similar observation was seen for the trophoblast cells where the dendrimer is largely found in interstitial spaces as compared to that being taken up in nuclei (FIG. 97B). Internalization of dendrimers into the lysozyme and cytoplasm by endocytosis in A549 lung epithelial cells has been previously reported. Further, colocalization of dendrimers in cytoplasm and nucleus of HeLa and cancer cells is known. Also transport of dendrimers by paracellular and transcellular pathway for Caco-2 cell line and microglial cell line is reported in the past. The dendrimer is indeed internalized in some of the trophoblast and stromal cells in fetal membranes.

Cellular permeation pathways exist in human fetal membranes and they are capable of differentiating between different molecular species. The transport data showed that the higher concentration of the dendrimer (3 mg/mL) at later time points (20-30 hours) did not show the proportionately higher transport across the membranes. This suggests that the concentration gradient was not the only driving force for the transport and there could be a possibility of dendrimer being retained in the cells. It is possible that the cells are saturated at higher concentration of dendrimer and hence the correspondingly higher transport at this concentration was not observed. The histology data for later time point 4 hours showed internalization of dendrimer in most stromal cells. A saturable phenomenon for transport was observed for higher concentration of valproic acid in trophoblast cells. The transtrophoblast transfer of D-glucose and 2-aminoisobutyrate showed both saturable and non-saturable pathways and accumulation in trophoblast cells. These previous results collectively with the transport data and histological evaluation of immunofluorescent images suggest that some dendrimer could be retained intracellularly in the layers of the chorioamnion membrane. There are reports indicating that certain types of particles are accumulated in the placental membrane cells rather than crossing the barriers after extended time periods. The gold nanoparticles 10-30 nm were internalized in the placental cells (trophoblast cells) and traceable amounts were not transported to the fetal side in 6 hours. Also, the energy dependant pathway for internalization of the small liposomes (70 nm) probably by endocytosis in the placental tissues was reported. Some amount of the liposomes (70 nm) was transported by endocytosis to the fetal side. The large multilamellar liposomes (300 nm) were minimally internalized and the anionic and neutral liposomes were preferentially internalized over the cationic liposomes.

The most significant observation from the present study is that the $G_4$-PAMAM dendrimers do not cross the intact human fetal membrane significantly (<3%) in 5 hours, and cross in relatively small amounts (~10%) over extended time periods up to hours. The dendrimer is mostly seen retained in chorionic regions. The results show that when compared to the smaller molecules (e.g. free FITC), which show rapid transport across the chorioamnion (intact membrane) the $G_4$-PAMAM dendrimers showed relatively negligible transport. The strength of this study is that it was conducted on the fetal membranes of women who underwent cesarean-section delivery and had intact fetal membranes. This investigation of transmembrane transport of dendrimer from intact fetal membranes is more relevant to correlate with the transport of dendrimers from formulations applied to pregnant women topically on the vaginal mucosa. The polylysine based dendrimers are used as topical microbicidal agents to treat genital herpes and the vaginal gels based formulations are currently under human clinical trials. Recently, the PAMAM dendrimers were reported to exhibit antimicrobial activity. The present study indicates that these dendrimers could be used as topical antimicrobial agents or as a component in any intravaginal dosage form (e.g. vaginal tablet, solution or gel) and possibly be used in pregnant women without affecting the fetus. These are the preliminary results and further extensive investigations are under way.

Conclusions

Selective treatment of the pregnant women without affecting the fetus is always desired which probes the search for effective drug delivery approaches. The transmembrane transport for $G_4$-PAMAM dendrimer and FITC was measured across intact human chorioamnion (fetal) membrane and through the stripped amnion and chorion membrane individually. Indeed, the $G_4$-PAMAM dendrimers (Mw ~16 kDa) tagged with FITC showed significantly slower rate of transport across the fetal (chorioamniotic) membranes when compared to the transplacental marker free FITC (Mw ~389 Da). The dendrimer transport was less than ≤3% from all the membranes upto 5 hours and increased slightly in 20 hours, with about 8.3% for chorioamnion (intact membrane), 22% for amnion and 10.5% for chorion, respectively. The transport of FITC was fastest across the amnion with almost complete FITC seen on the receptor side in 2 hours (49%), about 26% in 5 hours from chorion and 20% across chorioamnion in 5 hours, respectively. The biodistribution study showed that the dendrimer is mostly retained in the decidual stromal cells in 30 min to 2 hours. With progression in time the dendrimer traverses upto the chorionic trophoblast cells (2.5 to 4 hours). To some extent, the dendrimer is internalized in nuclei of trophoblast cells and nuclei and cytoplasm of stromal cells. Largely, the dendrimer is seen in the interstitial regions of stromal and trophoblast cells indicating the passive diffusion as major transport route. The results suggest that dendrimers could be used as topical antimicrobial agents or as components of intravaginal dosage forms for selective treatment of pregnant women without affecting the fetus. The overall findings further show that entry of drugs conjugated to macromolecules would be restricted across the human fetal membrane when administered topically by intravaginal route.

TABLE 7

Permeation coefficients of G4-PAMAM-O-GABA-NH-FITC (D-FITC) dendrimer and free FITC

| Compounds | Permeability coefficients cm$^2$/s | | |
|---|---|---|---|
| | Chorioamnion | Chorion | Amnion |
| D-FITC 0.6 mg/mL | $7.5 \times 10^{-8}$ | $2.94 \times 10^{-8}$ | $1.86 \times 10^{-8}$ |
| D-FITC 3 mg/mL | $5.8 \times 10^{-8}$ | $2.94 \times 10^{-8}$ | $2.08 \times 10^{-7}$ |
| FITC 0.3 mg/mL | $7.93 \times 10^{-7}$ | $1.32 \times 10^{-6}$ | $2.26 \times 10^{-6}$ |

FIG. 104 shows the schematic representation for the synthesis of fluorescently labeled $G_4$-PAMAM-dendrimers; G4-PAMAM-O-GABA-NH-FITC (1) and G4-PAMAM-O-GABA-NH-Alexa (2).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

REFERENCES

1. Svenson S, Tomalia D A: Dendrimers in biomedical applications—reflections on the field. *Adv. Drug Delivery Rev.* 57(15), 2106-2129 (2005).
2. Patil M L, Zhang M, Taratula O et al.: Internally cationic polyamidoamine PAMAM-OH dendrimers for siRNA delivery: effect of the degree of quaternization and cancer targeting. *Biomacromolecules* 10 (2), 258-266 (2009).
3. Huang R Q, Qu Y H, Ke W L et al.: Efficient gene delivery targeted to the brain using a transferrin-conjugated polyethyleneglycol-modified polyamidoamine dendrimer. *FASEB,* 21(4), 1117-1125 (2007).
4. Li S D, Huang L: Pharmacokinetics and biodistribution of nanoparticles. *Mol. Pharm.* 5(4), 496-504 (2008).
5. Barrett T, Ravizzini G, Choyke P L, Kobayashi H: Dendrimers in medical nanotechnology. *IEEE. Eng. Med. Biol. Mag.* 28(1), 12-22 (2009).
6. Kolhe P, Misra E, Kannan R M, Kannan S, Lieh-Lai M: Drug complexation, in vitro release and cellular entry of dendrimers and hyperbranched polymers. *Int. J. Pharm.* 259, 143-160 (2003).
7. Kobayashi H, Koyama Y, Barrett T et al.: Multimodal nanoprobes for radionuclide and five-color near-infrared optical lymphatic imaging. *ACS Nano.* 1 (4), 258-264. (2007).
8. Kang H, DeLong R, Fisher M H, Juliano R L: Tat-conjugated PAMAM dendrimers as delivery agents for antisense and siRNA oligonucleotides. *Pharm. Res.* 22, 2099-2106 (2005).
9. Khan M K, Nigavekar S S, Minc L D et al.: In vivo biodistribution of dendrimers and dendrimer nanocomposites—implications for cancer imaging and therapy. *Technol. Cancer. Res. Treat.* 4(6), 603-613 (2005).
10. Lesniak W G, Kariapper M S, Nair B M et al.: Synthesis and characterization of PAMAM dendrimer-based multifunctional nanodevices for targeting alphavbeta3 integrins. *Bioconjug. Chem.* 18(4), 1148-54 (2007).
11. Roy K, Mao H Q, Huang S K, Leong K W: Oral gene delivery with chitosan—DNA nanoparticles generates immunologic protection in a murine model of peanut allergy. *Nature. Med.* 5, 387-391 (1999).
12. Nigavekar S S, Sung L Y, Llanes M et al.: 3H dendrimer nanoparticle organ/tumor distribution. *Pharm. Res.* 21(3), 476-483 (2004).
13. Malik N, Wiwattanapatapee R, Klopsch R et al.: Dendrimers: relationship between structure and biocompatibility in vitro, and preliminary studies on the biodistribution of 125I-labelled polyamidoamine dendrimers in vivo. *J. Control. Release* 65, 133-148 (2000).
14. Almutairi A, Akers W J, Berezin M Y, Achilefu S, Frechet J M: Monitoring the biodegradation of dendritic near-infrared nanoprobes by in vivo fluorescence imaging. *Mol. Pharm.* 5(6), 1103-1110 (2008).
15. Almutairi A, Rossin R, Shokeen M et al.: Biodegradable dendritic positron-emitting nanoprobes for the noninvasive imaging of angiogenesis. *Proc. Natl. Acad. Sci. USA.* 106(3), 685-690 (2009).
16. Kirpotin D B, Drummond D C, Shao Y et al.: Antibody targeting of long-circulating lipidic nanoparticles does not increase tumor localization but does increase internalization in animal models. *Cancer Res.* 66(13), 6732-4670 (2006).
17. Chandrasekar D, Sistla R, Ahmad F J, Khar R K, Diwan P V: The development of folate-PAMAM dendrimer conjugates for targeted delivery of anti-arthritic drugs and their pharmacokinetics and biodistribution in arthritic rats. *Biomaterials.* 28(3), 504-512 (2007).
18. Bennewitz M F, Saltzman W M: Nanotechnology for delivery of drugs to the brain for epilepsy. *Neurotherapeutics* 6(2), 323-336 (2009).
19. Yan Q, Matheson C, Sun J et al.: Distribution of intracerebral ventricularly administered neurotrophins in rat brain and its correlation with trk receptor expression. *Exp Neurol.* 127, 23-36 (1994).
20. Kannan S, Saadani-Makki F, Muzik O et al.: Microglial activation in perinatal rabbit brain induced by intrauterine inflammation: detection with 11C-(R)-PK11195 and small-animal PET. *J. Nucl. Med.* 48(6), 946-954 (2007).
21. Saadani-Makki F, Kannan S, Lu X et al.: Intrauterine administration of endotoxin leads to motor deficits in a rabbit model: a link between prenatal infection and cerebral palsy. *Am. J. Obstet. Gynecol.* 199(6), 651-659 (2008).
22. Régina A, Demeule M, Ché C et al.: Antitumour activity of ANG1005, a conjugate between paclitaxel and the new brain delivery vector Angiopep-2. *Br. J. Pharmacol.* 155 (2), 185-197 (2008).
23. Fung L K, Shin M, Tyler B, Brem H, Saltzman W M: Chemotherapeutic drugs released from polymers: distribution of 1,3-bis(2-chloroethyl)-1-nitrosourea in the rat brain. *Pharm. Res.* 13, 671-682 (1996).
24. Pardridge W M: Blood-brain barrier delivery. *Drug. Discov. Today.* 12(1-2), 54-61 (2007).
25. Allard E, Passirani C, Benoit J P: Convection-enhanced delivery of nanocarriers for the treatment of brain tumors. *Biomaterials.* 30(12), 2302-2318 (2009).
26. Neeves K B, Sawyer A J, Foley C P, Saltzman W M, Olbricht W L: Dilation and degradation of the brain extracellular matrix enhances penetration of infused polymer nanoparticles. *Brain Res.* 1180, 121-132 (2007).
27. Perumal O P, Inapagolla R, Kannan S, Kannan R M: The effect of surface functionality on cellular trafficking of dendrimers. *Biomaterials* 29(24-25), 3469-3476 (2008).
28. Wang B, Navath R S, Romero R, Kannan S, Kannan R: Anti-inflammatory and anti-oxidant activity of anionic dendrimer-N-acetyl cysteine conjugates in activated microglial cells. *Int. J. Pharm.* 377(1-2), 159-68 (2009).
29. Block M L, Zecca L, Hong J S: Microglia-mediated neurotoxicity: uncovering the molecular mechanisms. *Nat. Rev. Neurosci.* 8, 57-69 (2007).
30. Nimmerjahn A, Kirchhoff F, Helmchen F: Resting microglial cells are highly dynamic surveillants of brain parenchyma in vivo. *Science.* 308, 1314-1318 (2005).
31. Napoli I, Neumann H: Microglial clearance function in health and disease. *Neuroscience.* 158, 1030-1038 (2009).
32. Stence N, Waite M, Dailey M E: Dynamics of microglial activation: a confocal time-lapse analysis in hippocampal slices. Glia. 33(3), 256-266 (2001).
33. Carbonell W S, Murase S, Horwitz A F, Mandell J W: Migration of perilesional microglia after focal brain injury and modulation by CC chemokine receptor 5: an in situ time-lapse confocal imaging study. J Neurosci. 27, 25(30):7040-7047 (2005).
34. Meyer-Luehmann M, Spires-Jones T L, Prada C, et al.: Rapid appearance and local toxicity of amyloid-beta plaques in a mouse model of Alzheimer's disease. *Nature;* 451, 720-724 (2008).
35. Navath R S, Kurtoglu Y E, Wang B et al.: Dendrimer-drug conjugates for tailored intracellular drug release based on glutathione levels. *Bioconjug. Chem.* 19, 2446-2455 (2008).
36. Kurtoglu Y E, Navath R S, Wang B et al.: Poly (amidoamine) dendrimer-drug conjugates with disulfide linkages for intracellular drug delivery. *Biomaterials* 30, 2112-2121 (2009).
37. Kannan R M, Kannan S, Romero R et al.: Dendrimer Based Nanodevices for Therapeutic and Imaging Purposes. U.S. Provisional Patent Application No. 61/187, 263 (2009).
38. Aslama, S. N. S., P. C.; Kokubun, T.; Halla, D. R., 2009. Antibacterial and antifungal activity of cicerfuran and related 2-arylbenzofurans and stilbenes. Microbiol Res 164, 191-195.
39. Balogh, L. S., D. R.; Tomalia, D. A.; Hagnauer, G. L.; McManus, A. T., 2001. Dendrimer-Silver Complexes and Nanocomposites as Antimicrobial Agents. Nano Lett 1, 18-21.
40. Benz, R., 1988. Strcture and fuction of porins from gram negative bacteria. Microbial 42, 359-393.
41. Bourne, N., Stanberry, L. R., Kern, E. R., Holan, G., Matthews, B., Bernstein, D. I., 2000. Dendrimers, a new class of candidate topical microbicides with activity against herpes simplex virus infection. Antimicrobial agents and chemotherapy 44, 2471-2474.
42. Cakara, D., Borkovecb, 2007. Microscopic M, Protonation Mechanism of Branched Polyamines: Poly(amido-amine) versus Poly(propyleneimine) Dendrimers. Croat Chem Acta 80 421-428.
43. Cakara, D. K., J.; Borkovec, M., 2003. Protonation Equilibria of Poly(amidoamine) Dendrimers from Macroscopic Titrations. Macromolecules 36, 4201-4207.
44. Calabretta, M. K., Kumar, A., McDermott, A. M., Cai, C., 2007. Antibacterial activities of poly(amidoamine) dendrimers terminated with amino and poly(ethylene glycol) groups. Biomacromolecules 8, 1807-1811.
45. Chaim, W., Mazor, M., Leiberman, J. R., 1997. The relationship between bacterial vaginosis and preterm birth. A review. Archives of gynecology and obstetrics 259, 51-58.
46. Chen, C. Z., Beck-Tan, N. C., Dhurjati, P., van Dyk, T. K., LaRossa, R. A., Cooper, S. L., 2000. Quaternary ammonium functionalized poly(propylene imine) dendrimers as effective antimicrobials: structure-activity studies. Biomacromolecules 1, 473-480.
47. Chen, C. Z., Cooper, S. L., 2002. Interactions between dendrimer biocides and bacterial membranes. Biomaterials 23, 3359-3368.
48. Cheng Y, Q. H., Ma M, Xu Z, Xu P, Fang Y, Xu T., 2007. Polyamidoamine (PAMAM) dendrimers as biocompatible carriers of quinolone antimicrobials: An in vitro study Eur J Med Chem 42, 1032-1038.
49. Cloninger, M. J., 2002. Biological applications of dendrimers. Current opinion in chemical biology 6, 742-748.
50. Dickinson, M. A., Harnett, E. L., Venditti, C. C., Smith, G. N., 2009. Transient lipopolysaccharide-induced 51. Dutta, T., Garg, M., Jain, N. K., 2008. Poly(propyleneimine) dendrimer and dendrosome mediated genetic immunization against hepatitis B. Vaccine 26, 3389-3394.
52. Ellison, R.T., 3rd, Giehl, T. J., LaForce, F. M., 1988. Damage of the outer membrane of enteric gram-negative bacteria by lactoferrin and transferrin. Infect Immun 56, 2774-2781.
53. Ethier-Chiasson, M. F., J-C.; Giguere, Y.; Masse, A.; Marseille-Tremblay, C.; Levy, E.; Lafond. J., 2008. Modulation of placental protein expression of OLR1: implication in pregnancy-related disorders or pathologies. Reproduction 136, 491-502.
54. Halford, B., 2005. Dendrimers branch out. C&EN. 83, 30-36.
55. Harnett, E. L., Dickinson, M. A., Smith, G. N., 2007. Dose-dependent lipopolysaccharide-induced fetal brain injury in the guinea pig. American journal of obstetrics and gynecology 197, 179 e171-177.
56. Helander, I. M., Mattila-Sandholm, T., 2000. Fluorometric assessment of gram-negative bacterial permeabilization. J Appl Microbiol 88, 213-219.
57. Hong, S., Leroueil, P. R., Janus, E. K., Peters, J. L., Kober, M. M., Islam, M. T., Orr, B. G., Baker, J. R., Jr., Banaszak Holl, M. M., 2006. Interaction of polycationic polymers with supported lipid bilayers and cells: nanoscale hole formation and enhanced membrane permeability. Bioconjug Chem 17, 728-734.
58. Hou, S., Zhou, C., Liu, Z., Young, A. W., Shi, Z., Ren, D., Kallenbach, N. R., 2009. Antimicrobial dendrimer active against Escherichia coli biofilms. Bioorg Med Chem Lett 19, 5478-5481.
59. Ibrahim, H. R. K., A.; Kobayashi, K., 1991. Antimicrobial Effects of Lysozyme against Gram-Negative Bacteria Due to Covalent Binding of Palmitic Acid. J Agric Food Chem 39, 2077-2082.
60. Je, J. Y., Kim, S. K., 2006a. Antimicrobial action of novel chitin derivative. Biochim Biophys Acta 1760, 104-109.
61. Je, J. Y., Kim, S. K., 2006b. Chitosan derivatives killed bacteria by disrupting the outer and inner membrane. J Agric Food Chem 54, 6629-6633.
62. Jevprasesphant, R., Penny, J., Jalal, R., Attwood, D., McKeown, N. B., D'Emanuele, A., 2003. The influence of surface modification on the cytotoxicity of PAMAM dendrimers. Int J Pharm 252, 263-266.
63. Jucker, B. A. H., H.; Hug, S. J.; Zehnder, A. J. B., 1997. Adsorption of bacterial surface polysaccharides on mineral oxides is mediated by hydrogen bonds Colloids and Surfaces B: Biointerfaces, 9 331-343.
64. Jucker, B. Z., A. B. D.; Harms, H., 1998. Quantification of Polymer Interactions in Bacterial Adhesion. Environ Sci Technol 32, 2909-2915.
65. Keelan, J. A., Marvin, K. W., Sato, T. A., Coleman, M., McCowan, L. M., Mitchell, M. D., 1999. Cytokine abundance in placental tissues: evidence of inflammatory activation in gestational membranes with term and preterm parturition. American journal of obstetrics and gynecology 181, 1530-1536.
66. Khan M. A. S, N. S., Ogawa M, Akita E, Azakami H, Kato A., 2000. Bactericidal Action of Egg Yolk Phosvitin against Escherichia coli under Thermal Stress. J Agric Food Chem 48, 1503-1506.
67. Kim, Y., Klutz, A. M., Jacobson, K. A., 2008. Systematic investigation of polyamidoamine dendrimers surface-modified with poly(ethylene glycol) for drug delivery applications: synthesis, characterization, and evaluation of cytotoxicity. Bioconjug Chem 19, 1660-1672.
68. Kolhatkar, R. B., Kitchens, K. M., Swaan, P. W., Ghandehari, H., 2007. Surface acetylation of polyamidoamine (PAMAM) dendrimers decreases cytotoxicity while maintaining membrane permeability. Bioconjug Chem 18, 2054-2060.
69. Kolhe, P., Khandare, J., Pillai, O., Kannan, S., Lieh-Lai, M., Kannan, R. M., 2006. Preparation, cellular transport, and activity of polyamidoamine-based dendritic nanodevices with a high drug payload. Biomaterials 27, 660-669.
70. Lebreton, S. N., N.; Bradley, M., 2003. Antibacterial single-bead screening. Tetrahedron 59, 10213-10222.
71. Lopez, A. I., Reins, R. Y., McDermott, A. M., Trautner, B. W., Cai, C., 2009. Antibacterial activity and cytotoxicity of PEGylated poly(amidoamine) dendrimers. Mol Biosyst 5, 1148-1156.
72. Mecke, A., Majoros, I. J., Patri, A. K., Baker, J. R., Jr., Holl, M. M., Orr, B. G., 2005. Lipid bilayer disruption by polycationic polymers: the roles of size and chemical functional group. Langmuir 21, 10348-10354.
73. Milovic, N. M., Wang, J., Lewis, K., Klibanov, A. M., 2005. Immobilized N-alkylated polyethylenimine avidly kills bacteria by rupturing cell membranes with no resistance developed. Biotechnol Bioeng 90, 715-722.
74. Mumper, R. J., Bell, M. A., Worthen, D. R., Cone, R. A., Lewis, G. R., Paull, J. R., Moench, T. R., 2009. Formulating a sulfonated antiviral dendrimer in a vaginal microbicidal gel having dual mechanisms of action. Drug development and industrial pharmacy 35, 515-524.
75. Myers, R. P., 1928. The Effect of Hydroxyl Ion Concentration on the Thermal Death Rate of Bacterium Coli. J Bacteriol 15, 341-356.
76. Naberezhnykh, G. A., Gorbach, V. I., Likhatskaya, G. N., Davidova, V. N., Solov'eva, T. F., 2008. Interaction of chitosans and their N-acylated derivatives with lipopolysaccharide of gram-negative bacteria. Biochemistry (Mosc) 73, 432-441.
77. Ortega, P. C.-P., J. L.; Munoz-Fernandez, M. A.; Soliveri, J.; Gomez, R.; Mata, F. Jdela., 2008. Amine and ammonium functionalization of chloromethylsilane-ended dendrimers. Antimicrobial activity studies. Org Biomol Chem. 6, 3264-3269.
78. Patrick, L. A., Gaudet, L. M., Farley, A. E., Rossiter, J. P., Tomalty, L. L., Smith, G. N., 2004. Development of a guinea pig model of chorioamnionitis and fetal brain injury. American journal of obstetrics and gynecology 191, 1205-1211.
79. Romero, R., Chaiworapongsa, T., Espinoza, J., 2003. Micronutrients and intrauterine infection, preterm birth and the fetal inflammatory response syndrome. The Journal of nutrition, 1668S-1673S.
80. Tang, Y. L., Shi, Y. H., Zhao, W., Hao, G., Le, G. W., 2008. Insertion mode of a novel anionic antimicrobial peptide MDpep5 (Val-Glu-Ser-Trp-Val) from Chinese traditional edible larvae of housefly and its effect on surface potential of bacterial membrane. J Pharm Biomed Anal 48, 1187-1194.
81. Tulu, M., Aghatabay, N. M., Senel, M., Dizman, C., Parali, T., Dulger, B., 2009. Synthesis, characterization and antimicrobial activity of water soluble dendritic macromolecules. Eur J Med Chem 44, 1093-1099.
82. Tziveleka, L. A., Psarra, A. M., Tsiourvas, D., Paleos, C. M., 2007. Synthesis and characterization of guanidinylated poly(propylene imine) dendrimers as gene transfection agents. J Control Release 117, 137-146.

83. Ugwumadu, A., 2007. Role of antibiotic therapy for bacterial vaginosis and intermediate flora in pregnancy. Best practice & research 21, 391-402.
84. Urakuboa, A. J., L. F.; Liebermana, J. A.; Gilmore, J. H., 2001 Prenatal exposure to maternal infection alters cytokine expression in the placenta, amniotic fluid, and fetal brain. Schizophrenia Research. 47, 27-36.
85. Wiegand, I., Hilpert, K., Hancock, R. E., 2008. Agar and broth dilution methods to determine the minimal inhibitory concentration (MIC) of antimicrobial substances. Nature protocols 3, 163-175.
86. Yang, H., Lopina, S. T., DiPersio, L. P., Schmidt, S. P., 2008. Stealth dendrimers for drug delivery: correlation between PEGylation, cytocompatibility, and drug payload. J Mater Sci Mater Med 19, 1991-1997.
87. Alexandre, J., Batteux, F., Nicco, C., Chereau, C., Laurent, A., Guillevin, L., Weill, B., Goldwasser, F., 2006. Accumulation of hydrogen peroxide is an early and crucial step for paclitaxel-induced cancer cell death both in vitro and in vivo. Int. J. Cancer 119, 41-48.
88. Cheng, Y., Wang, J., Rao, T., He, X., Xu, T., 2008. Pharmaceutical applications of dendrimers: promising nanocarriers for drug delivery. Front. Biosci. 13, 1447-1471.
89. El-Remessy, A. B., Tang, Y., Zhu, G., Matragoon, S., Khalifa, Y., Liu, E. K., Liu, J.-Y., Hanson, E., Mian, S., Fatteh, N., Liou, G. I., 2008. Neuroprotective effects of cannabidiol in endotoxin-induced uveitis: critical role of p38 MAPK activation. Mol. Vis. 14, 2190-2203.
90. Gomez, R., Romero, R., Nien, J., Medine, L., Carstens, M., Kim, Y. M., Espinoza, J., Chaiworapongsa, T., Gonzalez, R., Iams, J. D., Rojas, I., 2007. Antibiotic administration to patients with preterm premature rupture of membranes does not eradicate intra-amniotic infection. J. Matern. Fetal Neonatal Med. 20, 167-173.
91. Gurdag, S., Khandare, J., Staples, S., Kannan, R. M., Matherly, L., 2005. Activity of dendrimer-methotrexate conjugates in sensitive and resistant cell lines. Bioconjugate Chem. 17, 275-283.
92. Kannan, S., Kolhe, P., Raykova, V., Glibatec, M., Kannan, R. M., Lai, M. L., Bassett, D., 2004. Dynamics of cellular entry and drug delivery by dendritic polymers into human epithelial carcinoma cells. J. Biomater. Sci. Polym. Edn. 15, 311-330.
93. Kannan, R. M., Iezzi, R., Rajaguru, B., Kannan, S. Dendrimer-containing particles for sustained release of compounds (U S/International patent filed, U.S. Patent application No. 60/997,987).
94. Khandare, J., Kolhe, P., Pillai, O., Kannan, S., Lai, M. L., Kannan, R. M., 2005. Synthesis, cellular transport, and activity of polyamidoamine dendrimer-methylprednisolone conjugates. *Bioconjugate Chem.* 16, 330-337.
95. Kim, M. Y., Wogan, G. N., 2006. Mutagenesis of the supF gene of pSP189 replicating in AD293 cells cocultivated with activated macrophages: roles of nitric oxide and reactive oxygen species. Chem. Res. Toxicol. 19, 1483-1491.
96. Lee, C. C., MacKay, J. A., Frechet, J. M. J., Szoka, F. C., 2005. Designing dendrimers for biological applications. Biotechnology 23, 1517-1526.
97. Lessio, C., Assunc, F. D., Gloria, A. M., Beatriz, A., Tommaso, G. D., Mouro, M. G., Marco, G. S. D., Schor, N., Higa, E. M. S., 2005. Cyclosporine A and NAC on the inducible nitric oxide synthase expression and nitric oxide synthesis in rat renal artery cultured cells. Kidney Int. 68, 2508-2516.
98. Lu, D. Y., Tang, C. H., Liou, H. C., Teng, C. M., Jeng, K. C. G., Kuo, S. C., Lee, F. Y., Fu, W. M., 2007. YC-1 attenuates LPS-induced proinflammatory responses and activation of nuclear factor-kB in microglia. Br. J. Pharmacol. 151, 396-405.
99. Makki, F. S., Kannan, S., Lu, Janisse, X., Dawe, J. E., Edwin, S., Romero, R., Chugani, D., 2008. Intrauterine administration of endotoxin leads to motor deficits in a rabbit model: a link between prenatal infection and cerebral palsy. Am. J. Obstet. Gynecol. 199, 651-1651.
100. Min, K. J., Jou, I., Joe, E., 2003. Plasminogen-induced IL-1β and TNFα production in microglia is regulated by reactive oxygen species. Biochem. Biophys. Res. Commun. 312, 969-974.
101. Noack, H., Possel, H., Chatterjee, S., Keilhoff, G., Wolf, G., 2000. Nitrosative stress in primary glial cultures after induction of the inducible isoform of nitric oxide synthase (i-NOS). Toxicology 148, 133-142.
102. Paintlia, M. K., Paintlia, A. S., Contreras, M. A., Singh, I., Singh, A. K., 2008. Lipopolysaccharide-induced peroxisomal dysfunction exacerbates cerebral white matter injury: attenuation by N-acetyl cysteine. Exp. Neurol. 210, 560-576.
103. Romero, R., Gomez, R., Ghezzi, F., Yoon, B. H., Mazor, M., Edwin, S., Berry, S., 1998. A fetal systemic inflammatory response is followed by the spontaneous onset of preterm parturition. Am. J. Obstet. Gynecol. 179, 186-193.
104. Romero, R., Gotsch, F., Pineles, B., Kusanovic, J. P., 2007a. Inflammation in pregnancy: its roles in reproductive physiology, obstetrical complications, and fetal injury. Nutr. Rev. 65, S194-S202.
105. Romero, R., Espinoza, J., Goncalves, L. F., Kusanovic, J. P., Friel, L., Hassan, S., 2007b. The role of inflammation and infection in preterm birth. Semin. Reprod. Med. 25, 21-39.
106. Romero, R., Espinoza, J., Kusanovic, J. P., Gotsch, F., Hassan, S., Erez, O., Chaiworapongs, T.,Mazorc, M., 2006. The preterm parturition syndrome. Int. J. Obstet. Gynaecol. 113, 17-42.
107. Roy, A., Jana, A., Yatish, K., Freidt, M. B., Fung, Y. K., Martinson, J. A., Pahan, K., 2008. Reactive oxygen species up-regulate CD11b in microglia via nitric oxide: implications for neurodegenerative diseases. Free Radic. Biol. Med. 26, 116-121.
108. Villalonga-Barber, C., Micha-Screttas, M., Steele, B. R., 2008. Dendrimers as biopharmaceuticals: synthesis and properties. Curr. Top. Med. Chem. 8 (14), 1294-1309.
109. Wang, X., Svedin, P., Nie, C., Lapatto, R., Zhu, C., Gustavsson, M., Sandberg, M., Karlsson, J. O., Romero, R., Hagberg, H., Mallard, C., 2007. N-acetylcysteine reduces lipopolysaccharide-sensitized hypoxic-ischemic brain injury. Ann. Neurol. 61, 263-271.
110. Waseem, T., Duxbury, M., Ito, H., Ashley, S. W., Robinson, M. K., 2008. Exogenous ghrelin modulates release of pro-inflammatory and anti-inflammatory cytokines in LPS stimulated macrophages through distinct signaling pathways. Surgery 143, 334-342.
111. Wiwattanapatapee, R., Gómez, B. C., Malik, N., Duncan, R., 2004. Anionic PAMAM dendrimers rapidly cross adult rat intestine in vitro: a potential oral delivery system. Pharm. Res. 2, 991-998.
112. Wolinsky, J. B., Grinstaff, M. W., 2008. Therapeutic and diagnostic applications of dendrimers for cancer treatment. Adv. Drug Deliv. Rev. 60 (9), 1037-1055.

113. Esfand R, Tomalia D A. Poly(amidoamine) (PAMAM) dendrimers: from biomimicry to drug delivery and biomedical applications. Drug Discov Today 2001; 6:427-36.
114. Duncan R, Izzo L. Dendrimer biocompatibility and toxicity. Adv Drug Deliv Rev 2005; 57:2215-37.
115. Sato N, Kobayashi H, Hiraga A, Saga T, Togashi K, Konishi J, et al. Pharmacokinetics and enhancement patterns of macromolecular M R contrast agents with various sizes of polyamidoamine dendrimer cores. Magn Reson Med 2001; 46:1169-73.
116. Matsumura Y, Maeda H. A new concept for macromolecular therapeutics in cancer chemotherapy: mechanism of tumoritropic accumulation of proteins and the antitumor agent. Cancer Res 1986; 46:6387-92.
117. Kukowska-Latallo J F, Candido K A, Cao Z, Nigavekar S S, Majoros I J, Thomas T P, et al. Nanoparticle targeting of anticancer drug improves therapeutic response in animal model of human epithelial cancer. *Cancer Res* 2005; 65:5317-24.
118. Malik N, Evagorou E G, Duncan R. Dendrimer-platinate: a novel approach to cancer chemotherapy. Anticancer Drugs 1999; 10:767-76.
119. Zhuo R X, Du B, Lu Z R. In vitro release of 5-fluorouracil with cyclic core dendritic polymer. J Control Release 1999; 57:249-57.
120. Lee C C, Gillies E R, Fox M E, Guillaudeu S J, Fréchet J M J, Dy E E, et al. A single dose of doxorubicin-functionalized bow-tie dendrimer cures mice bearing C-26 colon carcinomas. Proc Natl Acad Sci USA 2006; 103:16649-56.
121. Wiwattanapatapee R, Lomlim L, Saramunee K. Dendrimers conjugates for colonic delivery of 5-aminosalicylic acid. J Control Release 2003; 88:1-9.
122. Najlah M, Freeman S, Attwood D, D'Emanuele A. Synthesis, characterization and stability of dendrimer prodrugs. Int J Pharm 2006; 308:175-82.
123. Zafarullah M, Li W Q, Sylvester J, Ahmad M. Molecular mechanisms of N-acetyl cysteine actions. Cell Mol Life Sci 2003; 60:6-20.
124. Khan M, Sekhon B, Jatana M, Giri S, Gilg A G, Sekhon C, et al. Administration of N-acetyl cysteine after focal cerebral ischemia protects brain and reduces inflammation in a rat model of experimental stroke. J Neurosci Res 2004; 4:519-27.
125. Dekhuijzen P N R. Antioxidant properties of N-acetyl cysteine: their relevance in relation to chronic obstructive pulmonary disease. Eur Respir J 2004; 23:629-36.
126. Harada D, Naito S, Otagiri M. Kinetic analysis of covalent binding between N-acetyl-L-cysteine and albumin through the formation of mixed disulfides in human and rat serum in vitro. Pharm Res 2002; 19:1648-54.
127. Yip L, Dart R C, Hurlbut K M. Intravenous administration of oral N-acetyl cysteine. Crit Care Med 1998; 26:40-3.
128. Patri A K, Kukowska-Latallo J F, Baker Jr J R. Targeted drug delivery with dendrimers: comparison of the release kinetics of covalently conjugated drug and non-covalent drug inclusion complex. Adv Drug Deliv Rev 2005; 57:2203-14.
129. De Jesus O L P, Ihre H R, Gagne L, Frechet J M J, Szoka Jr F C. Polyester dendritic systems for drug delivery applications: in vitro and in vivo evaluation. Bioconjug Chem 2002; 13:453-61.
130. Bracci L, Falciani C, Lelli B, Lozzi L, Runci Y, Pini A, et al. Synthetic peptides in the form of dendrimers become resistant to protease activity. J Biol Chem 2003; 278: 46590-5.
131. Meister A, Anderson M E. Glutathione. Annu Rev Biochem 1983; 52:711-60.
132. Arrick B A, Nathan C F. Glutathione metabolism as a determinant of therapeutic efficacy: a review. Cancer Res 1984; 44:4224-32.
133. Saito G, Swanson J A, Lee K. Drug delivery strategy utilizing conjugation via reversible disulfide linkages: role and site of cellular reducing activities. Adv Drug Deliv Rev 2003; 55:199-215.
134. Zhang W, Tichy S E, Perez L M, Maria G C, Lindahl P A, Simanek E E. Evaluation of multivalent dendrimers based on melamine: kinetics of thiol-disulfide exchange depends on the structure of the dendrimer. J Am Chem Soc 2003; 25:5086-94.
135. Cuchelkar V, Kopeckova P, Kopecek J. Synthesis and biological evaluation of disulfide-linked HPMA copolymer-mesochlorin e6 conjugates. Macromol Biosci 2008; 8:375-83.
136. Roy A, Jana A, Yatich K, Freidt M B, Fung Y K, Martinson J A, et al. Reactive oxygen species up-regulate CD11b in microglia via nitric oxide: implications for neurodegenerative diseases. Free Radic Biol Med 2008; 45:686-99.
137. Winterbourn C C, Metodiewa D. Reactivity of biologically important thiol compounds with superoxide and hydrogen peroxide. Free Radic Biol Med 1999; 27:322-8.
138. Kitchens K M, Foraker A B, Kolhatkar R B, Swaan P W, Eddington N D, Ghandehari H. Endocytosis and interaction of poly(amidoamine) Dendrimers with caco-2 cells. Pharm Res 2007; 24:2138-45.
139. Flora S J, Poande M, Kannan G M, Mehta A. Lead induced oxidative stress and its recovery following co-administration of melatonin or N-acetyl cysteine during chelation with succimer in male rats. Cell Mol Biol 2004; 50:543-5.
140. Louwerse, E. S., Weverling, G. J., and Bossuyt, P. M. (1995) Randomized, double-blind, controlled trial of acetylcysteine in amyotrophic lateral sclerosis. *Arch. Neurol.* 52, 559-564.
141. Ferrari, G., Yan, C. Y., and Greene, L. A. (1995) NAcetylcysteine (D- and L-stereoisomers) prevents apoptotic death of neuronal cells. *J. Neurosci.* 15, 2857-2866.
142. Beloosesky, R, Gayle, A. D, and Ross, G. M. (2006) Maternal N-acetyl cystein suppress fetal inflammatory cytokine responses to materal lipopolysaccharide. *Am. J. Obstet. Gynecol.* 195, 1053-1057.
143. Beichert, M., Nebe, C. T, Hack, V., Edler, L., Droge, W., Pittack, N, Daniel, V., Breitkreutz, R., Schuster, D., and Brust, J. (2000) Improvement of immune functions in HIV infection by sulfur supplementation: two randomized trials. *J. Mol. Med.* 78, 55-62.
144. Estensen, R. D, Levy, M., and Klopp, S, J. (1999) N-Acetyl cysteine suppression of the proliferative index in the colon of patients with previous adenomatous colonic polyps. *Cancer Lett.* 147, 109-114.
145. Ballatori, N. (1998) N-Acetyl cysteine as an antidote in methyl mercury poisoning. *EnViron. Health Perspect.* 106 (5), 267-271.
146. Dilger, R. N, and Baker, D. H. (2007) Oral N-acetyl L-cysteine is a safe and effective precursor of cysteine. *J. Anim. Sci.* 19, 1-26.
147. Beloosesky, R., Gayle, D. A., and Amidi, F. (2006) N-acetylcysteine suppresses amniotic fluid and placenta inflammatory cytokine responses to lipopolysaccharide in rats. *Am. J. Obstet. Gynecol.* 194, 268-273.
148. Xu, D. X., Chen, Y. H., and Wang, H. (2005) Effect of N-acetylcysteine on lipopolysaccharide-induced intra- 148. (continued) uterine fetal death and intra-uterine growth retardation in mice. *Toxicol. Sci* 88, 525-533.

149. Buhimschi, I. A., Buhimschi, C. S., and Weiner, C. P. (2003) Protective effect of N-acetylcysteine against fetal death and preterm labor induced by maternal inflammation. *Am. J. Obstet. Gynecol.* 188, 203-208.

150. Van Schayck, C. P., Dekhuijzen, P. N., and Gorgels, W. J. (1998) Are anti-oxidant and anti-inflammatory treatments effective in different subgroups of COPD. A hypothesis. *Respir. Med.* 92, 1259-1264.

151. Ben-Ari, Z., Vaknin, H., and Tur-Kaspa, R. (2000) N-Acetylcysteine in acute hepatic failure (non-paracetamol-induced). *Hepatogastroenterology* 47 (33), 786-789.

152. Vale, J. A., and Proudfoot, A. T. (1995) Paracetamol (acetaminophen) poisoning. *Lancet* 346, 547-552.

153. Tepel, M., Van der Giet, M., and Schwarzfeld, C. (2000) Prevention of radiographic-contrast-agent-induced reductions in renal function by acetylcysteine. *N. Engl. J. Med.* 343, 180-184.

154. Borgström, L, Kågedal, B., and Paulsen, O. (1986) Pharmacokinetics of N-acetylcysteine in man. *Eur. J. Clin. Pharmacol.* 31, 217-222.

155. Dilger, R. N., Toue, S., Kimura, T., Sakai, R., and Baker, D. H. (2007) Excess dietary L-cysteine, but not L-cystine, is lethal for chicks but not for rats or pigs. *J. Nutr.* 322, 331-338.

156. Palmer, L. A., Doctor, A., Chhabra, P., Sheram, M. L., Laubach, V. E., Karlinsey, M. Z., Forbes, M. S., Macdonald, T, and Gaston, B. (2007) S-Nitrosothiols signal hypoxia-mimetic vascular pathology. *J. Clin. InVest.* 117, 2592-601.

157. Rui, Y, Wang, S., Low, P. S., and Thompson, D. H., (1998) Diplasmenylcholine-folate liposomes: an efficient vehicle for intracellular drug delivery. *J. Am. Chem. Soc.* 120, 11213-11218.

158. Gillies, E. R, and Frechet, J. M. J. (2005) Dendrimers and dendritic polymers in drug delivery. *Drug Discovery Today* 10, 35-43.

159. Alving, R. C., Steckt, A. E., Chapman, L. W., Waits, B. V., Jr., Hendrickst, D. L., Swartz, M. G, Jr., and Hansont, L. I. (1978) Therapy of leishmaniasis: Superior efficacies of liposomeencapsulated drugs. *Proc. Natl. Acad. Sci. U.S.A.* 75, 2959-2963.

160. Ulbrich, K., Etrych, T., Chytil, P., Jelinkova, M., and Rihova, B. (2003) HPMA copolymers with pH-controlled release of doxorubicin: In vitro cytotoxicity and in vivo antitumor activity. *J. Controlled Release* 87, 33-47.

161. Duncan, R. (2003) The dawning era of polymer therapeutics. *Nat. Rev. Drug Discovery* 2, 347-360.

162. Giri, S., Trewyn, B. G. P., Stellmaker, M. P., and Lin, V. S.-Y. (2005) Stimuli-responsive controlled-release delivery system based on mesoporous silica nanorods capped with magnetic nanoparticles. *Angew. Chem., Int Ed.* 44, 5038-5044.

163. Kam, N. W. S., Liu, Z., and Dai, H. (2005) Functionalization of carbon nanotubes via cleavable disulfide bonds for efficient intracellular delivery of siRNA and potent gene silencing. *J. Am. Chem. Soc.* 127, 12492-12493.

164. Perry, R. R., Mazetta, J., Levin, M., and Barranco, S. C. (1993) Glutathione levels and variability in breast tumors and normal tissue. *Cancer* 72, 783-787.

165. Yeh, C. C., Hou, M. F., Wu, S. H., Tsai, S. M., Lin, S. K., Hou, L. A., Ma, H., and Tsai., L. Y. (2006) A study of glutathione status in the blood and tissues of patients with breast cancer. *Cell. Biochem. Funct.* 24, 555-559.

166. Hong, R., Han, G., Fernandez, M. J., Kim, J. B., Forbes, S. N., and Rotello, M. V. (2006) Glutathione-mediated delivery and release using monolayer protected nanoparticle carriers. *J. Am. Chem. Soc.* 128, 1078-1079.

167. Kou, X., Zhang, S., Yang, Z., Tsung, K. C., Stucky, D. G., Sun, L., Wang, J., and Yan, C. (2007) Glutathione- and cysteine-induced transverse overgrowth on gold nanorods. *J. Am. Chem. Soc.* 129, 6402-6404.

168. Verma, A., Simard, M. J., Worrall, W. E. J., and Rotello, M. V. (2004) Tunable reactivation of nanoparticle-inhibited-galactosidase by glutathione at intracellular concentrations. *J. Am. Chem. Soc.* 126, 13987-13991.

169. You, Zi-Ye., Manickam, S. D., Zhou, H. Q., and Oupicky, D. (2007) Reducible poly(2-dimethylaminoethyl methacrylate): Synthesis, cytotoxicity, and gene delivery activity. *J. Controlled Release* 122, 217-225.

170. Zugates, T. G., Anderson, G. D., Little, R. S., Lawhorn, E. B. I., and Langer, R. (2006) Synthesis of poly(_-amino esters) with thiol-reactive side chains for DNA delivery. *J. Am. Chem. Soc.* 128, 12726-12734.

171. Kommareddy, S., and Amiji, M. (2005) Preparation and evaluation of thiol-modified gelatin nanoparticles for intracellular DNA delivery in response to glutathione. *Bioconjugate Chem.* 16, 1423-1432.

172. Oupicky, D., Parker, L. A., and Seymour, W. L. (2002) Laterally stabilized complexes of DNA with linear reducible polycations: strategy for triggered intracellular activation of DNA delivery vectors. *J. Am. Chem. Soc.* 124, 8-9.

173. Wagner, E., Cotten, M., Mechtler, K., Kirlappos, H., and Birnstiel, L. M. (1991) DNA-binding transferrin conjugates as functional gene-delivery agents: synthesis by linkage of polylysine or ethidium homodimer to the transferrin carbohydrate moiety. *Bioconjugate Chem.* 2, 226-231.

174. Rajur, B. S., Roth, M. C., Morgan, R. J., and Yarmush, L. M. (1997) Covalent protein-oligonucleotide conjugates for efficient delivery of antisense molecules. *Bioconjugate Chem.* 8, 935-940.

175. Filipovska, A., Eccles, M. R., Smith, R. A., and Murphy, M. P. (2004) Delivery of antisense peptide nucleic acids (PNAs) to the cytosol by disulphide conjugation to a lipophilic cation. *FEBS Lett.* 556, 180-186.

176. Reiter, Y., Kreitman, J. R., Brinkmann, U., and Pastan, I. (1994) Cytotoxic and antitumor activity of a recombinant immunotoxin composed of disulfide-stabilized anti-TAC Fv fragment and truncated pseudomonas exotoxin. *Int. J. Cancer* 58, 142-149.

177. Hinman, M. L., Hamann, R. P., Wallace, R., Menendez, T. A., and Durr, F. E. (1993) Upeslacis, Preparation and characterization of monoclonal antibody conjugates of the calicheamicins: A novel and potent family of antitumor antibiotics. *J. Cancer Res.* 53, 3336-3342.

178. Najlah, M., Freeman, S., Attwood, D. D., and Emanuele, A. (2007) In vitro evaluation of dendrimer prodrugs for oral drug delivery. *Int. J. Pharm.* 336, 183-190.

179. Pillai, O., Inapagolla, R., Kannan, S., and Kannan, R. M. (2008) The effect of surface functionality on cellular trafficking of dendrimers. *Biomaterials* 29, 3469-3476.

What is claimed is:

1. A composition comprising a polyamidoamine (PAMAM) dendrimer linked to N-acetyl cysteine, optionally via one or more spacers.

2. The composition of claim 1, wherein the PAMAM dendrimer is a generation 3, generation 4, generation 5, generation 6, generation 7, generation 8, generation 9, or generation 10 PAMAM dendrimer.

3. The composition of claim 2, wherein the PAMAM dendrimer is a generation 4 PAMAM dendrimer.

4. The composition of claim 3, wherein the generation 4 PAMAM dendrimer has one or more terminal functional groups selected from the group consisting of carboxylic, amine, and hydroxyl groups.

5. The composition of claim 1, wherein the dendrimer is linked to N-acetyl cysteine via one or more spacers.

6. The composition of claim 5, wherein the one or more spacers are selected from the group consisting of N-Succinimidyl 3-(2-pyridyldithio)-propionate, Glutathione, Gamma-aminobutyric acid, and combinations thereof.

7. The composition of claim 1, wherein the dendrimer is linked to N-acetyl cysteine via disulfide bonds.

8. The composition of claim 1, wherein the composition is in an amount effective to treat inflammation or neuroinflammation in a subject in need thereof.

9. The composition of claim 1, wherein the composition is in an amount effective for targeting to activated microglia and astrocytes of the central nervous system.

10. The composition of claim 1, wherein the composition is in an amount effective to reduce the level of hydrogen peroxide, and/or nitrite in activated microglia and astrocytes of the central nervous system.

11. The composition of claim 1, wherein the composition is in an amount effective to treat and or prevent one or more symptoms of cerebral palsy or white matter injury in the brain.

12. The composition of claim 1 formulated for parenteral, topical or oral administration.

13. The composition of claim 1 formulated in a form selected from the group consisting of hydrogels, nanoparticle or microparticles, suspensions, gels, ointments, powders, tablets, capsules and solutions.

14. A method of reducing or preventing inflammation comprises administering an effective amount of composition according to claim 1.

15. The method of claim 14, wherein the inflammation is chronic inflammation associated with heart attack, Alzheimer's disease, congestive heart failure, stroke, arthritis, aortic valve stenosis, kidney failure, lupus, asthma, psoriasis, pancreatitis, allergies, fibrosis, surgical complications, anemia, fibromyalgia, or combinations thereof.

16. The method of claim 14, wherein the inflammation is neuroinflammation.

17. The method of claim 16, wherein the neuroinflammation has pathogenesis associated with activated microglia and/or astrocytes.

18. The method of claim 16, wherein the neuroinflammation is associated with cerebral palsy.

19. A method of reducing or preventing microbial growth in a subject in need thereof comprising administering an effective amount of the composition according to claim 1.

20. The method of claim 19, wherein the method of reducing or preventing microbial growth comprises administering via a route selected from the group consisting of vaginal, cervical, and rectal routes.

* * * * *

UNITED STATES PATENT AND TRADEMARK OFFICE
CERTIFICATE OF CORRECTION

| | |
|---|---|
| PATENT NO. | : 10,561,673 B2 |
| APPLICATION NO. | : 16/223793 |
| DATED | : February 18, 2020 |
| INVENTOR(S) | : Kannan Rangaramanujam et al. |

It is certified that error appears in the above-identified patent and that said Letters Patent is hereby corrected as shown below:

In the Specification

Figure 82A:
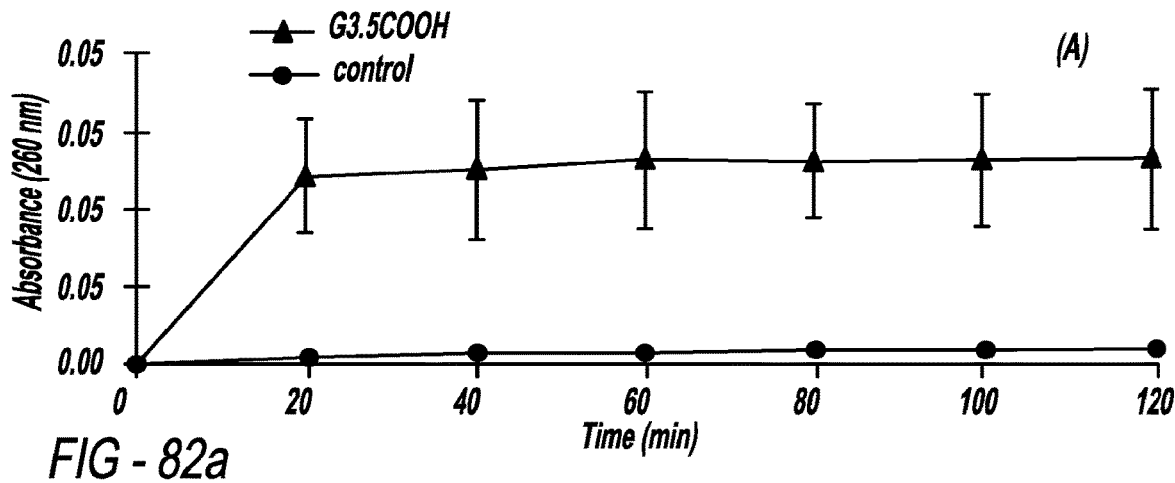
FIG. 82 show the release of intracellular components of *E. coli* suspensions treated with (A) $G_{3.5}$-PAMAM-COOH, (B) $G_4$-PAMAM-OH and (C) $G_4$-PAMAM-$NH_2$. Four samples were evaluated in each group. The increase in the absorbance is an indicator of the compromised cell integrity resulting in leaching of the nuclear components which are absorbed at 260 nm.
Figure 82B:
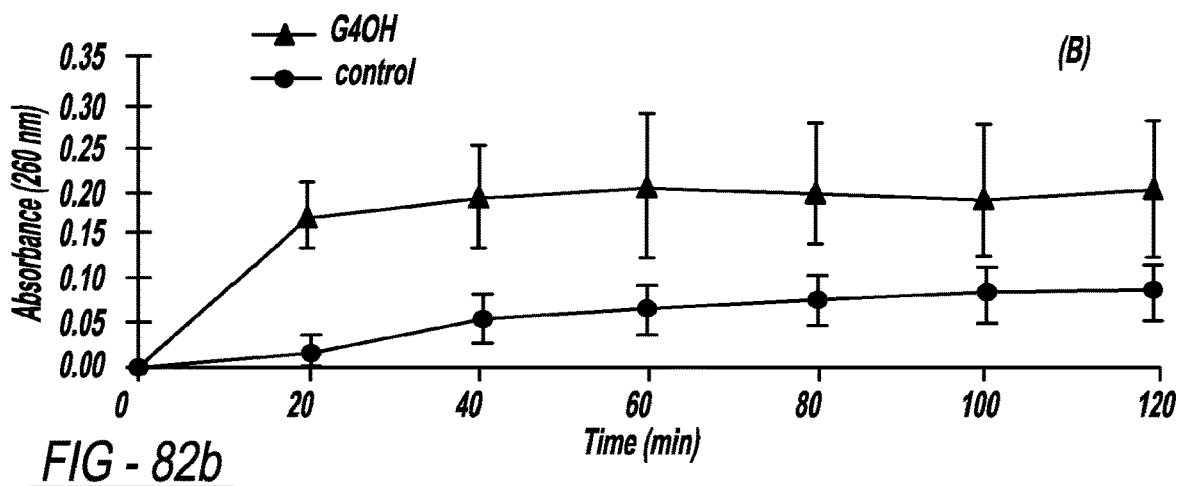
Figure 82C:
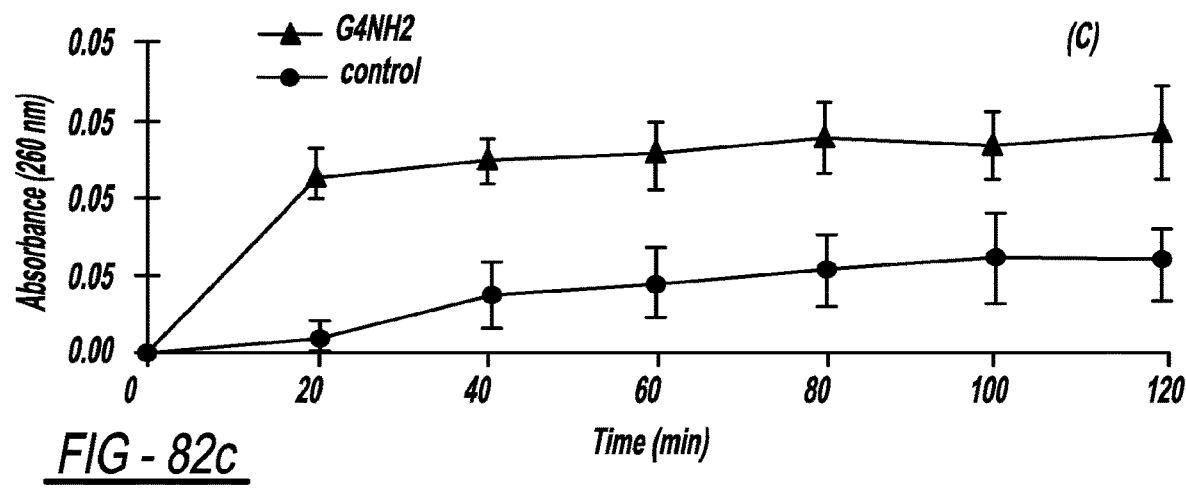
Figure 83A:
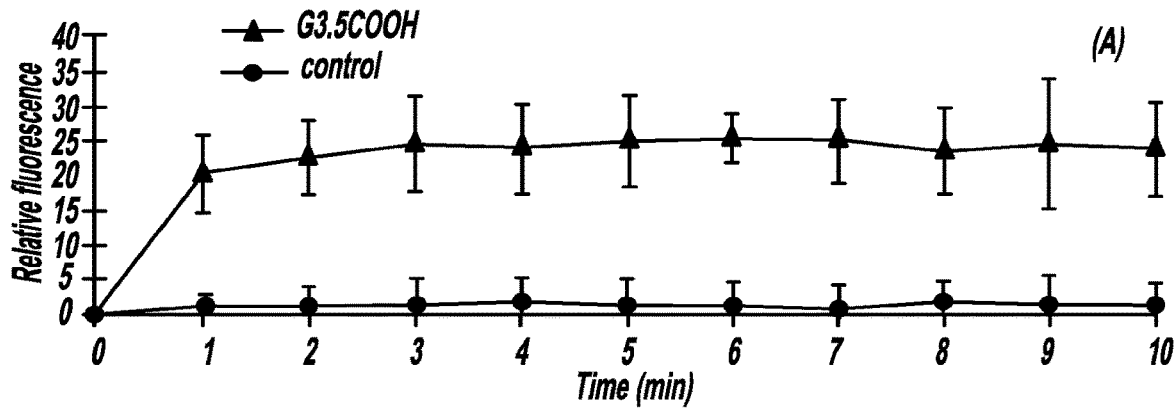
FIG. 83 show the uptake of NPN by *E. coli* suspensions treated with (A) $G_{3.5}$-PAMAM-COOH, (B) $G_4$-PAMAM-OH and (C) $G_4$-PAMAM-$NH_2$. Four samples were in each group.
Figure 83B:
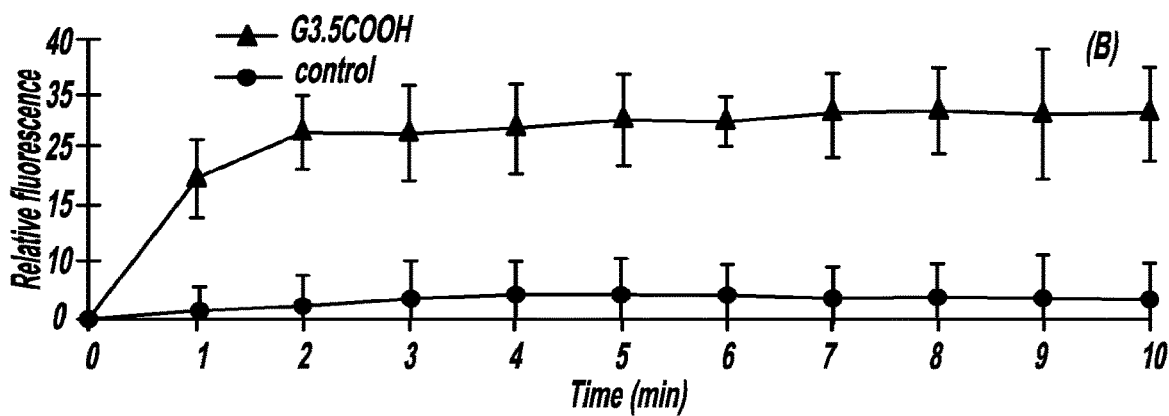
Figure 83C:
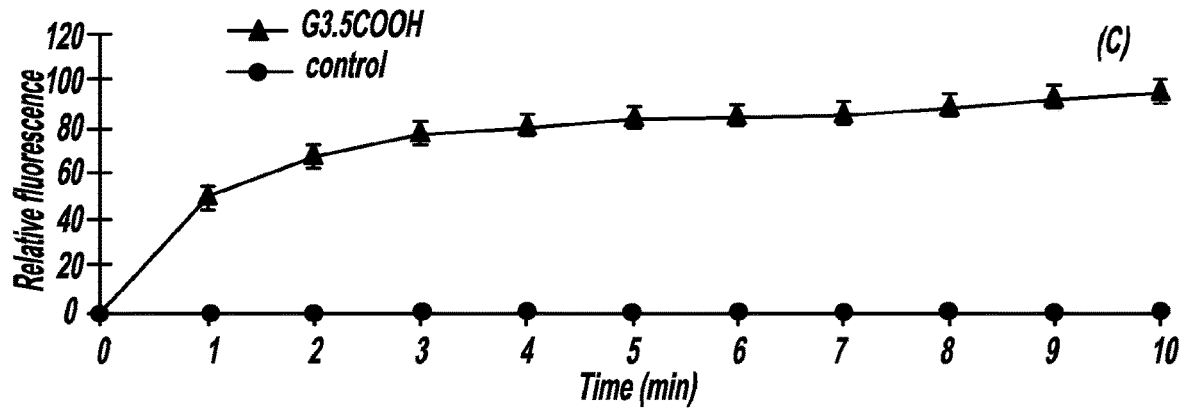
Figure 84A:
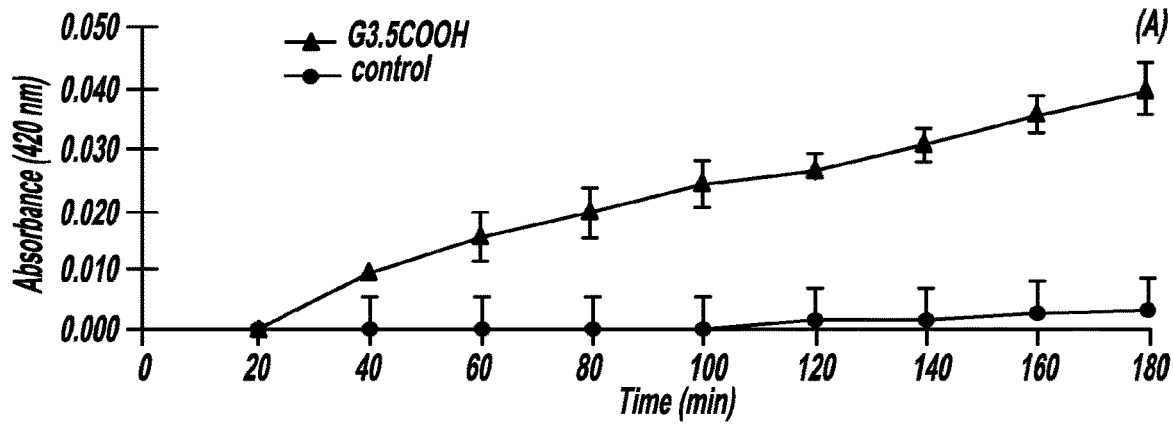
FIG. 84 show the release of cytoplasmic β-galactosidase of *E. coli* treated with (A) $G_{3.5}$-PAMAM-COOH, (B) $G_4$-PAMAM-OH and (C) $G_4$-PAMAM-$NH_2$. Four samples were in each group.
Figure 84B:
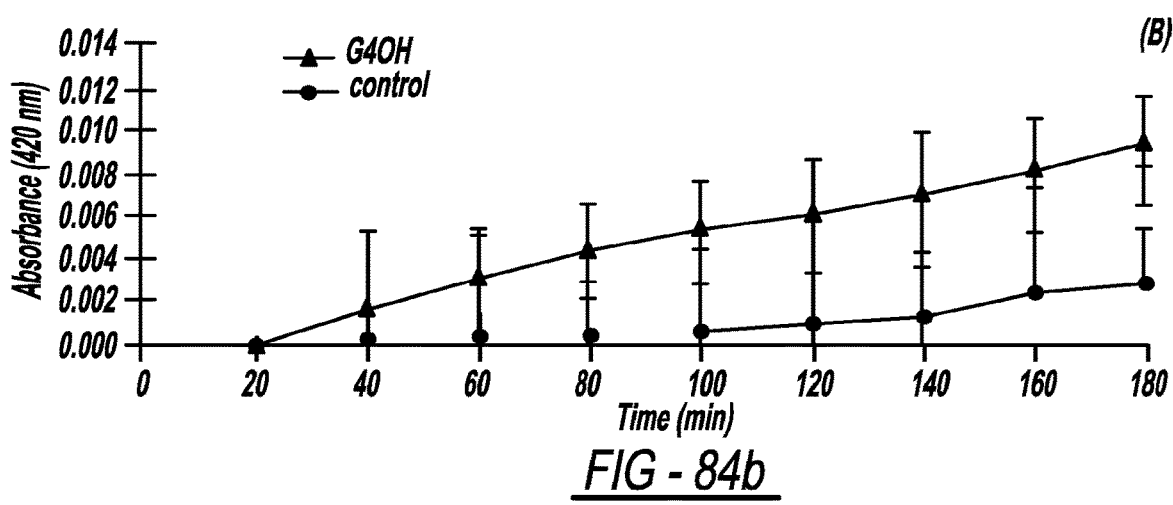
Figure 84C:
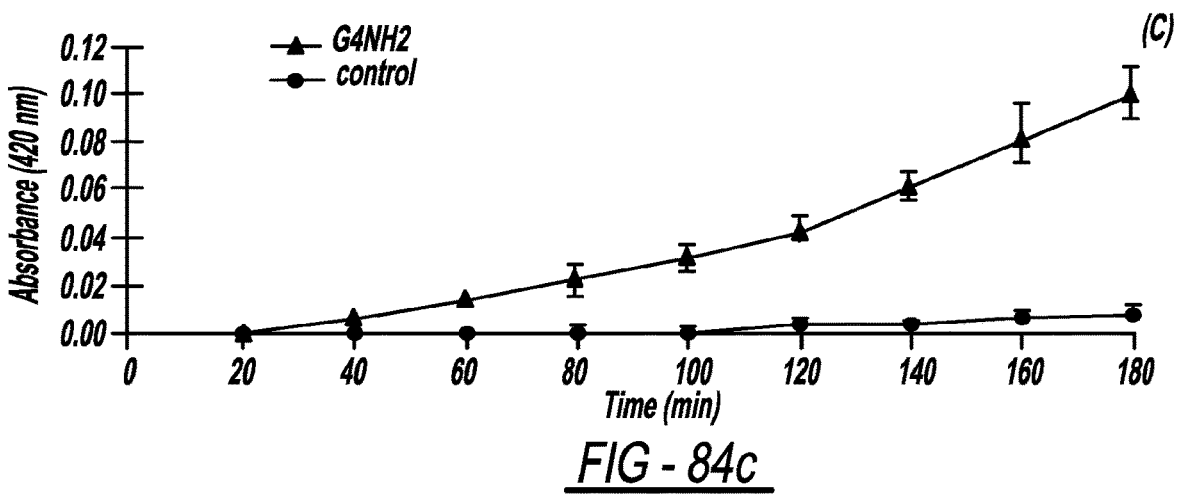

Column 1, Line 21, please insert the following paragraph prior to the paragraph titled "Background Art":
--STATEMENT REGARDING FEDERALLY SPONSORED RESEARCH
This invention was made with government support under HD023342 awarded by the National Institutes of Health. The government has certain rights in the invention.--.
Column 2, Line 60, please replace the term "or or" with "or".
Column 2, Line 65, please replace the term "or or" with "or".
Column 3, Line 3, please replace the term "or or" with "or".
Column 3, Line 4, please replace the term "or or" with "or".
Column 3, Line 6, please replace the term "or or" with "or".
Column 3, Line 20, please replace the term "GSH on" with "GSH".
Column 3, Line 25, please replace the term "disulfide" with "disulfide.".
Column 3, Line 53, please replace the term "molecules of" with "molecules".
Column 3, Line 60, please replace the term "molecules of" with "molecules".
Column 3, Line 66, please replace the term "molecules of" with "molecules".
Column 4, Line 17, please replace the term "land" with "1 and".
Column 4, Line 20, please replace the term "2 its" with "2 and its".
Column 4, Line 30, please replace the term "correspond" with "corresponding".
Column 9, Line 1, please replace the term "FIG. 80" with "FIGS. 80A-80F".
Column 9, Line 16, please replace the term "FIG. 82" with "FIGS. 82A-82C".
Column 9, Line 23, please replace the term "FIG. 83" with "FIGS. 83A-83C".
Column 9, Line 27, please replace the term "FIG. 84" with "FIGS. 84A-84C".
Column 9, Line 31, please replace the term "FIG. 85" with "FIGS. 85A-85B".
Column 9, Line 39, please replace the term "FIG. 86" with "FIGS. 86A-86B".
Column 12, Line 28, please replace the phrase "herein it intended" with "herein is intended".
Column 16, Line 5, please replace the phrase "polymer has has" with "polymer has".
Column 16, Line 19, please replace the term "funtionalized" with "functionalized".
Column 16, Line 39, please replace the term "Since," with "Since".

Signed and Sealed this
Twenty-second Day of December, 2020

Andrei Iancu
*Director of the United States Patent and Trademark Office*

CERTIFICATE OF CORRECTION (continued)
U.S. Pat. No. 10,561,673 B2

Column 17, Line 60, please replace the phrase "concentration 10 mg/kg, 10 mg elicit" with "concentration 10 mg/kg elicit".
Column 20, Line 1, please replace the phrase "lyophilized get" with "lyophilized to get".
Column 20, Line 36, please replace the phrase "at room for 4 hours" with "at room temperature for 4 hours".
Column 26, Line 62, please replace the phrase "n PBS buffer" with "in PBS buffer".
Column 28, Line 17, please replace the term "AMAM-O-GABA-NH" with "PAMAM-O-GABA-NH".
Column 28, Lines 46-47, please replace the phrase "confirmed HPLC" with "confirmed by HPLC".
Column 39, Line 10, please replace the term "weighted" with "weighed".
Column 55, Line 23, please replace the phrase "efficacious that free drug" with "efficacious than free drug".
Column 65, Line 63, please replace the term "choriomanionitis" with "chorioamnionitis".

In the Claims

Claim 14, Column 96, Line 46, please replace the term "comprises" with "comprising".
Claim 14, Column 96, Line 46, please replace the phrase "amount of composition" with "amount of the composition".